(12) United States Patent
Ecker et al.

(10) Patent No.: US 9,149,473 B2
(45) Date of Patent: *Oct. 6, 2015

(54) TARGETED WHOLE GENOME AMPLIFICATION METHOD FOR IDENTIFICATION OF PATHOGENS

(75) Inventors: David J. Ecker, Encinitas, CA (US); Mark W. Eshoo, Solana Beach, CA (US)

(73) Assignee: IBIS BIOSCIENCES, INC., Carlsbad, CA (US)

( * ) Notice: Subject to any disclaimer, the term of this patent is extended or adjusted under 35 U.S.C. 154(b) by 600 days.

This patent is subject to a terminal disclaimer.

(21) Appl. No.: 12/441,329

(22) PCT Filed: Sep. 14, 2007

(86) PCT No.: PCT/US2007/020045
§ 371 (c)(1),
(2), (4) Date: Jun. 17, 2009

(87) PCT Pub. No.: WO2008/143627
PCT Pub. Date: Nov. 27, 2008

(65) Prior Publication Data
US 2010/0035232 A1    Feb. 11, 2010

Related U.S. Application Data

(60) Provisional application No. 60/825,703, filed on Sep. 14, 2006, provisional application No. 60/946,367, filed on Jun. 26, 2007.

(51) Int. Cl.
C12Q 1/68 (2006.01)
C12P 19/34 (2006.01)
A61K 31/4741 (2006.01)

(52) U.S. Cl.
CPC ............. *A61K 31/4741* (2013.01); *C12P 19/34* (2013.01); *C12Q 1/68* (2013.01); *C12Q 1/6806* (2013.01); *C12Q 1/686* (2013.01); *C12Q 1/6848* (2013.01); *C12Q 1/689* (2013.01)

(58) Field of Classification Search
CPC .................................. C12Q 1/68; C12P 19/34
USPC ............................ 435/5, 6.12, 91.1, 6.1, 91.2
See application file for complete search history.

(56) References Cited

U.S. PATENT DOCUMENTS

| | | |
|---|---|---|
| 4,075,475 A | 2/1978 | Risby et al. |
| 4,683,195 A | 7/1987 | Mullis et al. |
| 4,683,202 A | 7/1987 | Mullis |
| 4,965,188 A | 10/1990 | Mullis et al. |
| 5,015,845 A | 5/1991 | Allen et al. |
| 5,072,115 A | 12/1991 | Zhou |
| 5,143,905 A | 9/1992 | Sivasubramanian et al. |
| 5,213,961 A | 5/1993 | Bunn et al. |
| 5,219,727 A | 6/1993 | Wang et al. |
| 5,288,611 A | 2/1994 | Kohne |
| 5,436,129 A | 7/1995 | Stapleton |
| 5,451,500 A | 9/1995 | Stapleton |
| 5,472,843 A | 12/1995 | Milliman |
| 5,476,774 A | 12/1995 | Wang et al. |
| 5,484,908 A | 1/1996 | Froehler et al. |
| 5,502,177 A | 3/1996 | Matteucci et al. |
| 5,503,980 A | 4/1996 | Cantor |
| 5,504,327 A | 4/1996 | Sproch et al. |
| 5,504,329 A | 4/1996 | Mann et al. |
| 5,523,217 A | 6/1996 | Lupski et al. |
| 5,527,669 A | 6/1996 | Resnick et al. |
| 5,527,675 A | 6/1996 | Coull et al. |
| 5,547,835 A | 8/1996 | Koster |
| 5,567,587 A | 10/1996 | Kohne |
| 5,576,204 A | 11/1996 | Blanco et al. |
| 5,580,733 A | 12/1996 | Levis et al. |
| 5,605,798 A | 2/1997 | Koster |
| 5,608,217 A | 3/1997 | Franzen et al. |
| 5,612,179 A | 3/1997 | Simons |
| 5,622,824 A | 4/1997 | Koster |
| 5,625,184 A | 4/1997 | Vestal et al. |
| 5,639,606 A | 6/1997 | Willey |
| 5,641,632 A | 6/1997 | Kohne |
| 5,645,985 A | 7/1997 | Froehler et al. |
| 5,683,869 A | 11/1997 | Ramsay Shaw et al. |
| 5,686,242 A | 11/1997 | Bruice et al. |
| 5,691,141 A | 11/1997 | Koster |
| 5,700,642 A | 12/1997 | Monforte et al. |
| 5,702,895 A | 12/1997 | Matsunaga et al. |

(Continued)

FOREIGN PATENT DOCUMENTS

| | | |
|---|---|---|
| DE | 19732086 A1 | 1/1999 |
| DE | 19802905 A1 | 7/1999 |

(Continued)

OTHER PUBLICATIONS

Talaat et al., Genome-directed primers for selective labeling of bacterial transcripts for DNA microarray analysis, Nature Biotechnology vol. 18 Jun. 2000 pp. 679-682, http://biotech.nature.com.*
Buck et al., Design Strategies and Performance of Custom DNA Sequencing Primers BioTechniques 27:pp. 528-536 (Sep. 1999).*
Tang et al., Mining Disease Susceptibility Genes through SNP Analyses and Expression Profiling Using MALDI-TOF Mass Spectrometry, Journal of Proteome Research 2004, 3, pp. 218-227.*
Anthony et al., Rapid Diagnosis of Bacteremia by Universal Amplification of 23S Ribosomal DNA Followed by Hybridization to an Oligonucleotide Array, Journal of Clinical Microbiology Feb. 2000, p. 781-788.*
Talaat AM, Hunter P, Johnston SA. Genome-directed primers for selective labeling of bacterial transcripts for DNA microarray analysis. Nat Biotechnol. 2000. 18(6):679-82.*

(Continued)

*Primary Examiner* — Ardin Marschel
(74) *Attorney, Agent, or Firm* — David A. Casimir; Casimir Jones, S.C.

(57) ABSTRACT

The methods disclosed herein relate to methods and compositions for amplifying nucleic acid sequences, more specifically, from nucleic acid sequences of pathogens by targeted whole genome amplification.

79 Claims, 9 Drawing Sheets

(56) References Cited

U.S. PATENT DOCUMENTS

| | | | |
|---|---|---|---|
| 5,707,802 A | 1/1998 | Sandhu et al. | |
| 5,712,125 A | 1/1998 | Uhlen | |
| 5,716,825 A | 2/1998 | Hancock et al. | |
| 5,719,028 A * | 2/1998 | Dahlberg et al. | 435/5 |
| 5,727,202 A | 3/1998 | Kucala | |
| 5,745,751 A | 4/1998 | Nelson et al. | |
| 5,747,246 A | 5/1998 | Pannetier et al. | |
| 5,747,251 A | 5/1998 | Carson et al. | |
| 5,753,467 A | 5/1998 | Jensen et al. | |
| 5,753,489 A | 5/1998 | Kistner et al. | |
| 5,759,771 A | 6/1998 | Tilanus | |
| 5,763,169 A | 6/1998 | Sandhu et al. | |
| 5,763,588 A | 6/1998 | Matteucci et al. | |
| 5,770,367 A | 6/1998 | Southern et al. | |
| 5,777,324 A | 7/1998 | Hillenkamp | |
| 5,814,442 A | 9/1998 | Natarajan et al. | |
| 5,822,824 A | 10/1998 | Dion | |
| 5,828,062 A | 10/1998 | Jarrell et al. | |
| 5,830,653 A | 11/1998 | Froehler et al. | |
| 5,830,655 A | 11/1998 | Monforte et al. | |
| 5,830,853 A | 11/1998 | Backstrom et al. | |
| 5,832,489 A | 11/1998 | Kucala | |
| 5,834,255 A | 11/1998 | Van Gemen et al. | |
| 5,845,174 A | 12/1998 | Yasui et al. | |
| 5,849,492 A | 12/1998 | Rogan | |
| 5,849,497 A | 12/1998 | Steinman | |
| 5,849,901 A | 12/1998 | Mabilat et al. | |
| 5,851,765 A | 12/1998 | Koster | |
| 5,856,174 A | 1/1999 | Lipshutz et al. | |
| 5,864,137 A | 1/1999 | Becker et al. | |
| 5,866,429 A | 2/1999 | Bloch | |
| 5,869,242 A | 2/1999 | Kamb | |
| 5,871,697 A | 2/1999 | Rothberg et al. | |
| 5,872,003 A | 2/1999 | Koster | |
| 5,876,936 A | 3/1999 | Ju | |
| 5,876,938 A | 3/1999 | Stolowitz et al. | |
| 5,885,775 A | 3/1999 | Haff et al. | |
| 5,900,481 A | 5/1999 | Lough et al. | |
| 5,928,905 A | 7/1999 | Stemmer et al. | |
| 5,928,906 A | 7/1999 | Koster et al. | |
| 5,965,363 A | 10/1999 | Monforte et al. | |
| 5,965,383 A | 10/1999 | Vogel et al. | |
| 5,972,693 A | 10/1999 | Rothberg et al. | |
| 5,976,798 A | 11/1999 | Parker et al. | |
| 5,981,176 A | 11/1999 | Wallace | |
| 5,981,190 A | 11/1999 | Israel | |
| 5,994,066 A | 11/1999 | Bergeron et al. | |
| 6,001,564 A | 12/1999 | Bergeron et al. | |
| 6,005,096 A | 12/1999 | Matteucci et al. | |
| 6,007,690 A | 12/1999 | Nelson et al. | |
| 6,007,992 A | 12/1999 | Lin et al. | |
| 6,015,666 A | 1/2000 | Springer et al. | |
| 6,018,713 A | 1/2000 | Coli et al. | |
| 6,024,925 A | 2/2000 | Little et al. | |
| 6,028,183 A | 2/2000 | Lin et al. | |
| 6,043,031 A | 3/2000 | Koster et al. | |
| 6,046,005 A | 4/2000 | Ju et al. | |
| 6,051,378 A | 4/2000 | Monforte et al. | |
| 6,054,278 A | 4/2000 | Dodge et al. | |
| 6,055,487 A | 4/2000 | Margery et al. | |
| 6,060,246 A | 5/2000 | Summerton et al. | |
| 6,061,686 A | 5/2000 | Gauvin et al. | |
| 6,063,031 A | 5/2000 | Cundari et al. | |
| 6,074,823 A | 6/2000 | Koster | |
| 6,074,831 A | 6/2000 | Yakhini et al. | |
| 6,090,558 A | 7/2000 | Butler et al. | |
| 6,104,028 A | 8/2000 | Hunter et al. | |
| 6,110,710 A | 8/2000 | Smith et al. | |
| 6,111,251 A | 8/2000 | Hillenkamp | |
| 6,133,436 A | 10/2000 | Koster et al. | |
| 6,140,053 A | 10/2000 | Koster | |
| 6,146,144 A | 11/2000 | Fowler et al. | |
| 6,146,854 A | 11/2000 | Koster et al. | |
| 6,153,389 A | 11/2000 | Haarer et al. | |
| 6,159,681 A | 12/2000 | Zebala | |
| 6,180,339 B1 | 1/2001 | Sandhu et al. | |
| 6,180,372 B1 | 1/2001 | Franzen | |
| 6,187,842 B1 | 2/2001 | Kobayashi et al. | |
| 6,194,144 B1 | 2/2001 | Koster | |
| 6,197,498 B1 | 3/2001 | Koster | |
| 6,214,555 B1 | 4/2001 | Leushner et al. | |
| 6,218,118 B1 | 4/2001 | Sampson et al. | |
| 6,221,587 B1 | 4/2001 | Ecker et al. | |
| 6,221,598 B1 | 4/2001 | Schumm et al. | |
| 6,221,601 B1 | 4/2001 | Koster et al. | |
| 6,221,605 B1 | 4/2001 | Koster | |
| 6,225,450 B1 | 5/2001 | Koster | |
| 6,235,476 B1 | 5/2001 | Bergmann et al. | |
| 6,235,478 B1 | 5/2001 | Koster | |
| 6,235,480 B1 | 5/2001 | Shultz et al. | |
| 6,238,871 B1 | 5/2001 | Koster | |
| 6,238,927 B1 | 5/2001 | Abrams et al. | |
| 6,239,159 B1 | 5/2001 | Brown et al. | |
| 6,258,538 B1 | 7/2001 | Koster et al. | |
| 6,261,769 B1 | 7/2001 | Everett et al. | |
| 6,265,716 B1 | 7/2001 | Hunter et al. | |
| 6,265,718 B1 | 7/2001 | Park et al. | |
| 6,266,131 B1 | 7/2001 | Hamada et al. | |
| 6,266,144 B1 | 7/2001 | Li | |
| 6,268,129 B1 | 7/2001 | Gut et al. | |
| 6,268,131 B1 | 7/2001 | Kang et al. | |
| 6,268,144 B1 | 7/2001 | Koster | |
| 6,268,146 B1 | 7/2001 | Shultz et al. | |
| 6,270,973 B1 | 8/2001 | Lewis et al. | |
| 6,270,974 B1 | 8/2001 | Shultz et al. | |
| 6,274,726 B1 | 8/2001 | Laugharn, Jr. et al. | |
| 6,277,573 B1 | 8/2001 | Koster | |
| 6,277,578 B1 | 8/2001 | Shultz et al. | |
| 6,277,634 B1 | 8/2001 | McCall et al. | |
| 6,300,076 B1 | 10/2001 | Koster | |
| 6,303,297 B1 | 10/2001 | Lincoln et al. | |
| 6,312,893 B1 | 11/2001 | Van Ness et al. | |
| 6,312,902 B1 | 11/2001 | Shultz et al. | |
| 6,322,970 B1 | 11/2001 | Little et al. | |
| 6,361,940 B1 | 3/2002 | Van Ness et al. | |
| 6,372,424 B1 | 4/2002 | Brow et al. | |
| 6,389,428 B1 | 5/2002 | Rigault et al. | |
| 6,391,551 B1 | 5/2002 | Shultz et al. | |
| 6,393,367 B1 | 5/2002 | Tang et al. | |
| 6,419,932 B1 | 7/2002 | Dale | |
| 6,423,966 B2 | 7/2002 | Hillenkamp et al. | |
| 6,428,955 B1 | 8/2002 | Koster et al. | |
| 6,428,956 B1 | 8/2002 | Crooke et al. | |
| 6,432,651 B1 | 8/2002 | Hughes et al. | |
| 6,436,635 B1 | 8/2002 | Fu et al. | |
| 6,436,640 B1 | 8/2002 | Simmons et al. | |
| 6,453,244 B1 | 9/2002 | Oefner | |
| 6,458,533 B1 | 10/2002 | Felder et al. | |
| 6,468,743 B1 | 10/2002 | Romick et al. | |
| 6,468,748 B1 | 10/2002 | Monforte et al. | |
| 6,475,143 B2 | 11/2002 | Iliff | |
| 6,475,736 B1 | 11/2002 | Stanton, Jr. | |
| 6,475,738 B2 | 11/2002 | Shuber et al. | |
| 6,479,239 B1 | 11/2002 | Anderson et al. | |
| 6,500,621 B2 | 12/2002 | Koster | |
| 6,553,317 B1 | 4/2003 | Lincoln et al. | |
| 6,558,902 B1 | 5/2003 | Hillenkamp | |
| 6,563,025 B1 | 5/2003 | Song et al. | |
| 6,566,055 B1 | 5/2003 | Monforte et al. | |
| 6,568,055 B1 | 5/2003 | Tang et al. | |
| 6,582,916 B1 | 6/2003 | Schmidt et al. | |
| 6,586,584 B2 | 7/2003 | McMillian et al. | |
| 6,589,485 B2 | 7/2003 | Koster | |
| 6,602,662 B1 | 8/2003 | Koster et al. | |
| 6,605,433 B1 | 8/2003 | Fliss et al. | |
| 6,610,492 B1 | 8/2003 | Stanton, Jr. et al. | |
| 6,613,509 B1 | 9/2003 | Chen | |
| 6,613,520 B2 | 9/2003 | Ashby | |
| 6,623,928 B2 | 9/2003 | Van Ness et al. | |
| 6,638,714 B1 | 10/2003 | Linnen et al. | |
| 6,680,476 B1 | 1/2004 | Hidalgo et al. | |
| 6,682,889 B1 | 1/2004 | Wang et al. | |
| 6,705,530 B2 | 3/2004 | Kiekhaefer | |
| 6,706,530 B2 | 3/2004 | Hillenkamp | |

(56) References Cited

U.S. PATENT DOCUMENTS

| | | |
|---|---|---|
| 6,783,939 B2 | 8/2004 | Olmsted et al. |
| 6,800,289 B2 | 10/2004 | Nagata et al. |
| 6,813,615 B1 | 11/2004 | Colasanti et al. |
| 6,836,742 B2 | 12/2004 | Brekenfeld |
| 6,852,487 B1 | 2/2005 | Barany et al. |
| 6,856,914 B1 | 2/2005 | Pelech |
| 6,875,593 B2 | 4/2005 | Froehler et al. |
| 6,906,316 B2 | 6/2005 | Sugiyama et al. |
| 6,906,319 B2 | 6/2005 | Hoyes |
| 6,914,137 B2 | 7/2005 | Baker |
| 6,977,148 B2 | 12/2005 | Dean et al. |
| 6,994,962 B1 | 2/2006 | Thilly |
| 7,022,835 B1 | 4/2006 | Rauth et al. |
| 7,024,370 B2 | 4/2006 | Epler et al. |
| 7,108,974 B2 | 9/2006 | Ecker et al. |
| 7,198,893 B1 | 4/2007 | Köster et al. |
| 7,217,510 B2 | 5/2007 | Ecker et al. |
| 7,226,739 B2 | 6/2007 | Ecker et al. |
| 7,255,992 B2 | 8/2007 | Ecker et al. |
| 7,285,422 B1 | 10/2007 | Little et al. |
| 7,312,036 B2 | 12/2007 | Sampath et al. |
| 7,321,828 B2 | 1/2008 | Cowsert et al. |
| 7,349,808 B1 | 3/2008 | Kreiswirth et al. |
| 7,390,458 B2 | 6/2008 | Burow et al. |
| 7,419,787 B2 | 9/2008 | Köster |
| 7,501,251 B2 | 3/2009 | Köster et al. |
| 7,666,588 B2 | 2/2010 | Ecker et al. |
| 7,718,354 B2 | 5/2010 | Ecker et al. |
| 7,741,036 B2 | 6/2010 | Ecker et al. |
| 7,781,162 B2 | 8/2010 | Ecker et al. |
| 8,073,627 B2 * | 12/2011 | Ecker et al. ............ 702/19 |
| 2001/0039263 A1 | 11/2001 | Matthes et al. |
| 2002/0006611 A1 | 1/2002 | Portugal et al. |
| 2002/0042112 A1 | 4/2002 | Koster et al. |
| 2002/0042506 A1 | 4/2002 | Kristyanne et al. |
| 2002/0045178 A1 | 4/2002 | Cantor et al. |
| 2002/0055101 A1 | 5/2002 | Bergeron et al. |
| 2002/0120408 A1 | 8/2002 | Kreiswirth et al. |
| 2002/0137057 A1 | 9/2002 | Wold et al. |
| 2002/0138210 A1 | 9/2002 | Wilkes et al. |
| 2002/0150927 A1 | 10/2002 | Matray et al. |
| 2002/0168630 A1 | 11/2002 | Fleming et al. |
| 2002/0187490 A1 | 12/2002 | Tiedje et al. |
| 2003/0017487 A1 | 1/2003 | Xue et al. |
| 2003/0027135 A1 | 2/2003 | Ecker et al. |
| 2003/0039976 A1 | 2/2003 | Haff |
| 2003/0050470 A1 | 3/2003 | An et al. |
| 2003/0064483 A1 | 4/2003 | Shaw et al. |
| 2003/0073112 A1 | 4/2003 | Zhang et al. |
| 2003/0084483 A1 | 5/2003 | Simpson et al. |
| 2003/0101172 A1 | 5/2003 | De La Huerga |
| 2003/0104410 A1 | 6/2003 | Mittmann |
| 2003/0104699 A1 | 6/2003 | Minamihaba et al. |
| 2003/0113738 A1 | 6/2003 | Liu et al. |
| 2003/0113745 A1 | 6/2003 | Monforte et al. |
| 2003/0118998 A1 * | 6/2003 | Dean et al. ............ 435/6 |
| 2003/0119018 A1 | 6/2003 | Omura et al. |
| 2003/0129589 A1 | 7/2003 | Koster et al. |
| 2003/0134312 A1 | 7/2003 | Burgoyne |
| 2003/0148281 A1 | 8/2003 | Glucksmann |
| 2003/0148284 A1 | 8/2003 | Vision et al. |
| 2003/0167133 A1 | 9/2003 | Ecker et al. |
| 2003/0167134 A1 | 9/2003 | Ecker et al. |
| 2003/0175695 A1 | 9/2003 | Ecker et al. |
| 2003/0175696 A1 | 9/2003 | Ecker et al. |
| 2003/0175697 A1 | 9/2003 | Ecker et al. |
| 2003/0175729 A1 | 9/2003 | Van Eijk et al. |
| 2003/0186247 A1 | 10/2003 | Smarason et al. |
| 2003/0187588 A1 | 10/2003 | Ecker et al. |
| 2003/0187593 A1 | 10/2003 | Ecker et al. |
| 2003/0190605 A1 | 10/2003 | Ecker et al. |
| 2003/0190635 A1 | 10/2003 | McSwiggen |
| 2003/0194699 A1 | 10/2003 | Lewis et al. |
| 2003/0203398 A1 | 10/2003 | Bramucci et al. |
| 2003/0220844 A1 | 11/2003 | Marnellos et al. |
| 2003/0224377 A1 | 12/2003 | Wengel et al. |
| 2003/0225529 A1 | 12/2003 | Ecker et al. |
| 2003/0228571 A1 | 12/2003 | Ecker et al. |
| 2003/0228597 A1 | 12/2003 | Cowsert et al. |
| 2003/0228613 A1 | 12/2003 | Bornarth et al. |
| 2004/0005555 A1 | 1/2004 | Rothman et al. |
| 2004/0013703 A1 | 1/2004 | Ralph et al. |
| 2004/0014957 A1 | 1/2004 | Eldrup et al. |
| 2004/0023207 A1 | 2/2004 | Polansky |
| 2004/0023209 A1 | 2/2004 | Jonasson |
| 2004/0029129 A1 | 2/2004 | Wang et al. |
| 2004/0038206 A1 | 2/2004 | Zhang et al. |
| 2004/0038208 A1 | 2/2004 | Fisher et al. |
| 2004/0038234 A1 | 2/2004 | Gut et al. |
| 2004/0038385 A1 | 2/2004 | Langlois et al. |
| 2004/0081993 A1 | 4/2004 | Cantor et al. |
| 2004/0101809 A1 | 5/2004 | Weiss et al. |
| 2004/0110169 A1 | 6/2004 | Ecker et al. |
| 2004/0111221 A1 | 6/2004 | Beattie et al. |
| 2004/0117129 A1 | 6/2004 | Ecker et al. |
| 2004/0117354 A1 | 6/2004 | Azzaro et al. |
| 2004/0121309 A1 | 6/2004 | Ecker et al. |
| 2004/0121310 A1 | 6/2004 | Ecker et al. |
| 2004/0121311 A1 | 6/2004 | Ecker et al. |
| 2004/0121312 A1 | 6/2004 | Ecker et al. |
| 2004/0121313 A1 | 6/2004 | Ecker et al. |
| 2004/0121314 A1 | 6/2004 | Ecker et al. |
| 2004/0121315 A1 | 6/2004 | Ecker et al. |
| 2004/0121329 A1 | 6/2004 | Ecker et al. |
| 2004/0121335 A1 | 6/2004 | Ecker et al. |
| 2004/0121340 A1 | 6/2004 | Ecker et al. |
| 2004/0122598 A1 | 6/2004 | Ecker et al. |
| 2004/0122857 A1 | 6/2004 | Ecker et al. |
| 2004/0126764 A1 * | 7/2004 | Lasken et al. ............ 435/6 |
| 2004/0137013 A1 | 7/2004 | Katinger et al. |
| 2004/0185438 A1 | 9/2004 | Ecker |
| 2004/0191769 A1 | 9/2004 | Marino et al. |
| 2004/0202997 A1 | 10/2004 | Ecker et al. |
| 2004/0209260 A1 | 10/2004 | Ecker et al. |
| 2004/0209298 A1 * | 10/2004 | Kamberov et al. ............ 435/6 |
| 2004/0253583 A1 | 12/2004 | Ecker et al. |
| 2004/0253619 A1 | 12/2004 | Ecker et al. |
| 2005/0026147 A1 | 2/2005 | Walker et al. |
| 2005/0026641 A1 | 2/2005 | Hokao |
| 2005/0027459 A1 | 2/2005 | Ecker et al. |
| 2005/0065813 A1 | 3/2005 | Mishelevich et al. |
| 2005/0130196 A1 | 6/2005 | Hofstadler et al. |
| 2005/0130216 A1 | 6/2005 | Becker et al. |
| 2005/0142584 A1 | 6/2005 | Willson et al. |
| 2005/0250125 A1 | 11/2005 | Novakoff |
| 2005/0266397 A1 | 12/2005 | Ecker et al. |
| 2005/0266411 A1 | 12/2005 | Hofstadler et al. |
| 2006/0020391 A1 | 1/2006 | Kreiswirth et al. |
| 2006/0046246 A1 * | 3/2006 | Zeng et al. ............ 435/5 |
| 2006/0121520 A1 | 6/2006 | Ecker et al. |
| 2006/0172330 A1 | 8/2006 | Osborn et al. |
| 2006/0188875 A1 * | 8/2006 | Cox et al. ............ 435/6 |
| 2006/0205040 A1 | 9/2006 | Sampath |
| 2006/0240412 A1 | 10/2006 | Hall et al. |
| 2006/0259249 A1 | 11/2006 | Sampath et al. |
| 2007/0218467 A1 | 9/2007 | Ecker et al. |
| 2008/0160512 A1 | 7/2008 | Ecker et al. |
| 2008/0311558 A1 | 12/2008 | Ecker et al. |
| 2009/0004643 A1 | 1/2009 | Ecker et al. |
| 2009/0023150 A1 | 1/2009 | Koster et al. |
| 2009/0042203 A1 | 2/2009 | Koster |
| 2009/0092977 A1 | 4/2009 | Koster |
| 2009/0125245 A1 | 5/2009 | Hofstadler et al. |
| 2009/0148829 A1 | 6/2009 | Ecker et al. |
| 2009/0148836 A1 | 6/2009 | Ecker et al. |
| 2009/0148837 A1 | 6/2009 | Ecker et al. |
| 2009/0182511 A1 | 7/2009 | Ecker et al. |
| 2009/0239224 A1 | 9/2009 | Ecker et al. |

(56) References Cited

U.S. PATENT DOCUMENTS

| | | |
|---|---|---|
| 2010/0070194 A1 | 3/2010 | Ecker et al. |
| 2010/0145626 A1 | 6/2010 | Ecker et al. |
| 2010/0184035 A1 | 7/2010 | Hall et al. |

FOREIGN PATENT DOCUMENTS

| | | | |
|---|---|---|---|
| DE | 19824280 A1 | 12/1999 | |
| DE | 19852167 A1 | 5/2000 | |
| DE | 19943374 A1 | 3/2001 | |
| DE | 10132147 A1 | 2/2003 | |
| EP | 0 990 047 B1 * | 7/1988 | ............... C12Q 1/68 |
| EP | 281390 A2 | 9/1988 | |
| EP | 633321 A1 | 1/1995 | |
| EP | 620862 B1 | 4/1998 | |
| EP | 1035219 A1 | 9/2000 | |
| EP | 1138782 A2 | 10/2001 | |
| EP | 1234888 A2 | 8/2002 | |
| EP | 1308506 A1 | 5/2003 | |
| EP | 1310571 A2 | 5/2003 | |
| EP | 1333101 A1 | 8/2003 | |
| EP | 1365031 A1 | 11/2003 | |
| EP | 1234888 A3 | 1/2004 | |
| EP | 1748072 A1 | 1/2007 | |
| FR | 2811321 A1 | 1/2002 | |
| GB | 2325002 A | 11/1998 | |
| GB | 2339905 A | 2/2000 | |
| JP | 5276999 A2 | 10/1993 | |
| JP | 11137259 A | 5/1999 | |
| JP | 24024206 A2 | 1/2004 | |
| JP | 2004000200 A2 | 1/2004 | |
| JP | 24201679 A2 | 7/2004 | |
| JP | 2004201641 A | 7/2004 | |
| JP | 2005523700 A | 8/2005 | |
| JP | 2007512014 A | 5/2007 | |
| JP | 2008526248 A | 7/2008 | |
| WO | WO8803957 A1 | 6/1988 | |
| WO | WO9015157 A1 | 12/1990 | |
| WO | WO9205182 A1 | 4/1992 | |
| WO | WO9208117 A1 | 5/1992 | |
| WO | WO9209703 A1 | 6/1992 | |
| WO | WO9219774 A1 | 11/1992 | |
| WO | WO9303186 A1 | 2/1993 | |
| WO | WO9305182 A1 | 3/1993 | |
| WO | WO9308297 A1 | 4/1993 | |
| WO | WO9416101 A2 | 7/1994 | |
| WO | WO9419490 A1 | 9/1994 | |
| WO | WO9421822 A1 | 9/1994 | |
| WO | WO9504161 A1 | 2/1995 | |
| WO | WO9511996 A1 | 5/1995 | |
| WO | WO9513395 A1 | 5/1995 | |
| WO | WO9513396 A2 | 5/1995 | |
| WO | WO9531997 A1 | 11/1995 | |
| WO | WO9606187 A1 | 2/1996 | |
| WO | WO9616186 A1 | 5/1996 | |
| WO | WO9629431 A2 | 9/1996 | |
| WO | WO9632504 A2 | 10/1996 | |
| WO | WO9635450 A1 | 11/1996 | |
| WO | WO9637630 A1 | 11/1996 | |
| WO | WO9733000 A1 | 9/1997 | |
| WO | WO9734909 A1 | 9/1997 | |
| WO | WO9737041 A2 | 10/1997 | |
| WO | WO9747766 A1 | 12/1997 | |
| WO | WO9803684 A1 | 1/1998 | |
| WO | WO9812355 A1 | 3/1998 | |
| WO | WO9814616 A1 | 4/1998 | |
| WO | WO9815652 A1 | 4/1998 | |
| WO | WO9820020 A2 | 5/1998 | |
| WO | WO9820157 A2 | 5/1998 | |
| WO | WO9820166 A2 | 5/1998 | |
| WO | WO9826095 A1 | 6/1998 | |
| WO | WO9831830 A1 | 7/1998 | |
| WO | WO9835057 A1 | 8/1998 | |
| WO | WO9840520 A1 | 9/1998 | |
| WO | WO9854571 A1 | 12/1998 | |
| WO | WO9854751 A1 | 12/1998 | |
| WO | WO9905319 A2 | 2/1999 | |
| WO | WO9912040 A2 | 3/1999 | |
| WO | WO9913104 A1 | 3/1999 | |
| WO | WO9914375 A2 | 3/1999 | |
| WO | WO9929898 A2 | 6/1999 | |
| WO | WO9931278 A1 | 6/1999 | |
| WO | WO9957318 A2 | 11/1999 | |
| WO | WO9958713 A2 | 11/1999 | |
| WO | WO9960183 A1 | 11/1999 | |
| WO | WO0032750 A1 | 6/2000 | |
| WO | WO0038636 A1 | 7/2000 | |
| WO | WO0063362 A1 | 10/2000 | |
| WO | WO0066762 A2 | 11/2000 | |
| WO | WO0066789 A2 | 11/2000 | |
| WO | WO0077260 A1 | 12/2000 | |
| WO | WO0100828 A2 | 1/2001 | |
| WO | WO0107648 A1 | 2/2001 | |
| WO | WO0112853 A1 | 2/2001 | |
| WO | WO0120018 A2 | 3/2001 | |
| WO | WO0123604 A2 | 4/2001 | |
| WO | WO0123608 A2 | 4/2001 | |
| WO | WO0132930 A1 | 5/2001 | |
| WO | WO0140497 A2 | 6/2001 | |
| WO | WO0146404 A1 | 6/2001 | |
| WO | WO0151661 A2 | 7/2001 | |
| WO | WO0151662 A1 | 7/2001 | |
| WO | WO0157263 A1 | 8/2001 | |
| WO | WO0157518 A2 | 8/2001 | |
| WO | WO0173119 A2 | 10/2001 | |
| WO | WO0173199 A1 | 10/2001 | |
| WO | WO0177392 A2 | 10/2001 | |
| WO | WO0196388 A2 | 12/2001 | |
| WO | WO0202811 A2 | 1/2002 | |
| WO | WO0210186 A1 | 2/2002 | |
| WO | WO0210444 A1 | 2/2002 | |
| WO | WO0218641 A2 | 3/2002 | |
| WO | WO0221108 A2 | 3/2002 | |
| WO | WO0222873 A1 | 3/2002 | |
| WO | WO0224876 A2 | 3/2002 | |
| WO | WO0250307 A1 | 6/2002 | |
| WO | WO02057491 A2 | 7/2002 | |
| WO | WO02070664 A2 | 9/2002 | |
| WO | WO02070728 A2 | 9/2002 | |
| WO | WO02070737 A2 | 9/2002 | |
| WO | WO02077278 A1 | 10/2002 | |
| WO | WO02099034 A2 | 12/2002 | |
| WO | WO02099095 A2 | 12/2002 | |
| WO | WO02099129 A2 | 12/2002 | |
| WO | WO02099130 A2 | 12/2002 | |
| WO | WO03/001976 * | 1/2003 | |
| WO | WO03001976 A2 | 1/2003 | |
| WO | WO03002750 A1 | 1/2003 | |
| WO | WO03008636 A2 | 1/2003 | |
| WO | WO03012058 A2 | 2/2003 | |
| WO | WO03012074 A2 | 2/2003 | |
| WO | WO03014382 A2 | 2/2003 | |
| WO | WO03016546 A1 | 2/2003 | |
| WO | WO03018636 A2 | 3/2003 | |
| WO | WO03020890 A2 | 3/2003 | |
| WO | WO03033732 A2 | 4/2003 | |
| WO | WO03054162 A2 | 7/2003 | |
| WO | WO03054755 A2 | 7/2003 | |
| WO | WO03060163 A2 | 7/2003 | |
| WO | WO03075955 A1 | 9/2003 | |
| WO | WO03088979 A2 | 10/2003 | |
| WO | WO03093506 A1 | 11/2003 | |
| WO | WO03097869 A2 | 11/2003 | |
| WO | WO03100035 A2 | 12/2003 | |
| WO | WO03100068 A1 | 12/2003 | |
| WO | WO03102191 A1 | 12/2003 | |
| WO | WO03104410 A1 | 12/2003 | |
| WO | WO03106635 A2 | 12/2003 | |
| WO | WO2004003511 A2 | 1/2004 | |
| WO | WO2004009849 A1 | 1/2004 | |
| WO | WO2004011651 A1 | 2/2004 | |
| WO | WO2004013357 A2 | 2/2004 | |
| WO | WO2004040013 A1 | 5/2004 | |
| WO | WO2004044123 A2 | 5/2004 | |

(56) References Cited

FOREIGN PATENT DOCUMENTS

| | | | |
|---|---|---|---|
| WO | WO2004044247 A2 | 5/2004 |
| WO | WO2004052175 A2 | 6/2004 |
| WO | WO2004053076 A2 | 6/2004 |
| WO | WO2004053141 A2 | 6/2004 |
| WO | WO2004053164 A1 | 6/2004 |
| WO | WO2004058987 A2 | 7/2004 |
| WO | WO2004060278 A2 | 7/2004 |
| WO | WO2004070001 A2 | 8/2004 |
| WO | WO2004072230 A2 | 8/2004 |
| WO | WO2004072231 A2 | 8/2004 |
| WO | WO2004101809 A2 | 11/2004 |
| WO | WO2005003384 A1 | 1/2005 |
| WO | WO2005009202 A2 | 2/2005 |
| WO | WO2005012572 A1 | 2/2005 |
| WO | WO2005024046 A2 | 3/2005 |
| WO | WO2005036369 A2 | 4/2005 |
| WO | WO2005054454 A1 | 6/2005 |
| WO | WO2005075686 A1 | 8/2005 |
| WO | WO2005086634 A2 | 9/2005 |
| WO | WO2005091971 A2 | 10/2005 |
| WO | WO2005098047 A2 | 10/2005 |
| WO | WO2005116263 A2 | 12/2005 |
| WO | WO2006089762 A1 | 8/2006 |
| WO | WO2006094238 A2 | 9/2006 |
| WO | WO2006135400 A2 | 12/2006 |
| WO | WO2007014045 A2 | 2/2007 |
| WO | WO2007086904 A2 | 8/2007 |
| WO | WO2008104002 A2 | 8/2008 |
| WO | WO2008118809 A1 | 10/2008 |

OTHER PUBLICATIONS

Buck et al., Design Strategies and Performance of Custom DNA Sequencing Primers. BioTechniques 27:pp. 528-536. Sep. 1999.*

Tang K, Oeth P, Kammerer S, Denissenko MF, Ekblom J, Jurinke C, van den Boom D, Braun A, Cantor CR. Mining disease susceptibility genes through SNP analyses and expression profiling using MALDI-TOF mass spectrometry. J Proteome Res. 2004. 3(2):218-27.*

Anthony RM, Brown TJ, French GL. Rapid diagnosis of bacteremia by universal amplification of 23S ribosomal DNA followed by hybridization to an oligonucleotide array. J Clin Microbiol. 2000. 38(2):781-8.*

Final Office Action mailed Jun. 14, 2011 for U.S. Appl. No. 12/616,422, filed Nov. 11, 2009.

Notice of Allowance mailed Jun. 9, 2011 for U.S. Appl. No. 11/331,987, filed Jan. 13, 2006.

Aaserud D.J., et al., "Accurate Base Composition of Double-Strand DNA by Mass Spectrometry," American Society for Mass Spectrometry, 1996, vol. 7 (12), pp. 1266-1269.

Aaserud D.J., et al., "DNA Sequencing with Blackbody Infrared Radioactive Dissociation of Electrosprayed Ions," International Journal of Mass Spectrometry and Icon Processes, 1997, vol. 167/168, pp. 705-712.

Adam E., et al., "Characterization of Intertype Specific Epitopes on Adenovirus Hexons," Archives of Virology, 1998, vol. 143 (9), pp. 1669-1682.

Adam E., et al., "Intertype Specific Epitope Structure of Adenovirus Hexon," Acta Microbiologica et Immunologica Hungarica, 1998, vol. 45 (3-4), pp. 311-316.

Adam E., et al., "Molecular Structure of the Two-Dimensional Hexon Crystalline Array and of Adenovirus Capsid," Acta Microbiologica et Immunologica Hungarica, 1998, vol. 45 (3-4), pp. 305-310.

Adrian T., et al., "DNA Restriction Analysis of Adenovirus Prototypes 1 to 41," Archives of Virology, 1986, vol. 91 (3-4), pp. 277-290.

Adzhar A., et al., "Universal Oligonucleotides for the Detection of Infectious Bronchitis Virus by Thepolymerase Chain Reaction," Avian Pathology, 1996, vol. 25 (4), pp. 817-836.

Agostini H.T., et al., "Complete Genome of a JC Virus Genotype Type 6 from the Brain of an African American with Progressive Multifocal Leukoencephalopathy," Journal of Human Virology, 1998, vol. 1 (4), pp. 267-272.

Aires De Sousa M., et al., "Bridges from Hospitals to the Laboratory: Genetic Portraits of Methicillin-Resistant Staphylococcus aureus Clones," FEMS Immunology and Medical Microbiology, 2004, vol. 40 (2), pp. 101-111.

Akalu A., et al., "Rapid Identification of Subgenera of Human Adenovirus by Serological and PCR Assays," Journal of Virological Methods, 1998, vol. 71 (2), pp. 187-196.

Alba M.M., et al., "VIDA: A Virus Database System for the Organization of Animal Virus Genome Open Reading Frames," Nucleic Acids Research, 2001, vol. 29 (1), pp. 133-136.

Allaouchiche B., et al., "Clinical Impact of Rapid Oxacillin Susceptibility Testing Using a PCR Assay in Staphylococcus aureus Bactaeremia," The Journal of Infection, 1999, vol. 39 (3), pp. 198-204.

Allawi H.T., et al., "Thermodynamics and NMR of Internal G.T. Mismatches in DNA," Biochemistry, 1997, vol. 36 (34), pp. 10581-10594.

Altschuel S.F., et al., "Basic Local Alignment Search Tool," Journal of Molecular Biology, 1990, vol. 215 (3), pp. 403-410.

Altschuel S.F., et al., "Gapped BLAST and PSI-BLAST: A New Generation of Protein Database Search Programs," Nucleic Acids Research, 1997, vol. 25 (17), pp. 3389-3402.

Alves-Silva J., et al., "The Ancestry of Brazilian mtDNA Linages," The American Journal of Human Genetics, 2000, vol. 67 (2), pp. 444-461.

Amano Y., et al., "Detection of Influenza Virus: Traditional Approaches and Development of Biosensors," Analytical and Bioanalytical Chemistry, 2005, vol. 381 (1), pp. 156-164.

Amexis G., et al., "Quantitative Mutant Analysis of Viral Quasispecies by Chip-Based Matrix Assisted LaserDesorption Ionization Time-of-Flight Mass Spectrometry," Proceedings of the National Academy of Sciences, 2001, vol. 98 (21), pp. 12097-12102.

Anderson M.L.M., "Quantitative Filter Hybridization" in: Nucleic Acid Hybridization, Names B.D., ed., IRL Press, 1985, pp. 73-111.

Anderson S., et al., "Sequence and Organization of the Human Mitochondrial Genome," Nature, 1981, vol. 290 (5806), pp. 457-465.

Andreasson H., et al., "Mitochondrial Sequence Analysis for Forensic Identification Using Pyrosequencing Technology," BioTechniques, 2002, vol. 32 (1), pp. 124-133.

Anthony R.M., et al., "Use of the Polymerase Chain Reaction for Rapid Detection of High-Level Mupirocin Resistance in Staphylococci," European Journal of Clinical Microbiology & Infectious Diseases, 1999, vol. 18 (1), pp. 30-34.

Arbique J., et al., "Comparison of the Velogene Rapid MRSA Identification Assay, Denka MRSAScreen Assay, and BBL Crystal MRSA ID System for Rapid Identification of Methicillin-Resistant Staphylococcus aureus," Diagnositic Microbiology and Infectious Diseases, 2001, vol. 40 (1-2), pp. 5-10.

Archer G.L., et al., "Detection of Methicillin Resistance in Staphylococci by Using a DNA Probe," Antimicrobial Agents and Chemotherapy, 1990, vol. 34 (9), pp. 1720-1724.

Armstrong P., et al., "Sensitive and Specific Colorimetric Dot Assay to Detect Eastern Equine Encephalomyelitis Viral RNA in Mosquitoes After PCR Amplification," Journal of Medicinal Entomology, 1995, vol. 32 (1), pp. 42-52.

Arnal C., et al., "Quantification of Hepatitis A Virus in Shellfish by Competitive Reverse Transcription PCR with Coextraction of Standard RNA," Applied and Environmental Microbiology, 1999, vol. 65 (1), pp. 322-326.

Aronsson F., et al., "Persistence of the Influenza A/WSN/33 Virus RNA at Midbrain Levels of Immunodefective Mice," Journal of Neurovirology, 2001, vol. 7 (2), pp. 117-124.

Ausubel F.M., et al., Eds., Current Protocols in Molecular Biology, vol. 1, John Wiley & Sons Inc., 2004, Table of Contents.

Ausubel F.M., et al., eds., Short Protocols in Molecular Biology: A Compendium of Methods from Current Protocols in Molecular Biology, 2nd Edition, John Wiley & Sons, 1992, Units 2.9, 3.4-3.17, 4.6-4.10, and 10.8.

Ausubel F.M., et al., "Unit 2.11 "Synthesis and Purification of Oligonucleotides," in: Current Protocols in Molecular Biology," 1998, John Wiley & Sons, Inc., pp. 2.11-2.11.21.

(56) References Cited

OTHER PUBLICATIONS

Avellon A., et al., "Rapid and Sensitive Diagnosis of Human Adenovirus Infections by a Generic Polymerase Chain Reaction," Journal of Virological Methods, 2001, vol. 92 (2), pp. 113-120.

Azevedo A.M., et al., "Detection of Influenza, Parainfluenza, Adenovirus and Respiratory Syncytial Virus during Asthma Attacks in Children Older than 2 Years Old," Allergologia Immunopathologia, 2003, vol. 31 (6), pp. 311-317.

Baba T., et al., "Genome and Virulence Determinants of High Virulence Community-Acquired MRSA," Lancet, 2002, vol. 359 (9320), pp. 1819-1827.

Bahrmahd A.R., et al., "Polymerise Chain Reaction of Bacterial Genomes with Single Universal Primer: Application to Distinguishing *Mycobacteria* Species," Molecular and Cellular Probes, 1996, vol. 10 (2), pp. 117-122.

Bahrmahd A.R., et al., "Use of Restriction Enzyme Analysis of Amplified DNA Coding for the hsp65 Gene and Polymerase Chain Reaction with Universal Primer for Rapid Differtiation of *Mycobacterium* Species in the Clinical Laboratory," Scandinavian Journal of Infectious Diseases, 1998, vol. 30 (5), pp. 477-480.

Bai J., et al., "Matrix-Assisted Laser Desorption/Ionization Mass Spectrometry of Restriction Enzyme-Digested Plasmid DNA Using an Active Nafion Substrate," Rapid Communications in Mass Spectrometry, 1994, vol. 8 (9), pp. 687-691.

Baker G.C., et al., "Review and Re-Analysis of Domain-Specific 16S Primers," Journal of Microbiological Methods, 2003, vol. 55 (3), pp. 541-555.

Banik U., et al., "Multiplex PCR Assay for Rapid Identification of Oculopathogenic Adenoviruses by Amplification of the Fiber and Hexon Genes," Journal of Clincal Microbiology, 2005, vol. 43 (3), pp. 1064-1068.

Barbour A.G., et al., "Identification of an Uncultivatable *Borrelia* Species in the Hard Tick *Amblyomma americanum*: Possible Agent of a Lyme Disease-Like Illness," The Journal of Infectious Diseases, 1996, vol. 173 (2), pp. 403-409.

Barns S.M., et al., "Detection of Diverse New Francisella-like Bacteria in Environmental Samples," Applied and Environmental Microbiology, 2005, vol. 71 (9), pp. 5494-5500.

Baron E.J., "Genetic Aspects of Methicillin Resistance in *Staphylococcus aureus* and MethodsUsed for its Detection in Clinical Laboratories in the United States," Journal of Chemotherapy, 1995, vol. 7 (Suppl. 3), pp. 87-92.

Barr I.G., et al., "An Influenza A(H3) Reassortant was Epidemic in Australia and New Zealand in 2003," Journal of Medical Virology, 2005, vol. 76 (3), pp. 391-397.

Barski P., et al., "Rapid Assay for Detection of Methicillin-Resistant *Staphylococcus aureus* Using Multiplex PCR," Molecular and Cellular Probes, 1996, vol. 10 (6), pp. 471-475.

Bastia T., et al., "Organelle DNA Analysis of Solanum and Brassica Somatic Hybrids by PCR with Universal Primers," Theoretical and Applied Genetics, 2001, vol. 102 (8), pp. 1265-1272.

Batey R.T., et al., "Preparation of Isotopically Labeled Ribonucleotides for Multidimensional NMR Spectroscopy of RNA," Nucleic Acids Research, 1992, vol. 20 (17), pp. 4515-4523.

Baumer A., et al., "Age-Related Human mtDNA Deletions: A Heterogeneous Set of Deletions Arising at aSingle Pair of Directly Repeated Sequences," American Journal of Human Jenetics, 1994, vol. 54 (4), pp. 618-630.

Beall B., et al., "Sequencing emm-Specific PCR Products for Routine andAccurate Typing of Group A *Streptococci*," Journal of Clincal Microbiology, 1996, vol. 34 (4), pp. 953-958.

Beall B., et al., "Survey of emm Gene Sequences and T-Antigen Types from Systemic *Streptococcus pyogenes* Infection Isolates Collected in San Francisco, California; Atlanta, Georgia; and Connecticut in 1994 and 1995," Journal of Clincal Microbiology, 1997, vol. 35 (5), pp. 1231-1235.

Benko, M. et al., "Family Adenoviridae," Virus taxonomy. VIIIth report of the International Committee on Taxonomy of Viruses, 2004, Academic Press, New York, pp. 213-228.

Benson D.A., et al., "GenBank," Nucleic Acids Research, 1999, vol. 27 (1), pp. 12-17.

Benson L.M., et al, "Advantages of Thermococcus Kodakaraenis (KOD) DNA Polymerase for PCR-Mass Spectrometry Based Analyses," American Society for Mass Spectrometry, 2003, vol. 14 (6), pp. 601-604.

Berencsi G., et al., "Molecular Biological Characterization of Adenovirus DNA," Acta Microbiologica et Immunologica Hungarica, 1998, vol. 45 (3-4), pp. 297-304.

Bishop M.J., et al., "Molecular Sequence Databases" in: Nucleic Acid and Protein Sequence Analysis, 4th Chapter, Bishop M.J., et al., Eds, IRL Press, 1987, pp. 83-113.

Bisno A.L., "*Streptococcus pyogenes*" in: Infectious Diseases and Their Etiologic Agents, vol. 2, Mandell, Eds., Churchill Livingston, New York, pp. 1786-1799.

Black R.M., et al., "Detection of Trace Levels of Tricothecene Mycotoxins in Human Urineby Gas Chromatography-Mass Spectrometry," Journal of Chromatography, 1986, vol. 367 (1), pp. 103-115.

Blaiotta G., et al., "PCR Detection of Staphylococcal Enterotoxin Genes in *Staphyiococcus* Spp. Strains Isolated from Meat and Dairy Products. Evidence for New Variants of seG and Sel in *S. aureus* AB-8802," Journal of Applied Microbiology, 2004, vol. 97 (4), pp. 719-730.

Blast Search results, Mar. 7, 2006.

Boivin-Jahns V., et al., "Bacterial Diversity in a Deep-Subsurface Clay Environment," Applied and Environmental Microbiology, 1996, vol. 62 (9), pp. 3405-3412.

Bolton E.T., et al., "A General Method for the Isolation of RNA Complementary to DNA," Proceedings of the National Academy of Sciences, 1962, vol. 48, pp. 1390-1397.

Bonk T., et al., "Matrix-Assisted Laser Desorption/Ionization Time-of-Flight Mass Spectrometry-Based Detection of Microsatellite Instabilities in Coding DNA Sequences: A Novel Approach to Identify DNA-Mismatch Repair-Deficient Cancer Cells," Clinical Chemistry, 2003, vol. 49 (4), pp. 552-561.

Borrow R., et al., "SiaD PCR Elisa for Confirmation and Identification of Serogroup Y and W135 Meningococcal Infections," FEMS Microbiology Letters, 1998, vol. 159 (2), pp. 209-214.

Boubaker K., et al., "Panton-Valentine Leukocidin and Staphylococcal Skin Infections in Schoolchildren," Emerging Infectious Diseases, 2004, vol. 10 (1), pp. 121-124.

Bowen J.E., et al., "The Native Virulence Plasm id Combination Affects the Segregational Stability of a Thetareplicating Shuttle Vector in Bacillus Anthracis Var," Journal of Applied Microbiology, 1999, vol. 87 (2), pp. 270-278.

Bowers K.M., et al., "Screening for Methicillin Resistance in *Staphylococars aureus* and Coagulasenegative *Staphylococci*: Evaluation of Three Selective and Mastalex-MRSA latex Agglutination," British Journal of Biomedical Science, 2003, vol. 60 (2), pp. 71-74.

Brakstad O.G., et al., "Direct Identification of *Staphylococcus aureus* in Blood Cultures Bydetection of the Gene, Encoding the Thermostable Nuclease or the Gene Product," Acta Pathologica, Microbiologica et Immunologica Scandinavica, 1995, vol. 103 (3), pp. 209-218.

Brakstad O.G., et al., "Multiplex Polymerase Chain Reaction for Detection of Genes for *Staphylococcus aureus* Themonuclease and Methicillin Resistance and Correlation with Oxacillin Resistance," Acta Pathologica, Microbiologica et Immunologica Scandinavica, 1993, vol. 101 (9), pp. 681-688.

Brandt C.D., et al., "Infections in 18,000 Infants and Children in a Controlled Study of Respiratory Tract Disease. I. Adenovirus Pathogenicity in Relation to Serologic Type and Illness Syndrome," American Journal of Epidemiology, 1969, vol. 90 (6), pp. 484-500.

Brayshaw D.P., "Methicillin-Resistant *Staphylococcus aureus*: Evaluation of Detection Techniques on Laboratory-Passaged Organisms," British Journal of Biomedical Science, 1999, vol. 56 (3), pp. 170-176.

Brightwell G., et al., "Development of Internal Controls for PCR Detection of Bacillus Anthracis," Molecular and Cellular Probes, 1998, vol. 12 (6), pp. 367-377.

(56) References Cited

OTHER PUBLICATIONS

Brightwell G., et al., "Genetic Targets for the Detection and Identifiaction of Venezuelan Equine Encephalitis Viruses," Archives of Virology, 1998, vol. 143 (4), pp. 731-742.
Bronzoni R.V.M., et al., "Duplex Reverse Transcription-PCR Followed by Nested PCR Assays for Detection and Identification of Brazilian Alphaviruses and Flaviviruses," Journal of Clincal Microbiology, 2005, vol. 43 (2), pp. 696-702.
Bronzoni R.V.M., et al., "Multiplex Nested PCR for Brazilian Alphavirus Diagnosis," Transactions of the Royal Society of Tropical Medicine and Hygiene, 2004, vol. 98 (8), pp. 456-461.
Brown I.H., "Advances in Molecular Diagnostics for Avian Influenza," Developments in Biologicals, 2006, vol. 124, pp. 93-97.
Brownstein M.J., et al., "Modulation of Non-Templated Nucleotide Addition by Taq DNA Polymerase: Primer Modifications that Facilitate Genotyping," BioTechniques, 1996, vol. 20 (6), pp. 1004-1010.
Brunaud V., et al., "T-DNA Integration into the Arabidopsis Genome Depends on Sequence of Pre-Insertion Sites," EMBO Reports, 2002, vol. 3 (12), pp. 1152-1157.
Buck G.A., et al., "Design Strategies and Performance of Custom DNA Sequencing Primers," BioTechniques, 1999, vol. 27 (3), pp. 528-536.
Buetow K.H., et al., "High-Throughput Development and Characterization of a Genomewide Collection of Gene-Based Single Nucleotide Polymorphism Markers by Chip-Based Matrix-Assisted Laser Desorption/Ionization Time-of-Flight Mass Spectrometry," Proceedings of the National Academy of Sciences, 2001, vol. 98 (2), pp. 581-584.
Butel J.S., et al., "Cell and Molecular Biology of Simian Virus 40: Implications for Human Infections and Disease," Journal of the National Cancer Institute, 1999, vol. 91 (2), pp. 119-134.
Butler J., "DNA Profiling and Quantitation of Human DNA," CCQM Bio Analysis Working Group, 2005.
Butler J.M., et al., High Throughput Genotyping of Forensic STRs and SNPs using Time-of-Flight Mass Spectrometry, 9th International Symposium on Human Identification, 1998, Orlando FL.
Campbell W.P., et al., "Detection of California Serogroup Bunyavirus in Tissue Culture and Mosquito Pools by PCR," Journal of Virological Methods, 1996, vol. 57 (2), pp. 175-179.
Carracedo A., et al., "DNA Commission of the International Society for Forensic Genetics: Guidelines Formitochondrial DNA Typing," Forensic Science International, 2000, vol. 110 (2), pp. 79-85.
Carroll K.C., et al., "Rapid Detection of the Staphylococcal mecA Gene from Bactec BloodCulture Bottles by the Polymerase Chain Reaction," American Journal of Clincal Pathology, 1996, vol. 106 (5), pp. 600-605.
Case J.T., et al., "Maternal Inheritance of Mitochondrial DNA Polymorphisms in Cultured Human Fibroblasts," Somatic Cell Genetics, 1981, vol. 7 (1), pp. 103-108.
Cattoli G., et al., "Comparison of Three Rapid Detection Systems for Type A Influenza Virus on Tracheal Swabs of Experimentally and Naturally Infected Birds," Avian Pathology, 2004, vol. 33 (4), pp. 432-437.
Cavassini M., et al., "Evaluation of MRSA-Screen, a Simple Anti-PBP 2a Slide Latex AgglutinationKit, for Rapid Detection of Methicillin Resistance in *Staphylococcus aureus*," Journal of Clincal Microbiology, 1999, vol. 37 (5), pp. 1591-1594.
Certificate of Correction mailed Jan. 6, 2009 for U.S. Appl. No. 10/660,996, filed Sep. 12, 2003.
Certificate of Correction mailed Aug. 7, 2007 for U.S. Appl. No. 10/660,997, filed Sep. 12, 2003.
Certificate of Correction mailed Dec. 12, 2006 for U.S. Appl. No. 10/156,608, filed May 24, 2002.
Certificate of Correction mailed Jul. 17, 2007 for U.S. Appl. No. 09/891,793, filed Jun. 26, 2001.
Certificate of Correction mailed Mar. 31, 2008 for U.S. Appl. No. 09/891,793, filed Jun. 26, 2001.
Certificate of Correction mailed Mar. 31, 2008 for U.S. Appl. No. 10/156,608, filed May 24, 2002.
Certificate of Correction mailed Mar. 31, 2008 for U.S. Appl. No. 10/660,997, filed Sep. 12, 2003.
Cespedes A., et al., "Polymerase Chain Reaction-Restriction Fragment Length Polymorphism Analysis of a Short Fragment of the Cytochrome b Gene for Identification of Flatfish Species," Journal of Food Protection, 1998, vol. 61 (12), pp. 1684-1685.
Chamberlin M., et al., "New RNA Polymerase from *Escerichia coli* Infected with Bacteriophage T7," Nature, 1970, vol. 228 (5268), pp. 227-231.
Chandra S., et al., "Virus Reduction in the Preparation and Intravenous Globulin: In Vitro Experiments," Transfusion, 1999, vol. 39 (3), pp. 249-257.
Chang P.K., et al., "afIT, a MFS Transporter-Encoding Gene Located in the Aflatoxin Gene Cluster, does not have a Significant Role in Aflatoxin Secretion," Fungal Genetics and Biology, 2004, vol. 41 (10), pp. 911-920.
Chaves F., et al., "Molecular Characterization of Resistance to Mupirocin in Methicillin-Susceptible and -Resistant Isolates of *Staphylococcus aureus* from Nasal Samples," Journal of Clincal Microbiology, 2004, vol. 42 (2), pp. 822-824.
Chelly J., et al., "Transcription of the Dystrophin Gene in Human Muscle and Non-Muscle Tissue," Nature, 1988, vol. 333 (6176), pp. 858-860.
Chen C.A., et al., "Universal Primers for Amplification of Mitochondrial Small Subunit Ribosomal RNA-Encoding Gene in Scleractinian Corals," Marine Biotechnology, 2000, vol. 2 (2), pp. 146-153.
Chen C.H., et al., Laser Desorption Mass Spectrometry for FastDNA Sequencing [online], Nov. 1994, Retrieved from the Internet< URL:http://www.ornl.gove/sci/techresources/Human_Genome/publicat/94SANTA/sequencing/seqtoc.shtml>.
Chen J., et al., "A Universal PCR Primer to Detect Members of the Potyviridae and its Use to Examine the Taxonomic Status of Several Members of the Family," Archives of Virology, 2001, vol. 146 (4), pp. 757-766.
Chen N., et al., "The Genomic Sequence of Ectromelia Virus, the Causative Agent of Mousepox," Virology, 2003, vol. 317 (1), pp. 165-186.
Chen R., et al., "Trapping, Detection, and Charge and Mass Measurement of Large Individual Ions (up to $1.1 \times 10^8$ Daltons) by Electrospray Ionization FTICR MS," 42nd ASMS Conference on Mass Spectrometry, 1994.
Chen Y.Z., et al., "A BAC-Based STS-Content Map Spanning a 35-Mb Region of Human Chromosome 1p35-36," Genomics, 2001, vol. 74 (1), pp. 55-70.
Chen Z., et al., "Genetic Mapping of the Cold-Adapted Phenotype of B/Ann Arbor/1/66, the Master Donor Virus for Live Attenuated Influenza Vaccines (FluMist)," Virology, 2006, vol. 345 (2), pp. 416-423.
Chiu N.H., et al., "Mass Spectrometry of Single-Stranded Restriction Fragments Captured by an Undigested Complementary Sequence," Nucleic Acids Research, 2000, vol. 28 (8), pp. E31.
Chmielewicz B., et al., "Development of a PCR-Based Assay for Detection, Quantification, and Genotyping of Human Adenoviruses," Clinical Chemistry, 2005, vol. 51 (8), pp. 1365-1373.
Cho M., et al., "Application of the Ribonuclease P (RNaseP) RNA Gene Sequence for Phylogenetic Analysis of the Genus *Saccharomonospora*," International Journal of Systematic Bacteriology, 1998, vol. 48 (4), pp. 1223-1230.
Choi S., et al., "Real-Time PCR Quantification of Human Adenoviruses in Urban Rivers Indicates Genome Prevalence but Low Infectivity," Applied and Environmental Microbiology, 2005, vol. 71 (11), pp. 7426-7433.
Choi Y.K., et al., "Detection and Subtying of Swine Influenza H1 N1, H1 N2 and H3N2 Viruses in Clinical Samples Using Two Multiplex RT-PCR Assays," Journal of Virological Methods, 2002, vol. 102 (1-2), pp. 53-59.
Christel L.A., et al., "Rapid, Automated Nucleic Acid Probe Assays Using Silicon Microstructures for Nucleic Acid Concentration," Journal of Biomechanical Engineering, 1999, vol. 121 (1), pp. 22-27.
Claas E.C., et al., "Internally Controlled Real-Time PCT Monitoring of Adenovirus DNA Load inSerum or Plasma of Transplant Recipients," Journal of Clincal Microbiology, 2005, vol. 43 (4), pp. 1738-1744.

(56) References Cited

OTHER PUBLICATIONS

Cloney L., et al., "Rapid Detection of mecA in Methicillin Resistant *Staphylococcus aureus* Using Cycling Probe Technology," Molecular and Cellular Probes, 1999, vol. 13 (13), pp. 191-197.
Collins D.W., et al., "Numerical Classification of Coding Sequences," Nucleic Acids Research, 1992, vol. 20 (6), pp. 1405-1410.
Conrads G., et al., "16S-23S rDNA Internal Transcribed Spacer Sequences for Analysis of the Phylogenetic Relationships Among Species of the Genus *Fusobacterium*," International Journal of Systematic and Evolutionary Microbiology, 2002, vol. 52 (2), pp. 493-499.
Contreras-Salazar B., et al., "Up Regulation of the Epstein-Barr Virus (EBV)-Encoded Membrane Protein LMP in the Burkitt's Lymphoma Line Daudi after Exposure to N-Butyrate and after EBV Superinfection," Journal of Virology, 1990, vol. 64 (11), pp. 5441-5447.
Co-pending U.S. Appl. No. 10/318,463, filed Dec. 13, 2002.
Co-pending U.S. Appl. No. 10/323,186, filed Dec. 18, 2002.
Co-pending U.S. Appl. No. 10/323 187, filed Dec. 18, 2002.
Co-pending U.S. Appl. No. 10/324,721, filed Dec. 18, 2002.
Co-pending U.S. Appl. No. 10/521,662, filed Jul. 21, 2003.
Co-pending U.S. Appl. No. 10/754,415, filed Jan. 9, 2004.
Co-pending U.S. Appl. No. 10/807,019, filed Mar. 23, 2004.
Co-pending U.S. Appl. No. 10/845,052, filed May 12, 2004.
Co-pending U.S. Appl. No. 10/964,571, filed on Oct. 12, 2004.
Co-pending U.S. Appl. No. 11/209,439, filed Aug. 23, 2005.
Co-pending U.S. Appl. No. 11/674,538, filed Feb. 13, 2007.
Co-pending U.S. Appl. No. 11/682,259, filed Mar. 5, 2007.
Co-pending U.S. Appl. No. 11/929,910, filed Oct. 30, 2007.
Co-pending U.S. Appl. No. 11/930,108, filed Oct. 31, 2007.
Co-pending U.S. Appl. No. 11/930,741, filed Oct. 31, 2007.
Co-pending U.S. Appl. No. 90/010,209, filed Jun. 27, 2008.
Co-pending U.S. Appl. No. 90/010,210, filed Jun. 27, 2008.
Co-pending U.S. Appl. No. 90/010,447, filed Apr. 9, 2009.
Co-pending U.S. Appl. No. 90/010,448, filed Apr. 9, 2009.
Co-pending U.S. Appl. No. 60/639,068, filed Dec. 22, 2004.
Co-pending U.S. Appl. No. 60/648188, filed on Jan. 28, 2005.
Co-pending U.S. Appl. No. 60/369405, filed Apr. 1, 2002.
Co-pending U.S. Appl. No. 60/397,365, filed Jul. 19, 2002.
Co-pending U.S. Appl. No. 60/431,319.
Co-pending U.S. Appl. No. 60/443,443, filed Jan. 29, 2003.
Co-pending U.S. Appl. No. 60/443,788.
Co-pending U.S. Appl. No. 60/447,529, filed Feb. 14, 2003.
Co-pending U.S. Appl. No. 60/453,607, filed Mar. 10, 2003.
Co-pending U.S. Appl. No. 60/461,494.
Co-pending U.S. Appl. No. 60/470,175, filed May 12, 2003.
Co-pending U.S. Appl. No. 60/501,926, filed Sep. 11, 2003.
Co-pending U.S. Appl. No. 60/509,911.
Co-pending U.S. Appl. No. 60/604,329, filed Aug. 24, 2004.
Co-pending U.S. Appl. No. 60/615,387.
Co-pending U.S. Appl. No. 60/701,404, filed Jul. 21, 2005.
Co-pending U.S. Appl. No. 60/705,631, filed Aug. 3, 2005.
Co-pending U.S. Appl. No. 60/720,843, filed Sep. 27, 2005.
Co-pending U.S. Appl. No. 60/747607, filed May 18, 2006.
Co-pending U.S. Appl. No. 60/771,101, filed Feb. 6, 2006.
Co-pending U.S. Appl. No. 60/773,124, filed Feb. 13, 2006.
Co-pending U.S. Appl. No. 60/891,479.
Co-pending U.S. Appl. No. 60/941,641.
Cornel a.J., et al., "Polymerase Chain Reaction Species Diagnostic Assay for Anopheles Quadrimaculatus Cryptic Species (*Diptera:culicidae*) Based on Ribosomal DNA ITS2 Sequences," Journal of Medical Entomology, 1996, vol. 33 (1), pp. 109-116.
Couto I., et al., "Development of Methicillin Resistance in Clinical Isolates of *Staphylococcus sciuri* by Transcriptional Activation of the mecA Homologue Native to the Species," Journal of Bacteriology, 2003, vol. 185 (2), pp. 645-653.
Crain P.F., et al., "Applications of Mass Spectrometry to the Characterization of Oligonucleotides and Nucleic Acids," Current Opinion in Biotechnology, 1998, vol. 9 (1), pp. 25-34.

Crawford-Miksza L., et al., "Analysis of 15 Adenovirus Hexon Proteins Reveals the Location and Structure of Seven Hypervariable Regions Containing Serotype-Specific Residues," Journal of Virology, 1996, vol. 70 (3), pp. 1836-1844.
Crawford-Miksza L.K., et al., "Adenovirus Serotype Evolution is Driven by Illegitimate Recombination in the Hypervariable Regions of the Hexon Protein," Virology, 1996, vol. 224 (2), pp. 357-367.
Crawford-Miksza L.K., et al., "Strain Variation in Adenovirus Serotypes 4 and 7a Causing Acute Respiratory Disease," Journal of Clincal Microbiology, 1999, vol. 37 (4), pp. 1107-1112.
Crespillo M., et al., "Mitochondrial DNA Sequences for 118 Individuals from Northeastern Spain," International Journal of Legal Medicine, 2000, vol. 114 (1-2), pp. 130-132.
Cui L., et al., "Contribution of a Thickened Cell Wall and Its Glutamine Nonamidated Component to the Vancomycin Resistance Expressed by *Staphylococcus aureus* Mu50," Antimicrobial Agents and Chemotherapy, 2000, vol. 44 (9), pp. 2276-2285.
Dasen G., et al., "Classification and Identification of Propiolbacteria based on Ribosomal RNA Genes and PCR," Systematic and Applied Microbiology, 1998, vol. 21 (2), pp. 251-259.
De Jong J.C., et al., "Adenoviruses from Human Immunodeficiency Virus-Infected Individuals, Including Two Strains that Represent New Candidate Serotypes Ad50 and Ad51 of Species B1 and D, Respectively," Journal of Clincal Microbiology, 1999, vol. 37 (12), pp. 3940-3945.
De La Puente-Redondo V.A., et al., "Comparison of Different PCR Approaches for Typing of Francisella Tularensis Strains," Journal of Clinical Microbiology, 2000, vol. 38 (3), pp. 1016-1022.
Deforce D.L., et al., "Analysis of Oligonucleotides by ESI-MS," Advances in Chromatography, 2000, vol. 40, pp. 539-566.
Deforce D.L.D., et al., "Characterization of DNA Oligonudeotides by Coupling of Capillary zone Electrophoresis to Electrospray Ionization Q-TOF Mass Spectrometry," Analytical Chemistry, 1998, vol. 70 (14), pp. 3060-3068.
Del Blanco Garcia N., et al., "Genotyping of Francisella Tularensis Strains by Pulsed-field gel Electrophoresis, Amplified Fragment Length Polymorphism Fingerprinting, and 16S rRNA gene Sequencing," Journal of Clinical Microbiology, 2002, vol. 40 (8), pp. 2964-2972.
Del Vecchio V.G., et al., "Molecular Genotyping of Methicillin-Resistant *Staphylococcus aureus* via Fluorophore-Enhanced Repetitive-Sequence PCR," Journal of Clincal Microbiology, 1995, vol. 33 (8), pp. 2141-2144.
Demesure B., et al., "A Set of Universal Primers for Amplification of Polymorphic Non-Coding Regions of Mitochondrial and Chioroplast DNA in Plants," Molecular Ecology, 1995, vol. 4, pp. 129-131.
Denis M., et al., "Development of a Semiquantitative PCR Assay Using Internal Standard and Colorimetricdetection on Microwell Plate for Pseudorabies Virus," Molecular and Cellular Probes, 1997, vol. 11 (6), pp. 439-448.
Deurenberg R.H., et al., "Rapid Detection of Panton-Valentine Leukocidin from Clinical Isolates of *Staphylococcus aureus* Strains by Real-Time PCR," FEMS Microbiology Letters, 2004, vol. 240 (2), pp. 225-228.
Deurenberg R.H., et al., "The Prevalence of the Staphylococcus Aureus tst Gene among Community- and Hospital-Acquired Strains and Isolates from Wegener's Granulomatosis Patients," FEMS Microbiology Letters, 2005, vol. 245 (1), pp. 185-189.
Deyde V.M., et al., "Genomic Signature-Based Identification of Influenza A Viruses Using RT-PCR/Electro-Spray Ionization Mass Spectrometry (ESI-MS) Technology," PLoS One, 2010, vol. 5 (10), pp. e13293.
Di Guilmi A.M., et al., "Human Adenovirus Serotype 3 (Ad3) and the Ad3 fiber Protein Bind to a 130-kDa Membrane Protein on HLa Cells," Virus Research, 1995, vol. 38 (1), pp. 71-81.
Dias Neto E., et al., "Shotgun Sequencing of the Human Transcriptome with ORF Expressed Sequence Tags," Proceedings of the National Academy of Sciences, 2000, vol. 97 (7), pp. 3491-3496.
Diep B.A., et al., "Complete Genome Sequence of USA300, an Epidemic Clone of Community Acquired Meticillin-Resistant *Staphylococcus aureus*," Lancet, 2006, vol. 367 (9512), pp. 731-739.
Dinauer D.M., et al., "Sequence-Based Typing of HLA Class II DQB1," Tissue Antigens, 2000, vol. 55 (4), pp. 364-368.

(56) References Cited

OTHER PUBLICATIONS

Ding C., et al., "A High-Throughput Gene Expression Analysis Technique Using Compettiive PCR and Matrixassisted Laser Desorption Ionization Time-of-Flight MS," Proceedings of the National Academy of Sciences, 2003, vol. 100 (6), pp. 3059-3064.
Donehower L.A., et al., "The Use of Primers from Highly Conserved Pol Regions to Identify Uncharacterized Retroviruses by the Polymerase Chain Reaction," Journal of Virological Methods, 1990, vol. 28 (1), pp. 33-46.
Donofrio J.C., et al., "Detection of Influenza A and B in Respiratory Secretions with the Polymerase Chain Reaction," PCR Methods and Applications, 1992, vol. 1 (4), pp. 263-268.
Doty P., et al., "Strand Separation and Specific Recombination in Deoxyribonucleic Acids: Physical Chemical Studies," Proceedings of the National Academy of Sciences, 1960, vol. 46 (4), pp. 461-476.
Drosten C., et al., "Identification of a Novel Coronavirus in Patients with Severe Acute Respiratory Syndrome," New England Journal of Medicine, 2003, vol. 348 (20), pp. 1967-1976.
Dubernet S., et al., "A PCR-Based Method for Identification of Lactobacilli at to Genus Level," FEMS Microbiology Letters, 2002, vol. 214 (2), pp. 271-275.
Ebner K., et al., "Molecular Detection and Quantitative Analysis of the Entire Spectrum of Human Adenoviruses by a Two-Reaction Real-Time PCR Assay," Journal of Clinical Microbiology, 2005, vol. 43 (7), pp. 3049-3053.
Ebner K., et al., "Typing of Human Adenoviruses in Specimens from Immunosuppressed Patients by PCR-Fragment Length Analysis and Real-Time Quantitative PCR," Journal of Clinical Microbiology, 2006, vol. 44 (8), pp. 2808-2815.
Echavarria M., et al., "Detection of Adenoviruses (AdV) in Culture-Negative EnvironmentalSamples by PCR During an AdV-Associated Respiratory Disease Outbreak," Journal of Clinical Microbiology, 2000, vol. 38 (8), pp. 2982-2984.
Echavarria M., et al., "PCR Method for Detection of Adenovirus in Urine of Healthy and Human Immunodeficiency Virus-Infected Individuals," Journal of Clinical Microbiology, 1998, vol. 36 (11), pp. 3323-3326.
Echavarria M., et al., "Prediction of Severe Disseminated Adenovirus Infection by Serum PCR," Lancet, 2001, vol. 358 (9279), pp. 384-385.
Echavarria M., et al., "Rapid Detection of Adenovirus in Throat Swab Specimens by PCR During Respiratory Disease Outbreaks among Military Recruits," Journal of Clinical Microbiology, 2003, vol. 41 (2), pp. 810-812.
Echavarria M., et al., "Use of PCR to Demonstrate Presence of Adenovirus Species B, C, or F as Well as Coinfection with Two Adenovirus Species in Children with Flu-Like Symptoms," Journal of Clinical Microbiology, 2006, vol. 44 (2), pp. 625-627.
Ecker D.J., et al., "Ibis T5000: A Universal Biosensor Approach for Microbiology," Nature Reviews Microbiology, 2008, vol. 6 (7), pp. 553-558.
Ecker D.J., et al., "Rapid Identification and Strain-Typing of Respiratory Pathogens for Epidemic Surveillance," Proceedings of the National Academy of Sciences, 2005, vol. 102 (22), pp. 8012-8017.
Ecker D.J., et al., "The Ibis T5000 Universal Biosensor. An Automated Platform for Pathogen Identification and Strain Typing," Journal of the Association for Laboratory Automation, 2006, vol. 11 (6), pp. 341-351.
Edwards K.M., et al., "Adenovirus Infections in Young Children," Pediatrics, 1985, vol. 76 (3), pp. 420-424.
Ellis J.S., et al., "Molecular Diagnosis of Influenza," Reviews in Medical Virology, 2002, vol. 12 (6), pp. 375-389.
Ellis J.S., et al., "Multiplex Reverse Transcription—PCR for Surveillance of Influenza A and B Viruses in England and Wales in 1995 and 1996," Journal of Clinical Microbiology, 1997, vol. 35(8), pp. 2076-2082.
Elnifro E.M., et al., "PCR and Restriction Endonuclease Analysis for Rapid Identification of Adenovirus Subgenera," Journal of Clinical Microbiology, 2000, vol. 38 (6), pp. 2055-2061.

Elsayed S., et al., "Development and Validation of a Molecular Beacon Probe-Based Real-Time Polymerase Chain Reaction Assay for Rapid Detection of Methicillin Resistance in Staphylococcus aureus," Archives of Pathology and Laboratory Medicine, 2003, vol. 127 (7), pp. 845-849.
EMBL "Arabidopsis Thaliana T-DNA Flanking Sequence, Left Border, Clone 346C06," Accession No. AJ552897, Mar. 29, 2003.
EMBL"Dog (Clone: CXX.147) Primer for STS 147, 3" End, Sequence Tagged Site," Accession No. L15697, Mar. 4, 2000.
EMBL "Human, muscle, Mitochondrial Mutant, 22 nt, segment 2 of 2," Accession No. S90302, Sep. 1, 2004.
EMBL "Sequence 10 from U.S. Pat. No. 6,563,025," Accession No. AR321656, Aug. 18, 2003.
EMBL "Synthetic Construct DNA, Reverse Primer for Human STS sts-AA031654 at 1p36" Accession No. AB068711, May 21, 2003.
Enright M.C., et al., "A Multilocus Sequence Typing Scheme for Streptococcus pneumoniae: Identification of Clones Associated with Serious Invasive Disease," Microbiology, 1998, vol. 144 (Pt 11), pp. 3049-3060.
Enright M.C., et al., "Multilocus Sequence Typing for Characterization of Methicillin-Resistant and Methicillin-Susceptible Clones of Staphylococcus aureus," Journal of Clinical Microbiology, 2000, vol. 38 (3), pp. 1008-1015.
Enright M.C., et al., "Multilocus Sequence Typing of Streptococcus pyogenes and theRelationships between Emm Type and Clone," Infection and Immunity, 2001, vol. 69 (4), pp. 2416-2427.
Enright M.C., et al., "The Evolutionary History of Methicillin-Resistant Staphylococcus Aureus (MRSA)," Proceedings of the National Academy of Sciences, 2002, vol. 99 (11), pp. 7687-7692.
Enright M.C., "The Evolution of a Resistant Pathogen—the Case of MRSA," Current Opinion in Pharmacology, 2003, vol. 3 (5), pp. 474-479.
Eremeeva M.E., et al., "Evaluation of a PCR Assay for Quantitation of Rickettsia rickettsii and Closely Related Spotted Fever Group Rickettsiae," Journal of Clinical Microbiology, 2003, vol. 41 (12), pp. 5466-5472.
Erlich H.A., Ed., PCR Technology: Principles and Applications for DNA Amplification, W.H. Freeman and Company, 1989.
Esmans E.L., et al., "Liquid Chromatography-Mass Spectrometry in Nucleoside, Nucleotide and Modified Nucleotide Characterization," Journal of Chromatography, 1998, vol. 794, pp. 109-127.
Eugene-Ruellan G., et al., "Detection of Respiratory Syncytial Virus A and B and Parainfluenzavirus 3 Sequences in Respiratory Tracts of Infants by a Single PCR with Primers Targeted to the L-Polymerase Gene and Differential Hybridization," Journal of Clinical Microbiology, 1998, vol. 36 (3), pp. 796-801.
European Search Report for Application No. EP10175659.1, mailed on Feb. 9, 2011, 4 pages.
Evans P., et al., "Practical Algorithms for Universal DNA Primer Design: An Exercise in Algorithm Engineering," Currents in Computational Molecular Biology, 2001, pp. 25-26.
Ex Parte Re-Examination Certificate for U.S. Appl. No. 90/010,209 mailed Jul. 7, 2009.
Ex Parte Re-Examination Certificate for U.S. Appl. No. 90/010,210, mailed Dec. 28, 2010.
Ex Parte Re-Examination Certificate for U.S. Appl. No. 90/010,447 mailed Feb. 15, 2011.
Examiner Interview Summary mailed Oct. 3, 2005 for U.S. Appl. No. 10/326,046, filed Dec. 18, 2002.
Examiner Interview Summary mailed Nov. 6, 2008 for U.S. Appl. No. 10/728,486, filed Dec. 5, 2003.
Examiner Interview Summary mailed Jun. 7, 2011 for U.S. Appl. No. 11/930,108, filed Oct. 31, 2007.
Examiner Interview Summary mailed Aug. 10, 2004 for U.S. Appl. No. 09/798,007, filed Mar. 2, 2001.
Examiner Interview Summary mailed Aug. 10, 2004 for U.S. Appl. No. 09/891,793, filed Jun. 26, 2001.
Examiner Interview Summary mailed Aug. 10, 2004 for U.S. Appl. No. 10/156,608, filed May 24, 2002.
Examiner Interview Summary mailed Aug. 10, 2004 for U.S. Appl. No. 10/326,642, filed Dec. 18, 2002.
Examiner Interview Summary mailed May 19, 2003 for U.S. Appl. No. 09/891,793, filed Jun. 26, 2001.

(56) References Cited

OTHER PUBLICATIONS

Examiner Interview Summary mailed Oct. 24, 2008 for U.S. Appl. No. 11/582,859, filed Oct. 17, 2006.
Examiner Interview Summary mailed Feb. 27, 2006 for U.S. Appl. No. 10/326,644, filed Dec. 18, 2002.
Examiner Interview Summary mailed Jan. 27, 2006 for U.S. Appl. No. 10/323,211, filed Dec. 18, 2002.
Examiner Interview Summary mailed May 28, 2008 for U.S. Appl. No. 10/660,998, filed Sep. 12, 2003.
Examiner Interview Summary mailed Oct. 28, 2008 for U.S. Appl. No. 11/331,987, filed Jan. 13, 2006.
Examiner Interview Summary mailed Oct. 29, 2008 for U.S. Appl. No. 11/331,978, filed Jan. 13, 2006.
Examiner Interview Summary mailed Oct. 29, 2009 for U.S. Appl. No. 10/660,122, filed Sep. 11, 2003.
Examiner Interview Summary mailed Jul. 31, 2006 for U.S. Appl. No. 10/326,643, filed Dec. 18, 2002.
Extended European Search Opinion for Application No. EP10175659.1, mailed on Feb. 21, 2011, 5 pages.
Extended European Search Report for Application No. EP07874065.1, mailed on Jan. 24, 2011, 7 pages.
Extended European Search Report for Application No. EP10179789.2, mailed on Mar. 22, 2011, 9 pages.
Extended European Search Report for Application No. EP10179791.8, mailed on Mar. 17, 2011, 7 pages.
Extended European Search Report for Application No. EP10179795.9, mailed on Mar. 22, 2011, 9 pages.
Facklam R., et al., "Emm Typing and Validation of Provisional M Types for Group A *Streptococci*," Emerging Infectious Diseases, 1999, vol. 5 (2), pp. 247-253.
Fang H., et al., "Rapid Screening and Identification of Methicillin-Resistant *Staphylococcus aureus* from Clinical Samples by Selective-Broth and Real-Time PCR Assay," Journal of Clinical Microbiology, 2003, vol. 41 (7), pp. 2894-2899.
Farlow J., et al., "Francisella Tularensis Strain Typing Using Multiple-Locus, Variable-Number Tandem Repeat Analysis," Journal of Critical Microbiology, 2001, vol. 39 (9), pp. 3186-3192.
Farrell D.J., "The Reliability of Microscan Conventional and Rapid Panels to Identify *Staphylococcus aureus* and Detect Methicillin Resistance: An Evaluation Using the Tube Coagulase Test and mecA PCR," Pathology, 1997, vol. 29 (4), pp. 406-410.
Fedele C.G., et al., "Multiplex Polymerase Chain Reaction for the Simultaneous Detection and Typing of Polyomavirus JC, BK and SV40 DNA in Clinical Samples," Journal of Virological Methods, 1999, vol. 82 (2), pp. 137-144.
Fedele C.G., et al., "Quantitation of Polyomavirus DNA by a Competitive Nested Polymerase Chain Reaction," Journal of Virological Methods, 2000, vol. 88 (1), pp. 51-61.
Feng P., "Impact of Molecular Biology on the Detection of Food Pathogens," Molecular Biotechnology, 1997, vol. 7 (3), pp. 267-278.
Figueiredo L.M., et al., "Identification of Brazilian Flavivirus by a Simplified Reverse Transcription-Polymerase Chain Reaction Method Using Flavivirus Universal Primers," American Journal of Tropical Medicine and Hygiene, 1998, vol. 59 (3), pp. 357-362.
Final Office Action mailed Aug. 6, 2010 for U.S. Appl. No. 11/929,910, filed Oct. 30, 2007.
Final Office Action mailed Jul. 8, 2010 for U.S. Appl. No. 12/326,800, filed Dec. 2, 2008.
Final Office Action mailed May 12, 2010 for U.S. Appl. No. 11/674,538, filed Feb. 13, 2007.
Final Office Action mailed Apr. 14, 2011 for U.S. Appl. No. 12/049,949, filed Mar. 17, 2008.
Final Office Action mailed Oct. 14, 2009 for U.S. Appl. No. 10/943,344, filed Sep. 17, 2004.
Final Office Action mailed Nov. 17, 2009 for U.S. Appl. No. 11/582,875, filed Oct. 17, 2006.
Final Office Action mailed Feb. 18, 2010 for U.S. Appl. No. 10/754,415, filed Jan. 9, 2004.
Final Office Action mailed Nov. 20, 2009 for U.S. Appl. No. 11/331,987, filed Jan. 13, 2006.
Final Office Action mailed Jun. 23, 2010 for U.S. Appl. No. 11/930,017, filed Oct. 30, 2007.
Final Office Action mailed Feb. 26, 2009 for U.S. Appl. No. 11/582,863, filed Oct. 17, 2006.
Final Office Action mailed Jan. 30, 2009 for U.S. Appl. No. 10/844,938, filed May 12, 2004.
Flora J.W., et al, "Dual-Micro-ESI Source for Precise Mass Determination on a Quadrupole Time-of-Flight Mass Spectrometer for Genomic and Proteomic Applications," Analytical and Bioanalytical Chemistry, 2002, vol. 373 (7), pp. 538-546.
Fong W.K., et al., "Rapid Solid-Phase Immunoassay for Detection of Methicillin-Resistant*Staphylococcus aureus* Using Cycling Probe Technology," Journal of Clinical Microbiology, 2000, vol. 38 (7), pp. 2525-2529.
Fox A., et al., "Identification and Detection of Bacteria: Electrospray MS-MS Versus Derivatization/GC-MS," Proceedings of the ERDEC Scientific Conference on Chemical and Biological Defense Research, Aberdeen Proving Ground, MD, Nov. 15-18, 1994, pp. 39-44.
Fox A., et al., "Report of the Bioterrorism Workshop," Journal of Microbiological Methods, 2002, vol. 51 (3), pp. 247-254.
Fox J.P., et al., "The Virus Watch Program: A Continuing Surveillance of Viral Infections in Metropolitan New York Families," American Journal of Epidemiology, 1969, vol. 89 (1), pp. 25-50.
Fox K.F., et al., "Identification of *Brucella* by Ribosomal-Spacer-Region PCR and Differentiation of *Brucell canis* from Other *Brucella* Spp. Pathogenic for Humans by Carbohydrate Profiles," Journal of Clinical Microbiology, 1998, vol. 36 (11), pp. 3217-3222.
Francois J.C., et al., "Sequence-Specific Recognition and Cleavage of Duplex DNA via Triple-Helix Formation by Oligonucleotides Covalently Linked to a Phenanthroline-Copper Chelate," Proceedings of the National Academy of Sciences, 1989, vol. 86 (24), pp. 9702-9706.
Francois P., et al., "Rapid Detection of Methicillin-Resistant *Staphylococcus aureus* Directly from Sterile or Nonsterile Clinical Samples by a New Molecular Assay," Journal of Clinical Microbiology, 2003, vol. 41 (1), pp. 254-260.
Fraser C.M., et al., "The Mimimal Gene Complement of Mycoplasma Genitalium," Science, 1995, vol. 270 (5235), pp. 397-403.
Freiberg C., et al., "Genome-Wide mRNA Profiling: Impact on Compound Evaluation and Target Identification in Anti-Bacterial Research," Targets, 2002, vol. 1 (1), pp. 20-29.
Freymuth F., et al., "Comparison of Multiplex PCR Assays and Conventional Techniques for the Diagnostic of Respiratory Virus Infections in Children Admitted to Hospital With an Acute Respiratory Illness," Journal of Medical Virology, 2006, vol. 78 (11), pp. 1498-1504.
Freymuth F., et al., "Detection of Respiratory Syncytial Virus, Parainfluenzavirus 3, Adenovirus Andrhinovirus Sequences in Respiratory Tract of Infants by Polymerase Chain Reaction and Hybridization," Clinical and Diagnostic Virology, 1997, vol. 8 (1), pp. 31-40.
Fuerstenau S.D., et al., "Molecular Weight Determination of Megadalton DNA Electrospray Ions Using Charge Detection Time-of-flight Mass Spectrometry," Rapid Communications in Mass Spectrometry, 1995, vol. 9 (15), pp. 1528-1538.
Fujimoto T., et al., "Single-Tube Multiplex. PCR for Rapid and Sensitive Diagnosis of Subgenus B and Other Subgenera Adenoviruses in Clinical Samples," Microbiology and Immunology, 2000, vol. 44 (10), pp. 821-826.
Fujimura S., et al., "Characterization of the mupA Gene in Strains of Methicillin-Resistant *Staphylococcus aureus* with a Low Level of Resistance to Mupirocin," Antimicrobial Agents and Chemotheraphy, 2001, vol. 45 (2), pp. 641-642.
Fujimura S., et al., "Isoleucyl-tRNA Synthetase Mutations in *Staphylococcus aureus* Clinicallsolates and in Vitro Selection of Low-Level Mupirocin-Resistant Strains," Antimicrobial Agents and Chemotheraphy, 2003, vol. 47 (10), pp. 3373-3374.
Fujioka S., et al., "Analysis of Enterovirus Genotypes using Single-Strand Conformation Polymorphisms of Polymerase Chain Reaction Product," Journal of Virological Methods, 1995, vol. 51 (2-3), pp. 253-258.

(56) References Cited

OTHER PUBLICATIONS

Gabriel M.N., et al., "Improved mtDNA Sequence Analysis of Forensic Remains using a "Mini-Primer Set" Amplification Strategy," Journal of Forensic Sciences, 2001, vol. 46 (2), pp. 247-253.

Gall J.G., et al., "Construction and Characterization of Hexon-Chimeric Adenoviruses: Specification of Adenovirus Serotype," Journal of Virology, 1998, vol. 72 (12), pp. 10260-10264.

Gammelin M., et al., "Two Subtypes of Nucleoproteins (NP) of Influenza A Viruses," Virology, 1989, vol. 170 (1), pp. 71-80.

Garcia S., et al., "Quantitative Real-Time PCR Detection of Rift Valley Fever Virus and Its Application to Evaluation of Antiviral Compounds," Journal of Clinical Microbiology, 2001, vol. 39 (12), pp. 4456-4461.

Garcia-Martinez J., et al., "Use of the 16s-23s Ribosomal Genes Spacer Region in Studies of Prokaryotic Diversity," Journal of Microbiological Methods, 1999, vol. 36 (1-2), pp. 55-64.

Gattermann N., et al., "Heteroplasmic Point Mutations of Mitochondrial DNA Affecting Subunit I of Cytochrome c Oxidise in Two Patients with Acquired Idiopathic Siderblastic Anemia," Blood, 1997, vol. 90 (12), pp. 4961-4972.

Gaydos C.A., et al., "Adenovirus Vaccines in the U.S. Military," Military Medicine, 1995, vol. 160 (6), pp. 300-304.

Geha D.J., et al., "Multiplex PCR for Identification of Methicillin-Resistant *Staphylococci* in the Clinical Laboratory," Journal of Clinical Microbiology, 1994, vol. 32 (7), pp. 1768-1772.

GenBank, "{Deletion 6} [Human, Muscle, Mitochondrial Mutant, 22 nt, Segment 2 of 2]," Accession No. S90302.1, Jun. 10, 1992.

GenBank, "Acinetobacter Genomosp. 10 Strain CIP 70.12 RNA Polymerase Subunit B (rpoB) Gene, Complete Cds," Accession No. 78099429, Mar. 11, 2006.

GenBank, "Bovine Parainfluenza Virus 3 Strain Shipping Fever, Complete Genome," Accesion No. AF178655, Sep. 19, 2000.

GenBank, "Clostridium Tetani E88, Complete Genome," Accession No. AE015927.1, Feb. 4, 2003.

GenBank, "*E. coli* Operon rpoBC Coding for the Beta- and Beta"-Subunits of RNA Polymerase (Genes rpoC and rpoB), and Genes rpIL, rlpJ, rpIA, and rpIK Coding for 50S Ribosomal Subunit Proteins L7/L12, L10, L1, and L11, Respectively. (Map position 89-90 min.), Accession No. 42813, Feb. 28, 1992.

GenBank, "*E. coli* 16S Ribosomal RNA," Accession No. 174375, Aug. 11, 1995.

GenBank, "*E. coli* Open Reading Frame Upstream of Leu Operon," Accession No. M21150, Sep. 15, 1990.

GenBank, "*E. coli* rRNA Operon (rrnB) Coding for Glu-tRNA-2, 5S, 16S and 23S rRNA," Accession No. 147581, Sep. 14, 1992.

GenBank, "Enterococcus Malodoratus Strain ATCC43197 Elongation Factor Tu (tufA) Gene, Partial Cds," Accession No. AF274728, Dec. 11, 2000.

GenBank "*Escherichia coli* str. K-12 substr. MG1655, Complete Genome," Accession No. NC000913, Oct. 15, 2001.

GenBank, "*Homo sapiens* Haplotype V Mitochondrion, Complete Genome", Accession No. AF381990.1, Dec. 28, 2001.

GenBank, "Human Adenovirus Type 4 Hexon Gene," for Accession No. X84646, Jun. 30, 1995.

GenBank, "Human Coronavirus 229E, Complete Genome," Accession No. AF304460, Jul. 11, 2001.

GenBank, "Human Isolate L34 Mitochondrion D-loop Region", Accession No. U08081.1, Aug. 16, 1994.

GenBank, "il11b08.y1 Human insulinoma *Homo sapiens* cDNA clone Image:60295345—similar to SW:COX3_Human P00414 Cytochrome C Oxidase Polypeptide III ;, mRNA sequence", Accession No. BQ581956.1, Jun. 20, 2002.

GenBank, "Influenza B Virus B/Panama/45/90 Polymerase (PB2) mRNA, Complete Cds", Accession No. AF005737, Oct. 4, 1997, pp. 1-3.

GenBank, "Mastadenovirus h7 Hexon Gene," Accession No. Z48571, Apr. 18, 2005.

GenBank, "or72a01.s1 NCI_CGAP_Lu5 *Homo sapiens* cDNA Clone Image:1601352 3- similar to SW:COX1_Human P00395 Cytochrome C Oxidase Polypeptide I ;, mRNA sequence", Accession No. A1002209.1, Jun. 10, 1998.

GenBank "*Staphylococcus aureus* RN4220 ErmC Gene, Partial Cds," Accession No. 18542231, Sep. 16, 2003.

GenBank "*Staphylococcus aureus* Strain MSSA476, Complete Genome," Accession No. BX571857.1, Jun. 24, 2004.

GenBank, "*Staphylococcus aureus* Subsp. *aureus* Mu50, Complete Genome," Accession No. 15922990, Oct. 4, 2001.

GenBank "*Staphylococcus aureus* Subsp. *aureus* MW2, Complete Genome," Accession No. G121281729, May 31, 2002.

GenBank, "*Staphylococcus epidermidis* ATCC 12228, Complete Genome," Accession No. AE015929.1, Jan. 2, 2003.

GenBank "*Streptococcus agalactiae* 2603V/R, Complete Genome," Accession No. AE009948.1, Aug. 28, 2002.

GenBank, "*Streptococcus anginosus* Elongation Factor Tu (tuf) Gene, Partial cds," Accession No. AF276257.1, Jul. 1, 2001.

GenBank, "*Streptococcus pneumoniae* Isolate 95.1In00S DNA Gyrase Subunit B (gyrB) Gene, Complete Cds," Accession No. 73916349, Sep. 30, 2005.

GenBank, "*Streptococcus pyogenes* Strain MGAS8232, Complete Genome," Accession No. AE009949.1, Apr. 3, 2002.

GenBank, "Venezuelan Equine Encephalitis Virus Nonstructural Polyprotein and Structural Polyprotein Genes, Complete Cds," Accession No. AF375051.1, Jun. 26, 2001.

Gendel S.M., "Computational Analysis of the Specificity of 16S rRNA-Derived Signature Sequencesfor Identifying Food-Related Microbes," Food Microbiology, 1996, vol. 13, pp. 1-15.

Gibb T.R., et al., "Development and Evaluation of a 5" Fluorogenic Nuclease Assay to Detect and Differentiate Between Ebola Virus Subtypes Zaire and Sudan," Journal of Clinical Microbiology, 2001, vol. 39 (11), pp. 4125-4130.

Gilbert N., et al., "Comparison of Commercial Assays for the Quantitation of HBV DNA Load in Healthcare Workers: Calibration Differences," Journal of Virological Methods, 2002, vol. 100 (1-2), pp. 37-47.

Giles R.E., et al., "Maternal Inheritance of Human Mitochondrial DNA," Proceedings of the National Academy of Sciences, 1980, vol. 77 (11), pp. 6715-6719.

Gill S.R., et al., "Insights on Evolution of Virulence and Resistance from the Complete Genome Analysis of an Early Methicillin-Resistant *Staphylococcus aureus* Strain and a Biofilm-Producing Methicillin-Resistant *Staphylococcus epidemidis* Strain," Journal of Bacteriology, 2005, vol. 187 (7), pp. 2426-2438.

Gilliland G., et al., "Analysis of Cytokine mRNA and DNA: Detection and Quantitation by Competitive Polymerase Chain Reaction," Proceedings of the National Academy of Sciences, 1990, vol. 87 (7), pp. 2725-2729.

Ginther C., et al., "Identifying Individuals by Sequencing Mitochondrial DNA from Teeth," Nature Genetics, 1992, vol. 2 (2), pp. 135-138.

Gjoen K.V., et al., "Specific Detection of Coxsackie Viruses A by the Polymerase Chain Reaction," Clinical and Diagnostic Virology, 1997, vol. 8 (3), pp. 183-188.

Golden M.R., et al., "Pilot Study of COBAS PCR and Ligase Chain Reaction for Detection of Rectal Infections Due to Chlamydia Trachomatis," Journal of Clinical Microbiology, 2003, vol. 41 (5), pp. 2174-2175.

Goto K., et al., "Applications of the Partial 16S rDNA Sequence as an Index for Rapid Identification of Species in the Genus *Bacillus*," Journal of General and Applied Microbiology, 2000, vol. 46 (1), pp. 1-8.

Gravet A., et al., "Characterization of a Novel Structural Member, LukE-LukD, of the Bi-Component Staphylococcal Leucotoxins Family," FEBS Letters, 1998, vol. 436 (2), pp. 202-208.

Gray G.C., et al., "Adult Adenovirus Infections: Loss of Orphaned Vaccines Precipitates Military Respiratory Disease Epidemics," Clinical Infectious Diseases, 2000, vol. 31, pp. 663-670.

Greenberg B.D., et al., "Intraspecific Nucleotide Sequence Variability Surrounding the Origin of Replicationin Human Mitochondrial DNA," Gene, 1983, vol. 21, pp. 33-49.

(56) References Cited

OTHER PUBLICATIONS

Griffey, et al., "Detection of Base Pair Mismatches in Duplex DNA and RNA Oligonucleotides Using Electrospray Mass Spectrometry," SPIE, 1997, vol. 2985, pp. 82-86.

Griffin T.J., et al., "Direct Genetic Analysis by Matrix-Assisted Laseer Desorption/Ionization Mass Spectrometry," Proceedings of the National Academy of Sciences, 1999, vol. 96 (11), pp. 6301-6306.

Griffin T.J., et al., "Single-Nucleotide Polymorphism Analysis by Maldi-TOF Mass Spectrometry," Trends in Biotechnology, 2000, vol. 18 (2), pp. 77-84.

Grondahl B., et al., "Rapid Identification of Nine Microorganisms Causing Acute Respiratory TractInfections by Single-Tube Multiplex Reverse Transcription-PCR: Feasibility Study," Journal of Clinical Microbiology, 1999, vol. 37 (1), pp. 1-7.

Grundmann H., et al., "Emergence and Resurgence of Meticillin-Resistant *Staphylococcus aureus* as a Public-Health Threat," Lancet, 2006, vol. 368 (9538), pp. 874-885.

Grzybowski T., et al., "Extremely High Levels of Human Mitochondrial DNA Heteroplasmy in Single Hair Roots," Electrophoresis, 2000, vol. 21 (3), pp. 548-553.

Gu Z., et al., "Multiplexed, Real-Time PCR for Quantitative Detection of Human Adenovirus," Journal of Clinical Microbiology, 2003, vol. 41 (10), pp. 4636-4641.

Guatelli J.C., et al., "Nucleic Acid Amplification In Vitro: Detection of Sequences with Low Copy Numbers and Application to Diagnosis of Human Immunodeficiency Virus Type 1 Infection," Clinical Microbiology Reviews, 1989, vol. 2 (2), pp. 217-226.

Haff L.A., et al., "Multiplex Genotyping of PCR Products with Mass Tag-Labeled Primers," Nucleic Acids Research, 1997, vol. 25 (18), pp. 3749-3750.

Hahner S., et al., "Analysis of Short Tandem Repeat Polymorphisms by Electrospray Ion Trap Mass Spectrometry," Nucleic Acids Research, 2000, vol. 28 (18), pp. E82.1-E82.8.

Haines J.D., et al., "Medical Response to Bioterrorism: Are We Prepared," Journal of Oklahoma State Medical Association, 2000, vol. 93, pp. 187-196.

Hall T.A., et al., "Base Composition Analysis of Human Mitochondrial DNA Using Electrospray Ionization Mass Spectrometry: A Novel Tool for the Identification and Differentiation of Humans," Analytical Biochemistry, 2005, vol. 344 (1), pp. 53-69.

Hamdad F., et al., "Detection of Methicillin/Oxacillin Resistance and Typing in Aminoglycoside-Susceptible Methicillin-Resistant and Kanamycin-TobramycinResistant Methicillin-Susceptible," Microbial Drug Resistance, 2006, vol. 12 (3), pp. 177-185.

Hamel S., et al., "Consensus PCR and Microarray for Diagnosis of the Genus *Staphylococcus*, Species, and Methicillin Resistance," Biotechniques, 2001, vol. 31 (6), pp. 1364-1372.

Hammerle T., et al., "A Sensitive PCR Assay System for the Quantitation of Viral Genome Equivalents:Hepatitis C Virus (HCV)," Archives of Virology, 1996, vol. 141 (11), pp. 2103-2114.

Hannis J.C., et al., "Accurate Characterization of the Tyrosine Hydroxylase Forensic Allele 9.3 through Development of Electrospray Ionization Fourier Transform Ion Cyclotron Resonance Mass Spectrometry," Rapid Communications in Mass Spectrometry, 1999, vol. 13 (10), pp. 954-962.

Hannis J.C., et al., "Detection of Double-Stranded PCR Amplicons at the Attomole Level Electrosprayed from Low Nanomolar Solutions using FT-ICR Mass Spectrometry," Fresenius Journal of Analytical Chemistry, 2001, vol. 369 (3-4), pp. 246-251.

Hannis J.C., et al., "Genotyping Complex Short Tandem Repeats Using Electrospray Ionzation Fourier Transform Ion Cyclotron Resonance Multi-Stage Mass Spectrometry," Proceedings of SPIE, 2000, vol. 3926, pp. 36-47.

Hannis J.C., et al., "Genotyping Short Tandem Repeats Using Flow Injection and Electrospray Ionization, Fourier Transform Ion Cyclotron Resonance Mass Spectrometry," Rapid Communications in Mass Spectrometry, 2001, vol. 15 (5), pp. 348-350.

Hannis J.C., et al., "Nanoelectrospray Mass Spectrometry Using Non-Metalized, Tapered (50-10 .mu.m) Fused-silica Capillaries," Rapid Communication in Mass spectrometry, 1998, vol. 12, pp. 443-448.

Hanssen A.M., et al., "Sccmecin *Staphylococci*: Genes on the Move," FEMS Immuol Medical Microbiol, 2006, vol. 46, pp. 8-20.

Hasebe F. et al., "Combined Detection and Genotyping of Chikungunya Virus by a Specific Reverse Transcription-Polymerase Chain Reaction," Journal of Medical Virology, 2002, vol. 67 (3), pp. 370-374.

Hassan A.A., et al., "Inter- and Intraspecies Variations of the 16S-23S rDNA Intergenic Spacer Region of Various Streptococcal Species," Systematic and Applied Microbiology, 2003, vol. 26 (1), pp. 97-103.

Haugland R.A., et al., "Identification of Putative Sequence Specific PCR Primers for Detection of the Toxygenic Fungal Species *Stachybotrys chartarum*," Molecular and Cellular Probes, 1998, vol. 12 (6), pp. 387-396.

Hayashi H., et al., "Phylogenetic Analysis of the Human Gut Microbiota Using 16S rDNA Clone Libraries and Strictly Anaerobic Culture-based Methods," Journal of Microbiology, Immunology, 2002, vol. 46 (8), pp. 535-548.

He L., et al, "Development of a Capillary High-performance Liquid Chromatography Tandem Mass Spectrometry System Using SWIFT Technology in an Ion Trap/Reflectron Time-of-flight Mass Spetrometer," Biochemical and Biophysical Research Communications, 1997, vol. 11, pp. 1739-1748.

Heim A., et al., "Rapid and Quantitative Detection of Human Adenovirus DNA by Real-Time PCR," Journal of Medical Virology, 2003, vol. 70, pp. 228-239.

Henchal E.A., et al., "Sensitivity and Specificity of a Universal Primer Set for the Rapid Diagnosis of Dengue Virus Infections by Polymerase Chain Reaction and Nucleic Acid Hybridization," American Journal of Tropical Medicine and Hygiene, 1991, vol. 45 (4), pp. 418-428.

Herrmann B., et al., "Differentiation of *Chlamydia* spp. by Sequence Determination and Restriction Endonuclease Cleavage of RNase P RNA Genes," Journal of Clinical Microbiology, 1996, vol. 34 (8), pp. 1897-1902.

Higgins G.S., et al., "Competitive Oligonucleotide Single-base Extension Combined with Mass Spectrometric Detection for Mutation Screening," Biotechniques, 1997, vol. 23 (4), pp. 710-714.

Higgins J.A., et al., "Sensitive and Rapid Identification of Biological Threat Agents," Annals of the New York Academy of Sciences, 1999, vol. 894, pp. 130-148.

Hill F., et al., "Polymerase Recognition of Synthetic Oligodeoxyribonucleotides Incorporating Degenerate Pyrimidine and Purine Bases," Proceedings of the National Academy of Sciences, 1998, vol. 95, pp. 4258-4263.

Hiramatsu K., et al., "The Emergence and Evolution of Methicillin-Resistant *Staphylococcus aureus*," Trends Microbiology, 2001, vol. 9 (10), pp. 486-493.

Hodgson J.E., et al., "Molecular Characterization of the Gene Encoding High-Level Mupirocin Resistancein *Staphylococcus aureus* J2870," Antimicrobial Agents and Chemotherapy, 1994, vol. 38 (5), pp. 1205-1208.

Hoffman E., et al., "Rescue of Influenza B Virus from Eight Plasmids," Proceedings of the National Academy of Sciences, 2002, vol. 99 (17), pp. 11411-11416.

Hoffmann E., et al., "Universal Primer Set for the Full-Length Amplification of all Influenza A Viruses," Archives of Virology, 2001, vol. 146 (12), pp. 2275-2289.

Hofstadler S.A., et al., "TIGER: The Universal Biosensor," International Journal of Mass Spectrometry, 2005, vol. 242, pp. 23-41.

Holden M.T., et al., "Complete Genomes of Two Clinical *Staphylocuccus aureus* Strain: Evidence for the Rapid Evolution of Virulence and Drug Resistance," Proceedings of the National Academy of Sciences, 2004, vol. 101 (26), pp. 9786-9791.

Holland M.M., et al., "Mitochondrial DNA Sequence Analsysis—Validation and Use for Forensic Casework," Forensic Science Review, 1999, vol. 11 (1), pp. 22-50.

(56) References Cited

OTHER PUBLICATIONS

Holland M.M., et al., "Mitochondrial DNA Sequence Analysis of Human Skeletal Remains: Identification of Remains from the Vietnam War," Journal of Forensic Sciences, 1993, vol. 38 (3), pp. 542-553.

Holm L., et al., "Removing Near-Neighbour Redundancy from Large Protein Sequence Collections," Bioinformatics, 1998, vol. 14 (5), pp. 423-429.

Holmes E.C., et al., "Whole-Genome Analysis of Human Influenza A Virus Reveals Multiple Persistent Lineages and Reassortment among Recent H3N2 Viruses," Public Library of Science Biology, 2005, vol. 3 (9), pp. 1579-1589.

Honda K., et al., "Universal Method of Hypersensitive Nested PCR Toward Forensic DNA typing," International Congress Series, 1998, vol. 7, pp. 28-30.

Hongoh Y., et al., "Evaluation of Primers and PCR Conditions for the Analysis of 16s rRNA Genes from a Naturalenvironment," FEMS Microbiology Letters, 2003, vol. 221 (2), pp. 299-304.

Hood E., et al., "Chemical and Biological Weapons: New Questions, New Answers," Environmental Health Perspectives, 1999, vol. 107 (12), pp. 931-932.

Houng H.S., et al., "Rapid Type-Specific Diagnosis of Adenovirus Type 4 Infection Using a Hexon-Based Quantitative Fluorogenic PCR," Diagnostic Microbiology and Infectious Disease, 2002, vol. 42 (4), pp. 227-236.

Howell N., et al., "Persistent Heteroplasmy of a Mutation in the Human mtDNA Control Region: Hypermutation as an Apparent Consequence of Simple-Repeat Expansion/Contraction," American Journal of Human Genetics, 2000, vol. 66 (5), pp. 1589-1598.

Huber C.G., et al., "On-Line Cation Exchange for Suppression of Adduct Formation in Negative-Ion Electrospray Mass Spectrometry of Nucleic Acids," Analytical Chemistry, 1998, vol. 70 (24), pp. 5288-5295.

Huletsky A., et al., "New Real-Time Pcr Assay for Rapid Detection of Methicillin- Resistant*Staphylococcus aureus* Directly from Specimens Containing a Mixture of *Staphylococci*," Journal of Clinical Microbiology, 2004, vol. 42 (5), pp. 1875-1884.

Hunag C., et al., "Detection of Arboviral RNA Directly from Mosquito Homogenates by Reverse Transcription-Polymerase Chain Reaction," Journal of Virological Methods, 2001, vol. 94 (1-2), pp. 121-128.

Hung E.C., et al., "Detection of SARS Coronavirus RNA in the Cerebrospinal Fluid of a Patient with Severe Acute Respiratory Syndrome," Clinical Chemistry, 2003, vol. 49 (12), pp. 2108-2109.

Hurdle J.G., et al., "Analysis of Mupirocin Resistance and Fitness in *Staphylococcus aureus* by Molecular Genetic and Structural Modeling Techniques," Antimicrobial Agents and Chemotherapy, 2004, vol. 48 (11), pp. 4366-4376.

Hurst G.B., et al., "Detection of Bacterial DNA Polymerase Chain Reaction Products by Matrix-Assisted Laser Desorptionfionization Mass Spectrometry," Rapid Communications in Mass Spectrometry, 1996, vol. 10 (3), pp. 377-382.

Hurst G.B., et al., "MALDI-TOF Analysis of Polymerase Chain Reaction Products from Methanotrophic Bacteria," Analytical Chemistry, 1998, vol. 70 (13), pp. 2693-2698.

Hutchison C.A., et al., "Maternal Inheritance of Mammalian Mitochondrial DNA," Nature, 1974, vol. 251 (5475), pp. 536-538.

Hyde-Deruyscher R., et al., "Polyomavirus Early-Late Switch is not Regulated at the Level of Transcription Initiation and is associated with changes in RNA Processing," Proceedings of the National Academy of Sciences, 1988, vol. 85, pp. 8993-8997.

Ieven M., et al., "Rapid Detection of Methicillin Resistance in Coagulase-Negative *Staphylococci* by Commercially Available Fluorescence Test," Journal of Clinical Microbiology, 1995, vol. 33 (8), pp. 2183-2185.

Ihle O., et al., "Efficient Purification of DNA Fragments using a Protein Binding Membrane," Nucleic Acids Research, 2000, vol. 28 (16), pp. e76.

Inglis T.J., et al., "Rapid Genotypic Confirmation of Methicillin Resistance," Pathology, 1996, vol. 28 (3), pp. 259-261.

Ingman M., et al., "Mitochondrial Genome Variation and the Origin of Modern Humans," Nature, 2000, vol. 408 (6813), pp. 708-713.

International Preliminary Examination Report for Application No. PCT/US2002/06763, mailed on Jun. 11, 2003, 6 pages.

International Preliminary Examination Report for Application No. PCT/US2002/20336, mailed on Apr. 26, 2004, 8 pages.

International Preliminary Examination Report for Application No. PCT/US2003/09802, mailed on Apr. 8, 2005, 7 pages.

International Preliminary Examination Report for Application No. PCT/US2003/22835, mailed on Mar. 5, 2005, 4 pages.

International Preliminary Examination Report for Application No. PCT/US2003/38505, mailed on Mar. 3, 2006, 5 pages.

International Preliminary Examination Report for Application No. PCT/US2003/38757, mailed on Feb. 2, 2007, 5 pages.

International Preliminary Examination Report for Application No. PCT/US2003/38761, mailed on Jun. 27, 2006, 6 pages.

"International Preliminary Report on Patentability and Written Opinion for Application No. PCT/US04/007236, mailed on Mar. 16, 2006, 7 pages."

International Preliminary Report on Patentability and Written Opinion for Application No. PCT/US2005/00386, mailed on Jul. 10, 2006, 6 pages.

International Preliminary Report on Patentability and Written Opinion for Application No. PCT/US2005/030058, mailed on Sep. 25, 2007, 6 pages.

International Preliminary Report on Patentability and Written Opinion for Application No. PCT/US2005/033707, mailed on Mar. 20, 2007, 6 pages.

International Preliminary Report on Patentability for Application No. PCT/US2004/033742, mailed on Jun. 20, 2006, 1 page.

International Preliminary Report on Patentability for Application No. PCT/US2006/028397, mailed on Jan. 22, 2008, 1 page.

International Preliminary Report on Patentability for Application No. PCT/US2007/020045, mailed on Mar. 17, 2009, 1 page.

International Preliminary Report on Patentability for Application No. PCT/US2008/054926, mailed on Aug. 26, 2009, 1 page.

International Preliminary Report on Patentability, Written Opinion and International Search Report for Application No. PCT/US2004/015123, mailed on Oct. 3, 2005, 8 pages.

International Preliminary Report on Patentabilty for Appplication No. PCT/US2005/018031, mailed on Nov. 29, 2006, 1 page.

International Search Report and Written Opinion for Application No. PCT/US2005/018031, mailed on Jun. 28, 2006, 14 pages.

International Search Report and Written Opinion for Application No. PCT/US2006/007747, mailed on Sep. 5, 2006, 13 pages.

International Search Report and Written Opinion for Application No. PCT/US2006/028397, mailed on Mar. 5, 2007, 14 pages.

International Search Report and Written Opinion for Application No. PCT/US2006/040747, mailed on Mar. 17, 2009, 19 pages.

International Search Report and Written Opinion for Application No. PCT/US2006/061307, mailed on Jan. 9, 2008, 21 pages.

International Search Report and Written Opinion for Application No. PCT/US2007/020045 mailed on Jan. 8, 2009, 17 pages.

International Search Report and Written Opinion for Application No. PCT/US2008/054926, mailed on Jan. 26, 2009, 15 pages.

International Search Report and Written Opinion for Application No. PCT/US2008/057901, mailed on Aug. 28, 2008, 14 pages.

International Search Report and Written Opinion for Application No. PCT/US2008/064891, mailed on Jun. 29, 2009, 15 pages.

International Search Report for Application No. PCT/US04/007236, mailed on Feb. 24, 2006, 2 pages.

International Search Report for Application No. PCT/US2002/06763, mailed on Oct. 23, 2002, 2 pages.

International Search Report for Application No. PCT/US2002/20336, mailed on Feb. 3, 2003, 4 pages.

International Search Report for Application No. PCT/US2003/009802, mailed on Aug. 3, 2004, 2 pages.

International Search Report for Application No. PCT/US2003/038505, mailed on Apr. 12, 2005, 2 pages.

International Search Report for Application No. PCT/US2003/038830, mailed on Aug. 25, 2004, 4 pages.

International Search Report for Application No. PCT/US2003/22835, mailed on Dec. 12, 2003, 1 page.

(56) References Cited

OTHER PUBLICATIONS

International Search Report for Application No. PCT/US2003/38757, mailed on Jun. 24, 2004, 2 pages.
International Search Report for Application No. PCT/US2003/38761, mailed on Dec. 30, 2005, 5 pages.
International Search Report for Application No. PCT/US2003/38795, mailed on Apr. 19, 2004, 3 pages.
International Search Report for Application No. PCT/US2004/012671, mailed on Sep. 28, 2007, 2 pages.
International Search Report for Application No. PCT/US2004/015123, mailed on Oct. 3, 2005, 2 pages.
International Search Report for Application No. PCT/US2004/015196, mailed on Jul. 1, 2005, 3 pages.
International Search Report for Application No. PCT/US2004/028869, mailed on Jul. 17, 2006, 4 pages.
International Search Report for Application No. PCT/US2004/033742, mailed on May 15, 2006, 2 pages.
International Search Report for Application No. PCT/US2005/000386, mailed on May 9, 2006, 3 pages.
International Search Report for Application No. PCT/US2005/005356, mailed on Aug. 7, 2007, 4 pages.
International Search Report for Application No. PCT/US2005/006133, mailed on Jul. 26, 2007, 4 pages.
International Search Report for Application No. PCT/US2005/009557, mailed on Sep. 19, 2005, 1 page.
International Search Report for Application No. PCT/US2005/018337, mailed on Oct. 10, 2006, 2 pages.
International Search Report for Application No. PCT/US2005/024799, mailed on Dec. 28, 2006, 4 pages.
International Search Report for Application No. PCT/US2005/030058, mailed on Aug. 20, 2007, 1 page.
International Search Report for Application No. PCT/US2005/033707, mailed on Feb. 6, 2006, 3 pages.
International Search Report for Application No. PCT/US2007/066194, mailed on Jan. 15, 2008, 4 pages.
International Search Report for Application No. PCT/US2008/065332, mailed on Nov. 28, 2008, 4 pages.
International Search Report for Application No. PCT/US2009/045635, mailed on Oct. 7, 2009, 9 pages.
Inyaku K., et al., "Rapid Detection and Identification of Mycobacteria in Sputum Samples by NestedPolymerase Chain Reaction and Restriction Fragment Length Polymorphisms of dnaJ Heat Shock Protein Gene," Journal of Medical Sciences, 1993, vol. 42 (1), pp. 21-31.
Iqbal S.S., et al., "A Review of Molecular Recognition Technologies for Detection of Biological Threat Agents," Biosensors & Bioelectronics, 2000, vol. 15 (11-12), pp. 549-578.
Isola N.R., et al., "MALDI-TOF Mass Spectrometric Method for Detection of Hybridized DNA Oligomers," Analytical Chemistry, 2001, vol. 73 (9), pp. 2126-2131.
Iteman I., et al., "Comparison of Conserved Structural and Regulatory Domains within Divergent 16S rRNA-23S rRNA Spacer Sequences of Cyanobacteria," Microbiology, 2000, vol. 146 (Pt 6), pp. 1275-1286.
Ito T., et al., "Insights on Antibiotic Resistance of *Staphylococcus aureus* from its Whole Genome: Genomic Island Scc," Drug Resistance Updates, 2003, vol. 6 (1), pp. 41-52.
Ito T., et al., "Structural Comparison of Three Types of Staphylococcal Cassette Chromosome mecIntegrated in the Chromosome in Methicillin-Resistant *Staphylococcus aureus*," Antimicrobial Agents and Chemotherapy, 2001, vol. 45 (5), pp. 1323-1336.
Jackson P.E., et al., "Mass Spectrometry for Genotyping: an Emerging Tool for Molecular Medicine," Molecular Medicine Today, 2000, vol. 6 (7), pp. 271-276.
James A.M., et al., "Borelia Lonestari Infection after a Bite by an *Amblyomma americanum* Tick," The Journal of Infectious Diseases, 2001, vol. 183 (12), pp. 1810-1814.
Jankowski K., et al., "Mass Spectrometry of DNA. Part 2 Quantitative Estimation of Base Composition," European Journal of Mass Spectrometry, 1980, vol. 1 (1), pp. 45-52.
Jansen R.C., et al., "Genotype-by-environment Interaction in Genetic Mapping of Multiple Quantitative Trait Loci," Theoretical and Applied Genetics, 1995, vol. 91, pp. 33-37.
Jaulhac B., et al., "Specific Detection of the Toxic Shock Syndrome Toxin-1 Gene Using the Polymerase Chain Reaction," Molecular and Cellular Probes, 1991, vol. 5, pp. 281-284.
Jaulhac B., et al., "Synthetic DNA Probes for Detection of Genes for Enterotoxins A, B, C, D, E and for Tsst-1 in Staphylococcal Strains," Journal of Applied Bacterial, 1992, vol. 72 (5), pp. 386-392.
Jensen M.A., et al., "Rapid Identification of Bacteria on the Basis of Polymcrase Chain Reaction-Amplified Ribosomal DNA Spacer Polymorphisms," Applied and Environmental Microbiology, 1993, vol. 59 (4), pp. 945-952.
Jeong J., et al., "Early Screening of Oxacillin-Resistant *Staphylococcus aureus* and *Staphylococcus epidermidis* from Blood Culture," Journal of Korean Medical Science, 2002, vol. 17, pp. 168-172.
Jiang C., et al., "Multiple Trait Analysis of Genetic Mapping for Quantitative Trait Loci Genetics," Genetics, 1995, vol. 140 (3), pp. 1111-1127.
Jiang Y., et al., "A Highly Efficient and Automated Method for Purifying and Desalting PCR Products for Analysis by Electrospray Ionization Mass Spectrometry," Analytical Biochemistry, 2003, vol. 316 (1), pp. 50-57.
Johansson A., et al., "Evaluation of PCR-based Methods for Discrimination of Francisella species and Subspecies and Development of a Specific PCR that Distinguishes the Two Major Subspecies of *Francisella tularensis*," Journal of Clinical Microbiology, 2000, vol. 38 (11), pp. 4180-4185.
Johnson W.M., et al., "Detection of Genes for Enterotoxins, Exfoliative Toxins, and Toxic Shock Syndrome Toxin 1 in *Staphylococcus aureus* by the Polymerase Chain Reaction," Journal of Clinical Microbiology, 1991, vol. 29 (3), pp. 426-430.
Johnson Y.A., et al., "Precise Molecular Weight Determination of PCR Products of the rRNA Intergenic Spacer Region Using Electrospray Quadrupole Mass Spectrometry for Differentiation of *B. subtilis* and *B. atrophaeus*, Closely Related Species of Bacilli," Journal of Microbiological Methods, 2000, vol. 40 (3), pp. 241-254.
Jonas D., et al., "Rapid PCR-Based Identification of Methicillin-Resistant *Staphylococcus aureus* from Screening Swabs," Journal of Clinical Microbiology, 2002, vol. 40 (5), pp. 1821-1823.
Jurinke C., et al., "Application of Nested PCR and Mass Spectrometry for DNA Based Virus Detection: HBV-DNA Detected in the Majority of Isolated Anti-Hbc Positive Sera," Genetic Analysis: Biomolecular Engineering, 1998, vol. 14 (3), pp. 97-102.
Jurinke C., et al., "Detection of Hepatitis B: Virus DNA in Serum Samples via Nested PCR and MALDI-TOF Mass Spectrometry," Genetic Analysis: Biomolecular Engineering, 1996, vol. 13 (3), pp. 67-71.
Jurinke C., et al., "MALDI-TOF Mass Spectrometry. A Versatile Tool for High-Performance DNA Analysis," Molecular Biotechnology, 2004, vol. 26 (2), pp. 147-163.
Kacian D.L., et al., "A Replicating RNA Molecule Suitable for a Detailed Analysis of Extracellular Evolution and Replication," Proceeding of the National Academy of Sciences, 1972, vol. 69 (10), pp. 3038-3042.
Kageyama A., et al. "Rapid Detection of Human Fecal Eubacterium Species and Related Genera by Tested PCR Method," Journal of Microbiology, Immunology, 2001, vol. 45 (4), pp. 315-318.
Kajon A.E., et al., "Genome Type Analysis of Brazilian Adenovirus Strains of Serotypes 1, 2, 3, 5,and 7 Collected Between 1976 and 1995," Journal of Medical, 1999, vol. 58 (4), pp. 408-412.
Kasai H., et al., "Construction of the gyrB Database for the Identification and Classification of Bacteria," Genome Informatics. Workshop on Genome Informatics, 1998, pp. 13-21.
Katano H., et al., "Identification of Adeno-Associated Virus Contamination in Cell and Virus Stocks by PCR," Biotechniques, 2004, vol. 36 (4), pp. 676-680.
Katayama Y., et al., "Genetic Organization of the Chromosome Region Surrounding mecA inClinical Staphylococcal Strains: Role of IS431-Mediated mecl Deletion in Expression of Resistance inmed-Canying, Low-Level Methicillin-Resistant *Staphylococcus haemolyticus*," Antimicrobial Agents and Chemotherapy, 2001, vol. 45 (7), pp. 1955-1963.

(56) References Cited

OTHER PUBLICATIONS

Ke D., et al., "Development of a PCR Assay for Rapid Detection of Enterococci," Journal of Clinical Microbiology, 1999, vol. 37 (11), pp. 3497-3503.

Kearns A.M., et al., "Rapid Detection of Methicillin-Resistant *Staphylococci* by Multiplex PCR," The Journal of Hospital Inspection, 1999, vol. 43 (1), pp. 33-37.

Keller A., et al., "Empirical Statistical Model to Estimate the Accuracy of Peptide Identifications Made by MS/MS and Database Search," Analytical Chemistry, 2002, vol. 74 (20), pp. 5383-5392.

Khan A.S., et al., "An Outbreak of Crimean-Congo Haemorrhagic Fever in the United Arab Emirates, 1994-1995," The American Journal of Tropical Medicine and Hygiene, 1997, vol. 57 (5), pp. 519-525.

Khan S.A., et al., "Simultaneous Detection of Erythromycin-Resistant Methylase Genes ermA and ermC from *Staphylococcus* Spp. By Multiplex-PCR," Molecular and Cellular Probes, 1999, vol. 13 (5), pp. 381-387.

Kidd A.H., et al., "Rapid Subgenus Identification of Human Adenovirus Isolates by a General PCR," Journal of Clinical Microbiology, 1996, vol. 34 (3), pp. 622-627.

Kidd-Ljunggren K., et al., "The Hepatitis B Virus X Gene: Analysis of Functional Domain Variation and Gene Phylogeny using Multiple Sequences," Journal of General Virology, 1995, vol. 76 (pt 9), pp. 2119-2130.

Kikuchi K., et al., "Restriction Fragment Length Polymorphism Analysis of Clinical Isolates of *Mycobacterium haemophilum*," Journal of Clinical Microbiology, 1994, vol. 32 (7), pp. 1763-1767.

Kilbourne E.D., "Influenza Pandemics of the 20th Century," Emerging Infectious Diseases Journal, 2006, vol. 12 (1), pp. 9-14.

Kilbourne E.D., "Influenza Pandemics: Can We Prepare for the Unpredictable," Viral Immunology, 2004, vol. 17 (3), pp. 350-357.

Kilpatrick D.R., et al., "Group-Specific Identification of Polioviruses by PCR Using Primer Containing Mixed-Base or Deoxyinosine Residues at Positions of Codon Degeneracy," Journal of Clinical Microbiology, 1996, vol. 34 (12), pp. 2990-2996.

Kim B.J., et al., "Identification of Mycobacterial Species by Comparative Sequence Analysis of the RNA Polymerase Gene (rpoB)," Journal of Clinical Microbiology, 1999, vol. 37 (6), pp. 1714-1720.

Kinney R.M., et al., "Nucleotide Sequences of the 26S mRNAs of the Viruses Defining the Venezuelan Equine Encephalitis Antigenic Complex," The American Journal of Tropical Medicine and Hygiene, 1998, vol. 59 (6), pp. 952-964.

Kirpekar F., et al., "Matrix Assisted Laser Desorption/Ionization Mass Spectrometry of Enzymatically Synthesized RNA up to 150 kDa," Nucleic Acids Research, 1994, vol. 22 (19), pp. 3866-3870.

Kitagawa Y., et al., "Rapid Diagnosis of Methicillin-Resistant *Staphylococcus aureus* Bacteremia by Nested Polymerase Chain Reaction," Annals of Surgery, 1996, vol. 224 (5), pp. 665-671.

Knoth K., et al., "Highly Degenerate, Inosine-Containing Primers Specifically Amplify Rare cDNA using the Polymerase Chain Reaction," Nucleic Acids Research, 1988, vol. 16 (22), pp. 10932.

Kolbert C.P., et al., "Branched-DNA Assay for Detection of the mecA Gene in Oxacillin-Resistant and Oxacillin-Sensitive *Staphylococci*," Journal of Clinical Microbiology, 1998, vol. 36 (9), pp. 2640-2644.

Kowalak J.A., et al., "A Novel Method for the Determination of Post-Transcriptional Modification in RNA by Mass Spectrometry," Nucleic Acids Research, 1993, vol. 21 (19), pp. 4577-4585.

Krafft A.E., et al., "Evaluation of PCR Testing of Ethanol-Fixed Nasal Swab Specimens as an Augmented Surveillance Strategy for Influenza Virus and Adenovirus Identification," Journal of Clincal Microbiology, 2005, vol. 43 (4), pp. 1768-1775.

Krahmer M.T., et al., "Electrospray Quadrupole Mass Spectrometry Analysis of Model Oligonucleotides and Polymerase Chain Reaction Products: Determination of Base Substitutions, Nucleotide Additions/Deletions, and Chemical Modifications," Analytical Chemistry, 1999, vol. 71 (14), pp. 2893-2900.

Krahmer M.T., et al, "MS for Identification of Single Nucleotide Polymorphisms and MS/MS for Discrimination of Isomeric PCR Products," Analytical Chemistry, 2000, vol. 72 (17), pp. 4033-4040.

Kramer L.D., et al., "Dection of Encephalitis Viruses in Mosquitoes (*Diptera: culicidea*) and Avian Tissues," Journal of Medical Entomology, 2002, vol. 39 (2), pp. 312-323.

Kramer L.D., et al., "Dection of St. Louis Encephalitis and Western Equine Encephalomyelitis RNA in Mosquitoes Tested Without Maintainance of a Cold Chain," Journal of the American Mosquito Control Association, 2001, vol. 17 (4), pp. 213-215.

Kresken M., et al., "Prevalence of Mupirocin Resistance in Clinical Isolates of *Staphylocccccus aureus* and *Staphylococcus epidermidis*: Results of the Antimicrobial Resistance Surveillance Study of the Paul-Ehrlich-Society for Chemotherapy, 2001," International Journal of Antimicrobial Agents, 2004, vol. 23 (6), pp. 577-581.

Krishnan P.U., et al., "Detection of Methicillin and Mupirocin Resistance in *Staphylococcus aureus* isolates Using Conventional and Molecular Methods: A Descriptive Study from a Burns Unit with High prevalence of MRSA," Journal of Clinical Pathology, 2002, vol. 55 (10), pp. 745-748.

Kroes I., et al., "Bacterial Diversity Within the Human Subgingival Crevice," Proceeding of the National Academy of Sciences, 1999, vol. 96 (25), pp. 14547-14552.

Krossoy B., et al., "The Putative Polymerase Sequence of Infectious Salmon Anemia Virus Suggests a New Genus within the Orthomyxoviridae," Journal of Virology, 1999, vol. 73 (3), pp. 2136-2142.

Ksiazek T.G., et al., "A Novel Coronavirus Associated with Severe Acute Respiratory Syndrome," The New England Journal of Medicine, 2003, vol. 348 (20), pp. 1953-1966.

Kupke T., et al., "Molecular Characterization of Lantibiotic-Synthesizing Enzyme EpiD Reveals a Function for Bacterial Dfp Proteins in Coenzyme A Biosynthesis," Journal of Biological Chemistry, 2000, vol. 275 (41), pp. 31838-31846.

Kuroda M., et al., "Whole Genome Sequencing of Meticillin-Resistant Staphylococcus Aureus," The Lancet, 2001, vol. 357 (9264), pp. 1225-1240.

Kwok S., et al., "Avoiding False Positives with PCR," Nature, 1989, vol. 339 (6221), pp. 237-238.

Labandeira-Rey, M. et al., "*Staphylococcus aureus* Panton Valentine Leukocidin Causes Necrotizing Pneumonia," ScienceExpress, 2007, 8 pages.

Lacroix J.M., et al, "PCR-Based Technique for the Detection of Bacteria in Semen and Urine," Journal of Microbiological Methods, 1996, vol. 26, pp. 61-71.

Lacroix L., et al., "Triplex Formation by Oligonucleotides Containing 5-(1-Propynyl)-2-deoxyuridine: Decreased Magnesium Dependence and Improved Intracellular Gene Targeting," Biochemistry, 1999, vol. 38 (6), pp. 1893-1901.

Laken S.J., et al., "Genotyping by Mass Spectrometric Analysis of Short DNA Fragments," Nature Biotechnology, 1998, vol. 16 (13), pp. 1352-1356.

Lamb R.A., et al., "Sequence of Interrupted and Uninterrupted mRNAs and Cloned DNA Coding for the Two Overlapping Nonstructural Proteins of Influenza Virus," Cell, 1980, vol. 21 (2), pp. 475-485.

Lambert A.J., et al., "Detection of North American Eastern and Western Equine Encephalitis Viruses by Nucleic Acid Amplification Assays," Journal of Clinical Microbiology, 2003, vol. 41 (1), pp. 379-385.

Lau L.T., et al, "A Real-Time PCR for SARS-Coronavirus Incorporating Target Gene Pre-Amplification," Biochemical and Biophysical Research Communications, 2003, vol. 312 (4), pp. 1290-1296.

Lau L.T., et al., "Nucleic Acid Sequence-Based Amplification Methods to Detect Avian Influenza Virus," Biochemical and Biophysical Research Communications, 2004, vol. 313 (2), pp. 336-342.

Le Cann P., et al., "Quantification of Human Astroviruses in Sewage Using Real-Time RT-PCR," Research in Microbiology, 2004, vol. 155 (1), pp. 11-15.

Lebedev Y., et al., "Oligonucleotides Containing 2-Aminoadenine and 5-Methycytosine are More Effective as Primers for PCR Amplification than their Nonmodified Counterparts," Genetic Analysis: Biomolecular Engineering, 1996, vol. 13 (1), pp. 15-21.

Lednicky J.A., et al., "Polyomaviruses and Human Tumors: A Brief Review of Current Concenpts and Interpretations," Frontiers Bioscience, 1999, vol. 4, pp. D153-D164.

(56) References Cited

OTHER PUBLICATIONS

Lee J.A., et al., "Rapid Identification of Human Adenovirus Types 3 and 7 from Respiratory Specimens via Multiplex Type-Specific PCR," Journal of Clinical Microbiology, 2005, vol. 43 (11), pp. 5509-5514.

Lee J.H., et al., "Simultaneous Detection of Three Mosquito-Borne Encephalitis Viruses (Eastern equine, La Crosse, and St. Louis) with a Single-Tube Multiplex Reverse Transcriptase Polymerase Chaine Reaction Assay," Journal of the American Mosquito Control Association, 2002, vol. 18 (1), pp. 26-31.

Leif H., et al., "Isolation and Characterization of the Proton-Translocating NADH: Ubiqu None Oxidoreductase from *Escherichia coli*," European Journal of Biochemistry, 1995, vol. 230 (2), pp. 538-548.

Lengyel A., et al., "Characterization of the Main Protein Components of Adenovirus Virion and its Possible Use in Laboratory Diagnostics," Acta Microbiologica Immunologica Hungarica, 1998, vol. 43 (3-4), pp. 281-283.

Leroy E.M., et al., "Diagnosis of Ebola Haemorrhagic Fever by RT-PCR in an Epidemic Setting," Journal of Medicinal Virology, 2000, vol. 60 (4), pp. 463-467.

Levi K., et al., "Evaluation of an Isothermal Signal Amplification Method for Rapid Detection of Methicillin-Resistant *Staphylococcus aureus* from Patient-Screening Swabs," Journal of Clinical Microbiology, 2003, vol. 41 (7), pp. 3187-3191.

Levine S.M., et al., "PCR-Based Detection of *Bacillus anthracis* in Formalin-Fixed Tissue from a Patient Receiving Ciprofloxacin," Journal of Clinical Microbiology, 2002, vol. 40 (11), pp. 4360-4362.

Levison P.R., et al., "Recent Developments of Magnetic Beads for Use in Nucleic Acid Purification," Journal of Chromatography, 1998, vol. A816, pp. 107-111.

Lewers K.S., et al., "Detection of Linked QTL for Soybean Brown Stem Rot Resistance in "BSR 101" as Expressed in a Growth Chamber Environment," Molecular Breeding, 1999, vol. 5, pp. 33-42.

Li C., et al., "Evolution of H9N2 Influenza Viruses from Domestic Poultry in Mainland China," Virology, 2005, vol. 340 (1), pp. 70-83.

Li J., et al., "Single Nucleotide Polymorphism Determination Using Primer Extension and Time-of-Flight Mass Spectrometry," Electrophoresis, 1999, vol. 20 (6), pp. 1258-1265.

Li Q., et al., "Genetic Variability of Hexon Loops 1 and 2 between Seven Genome Types of Adenovirus Serotype 7," Archives of Virology, 1999, vol. 144 (9), pp. 1739-1749.

Li Q., et al., "Screening of the High Yield Influenza B Virus on MDCK c14d Cloning of its Whole Genome," International Congress Series, 2004, vol. 1263, pp. 610-614.

Li Q.G., et al., "Analysis of 15 Different Genome Types of Adenovirus Type 7 Isolated on Five Continents," Journal of Virology, 1986, vol. 60 (1), pp. 331-335.

Li Q.G., et al., "Comparison of 17 Genome Types of Adenovirus Type 3 Identified among Strains Recovered from Six Continents," Journal of Clinical Microbiology, 1988, vol. 26 (5), pp. 1009-1015.

Liebermann H., et al., "Mapping of Epitopes on the Fiber Knobs of Human Adenovirus Serotypes 8 and 15," Intervirology, 2002, vol. 45 (1), pp. 59-66.

Liebermann H., et al., "Mapping of Linear Epitopes on Fibre Knob of Human Adenovirus Serotype 5," Virus Research, 2001, vol. 73 (2), pp. 145-151.

Lim L.P., et al., "The MicroRNAs of Caenorhabditis Elegans," Genes and Development, 2003, vol. 17 (8), pp. 991-1008.

Limbach P.A., et al., "Enzymatic Sequencing of Oligonucleotides with Electrospray Mass Spectrometry," 42nd ASMS Conference on Mass Spectrometry, 1994.

Limoncu M.H., et al., "Emergence of Phenotypic Resistance to Ciprofloxacin and Levofloxacin In methicillin-Resistant and Methicillin-Sensitive *Staphylococcus Aureus* Strains," International Journal of Antimicrobial Agents, 2003, vol. 21 (5), pp. 420-424.

Lin B., et al., "Use of Oligonucleotide Microarrays for Rapid Detection and Serotyping of Acute Respiratory Disease-Associated Adenoviruses," Journal of Clinical Microbiology, 2004, vol. 42 (7), pp. 3232-3239.

Lin P.H., et al., "Oxidative Damage to Mitochondrial DNA in Atrial Muscle of Patients with Atrial Fibrillation," Free Radical Biology and Medicine, 2003, vol. 35 (10), pp. 1310-1318.

Lina G., et al., "Bacterial Competition for Human Nasal Cavity Colonization: Role of Staphylococcalagr Alleles," Applied and Environmental Microbiology, 2003, vol. 69 (1), pp. 18-23.

Lina G., et al., "Involvement of Panton-Valentine Leukocidin-Producing *Staphylococcus aureus* in Primary Skin Infections and Pneumonia," Clinical Infectious Diseases, 1999, vol. 29 (5), pp. 1128-1132.

Linssen B., et al., "Development of Reverse Transcription-PCR Assays Specific for Detection of Equine Encephalitis Viruses," Journal of Clinical Microbiology, 2000, vol. 38 (4), pp. 1527-1535.

Little D.P., et al., "MALDI on a Chip: Analysis of Arrays of Low-Femtomole to Subfemtomole Quantities of Synthetic Oligonucleotides and DNA Diagnostic Products Dispensed by a Piezoelectric Pipet," Analytical Chemistry, 1997, vol. 69, pp. 4540-4546.

Little D.P., et al, "Rapid Sequencing of Oligonucleotides by High-Resolution Mass Spectrometry," Journal of the American Chemical Society, 1994, vol. 116 (11), pp. 4893-4897.

Liu C., et al., "Improving the Microdialysis Procedure for Electrospray Ionization Mass Spectrometry of Biological Samples," Journal of Mass Spectrometry, 1997, vol. 32 (4), pp. 425-431.

Liu J.H., et al., "Interregional Transmission of the Internal Protein Genes of H2 Influenza Virus in Migratory Ducks from North America to Eurasia," Virus Genes, 2004, vol. 29 (1), pp. 81-86.

Liu Y., et al., "An Unusual Gene Arrangement for the Putative Chromosome Replication Origin and Circadian expression of dnaN in *Synechococcus* sp. Strain PCC 7942," Gene, 1996, vol. 172 (1), pp. 105-109.

Livermore D.M., "The Threat from the Pink Corner," Annals of Medicine, 2003, vol. 35 (4), pp. 226-234.

Loakes D., et al., "Nitroindoles as Universal Bases," Nucleosides and Nucleotides, 1995, vol. 14 (3-5), pp. 1001-1003.

Loo J.A., et al., "Applying Charge Discrimination with Electrospray Ionization-Mass Spectrometry to Protein Analysis," Journal of American Society for Mass Spectrometry, 1995, vol. 6, pp. 1098-1104.

Lott T.J., et al., "Nucleotide Sequence Analysis of the 5-8s rDNA and Adjacent ITS2 Region of Candida albicans and Related Species," Yeast, 1993, vol. 9, pp. 1199-1206.

Louie L., et al., "Evaluation of Three Rapid Methods for Detection of Methicillin Resistance in *Staphylococcus aureus*," Journal of Clinical Microbiology, 2000, vol. 38 (6), pp. 2170-2173.

Love B.C., et al., "Cloning and Sequence of the GroESL Heat-Shock Operon of Pasteurella Multocida," Gene, 1995, vol. 166 (1), pp. 179-180.

Lovseth A., et al., "Modified Multiplex PCR Method for Detection of Pyrogenic Exotoxin Genes in Staphylococcal Isolates," Journal of Clinical Microbiology, 2004, vol. 42 (8), pp. 3869-3872.

Lowe T., et al., "A Computer Program for Selection of Oligonucleotide Primers for Polymerase Chain Reactions," Nucleic Acids Research, 1990, vol. 18 (7), pp. 1757-1761.

Lu X., et al., "Molecular Typing of Human Adenoviruses by PCR and Sequencing of a Partial Region of the Hexon Gene," Archives of Virology, 2006, vol. 151 (8), pp. 1587-1602.

Lubman D.M., Application for Continuation Grant by David Mitchell Lubman dated Jun. 4, 1996 and Jun. 14, 1996.

Lubman D.M., Application for Continuation Grant by David Mitchell Lubman dated Jun. 10, 1994 and Jun. 24, 1994.

Lubman D.M., Application for Grant by David Mitchell Lubman dated Sep. 1, 1994 and Sep. 27, 1994.

Lubman D.M., Application for Grant by David Mitchell Lubman dated Oct. 25, 1992 and Oct. 29, 1992.

Ludwig S.L., et al., "Prevalence of Antibodies to Adenovirus Serotypes 4 and 7 among Unimmunized US Army Trainees: Results of a Retrospective Nationwide Seroprevalence Survey," The Journal of Infectious Diseases, 1998, vol. 178 (6), pp. 1776-1778.

Ludwig W., et al., "Bacterial Phylogeny Based on 16S and 23S rRNA Sequence Analysis," FEMS Microbiolofy Reviews, 1994, vol. 15 (2-3), pp. 155-173.

(56) References Cited

OTHER PUBLICATIONS

Lukashov V.V., et al., "Evolutionary Relationships among Parvoviruses: Virus-Host Coevolution among Autonomous Primate Parvoviruses and Links between Adeno-Associated and Avian Parvoviruses," Journal of Virology, 2001, vol. 75 (6), pp. 2729-2740.
Ma X.X., et al., "Novel Type of Staphylococcal Cassette Chromosome Mec Identified in Community-Acquired Methicillin-Resistant *Staphylococcus aureus* Strains," Antimicrobial Agents and Chemotherapy, 2002, vol. 46 (4), pp. 1147-1152.
Mack D.H., et al., "A Sensitive Method for the Identification of Uncharacterized Viruses Related to known Virus Groups: Hepadnavirus Model System," Proceedings of the National Academy of Sciences, 1988, vol. 85 (18), pp. 6977-6981.
Magnuson V.L., et al., "Substrate Nucleotide-Determined Non-Templated Addition of Adenine by Taq DNA Polymerase: Implications for PCR-Based Genotyping and Cloning," BioTechniques, 1996, vol. 21 (4), pp. 700-709.
Maiwald M., et al., "Characterization of Contaminating DNA in Taq Polymerase which Occurs During Amplification with a Primer Set for Legionella 5S Ribosomal RNA," Molecular and Cellular Probes, 1994, vol. 8 (1), pp. 11-14.
Malasig M.D., et al., "Simplified Microneutralization Test for Serotyping Adenovirus Isolates," Journal of Clinical Microbiology, 2001, vol. 39 (8), pp. 2984-2986.
Mangrum J.D., et al., "Solution Composition and Thermal Denaturation for the Production of Single-Stranded PCR Amplicons: Piperidine-Induced Destabilization of the DNA Duplex," Journal of the American Society for Mass Spectrometry, 2002, vol. 13 (3), pp. 232-240.
Manian F.A., "Asymptomatic Nasal Carriage of Mupirocin-Resistant, Methicillin—*Staphylococcus aureus* (MRSA) in a Pet Dog Associated with MRSA Infection in Household Contacts," Clinical Infectious Diseases, 2003, vol. 36 (2), pp. e26-e28.
Marks F., et al., "Genotyping of Plasmodium Falciparum Pyrimethamine Resistance by Matrix-Assisted Laser Desorption-Ionization Time-of-Flight Mass Spectrometry," Antimicrobial Agents and Chemotherapy, 2004, vol. 48 (2), pp. 466-472.
Marmur J., et al., "Strand Separation and Specific Recombination in Deoxyribonucleic Acids: Biological Studies," Proceedings of the National Academy of Sciences, 1960, vol. 46 (4), pp. 453-461.
Martemyanov K.A., et al., "Extremely Thermostable Elongation Factor (3 from Aquifer aeolicus: Cloning, Expression, Purification, and Characterization in a Heterologous Translation System," Protein Expression and Purification, 2000, vol. 18 (3), pp. 257-261.
Martineau F., et al., "Development of a PCR Assay for Identification of *Staphylococci* at Genus and Species Levels," Journal of Clinical Microbiology, 2001, vol. 39 (7), pp. 2541-2547.
Martineau F., et al., "Species-Specific and Ubiquitous-DNA-Based Assays for Rapid Identification of *Staphylococcus aureus*," Journal of Clinical Microbiology, 1998, vol. 36 (3), pp. 618-623.
Martin-Lopez J.V., et al., "Simultaneous PCR Detection of Ica Cluster and Methicillin and Mupirocinresistance Genes in Catheter-Isolated *Staphylococcus*," International Microbiology, 2004, vol. 7 (1), pp. 63-66.
Mason V.P., et al., "Diversity and linkage of Replication and Mobilisation Genes in Bacillus Rolling Irclereplicating Plasmids from Diverse Geographical Origins," FEMS Microbiology Ecology, 2002, vol. 42 (2), pp. 235-241.
Matray T.J., et al., "Synthesis and Properties of RNA Analogs-Oligoribonucleotide N3—>p5 Phosphoramidates," Nucleic Acids Research, 1999, 27 (20), pp. 3976-3985.
Matsuoka M., et al., "Characteristic Expression of Three Genes, msr(a), mph(C) and erm(Y), Thatconfer Resistance to Macrolide Antibiotics on *Staphylococcus aureus*," FEMS Microbiology Letters, 2003, vol. 220 (2), pp. 287-293.
May A.C., "Percent Sequence Identity: The Need to be Explicit," Structure, 2004, vol. 12 (5), pp. 737-738.
McCabe K.M., et al., "Bacterial Species Identification After DNA Amplification with a Universal Primer Pair," Molecular Genetics and Metabolism, 1999, vol. 66 (3), pp. 205-211.

McLafferty F.W., et al., "Comparison of Algorithms and Databases for Matching Unknown Mass Spectra," Journal of the American Society for Mass Spectrometry, 1998, vol. 9 (1), pp. 92-95.
McLuckey S.A., et al., "Ion Trap Tandem Mass Spectrometry Applied to Small Multiply Charged Oligonucleotides with a Modified Base," Journal of the American Society for Mass Spectrometry, 1994, vol. 5, pp. 740-747.
Mehrotra M., et al., "Multiplex PCR for Detection of Genes for *Staphylococcus aureus* Enterotoxins, Exfoliative Toxins, Toxic Shock Syndrome Toxin 1, and Methicillin Resistance," Journal of Clinical Microbiology, 2000, vol. 38 (3), pp. 1032-1035.
Meiyu F., et al., "Detection of Flaviviruses by Reverse Transcriptase-Polymerase Chain Reaction with the Universal Primer Set," Microbiology and Immunology, 1997, vol. 41 (3), pp. 209-213.
Mellor J., et al., "Genotype Dependence of Hepatitis C Virus Load Measurement in Commercially Available Quantitative Assays," Journal of Clinical Microbiology, 1999, vol. 37 (8), pp. 2525-2532.
Merlino J., et al., "New Chromogenic Identification and Detection of *Staphylococcus aureus* and Methicillin-Resistant *S. aureus*," Journal of Clinical Microbiology, 2000, vol. 38 (6), pp. 2378-2380.
Merlino J., et al., "Rapid Detection of Non-Multidrug-Resistant and Multidrug-Methicillin-Resistant *Staphylococcus aureus* Using Cycling Probe Technology for the mecA Gene," European Journal of Clinical Microbiology and Infectious Diseases, 2003, vol. 22 (5), pp. 322-323.
Messmer T.O., et al., "Discrimination of *Streptococcus pneumoniae* from Other Upper respiratory tract *Streptococci* by Arbitrary Primed PCR," Clinical Biochemistry, 1995, vol. 28 (6), pp. 567-572.
Metzgar D., et al., "PCR Analysis of Egyptian Respiratory Adenovirus Isolates, Including Identification of Species, Serotypes and Coinfections," Journal of Clinical Microbiology, 2005, vol. 43 (11), pp. 5743-5752.
Miller K.W., et al., "A Compendium of Human Mitochondria! DNA Control Region: Development of an International Standard Forensic Database," Croatian Medical Journal, 2001, vol. 42 (3), pp. 315-327.
Miragaia M., et al., "Genetic Diversity among Methicillin-Resistant Staphylococcus Epidemidis(MRSE)," Microbial Drug Resistance, 2005, vol. 11 (2), pp. 83-93.
Miura-Ochiai R., et al., "Quantitative Detection and Rapid Identification of Human Adenoviruses," Journal of Clinical Microbiology, 2007, vol. 45 (3), pp. 958-967.
Mollet C., et al., "RpoB Sequence Analysis as a Novel Basis for Bacterial Identification," Molecular Microbiology, 1997, vol. 26 (5), pp. 1005-1011.
Monroy A.M., et al., "Exvaluation of Reverse Transcriptase Polymerase Chain Reaction for the Detection of Eastern Equine Encephalumyelitis Virus during Vector Surveillance," Journal of Medical Entomology, 1996, vol. 33 (3), pp. 449-457.
Moore C., et al., "Development and Evaluation of a Real-Time Nucleic Acid Sequence Based Amplification Assay for Rapid Detection of Influenza A," Journal of Medical Virology, 2004, vol. 74 (4), pp. 619-628.
Moricca S., et al., "Detection of Fusarium Oxysporum f.sp. Vasinfectum in Cotton Tissue by Polymerase Chain Reaction," Plant Pathology, 1998, vol. 47 (4), pp. 486- 494.
Morinaga N., et al., "Purification, Cloning and Charactarizarion of Variant LukE-LukD with Strong Leukocidal Activity of Staphylococcal Bi-Component Leukotoxin Family," Microbiology and Immunology, 2003, vol. 47 (1), pp. 81-90.
Morse R., et al., "Nucleotide Sequence of Part of the ropC Gene Encoding the B Subunit of DNA Dependent RNA Polymerase from some Gram-Positive Bacteria and Comparative Amino Acid Sequence Analysis," Systematic and Applied Microbiology, 1996, vol. 19, pp. 150-157.
Muddiman D.C., et al., "Application of Secondary Ion and Matrix-Assisted Laser Desorption-Ionization Time-of-Flight Mass Spectrometry for the Quantitative Analysis of Biological Molecules," Mass Spectrometry Reviews, 1995, vol. 14 (6), pp. 383-429.
Muddiman D.C., et al., "Characterization of PCR Products from Bacilli Using Electrospray Ionization FTICR Mass Spectrometry," Analytical Chemistry, 1996, vol. 68 (21), pp. 3705-3712.

(56) References Cited

OTHER PUBLICATIONS

Muddiman D.C., et al., "Important Aspects Concerning the Quantification of Biomolecules by Time-of-Flight Secondaryion Mass Spectrometry," Applied Spectrometry, 1996, vol. 50 (2), pp. 161-166.
Muddiman D.C., et al., "Length and Base Composition of PCR-Amplified Nucleic Acids Using Mass Measurements from Electrospray Ionization Mass Spectrometry," Analytical Chemistry, 1997, vol. 69 (8), pp. 1543-1549.
Muddiman D.C., et al., "Precise Mass Measurement of a Double-Stranded 500 Base-Pair (309 kDa) Polymerase Chain Reaction Product by Negative Ion Electrospray Ionization Fourier Transform Ion Cyclotron Resonance Mass Spectrometry," Rapid Communications in Mass Spectrometry, 1999, vol. 13 (2), pp. 1201-1204.
Muddiman D.C., et al., "Sequencing and Characterization of Larger Oligonucleotides by Electrospray Ionization Fourier Transform Ion Cyclotron Resonance Mass Spectrometry," Reviews in Analytical Chemistry, 1998, vol. 17 (1), pp. 1-68.
Muhammed W.T., et al., "Electrospray Ionization Quadrupole Time-of-Flight Mass Spectrometry and Guadrupole Mass Spectrometry for Genotyping Single Nucleotide Substitutions in Intact Polymerase Chain Reaction Products in K-Ras and p53," Rapid Communications in Mass Spectrometry, 2002, vol. 16 (24), pp. 2278-2285.
Murakami K., et al., "Identification of Methicillin-Resistant Strains of *Staphylococci* by Polymerase Chain Reaction," Journal of Clinical Microbiology, 1991, vol. 29 (10), pp. 2240-2244.
Mushegian A.R., et al., "A Minimal Gene Set for Cellular Life Derived by Comparison of Complete Bacterial Genomes," Proceedings of the National Academy of Science, 1996, vol. 93 (19), pp. 10268-10273.
Na B.K., et al., "Detection and Typing of Respiratory Adenoviruses in a Single-Tube Multiplex Polymerase Chain Reaction," Journal of Medical Virology, 2002, vol. 66 (4), pp. 512-517.
Nagpal M.L., et al., "Utility of 16S-23S rRNA Spacer Region Methodology: How Similar are Interspace Regions within a Genome and Between Strains for Closely Related Organisms?," Journal of Microbiological Methods, 1998, vol. 33, pp. 211-219.
Nagy M., et al., "Sequence Analysis of Porcine Adenovirus Serotype 5 Fibre Gene: Evidence for Recombination," Virus Genes, 2002, vol. 24 (2), pp. 181-185.
Naito Y., et al., "Molecular Mass Measurement of Polymerase Chain Reaction Products Amplified from Human Blood DNA by Electrospray Ionization Mass Spectrometry," Rapid Communications in Mass Spectrometry, 1995, vol. 9 (15), pp. 1484-1486.
Nakagawa S., et al., "Gene Sequences and Specific Detection for Panton-Valentine Leukocidin," Biochemical and Biophysical Research Communications, 2005, vol. 328 (4), pp. 995-1002.
Nakao H., et al., "Development of a Direct PCR Assay for Detection of the Diphtheria Toxin Gene," Journal of Clinical Microbiology, 1997, vol. 35 (7), pp. 1651-1655.
Narita S., et al., "Phage Conversion of Panton-Valentine Leukocidin in *Staphylococcus aureus*: Molecular Analysis of a PVL-Converting Phage, cpSLT," Gene, 2001, vol. 268 (1-2), pp. 195-206.
Naumov G.I., et al., "Discrimination Between the Soil Yeast Species Williopsis Saturnus and Williopsis Suaveolens by the Polymerase Chain Reaction with the Universal Primer N21," Microbiology, 2000, vol. 69 (2), pp. 229-233.
NEB Catalog, 1998/1999, pp. 1, 79, 121 and 284.
Neumann G., et al., "Host Range Restriction and Pathogenicity in the Context of Influenza Pandemic," Emerging Infectious Diseases, 2006, vol. 12 (6), pp. 881-886.
Newcombe J., et al., "PCR of Peripheral Blood for Diagnosis of Meningococcal Disease," Journal of Clinical Microbiology, 1996, vol. 34 (7), pp. 1637-1640.
Ng E.K., et al., "Quantitative Analysis an Prognostic Implication of SARS Coronavirus RNA in the Plasma and Serum of Patients with Severe Acute Respiratory Syndrome," Clinical Chemistry, 2003, vol. 49 (12), pp. 1976-1980.
Ng E.K., et al., "Serial Analysis of the Plasma Concentration of SARS Coronavirus RNA in Pediatric Patients with Severe Acute Respiratory Syndrome," Clinical Chemistry, 2003, vol. 49 (12), pp. 2085-2088.
Ni J., et al., "Interpretation of Oligonucleotide Mass Spectra for Determinationof Sequence Using Electrospray Ionization and Tandem Mass Spectrometry," Analytical Chemistry, 1996, vol. 68 (13), pp. 1989-1999.
Nilsson M., et al., "Evaluation of Mitochondrial DNA Coding Region Assays for Increased Discrimination in Forensic Analysis," Forensic Science International: Genetics, 2008, vol. 2 (1), pp. 1-8.
Nishikawa T., et al., "Reconstitution of Active Recombinant Ship Toxin (Stc)1 from Recombinant Stx1 -A and Sbt1 -B Subunits Independently Produced by *E. coli* Clones," FEMS Microbiol Letters, 1999, vol. 178 (1), pp. 13-18.
Non-Final Office Action mailed Feb. 2, 2007 for U.S. Appl. No. 10/844,938, filed May 12, 2004.
Non-Final Office Action mailed Oct. 2, 2009 for U.S. Appl. No. 11/929,707, filed Oct. 30, 2007.
Non-Final Office Action mailed Aug. 4, 2010 for U.S. Appl. No. 12/049,949, filed Mar. 17, 2008.
Non-Final Office Action mailed Apr. 6, 2009 for U.S. Appl. No. 11/331,987, filed Jan. 13, 2006.
Non-Final Office Action mailed Apr. 7, 2006 for U.S. Appl. No. 10/964,571, filed Oct. 12, 2004.
Non-Final Office Action mailed Aug. 7, 2007 for U.S. Appl. No. 10/844,938, filed May 12, 2004.
Non-Final Office Action mailed Jun. 10, 2009 for U.S. Appl. No. 10/844,938 filed May 12, 2004.
Non-Final Office Action mailed Jan. 12, 2010 for U.S. Appl. No. 11/491,376, filed Jul. 21, 2006.
Non-Final Office Action mailed Oct. 13, 2010 for U.S. Appl. No. 10/754,415, filed Jan. 9, 2004.
Non-Final Office Action mailed Sep. 16, 2009 for U.S. Appl. No. 11/233,630, filed Sep. 21, 2005.
Non-Final Office Action mailed Apr. 17, 2009 for U.S. Appl. No. 12/211,641, filed Sep. 16, 2008.
Non-Final Office Action mailed Nov. 19, 2003 for U.S. Appl. No. 09/798,007, filed Mar. 2, 2001.
Non-Final Office Action mailed Aug. 20, 2007 for U.S. Appl. No. 11/582,863, filed Oct. 17, 2006.
Non-Final Office Action mailed May 20, 2008 for U.S. Appl. No. 10/844,938, filed May 12, 2004.
Non-Final Office Action mailed Oct. 20, 2004 for U.S. Appl. No. 09/891,793, filed Jun. 26, 2001.
Non-Final Office Action mailed Feb. 23, 2009 for U.S. Appl. No. 10/660,122, filed Sep. 11, 2003.
Non-Final Office Action mailed May 26, 2010 for U.S. Appl. No. 11/869,449, filed Oct. 9, 2007.
Non-Final Office Action mailed Jul. 27, 2006 for U.S. Appl. No. 11/209,439, filed Aug. 8, 2005.
Non-Final Office Action mailed Jun. 28, 2010 for U.S. Appl. No. 11/930,002, filed Oct. 30, 2007.
Non-Final Office Action mailed Sep. 28, 2009 for U.S. Appl. No. 11/930,017, filed Oct. 30, 2007.
Non-Final Office Action mailed Dec. 29, 2010 for U.S. Appl. No. 12/616,422, filed Nov. 11, 2009.
Non-Final Office Action mailed Apr. 30, 2010 for U.S. Appl. No. 11/930,108 filed Oct. 31, 2007.
Norder H., et al., "Typing of Hepatitis B Virus Genomes by a Simplified Polymerase Chain Reaction," Journal of Medical Virology, 1990, vol. 31 (3), pp. 215-221.
Nordhoff E., et al., "Matrix Assisted Laser Desorption/Ionization Mass Spectrometry of Nucleic Acids with Wavelengths in the Ultraviolet and Infrared," Rapid Communications in Mass Spectrometry, 1992, vol. 6 (12), pp. 771-776.
Notice of Allowance mailed Apr. 1, 2011 for U.S. Appl. No. 11/233,630, filed Sep. 21, 2005.
Notice of Allowance mailed Jun. 3, 2009 for U.S. Appl. No. 11/331,978, filed Jan. 13, 2006.
Notice of Allowance mailed Aug. 5, 2010 for U.S. Appl. No. 11/233,630, filed Sep. 21, 2005.

(56) References Cited

OTHER PUBLICATIONS

Notice of Allowance mailed Aug. 6, 2009 for U.S. Appl. No. 10/728,486, filed Dec. 5, 2003.
Notice of Allowance mailed Jun. 9, 2011 for U.S. Appl. No. 11/491,376, filed Jul. 21, 2006.
Notice of Allowance mailed Dec. 10, 2010 for U.S. Appl. No. 11/233,630, filed Sep. 21, 2005.
Notice of Allowance mailed Dec. 10, 2010 for U.S. Appl. No. 11/491,376, filed Jul. 21, 2006.
Notice of Allowance mailed Nov. 12, 2009 for U.S. Appl. No. 10/728,486, filed Dec. 5, 2003.
Notice of Allowance mailed Dec. 15, 2008 for U.S. Appl. No. 11/331,978, filed Jan. 13, 2006.
Notice of Allowance mailed Sep. 18, 2009 for U.S. Appl. No. 10/660,998, filed Sep. 12, 2003.
Notice of Allowance mailed Nov. 24, 2009 for U.S. Appl. No. 11/331,978, filed Jan. 13, 2006.
Notice of Allowance mailed May 25, 2011 for U.S. Appl. No. 11/929,707, filed Oct. 30, 2007.
Notice of Allowance mailed Oct. 29, 2009 for U.S. Appl. No. 10/660,122, filed Sep. 11, 2003.
Nubel U., et al., "PCR Primers to Amplify 16S rRNA Genes from Cyanobacteria," Applied and Environmental Microbiology, 1997, vol. 63 (8), pp. 3327-3332.
Null Allison P., et al., "Enzymatic Strategies for the Characterization of Nucleic Acids by Electrospray Ionization Mass Spectrometry," Rapid Communications in Mass Spectrometry, 2003, vol. 17 (24), pp. 2699-2706.
Null A.P., et al., "Determination of a Correction to Improve Mass Measurement Accuracy of Isotopically Unresolved Polymerase Chain Reaction Amplicons by Electrospray Ionization Fourier Transform Ion Cyclotron Resonance Mass Spectrometry," Rapid Communications in Mass Spectrometry, 2003, vol. 17 (15), pp. 1714-1722.
Null A.P., et al., "Evaluation of Sample Preparation Techniques for Mass Measurements of PCR Products Using ESIFT-ICR Mass Spectrometry," The American Society for Mass Spectrometry, 2002, vol. 13 (4), pp. 338-344.
Null A.P., et al., "Genotyping of Simple and Compound Short Tandem Repeat Loci Using Electrospray Ionization Fourier Transform Ion Cyclotron Resonance Mass Spectrometry," Analytical Chemistry, 2001, vol. 73 (18), pp. 4514-4521.
Null A.P., et al., "Implications of Hydrophobicity and Free Energy of Solvation for Characterization of Nucleic Acids by Electrospray Ionization Mass Spectrometry," Analytical Chemistry, 2003, vol. 75 (6), pp. 1331-1339.
Null A.P., et al., "Perspectives on the Use of Electrospray Ionization Fourier Transform Ion Cyclotron Resonance Mass Spectrometry for Short Tandem Repeat Genotyping in the Post Genome Era," Journal of Mass Spectrometry, 2001, vol. 36 (6), pp. 589-606.
Null A.P., et al., "Preparation of Single-Stranded PCR Products for Electrospray Ionization Mass Spectrometry Using the DNA Repair Enzyme Lambda Exonuclease," Analyst, 2000, vol. 125 (4), pp. 619-626.
Nunes E.L., et al., "Detection of IleS-2 Gene Encoding Mupirocin Resistance in Methicillin-Resistant *Staphylococcus aureus* by Multiplex PCR," Diagnostic Microbiology and Infectious Disease, 1999, vol. 34 (2), pp. 77-81.
Nygren M., et al., "Quantification of HIV-1 Using Multiple Quantitative Polymerase Chain Reaction Standards and Bioluminometric Detection," Analytical Biochemistry, 2001, vol. 288 (1), pp. 28-38.
Oberacher H., et al., "Analysis of Polymerase Chain Reaction Products by On-Line Liquid Chromatography Mass Spectrometry for Genotyping of Polymeric Short tandem Repeat Loci," Analytical Chemistry, 2001, vol. 73 (21), pp. 5109-5115.
Oberacher H., et al., "Increased Foresnic Efficiency of DNA Fingerprints Through Simultaneous Resolution of Length and Nucleotide Variability by High-Performance Mass Spectrometry," Human Mutation, 2008, vol. 29 (3), pp. 427-432.

Oberste M.S., et al., "Improved Molecular Identification of Enteroviruses by RT-PCR and Amplicon Sequencing," Journal of Clinical Virology, 2003, vol. 26 (3), pp. 375-377.
Oberste M.S., et al., "Molecular Epidemiology and Type-Specific Detection of Echovirus 11 Isolates from the Americas, Europe, Africa, Australia, Southern Asia and the Middle East," Virus Research, 2003, vol. 91 (2), pp. 241-248.
Oberste M.S., et al., "Molecular Phylogeny and Proposed Classification of the Simian Picornaviruses," Journal of Virology, 2002, vol. 76 (3), pp. 1244-1251.
Office Action mailed Apr. 1, 2004 for U.S. Appl. No. 10/156,608, filed May 24, 2002.
Office Action mailed May 1, 2006 for U.S. Appl. No. 10/660,998, filed Sep. 12, 2003.
Office Action mailed Feb. 2, 2011 for U.S. Appl. No. 11/869,449, filed Oct. 9, 2007.
Office Action mailed Jan. 2, 2009 for U.S. Appl. No. 11/060,135 filed Feb. 17, 2005.
Office Action mailed Jun. 2, 2006 for U.S. Appl. No. 10/933,928, filed Sep. 3, 2004.
Office Action mailed Jun. 2, 2008 for U.S. Appl. No. 11/331,978, filed Jan. 13, 2006.
Office Action mailed Nov. 2, 2010 for Australian Application No. 2007353877 filed Sep. 14, 2007.
Office Action mailed Oct. 2, 2008 for U.S. Appl. No. 11/233,630, filed Sep. 21, 2005.
Office Action mailed Oct. 2, 2009 for Japanese Application No. 2005508560 filed Dec. 5, 2003.
Office Action mailed Aug. 3, 2006 for U.S. Appl. No. 10/660,998, filed Sep. 12, 2003.
Office Action mailed Aug. 3, 2009 for U.S. Appl. No. 11/754,174, filed May 25, 2007.
Office Action mailed Dec. 3, 2003 for U.S. Appl. No. 10/325,527, filed Dec. 18, 2002.
Office Action mailed Feb. 3, 2011 for U.S. Appl. No. 12/326,800, filed Dec. 2, 2008.
Office Action mailed Nov. 3, 2008 for U.S. Appl. No. 10/728,486, filed Dec. 5, 2003.
Office Action mailed Apr. 4, 2008 for U.S. Appl. No. 10/829,826, filed Apr. 22, 2004.
Office Action mailed Dec. 4, 2006 for Indian Application No. 1136KOLNP2003 filed Mar. 4, 2002.
Office Action mailed Feb. 4, 2009 for U.S. Appl. No. 11/404,561, filed Apr. 12, 2006.
Office Action mailed Jun. 4, 2009 for U.S. Appl. No. 10/754,415, filed Jan. 9, 2004.
Office Action mailed May 4, 2010 for U.S. Appl. No. 90/010,447, filed Apr. 9, 2009.
Office Action mailed May 4, 2010 for U.S. Appl. No. 90/010,448, filed Apr. 9, 2009.
Office Action mailed Nov. 4, 2009 for European Application No. 02709785.6 filed Mar. 4, 2002.
Office Action mailed Sep. 4, 2008 for Australian Application No. 2003297687 filed Dec. 5, 2003.
Office Action mailed Aug. 5, 2010 for European Application No. 02709785.6 filed Mar. 4, 2002.
Office Action mailed Sep. 5, 2006 for U.S. Appl. No. 10/660,996, filed Sep. 12, 2003.
Office Action mailed Jan. 6, 2011 for Israel Application No. 157661 filed Mar. 4, 2002.
Office Action mailed Jul. 6, 2006 for U.S. Appl. No. 10/660,122, filed Sep. 11, 2003.
Office Action mailed Jul. 6, 2007 for U.S. Appl. No. 10/829,826, filed Apr. 22, 2004.
Office Action mailed Mar. 6, 2009 for U.S. Appl. No. 11/233,630, filed Sep. 21, 2005.
Office Action mailed Nov. 6, 2002 for U.S. Appl. No. 09/798,007, filed Mar. 2, 2001.
Office Action mailed Apr. 7, 2009 for Canadian Application No. 2525498 filed May 13, 2004.
Office Action mailed Apr. 7, 2009 for European Application No. 07760292.8 filed Apr. 6, 2007.

(56) References Cited

OTHER PUBLICATIONS

Office Action mailed Apr. 7, 2009 for U.S. Appl. No. 10/660,998, filed Sep. 12, 2003.
Office Action mailed Aug. 7, 2007 for U.S. Appl. No. 10/660,998, filed Sep. 12, 2003.
Office Action mailed Feb. 7, 2008 for European Application No. 03796752.8 filed Dec. 5, 2003.
Office Action mailed Jun. 7, 2010 for European Application No. 06800205.4 filed Jul. 27, 2006.
Office Action mailed Jan. 8, 2003 for U.S. Appl. No. 09/798,007, filed Mar. 2, 2001.
Office Action mailed Jan. 8, 2007 for U.S. Appl. No. 09/891,793, filed Jun. 26, 2001.
Office Action mailed Mar. 8, 2005 for U.S. Appl. No. 09/891,793, filed Jun. 26, 2001.
Office Action mailed Mar. 8, 2007 for U.S. Appl. No. 11/060,135, filed Feb. 17, 2005.
Office Action mailed Sep. 8, 2006 for Chinese Application No. 02809122.1 filed Mar. 4, 2002.
Office Action mailed Dec. 9, 2004 for U.S. Appl. No. 10/156,608, filed May 24, 2002.
Office Action mailed Dec. 9, 2009 for U.S. Appl. No. 90/010,210, filed Jun. 27, 2008.
Office Action mailed Dec. 9, 2009 for U.S. Appl. No. 90/010,447, filed Apr. 9, 2009.
Office Action mailed Dec. 9, 2009 for U.S. Appl. No. 90/010,448, filed Apr. 9, 2009.
Office Action mailed Feb. 9, 2007 for Chinese Application No. 02809122.1 filed Mar. 4, 2002.
Office Action mailed Jan. 9, 2008 for Japanese Application No. 2002570692 filed Mar. 4, 2002.
Office Action mailed Jul. 9, 2008 for U.S. Appl. No. 10/660,122, filed Sep. 11, 2003.
Office Action mailed Jul. 9, 2008 for U.S. Appl. No. 11/331,987, filed Jan. 13, 2006.
Office Action mailed Mar. 9, 2004 for U.S. Appl. No. 09/891,793, filed Jun. 26, 2001.
Office Action mailed Nov. 9, 2010 for U.S. Appl. No. 11/331,987, filed Jan. 13, 2006.
Office Action mailed Dec. 10, 2008 for U.S. Appl. No. 10/829,826, filed Apr. 22, 2004.
Office Action mailed Dec. 10, 2009 for U.S. Appl. No. 11/929,910, filed Oct. 30, 2007.
Office Action mailed Feb. 10, 2005 for U.S. Appl. No. 09/798,007, filed Mar. 2, 2001.
Office Action mailed Feb. 10, 2006 for Australian Application No. 2002244250 filed Mar. 4, 2002.
Office Action mailed Jun. 10, 2009 for U.S. Appl. No. 90/010,210, filed Jun. 27, 2008.
Office Action mailed Jun. 10, 2010 for U.S. Appl. No. 90/010,447, filed Apr. 9, 2009.
Office Action mailed Jun. 10, 2010 for U.S. Appl. No. 90/010,448, filed Apr. 9, 2009.
Office Action mailed Oct. 10, 2007 for U.S. Appl. No. 10/754,415, filed Jan. 9, 2004.
Office Action mailed Sep. 10, 2008 for Australian Application No. 2003302236 filed Dec. 5, 2003.
Office Action mailed Aug. 11, 2005 for U.S. Appl. No. 09/891,793, filed Jun. 26, 2001.
Office Action mailed Aug. 11, 2010 for U.S. Appl. No. 90/010,447, filed Apr. 9, 2009.
Office Action mailed Aug. 11, 2010 for U.S. Appl. No. 90/010,448, filed Apr. 9, 2009.
Office Action mailed Dec. 11, 2007 for U.S. Appl. No. 10/660,998, filed Sep. 12, 2003.
Office Action mailed Jul. 11, 2003 for U.S. Appl. No. 09/798,007, filed Mar. 2, 2001.
Office Action mailed Jun. 11, 2010 for U.S. Appl. No. 90/010,210, filed Jun. 27, 2008.
Office Action mailed Mar. 11, 2005 for U.S. Appl. No. 10/325,527, filed Dec. 18, 2002.
Office Action mailed May 11, 2007 for U.S. Appl. No. 10/728,486, filed Dec. 5, 2003.
Office Action mailed Jul. 12, 2006 for U.S. Appl. No. 09/891,793, filed Jun. 26, 2001.
Office Action mailed Jul. 12, 2006 for U.S. Appl. No. 10/660,996, filed Sep. 12, 2003.
Office Action mailed Jun. 12, 2008 for U.S. Appl. No. 10/754,415, filed Jan. 9, 2004.
Office Action mailed Jun. 12, 2009 for Chinese Application No. 200480016187.9 filed May 13, 2004.
Office Action mailed May 12, 2002 for U.S. Appl. No. 09/798,007, filed Mar. 2, 2001.
Office Action mailed Aug. 13, 2009 for U.S. Appl. No. 11/674,538, filed Feb. 13, 2007.
Office Action mailed Jul. 13, 2004 for U.S Appl. No. 09/891,793, filed Jun. 26, 2001.
Office Action mailed Jul. 13, 2007 for U.S. Appl. No. 11/233,630, filed Sep. 21, 2005.
Office Action mailed Jul. 13, 2010 for U.S. Appl. No. 11/929,930, filed Oct. 30, 2007.
Office Action mailed Mar. 13, 2006 for U.S. Appl. No. 10/75,4415, filed Jan. 9, 2004.
Office Action mailed Nov. 13, 2003 for U.S. Appl. No. 09/891,793, filed Jun. 26, 2001.
Office Action mailed Sep. 13, 2006 for U.S. Appl. No. 09/891,793, filed Jun. 26, 2001.
Office Action mailed Jul. 14, 2004 for U.S. Appl. No. 10/326,642, filed Dec. 18, 2002.
Office Action mailed Jun. 14, 2004 for U.S. Appl. No. 09/891,793, filed Jun. 26, 2001.
Office Action mailed Mar. 14, 2011 for U.S. Appl. No. 11/930,002, filed Oct. 30, 2007.
Office Action mailed Aug. 15, 2008 for U.S. Appl. No. 11/331,978, filed Jan. 13, 2006.
Office Action mailed Dec. 15, 2008 for Israel Application No. 157661 filed Mar. 4, 2002.
Office action mailed Dec. 15, 2010 for Canadian Application No. 2508726 filed Dec. 5, 2003.
Office Action mailed Jan. 15, 2008 for Israel Application No. 157661 filed Mar. 4, 2002.
Office Action mailed Jul. 15, 2009 for U.S. Appl. No. 11/060,135, filed Feb. 17, 2005.
Office Action mailed Mar. 15, 2010 for European Application No. 08730682.5 filed Feb. 25, 2008.
Office Action mailed Nov. 15, 2007 for U.S. Appl. No. 11/331,978, filed Jan. 13, 2006.
Office Action mailed Sep. 15, 2005 for U.S. Appl. No. 10/156,608, filed May 24, 2002.
Office Action mailed Apr. 16, 2002 for U.S. Appl. No. 09/798,007, filed Mar. 2, 2001.
Office Action mailed Apr. 16, 2008 for U.S. Appl. No. 11/233,630, filed Sep. 21, 2005.
Office Action mailed Apr. 16, 2009 for U.S. Appl. No. 90/010,210, filed Jun. 27, 2008.
Office Action mailed Aug. 16, 2004 for U.S. Appl. No. 10/325,527, filed Dec. 18, 2002.
Office Action mailed Aug. 16, 2010 for U.S. Appl. No. 11/929,707, filed Oct. 30, 2007.
Office Action mailed Feb. 16, 2011 for U.S. Appl. No. 11/929,910, filed Oct. 30, 2007.
Office Action mailed Jul. 16, 2007 for U.S. Appl. No. 11/331,987, filed Jan. 13, 2006.
Office Action mailed Mar. 16, 2006 for U.S. Appl. No. 09/891,793, filed Jun. 26, 2001.
Office Action mailed Mar.16, 2010 for Canadian Application No. 2616281 filed Jul. 21, 2006.
Office Action mailed May 16, 2008 for U.S. Appl. No. 11/404,561, filed Apr. 12, 2006.
Office Action mailed Nov. 16, 2009 for Japanese Application No. 2005508488 filed Dec. 5, 2003.

(56) References Cited

OTHER PUBLICATIONS

Office Action mailed Jun. 17, 2008 for U.S. Appl. No. 11/582,863, filed Oct. 17, 2006.
Office Action mailed Mar. 17, 2006 for U.S. Appl. No. 10/660,122, filed Sep. 11, 2003.
Office Action mailed Nov. 17, 2006 for U.S. Appl. No. 10/754,415, filed Jan. 9, 2004.
Office Action mailed Oct. 17, 2007 for U.S. Appl. No. 10/728,486, filed Dec. 5, 2003.
Office Action mailed Oct. 17, 2008 for U.S. Appl. No. 11/331,978, filed Jan. 13, 2006.
Office Action mailed Sep. 17, 2008 for European Application No. 03796752.8 filed Dec. 5, 2003.
Office Action mailed Sep. 17, 2008 for U.S. Appl. No. 10/660,122, filed Sep. 11, 2003.
Office Action mailed Feb. 18, 2010 for European Application No. 03814656.9 filed Dec. 5, 2003.
Office Action mailed Jan. 18, 2011 for U.S. Appl. No. 11/930,108, filed Oct. 31, 2007.
Office Action mailed May 18, 2005 for New Zealand Application No. 527857 filed Mar. 4, 2002.
Office Action mailed Sep. 18, 2006 for U.S. Appl. No. 10/660,997, filed Sep. 12, 2003.
Office Action mailed Sep. 18, 2008 for Australian Application No. 2003298030 filed Dec. 5, 2003.
Office Action mailed Sep. 18, 2008 for U.S. Appl. No. 10/660,998, filed Sep. 12, 2003.
Office Action mailed Jan. 19, 2007 for U.S. Appl. No. 11/059,776, filed Feb. 17, 2005.
Office Action mailed May 19, 2005 for U.S. Appl. No. 09/891,793, filed Jun. 26, 2001.
Office Action mailed Nov. 19, 2004 for U.S. Appl. No. 10/156,608, filed May 24, 2002.
Office Action mailed Oct. 19, 2007 for U.S. Appl. No. 11/210,516, filed Aug. 24, 2005.
Office Action mailed Sep. 19, 2006 for U.S. Appl. No. 10/660,122, filed Sep. 11, 2003.
Office Action mailed Sep. 19, 2007 for U.S. Appl. No. 10/660,122, filed Sep. 11, 2003.
Office Action mailed Apr. 20, 2007 for U.S. Appl. No. 10/660,122, filed Sep. 11, 2003.
Office Action mailed Apr. 20, 2009 for U.S. Appl. No. 10/891,337, filed Jul. 14, 2004.
Office Action mailed Dec. 20, 2006 for U.S. Appl. No. 10/728,486, filed Dec. 5, 2003.
Office Action mailed Jul. 20, 2005 for U.S. Appl. No. 10/156,608, filed May 24, 2002.
Office Action mailed Jun. 20, 2002 for U.S. Appl. No. 09/798,007, filed Mar. 2, 2001.
Office Action mailed Nov. 20, 2003 for U.S. Appl. No. 10/323,438, filed Dec. 18, 2002.
Office Action mailed Nov. 20, 2006 for U.S. Appl. No. 09/891,793, filed Jun. 26, 2001.
Office Action mailed Nov. 20, 2006 for European Application No. 02709785.6 filed Mar. 4, 2002.
Office Action mailed Sep. 20, 2010 for U.S. Appl. No. 90/010,447, filed Apr. 9, 2009.
Office Action mailed Sep. 20, 2010 for U.S. Appl. No. 90/010,448, filed Apr. 9, 2009.
Office Action mailed Apr. 21, 2009 for U.S. Appl. No. 90/010,209, filed Jun. 27, 2008.
Office Action mailed Mar. 21, 2008 for U.S. Appl. No. 10/660,122, filed Sep. 11, 2003.
Office Action mailed May 21, 2008 for U.S. Appl. No. 10/943,344, filed Sep. 17, 2004.
Office Action mailed Nov. 21, 2003 for U.S. Appl. No. 10/326,642, filed Dec. 18, 2002.
Office Action mailed Nov. 21, 2006 for U.S. Appl. No. 10/660,997, filed Sep. 12, 2003.
Office Action mailed Oct. 21, 2005 for U.S. Appl. No. 10/326,641, filed Dec. 18, 2002.
Office Action mailed Oct. 21, 2009 for U.S. Appl. No. 12/326,800, filed Dec. 2, 2008.
Office Action mailed Apr. 22, 2009 for European Application No. 07874065.1 filed Sep. 14, 2007.
Office Action mailed Apr. 22, 2009 for U.S. Appl. No. 11/491,376, filed Jul. 21, 2006.
Office Action mailed Jul. 22, 2008 for U.S. Appl. No. 90/010,209, filed Jun. 27, 2008.
Office Action mailed Jul. 22, 2008 for U.S. Appl. No. 90/010,210, filed Jun. 27, 2008.
Office Action mailed Nov. 22, 2006 for U.S. Appl. No. 10/660,996, filed Sep. 12, 2003.
Office Action mailed Oct. 22, 2007 for U.S. Appl. No. 11/331,987, filed Jan. 13, 2006.
Office Action mailed Sep. 22, 2003 for U.S. Appl. No. 09/798,007, filed Mar. 2, 2001.
Office Action mailed Sep. 22, 2010 for Canadian Application No. 2510007 filed Dec. 5, 2003.
Office Action mailed Apr. 23, 2010 for U.S. Appl. No. 90/010,210, filed Jun. 27, 2008.
Office Action mailed Feb. 23, 2009 for U.S. Appl. No. 10/943,344, filed Sep. 17, 2004.
Office Action mailed Jan. 23, 2008 for U.S. Appl. No. 10/728,486, filed Dec. 5, 2003.
Office Action mailed Jan. 23, 2008 for U.S. Appl. No. 11/059,776, filed Feb. 17, 2005.
Office Action mailed Jun. 23, 2010 for European Application No. 07874065.1 filed Sep. 14, 2007.
Office Action mailed May 23, 2003 for U.S. Appl. No. 09/891,793, filed Jun. 26, 2001.
Office Action mailed May 23, 2005 for U.S. Appl. No. 10/156,608, filed May 24, 2002.
Office Action mailed Oct. 23, 2003 for New Zealand Application No. 527857 filed Mar. 4, 2002.
Office Action mailed Apr. 24, 2009 for U.S. Appl. No. 90/010,447, filed Apr. 9, 2009.
Office Action mailed Apr. 24, 2009 for U.S. Appl. No. 90/010,448, filed Apr. 9, 2009.
Office Action mailed Aug. 24, 2010 for U.S. Appl. No. 90/010,210, filed Jun. 27, 2008.
Office Action mailed Dec. 24, 2004 for New Zealand Application No. 527857 filed Mar. 4, 2002.
Office Action mailed Feb. 24, 2004 for U.S. Appl. No. 10/326,642, filed Dec. 18, 2002.
Office Action mailed Jan. 24, 2005 for U.S. Appl. No. 10/326,642, filed Dec. 18, 2002.
Office Action mailed Jan. 24, 2007 for U.S. Appl. No. 10/660,998, filed Sep. 12, 2003.
Office Action mailed Jul. 24, 2007 for Mexican Application No. PAA2003007927 filed Sep. 2, 2003.
Office Action mailed Jul. 24, 2007 for U.S. Appl. No. 11/060,135, filed Feb. 17, 2005.
Office Action mailed Jul. 24, 2009 for U.S. Appl. No. 11/754,182, filed May 25, 2007.
Office Action mailed Jun. 24, 2008 for European Application No. 06800205.4 filed Jul. 27, 2006.
Office Action mailed Mar. 24, 2011 for U.S. Appl. No. 11/929,930, filed Oct. 30, 2007.
Office Action mailed Nov. 24, 2009 for U.S. Appl. No. 90/010,210, filed Jun. 27, 2008.
Office Action mailed Sep. 24, 2009 for U.S. Appl. No. 90/010,210, filed Jun. 27, 2008.
Office Action mailed Aug. 25, 2009 for U.S. Appl. No. 11/754,169, filed May 25, 2007.
Office Action mailed Jun. 25, 2009 for U.S. Appl. No. 11/869,449, filed Oct. 9, 2007.
Office Action mailed Jun. 25, 2009 for U.S. Appl. No. 90/010,210, filed Jun. 27, 2008.
Office Action mailed Mar. 25, 2008 for U.S. Appl. No. 11/060,135, filed Feb. 17, 2005.

(56) References Cited

OTHER PUBLICATIONS

Office Action mailed May 25, 2011 for Canadian Application No. 2663029 filed Sep. 14, 2007.
Office Action mailed Aug. 26, 2003 for U.S. Appl. No. 09/891,793, filed Jun. 26, 2001.
Office Action mailed Aug. 26, 2010 for Canadian Application No. 2508584 filed Dec. 5, 2003.
Office Action mailed Jul. 26, 2004 for U.S. Appl. No. 10/323,438, filed Dec. 18, 2002.
Office Action mailed May 26, 2005 for U.S. Appl. No. 10/156,608, filed May 24, 2002.
Office Action mailed May 26, 2006 for U.S. Appl. No. 10/660,997, filed Sep. 12, 2003.
Office Action mailed Feb. 27, 2003 for U.S. Appl. No. 09/798,007, filed Mar. 2, 2001.
Office Action mailed Feb. 27, 2007 for U.S. Appl. No. 10/754,415, filed Jan. 9, 2004.
Office Action mailed Feb. 27, 2007 for U.S. Appl. No. 10/943,344, filed Sep. 17, 2004.
Office Action mailed Jul. 27, 2006 for U.S. Appl. No. 10/728,486, filed Dec. 5, 2003.
Office Action mailed Jul. 27, 2009 for Canadian Application No. 2439655 filed Mar. 4, 2002.
Office Action mailed Aug. 28, 2006 for U.S. Appl. No. 10/754,415, filed Jan. 9, 2004.
Office Action mailed Feb. 28, 2006 for U.S. Appl. No. 10/660,996, filed Sep. 12, 2003.
Office Action mailed Jul. 28, 2009 for U.S. Appl. No. 11/754,163, filed May 25, 2007.
Office Action mailed Jul. 28, 2010 for U.S. Appl. No. 90/010,210, filed Jun. 27, 2008.
Office Action mailed May 28, 2003 for U.S. Appl. No. 09/798,007, filed Mar. 2, 2001.
Office Action mailed Mar. 29, 2010 for Australian Application No. 2006272776 filed Jul. 21, 2006.
Office Action mailed May 29, 2007 for U.S. Appl. No. 11/059,776, filed Feb. 17, 2005.
Office Action mailed Oct. 29, 2009 for U.S. Appl. No. 90/010,447, filed Apr. 9, 2009.
Office Action mailed Oct. 29, 2009 for U.S. Appl. No. 90/010,448, filed Apr. 9, 2009.
Office Action mailed Aug. 30, 2007 for U.S. Appl. No. 10/754,415, filed Jan. 9, 2004.
Office Action mailed Jul. 30, 2008 for Australian Application No. 2004248107 filed Apr. 23, 2004.
Office Action mailed Jul. 30, 2009 for Japanese Application No. 2002570692 filed Mar. 4, 2002.
Office Action mailed Jun. 30, 2004 for U.S. Appl. No. 09/798,007, filed Mar. 2, 2001.
Office Action mailed Jun. 30, 2010 for U.S. Appl. No. 90/010,210, filed Jun. 27, 2008.
Office Action mailed Jun. 30, 2010 for U.S. Appl. No. 90/010,447, filed Apr. 9, 2009.
Office Action mailed Jun. 30, 2010 for U.S. Appl. No. 90/010,448, filed Apr. 9, 2009.
Office Action mailed May 30, 2006 for U.S. Appl. No. 10/660,996, filed Sep. 12, 2003.
Office Action mailed Nov. 30, 2009 for U.S. Appl. No. 10/660,122, filed Sep. 11, 2003.
Office Action mailed Sep. 30, 2005 for Chinese Application No. 02809122.1 filed Mar. 4, 2002.
Office Action mailed Aug. 31, 2010 for Canadian Application No. 2663029 filed Sep. 14, 2007.
Office Action mailed Jan. 31, 2003 for U.S. Appl. No. 09/798,007, filed Mar. 2, 2001.
Office Action mailed Jan. 31, 2007 for Philippines Application No. PH12003500824 filed Mar. 4, 2002.
O Guinn M.L., et al., "Field Detection of Eastern Equine Encephalitis Virus in the Amazon Basin Region of Peru Using Reverse Transcription-Polymerase Chain Reaction Adapted for FieldIdentification of Arthropod-Borne Pathogens," American Journal of Tropical Medicine and Hygiene, 2004, vol. 70 (2), pp. 164-171.
Oizumi N., et al., "Relationship Between Mutations in the DNA Gyrase and Topoisomerase IV Genes and Nadifloxacin Resistance in Clinically Isolated Quinolone-Resistant *Staphylococcus aureus*," Journal of Infection and Chemotherapy, 2001, vol. 7 (3), pp. 191-194.
Okada M., et al., "Detection and Sequence-Based Typing of Human Adenoviruses Using Sensitiveuniversal Primer Sets for the Hexon Gene," Archives of Virology, 2007, vol. 152 (1), pp. 1-9.
Okuma K., et al., "Dissemination of New Methicillin-Resistant *Staphylococcus aureus* Clones in the Community," Journal of Clinical Microbiology, 2002, vol. 40 (11), pp. 4289-4294.
Oliveira D.C., et al., "Genetic Organization of the Downstream Region of the mecA Element inMethicillin-Resistant *Staphylococcus aureus* Isolates Carrying Different Polymorphisms of This Region," Antimicrobial Agents and Chemotherapy, 2000, vol. 44 (7), pp. 1906-1910.
Oliveira D.C., et al., "Multiplex PCR Strategy for Rapid Identification of Structural Types and Variants of the mec Element in Methicillin-Resistant *Staphylococcus aureus*," Antimicrobial Agents and Chemotherapy, 2002, vol. 46 (7), pp. 2155-2161.
Olsen B., et al., "Transhemispheric Exchange of Lyme Disease Spyrochetes by Seabirds," Journal of Clinical Microbiology, 1995, vol. 33 (12), pp. 3270-3274.
Osiowy C., et al., "Direct Detection of Respiratory Syncytial Virus, Parainfluenza Virus, and Adenovirus in Clinical Respiratory Specimens by a Multiplex Reverse Transcription-PCR Assay," Journal of Clinical Microbiology, 1998, vol. 36 (11), pp. 3149-3154.
Ostrander E.A., et al., "Identification and Characterization of Dinucleotide Repeat (CA)n Markers for Genetic Mapping in Dog," Genomics, 1993, vol. 16 (1), pp. 207-213.
Ounissi H., et al., "Gene Homogeneity for Aminoglycoside-Modifying Enzymes in Gram-PositiveCocci," Antimicrobial Agents and Chemotherapy, 1990, vol. 34 (11), pp. 2164-2168.
Palys T., et al., "Discovery and Classification of Ecological Diversity in the Bacterial World: the Role of DNA Sequence Data," International Journal of Systematic Bacteriology, 1997, vol. 47 (4), pp. 1145-1156.
Pan Z.Q., et al., "Oligonucleotide-Targeted Degradation of U1 and U2 snRNAs Reveals Differential Interactions of Simian Virus 40 pre-mRNAs with snRNPs," Nucleic Acids Research, 1989, vol. 17 (16), pp. 6553-6568.
Pannetier C., et al., "Quantitative Titration of Nucleic Acids by Enzymatic Amplification Reactions Run to Saturation," Nucleic Acids Research, 1993, vol. 21 (3), pp. 577-583.
Parson W., et al., "Population Data for 101 Austrian Caucasian Mitochondrial DNA d-Loop Sequences: Application of mtDNA Sequence Analysis to a Forensic Case," International Journal of Legal Medicine, 1998, vol. 111 (3), pp. 124-132.
Partial European Search Report for Application No. EP01106974, mailed on Dec. 16, 2002, 2 pages.
Pastorino B., et al., "Development of a TaqMan PCR Assay Without RNA Extraction Step for the Detection and Quantification of African Chikungunya Viruses," Journal of Virological Methods, 2005, vol. 124 (1-2), pp. 65-71.
Paterson A.H., et al., "Fine Mapping of Quantitative Trait Loci Using Selected Overlapping Recombinant Chromosomes, in an Interspecies Cross of Tomato," Genetics, 1990, vol. 124 (3), pp. 735-742.
Pawa A., et al., "Co-Transfer of Plasmids in Association with Conjugative Transfer of Mupirocin or Mupirocin and Penicillin Resistance in Methicillin-Resistant *Staphylococcus aureus*," Journal of Medicinal Microbiology, 2000, vol. 49 (12), pp. 1103-1107.
Payne D., et al., "Antimicrobials: The Challenge of Antibiotic Resistant Bacterial Pathogens: The Medical Need, The Market and Prospects for New Antimicrobial Agents," Current Opinion in Microbiology, 2004, vol. 7, pp. 435-438.
Peng X., et al., "Rapid Detection of Shigella Species in Environmental Sewage by an Immunocapture PCR with Universal Primers," Applied and Environmental Microbiology, 2002, vol. 68 (5), pp. 2580-2583.

(56) References Cited

OTHER PUBLICATIONS

Perez-Roth E., et al., "Multiplex PCR for Simultaneous Identification of *Staphylococcus aureus* and Detection of Methicillin and Mupirocin Resistance," Journal of Clinical Microbiology, 2001, vol. 39 (11), pp. 4037-4041.
Peters S.E., et al., "Quantification of the Detection of Pneumocystis Carinii by DNA Amplification," Molecular and Cellur Probes, 1992, vol. 6 (2), pp. 115-117.
Pfeffer M., et al., "Genus-Specific Detection of Alphaviruses by a Semi-Nested ReverseTranscription-Polymerase Chain Reaction," American Journal of Tropical Medicine and Hygiene, 1997, vol. 57 (6), pp. 709-718.
Pfeffer M., et al., "Specific Detection of Chikungunya Virus Using a RT-PCR/Nested PCR Combination," Journal of Veterinary Medicine B, 2002, vol. 49 (1), pp. 49-54.
Pieles U., et al., "Matrix-Assisted Laser Desorption Ionization Time-of-Flight Spectrometry: APowerful Tool for the Mass and Sequence Analysis of Natural and Modified Oligonucleotides, 787 reexamination," Nucleic Acids Research, 1993, vol. 21 (14), pp. 3191-3196.
Pillai S.D., et al., "Rapid Molecular Detection of Microbial Pathogens: Breakthroughs and Challenges," Archives of Virology, 1997, vol. 13, pp. 67-82.
Piper J., et al., "Commercially Available Technique for Rapid Laboratory Detection of MethicillinResistance Among *Staphylococcus aureus*," Diagnostic Microbiology and Infectious Disease, 1988, vol. 11 (3), pp. 177-180.
Poddar S.K., et al., "Detection of Adenovirus using PCR and Molecular Beacon," Journal of Virological Methods, 1999, vol. 82 (1), pp. 19-26.
Pomerantz S.C., et al., "Determination of Oligonucleotide Composition from Mass Spectrometrically Measured Molecular Weight," Journal of the American Society for Mass Spectrometry, 1993, vol. 4 (3), pp. 204-209.
Pring-Akerblom P., et al., "Multiplex Polymerase Chain Reaction for Subgenus-Specific Detection of Human Adenoviruses in Clinical Samples," Journal of Medical Virology, 1999, vol. 58 (1), pp. 87-92.
Pring-Akerblom P., et al., "PCR-Based Detection and Typing of Human Adenoviruses in Clinical Samples," Research in Virology, 1997, vol. 148 (3), pp. 225-231.
Promega. T4 Polynucleotide Kinase, Technical Bulletin No. 519, 2002.
Puthavathana P., et al., "Molecular Characterization of the Complete Genome of Human Influenza H5N1 Virus Isolates from Thailand," Journal of General Virology, 2005, vol. 86 (2), pp. 423-433.
Qadri S.M., et al., "Rapid Detection of Methicillin-Resistant *Staphylococcus aureus* by CrystalMRSA ID System," Journal of Clinical Microbiology, 1994, vol. 32 (7), pp. 1830-1832.
Raaum R.L., et al., "Catarrhine Primate Divergence Dates Estimated from Complete Mitochondria Genomes: Concordance with Fossil and Nuclear DNA Evidence," Journal of Human Evolution, 2005, vol. 48 (3), pp. 237-257.
Ramisse V., et al., "Identification and Characterization of Bacillus Anthracis by Multiplex PCR Analysis of Sequences on Plasmids pX01 and pX02 and Chromosomal DNA," Fems Microbiology Letters, 1996, vol. 145 (1), pp. 9-16.
Reid S.M., et al., "Primary Diagnosis of Foot-and-Mouth Disease by Reverse Transcription Polymerase Chain Reaction," Journal of Virological Methods, 2000, vol. 89 (1-2), pp. 167-176.
Reilly K., et al., "Design and Use of 16s Ribosomal DNA-Directed Primers in Competitive PCRs to Enumerate Proteolytic Bacteria in the Rumen," Microbial Ecology, 2002, vol. 43 (2), pp. 259-270.
Reischl U., "Application of Molecular Biology-Based Methods to theDiagnosis of Infectious Diseases 1, e72-e77.," Frontiers in Bioscience, 1996, vol. 1 (1), pp. e72-e77.
Reischl U., et al., "Rapid Identification of Methicillin-Resistant *Staphylococcus aureus* and Simultaneous Species Confirmation Using Real-Time Fluorescence PCR," Journal of Clinical Microbiology, 2000, vol. 38 (6), pp. 2429-2433.

Roberts M.M., et al., "Three-Dimensional Structure of the Adenovirus Major Coat Protein Hexon," Science, 1986, vol. 232 (4754), pp. 1148-1151.
Roberts M.S., et al., "Recombination and Migration Rates in Natural Populations of Bacillus Subtilis and Bacillus Mojavensis," Evolution, 1995, vol. 49 (6), pp. 1081-1094.
Robinson D.A., et al., "Multilocus Sequence Typing and the Evolution of Methicillin-Resistant *Staphylococcus aureus*," Clinical Microbiology and Infection, 2004, vol. 10, pp. 92-97.
Rong S., et al., "Design and Application of 60mer Oligonucleotide Microarray in SARS Coronavirus Detection," Chinese Science Bulletin, 2003, vol. 48 (12), pp. 1165-1169.
Ross P., et al., "High Level Multiplex Genotyping by MALDI-TOF Mass Spectrometry," Nature Biotechnology, 1998, vol. 16 (13), pp. 1347-1351.
Ross P.L., et al., "Analysis of DNA Fragments from Conventional and Microfabricated PCR Devices Using Delayed Extraction MALDI-TOF Mass Spectrometry," Analytical Chemistry, 1998, vol. 70 (10), pp. 2067-2073.
Ross P.L., et al., "Discrimination of Single-Nucleotide Polymorphisms in Human DNA Using Peptide Nucleic Acid Probes Detected by MALDI-TOF Mass Spectrometry," Analytical Chemistry, 1997, vol. 69 (20), pp. 4197-4202.
Rota P.A., et al., "Sequencing of a cDNA Clone of the Nucleoprotein Gene of Influenza B/Ann Arbor/1/86," Nucleic Acids Research, 1989, vol. 17 (9), pp. 3595.
Ruan Y., et al., "Comparative Full-Length Genome Sequence Analysis of 14 SARS Coronavirus Isolates and Common Mutations Associated with the Putative Origins of Infection," The Lancet, 2003, vol. 361, pp. 1779-1785, 1832.
Ruest A., et al., "Comparison of the Directigen Flu A+B test, the QuickVue Influenza Test, and Clinical Case Definition to Viral Culture and Reverse Transcription-PCR for Rapid Diagnosis of Influenza Virus Infection," Journal of Clinical Microbiology, 2003, vol. 41 (8), pp. 3487-3493.
Rupf S., et al., "Quantitative Determination of *Streptococcus mutans* by using Competitive Polymerasechain Reaction," European Journal of Oral Sciences, 1999, vol. 107 (2), pp. 75-81.
Russell K.L., et al., "Transmission Dynamics and Prospective Environmental Sampling of Adenovirus in a Military Recruit Setting," Journal of Infectious Diseases, 2006, vol. 194 (7), pp. 877-885.
Sabat A., et al., "Comparison of PCR-Based Methods for Typing *Staphylococcus aureus* Isolates," Journal of Clinical Microbiology, 2006, vol. 44 (10), pp. 3804-3807.
Sackesen C., et al., "Use of Polymerase Chain Reaction for Detection of Adenovirus in Children Withor Without Wheezing," Turkish Journal of Pediatrics, 2005, vol. 47 (3), pp. 227-231.
Sakai H., et al., "Simultaneous Detection of *Staphylococcus aureus* and Coagulase-Negative *Staphylococci* in Positive Blood Cultures by Real-Time PCR with Two Fluorescence Resonance Energy Transfer Probe Sets," Journal of Clinical Microbiology, 2004, vol. 42 (12), pp. 5739-5744.
Sala M., et al., "Ambiguous Base Pairing of the Purine Analogue 1-(2-Deoxy-B-D-Ribofuranosyl)-Imidazole-4- Carboxamide During PCR," Nucleic Acids Research, 1996, vol. 24 (17), pp. 3302-3306.
Sambrook J., et al., "Molecular Cloning—A Laboratory Manual," 1989, Cold Spring Harbor Laboratory Press, Table of Contents.
Sampath R., et al., "Global Surveillance of Emerging Influenza Virus Genotypes by Mass Spectrometry," Plos ONE, 2007, vol. 2 (5), pp. e489.
Sampath R., et al., "Rapid Identification of Emerging Infectious Agents using PCR and Electrospray Ionization Mass Spectrometry," Annals of the New York Academy of Science, 2007, vol. 1102, pp. 109-120.
Sampath R., et al., "Rapid Identification of Emerging Pathogens: Coronavirus," Emerging Infectious Diseases, 2005, vol. 11 (3), pp. 373-379.
Sanchez A., et al., "Detection and Molecular Characterization of Ebola Viruses Causing Disease in Human and Nonhuman Primates," Journal of Infectious Diseases, 1999, vol. 179 (1), pp. S164-S169.
Sanchez J.L., et al., "Epidemic of Adenovirus-Induced Respiratory Illness Among US Military Recruits: Epidemiologic and Immuno-

(56) References Cited

OTHER PUBLICATIONS logic Risk Factors in Healthy, Young adults," Journal of Medical Virology, 2001, vol. 65 (4), pp. 710-718.
Sanchez-Seco M.P., et al., "A Generic Nested-RT-PCR followed by Sequencing for Detection and Identification of Members of the *Alphavirus* Genus," Journal of Virological Methods, 2001, vol. 95 (1-2), pp. 153-161.
Santos S.R., et al., "Identification and Phylogenetic Sorting of Bacterial Lineages with Universally Conserved Genes and Proteins," Environmental Microbiology, 2004, vol. 6 (7), pp. 754-759.
Sarantis H., et al., "Comprehensive Detection and Serotyping of Human Adenoviruses by PCR and Sequencing," Journal of Clinical Microbiology, 2004, vol. 42 (9), pp. 3963-3969.
Sauer S., et al., "A Novel Procedure for Efficient Genotyping of Single Nucleotide Polymorphisms," Nucleic Acids Research, 2000, vol. 28 (5), pp. E13.1-E13.8.
Scaramozzino N., et al., "Comparison of Flavivirus Universal Primer Pairs and Development of a Rapid, Highly Sensitive Heminested Reverse Transcription-PCR Assay for Detection of Flaviviruses Targeted to a Conserved Region of the NS5 Gene Sequences," Journal of Clinical Microbiology, 2001, vol. 39 (5), pp. 1922-1927.
Schabereiter-Gurtner C., et al., "Application of Broad-Range 16s rRNA PCR Amplification and DGGE Fingerprinting for Detection of Tick-Infecting Bacteria," The Journal of Microbiological Methods, 2003, vol. 52 (2), pp. 251-260.
Scheffner M., et al., "The E6 Oncoprotein Encoded by Human Papillomavirus Types 16 and 18 Promotes the Degradation of p53," Cell, 1990, vol. 63 (6), pp. 1129-1136.
Schena M., et al., "Genome Analysis with Gene Expression Microarrays," Bioessays, 1996, vol. 18 (5), pp. 427-431.
Scheuermann R.N., et al., "Polymerase Chain-Reaction-Based mRNA Quantification Using an Internal Standard: Analysis of Oncogene Expression," Methods in Enzymology, 1993, vol. 218, pp. 446-473.
Schlecht N.F., et al., "Viral Load as a Predictor of the Risk of Cervical Intraepithelial Neoplasia," British Journal of Cancer, 2003, vol. 103 (4), pp. 519-524.
Schmidt T.M., et al., "Analysis of a Marine Pikoplankton Community by 16s rRNA Gene Cloning and Sequencing," Journal of Bacteriology, 1991, vol. 173 (14), pp. 4371-4378.
Schmitz F.J., et al., "Development of a Multiplex-PCR for Direct Detection of the Genes for Enterotoxin B and C, and Toxic Shock Syndrome Toxin-1 in *Staphylococcus aureus* Isolates," Journal of Medical Microbiology, 1998, vol. 47 (4), pp. 335-340.
Schmitz F.J., et al., "Development of Resistance to Ciprofloxacin, Rifampin, and Mupirocin in Methicillin-Susceptible and -Resistant *Staphylococcus aureus* Isolates," Antimicrobial Agents and Chemotherapy, 2000, vol. 44 (11), pp. 3229-3231.
Schmitz F.J., et al., "Specific Information Concerning Taxonomy, Pathogenicity and Methicillin Esistance of *Staphylococci* Obtained by a Multiplex PCR," Journal of Medical Microbiology, 1997, vol. 46 (9), pp. 773-778.
Schram K.H., et al., "Mass Spectrometry of Nucleic Acid Components," Methods of Biochemical Analysis, 1990, vol. 34, pp. 203-280.
Schultz J.C., et al., "Polymerise Chain Reaction Products Analyzed by Charge Detection Mass Spectrometry," Rapid Communications in Mass Spectrometry, 1999, vol. 13 (1), pp. 15-20.
Schwartz M., et al., "Prenatal Diagnosis of Alpha-1-Antitrypsin Deficiency Using Polymerase Chainreaction (PCR). Comparison of Conventional RFLP Methods with PCR used in Combination with Allelespecific Oligonucleotides or RFLP Analysis," Clinical Genetics, 1989, vol. 36 (6), pp. 419-426.
Schweiger B., et al., "Application of a Fluorogenic PCR Assay for Typing and Subtyping of Influenza Viruses in Respiratory Samples," Journal of Clinical Microbiology, 2000, vol. 38 (4), pp. 1552-1558.
Sciacchitano C.J., "Analysis of Polymerase Chain Reaction-Amplified DNA Fragments of Clostridium Botulinum Type E Neurotoxin Gene by High Performance Capillary Electrophoresis," Journal of Liquid Chromatography & Related Technologies, 1996, vol. 19 (13), pp. 2165-2178.
Scott-Taylor T.H., et al., "Conserved Sequences of the Adenovirus Genome for Detection of all Human Adenovirus Types by Hybridization," Journal of Clinical Microbiology, 1992, vol. 30 (7), pp. 1703-1710.
Seifarth W., et al., "Rapid Identification of All Known Retroviral Reverse Transcriptase Sequences with a Novel Versatile Detection Assay," AIDS Research and Human Retroviruses, 2000, vol. 16 (8), pp. 721-729.
Sellner L., et al., "A Single-Tube Nested RT-PCR for the Detection of Ross River Virus," Methods in Molecular Biology, 1998, vol. 92, pp. 145-152.
Sellner L.N., et al., "Sensitive Detection of Ross River Virus—A One-Tube Nested RT-PCR," Journal of Virological Methods, 1994, vol. 49 (1), pp. 47-58.
Senko M.W., et al., "Determination of Monoisotopic Masses and Ion Populations for Large Biomoleculesfrom Resolved Isotopic Distributions," Journal of the American Society for Mass Spectrometry, 1995, vol. 6, pp. 229-233.
Seshadri R., et al., "Differential Expression of Translational Elements by Life Cycle Variants of Coxiella Burnetii," Infection and Immunity, 1999, vol. 67 (11), pp. 6026-6033.
Shadan F.F., et al., "N-Butyrate, A Cell Cycle Blocker, Inhibits the Replication of Polyomaviruses and Papillomaviruses but Not That of Adenoviruses and Herpesviruses," Journal of Virology, 1994, vol. 68 (8), pp. 4785-4796.
Shaver Y.J., et al., "Restriction Fragment Length Polymorphism of rRNA Operons for Discrimination and Intergenic Spacer Sequences for Cataloging of Bacilus Subtilis Sub-Groups," Journal of Microbiological Methods, 2002, vol. 50 (2), pp. 215-223.
Shaver Y.J., et al., "Variation in 16s-23s rRNA Intergenic Spacer Regions Among Bacilus Subtilis 168 Isolates," Molecular Microbiology, 2001, vol. 42 (1), pp. 101-109.
Shimaoka M., et al., "Detection of the Gene for Toxic Shock Syndrome Toxin 1 in *Siaphylococcus aureus* by Enzyme-Labelled Oligonucleotideprobes," Journal of Medical Microbiology, 1996, vol. 44 (3), pp. 215-218.
Shimaoka M., et al., "Development of Enzyme-Labeled Oligonucleotide Probe for Detection of MecA Gene in Methicillin-Resistant *Staphylococcus aureus*," Journal of Clinical Microbiology, 1994, vol. 32 (8), pp. 1866-1869.
Shrestha N.K., et al., "Rapid Identification of *Staphylococcus aureus* and the MecA Gene from BacT/ALERT Blood Culture Bottles by Using the Lightcycler System," Journal of Clinical Microbiology, 2002, vol. 40 (7), pp. 2659-2661.
Simonsen L., et al., "The Impact of Influenza Epidemics on Hospitalizations," Journal of Infectious Diseases, 2000, vol. 181 (3), pp. 831-837.
Skov R.L., et al., "Evaluation of a New 3-h Hybridization Method for Detecting the MecA Gene in *Staphylococcus aureus* and Comparison with Existing Genotypic and Phenotypic Susceptibility Testing Methods," Journal of Antimicrobial Chemotherapy, 1999, vol. 43 (4), pp. 467-475.
Smirnov I.P., et al., "Application of DNA-Binding Polymers for Preparation of DNA for Analysis by Matrix-Assisted Laser Desorption/Ionization Mass Spectrometry," Rapid Communications in Mass Spectrometry, 2001, vol. 15 (16), pp. 1427-1432.
Smith T.F., "Comparison of Biosequences," Advances in Applied Mathematics, 1981, vol. 2, pp. 482-489.
Song F., et al., "Identification of cry11-type Genes from Bacilus Thuringiensis Strains and Characterization of a Novel Cry11-Type Gene," Applied and Environmental Microbiology, 2003, vol. 69, pp. 5207-5211.
Spackman E., et al., "Development of a Real-Time Reverse Transcriptase PCR Assay for Type A Influenzavirus and The Avian H5 and H7 Hemagglutinin Subtypes," Journal of Clinical Microbiology, 2002, vol. 40 (9), pp. 3256-3260.
Spiess L., et al., "Trehalose is a Potent PCR Enhancer: Lowering of DNA Melting Temperature and Thermal Stabilization of Taq Polymerase by the Disaccharide Trehalose," Clinical Chemistry, 2004, vol. 50 (7), pp. 1256-1259.

(56) References Cited

OTHER PUBLICATIONS

Srinivasan J.R., et al., "Matrix-Assisted Laser Desorption/Ionization Time-of-Flight Mass Spectrometry as a Rapid Screening Method to Detect Mutations Causing Tay-Sachs Disease," Rapid Communications in Mass Spectrometry, 1997, vol. 11 (10), pp. 1144-1150.
Steffens D.L., et al., "Sequence Analysis of Mitochondrial DNA Hypervariable Regions Using Infrared Fluorescence Detection," BioTechniques, 1998, vol. 24 (6), pp. 1044-1046.
Stephensen C.B., et al., "Phylogenetic Analysis of a Highly Conserved Region of the Poymerase Gene from 11 Coronaviruses and Development of a Consensus Poymerase Chain Reaction Assay," Virus Research, 1999, vol. 60 (2), pp. 181-189.
Stone B., et al., "Rapid Detection and Simultaneous Subtype Differentiation of Influenza A Viruses by Real Time PCR," Journal of Virological Methods, 2004, vol. 117 (2), pp. 103-112.
Stoneking M., et al., "Population Variation of Human mtDNA Control Region Sequences Detected by Enzymatic Amplification and Sequence-Specific Oligonucleotide Probes," American Journal of Human Genetics, 1991, vol. 48 (2), pp. 370-382.
Stratagene Catalog, Gene Characterization Kits, 1988, pp. 39.
Strommenger B., et al., "Multiplex PCR Assay for Simultaneous Detection of Nine Clinically Relevant Antibiotic Resistance Genes in *Staphylococcus aureus*," Journal of Clinical Microbiology, 2003, vol. 41 (9), pp. 4089-4094.
Studdert M.J., et al., "Polymerase Chain Reaction Tests for the Identification of Ross River, Kunjin and Murray Valley Encephalitis Virus Infections in Horses," Australian Veterinary Journal, 2003, vol. 81 (1-2), pp. 76-80.
Stuhlmeier R., et al., "Fast, Simultaneous, and Sensitive Detection of *Staphylococci*," Journal of Clinical Pathology, 2003, vol. 56 (10), pp. 782-785.
Sumner J.W., et al., "PCR Amplification and Comparison of Nucleotide Sequences from the groESL Heat Shock Operon of *Ehrlichia* Species," Journal of Critical Microbiology, 1997, vol. 35 (8), pp. 2087-2092.
Sundsfjord A., et al., "Genetic Methods for Detection of Antimicrobial Resistance," APMIS : Acta Pathologica, Microbiologica, et Immunologica Scandinavica, 2004, vol. 112 (11-12), pp. 815-837.
Supplementary European Search Report for Application No. 04775904.8, mailed on Jul. 7, 2008, 8 pages.
Supplementary European Search Report for Application No. EP03796752.8, mailed on Aug. 7, 2007, 3 pages.
Supplementary European Search Report for Application No. EP03810055.8, mailed on Jun. 8, 2007, 4 pages.
Supplementary European Search Report for Application No. EP03814656, mailed on Oct. 16, 2007, 2 pages.
Supplementary European Search Report for Application No. EP04752257.8, mailed on Feb. 15, 2006, 2 pages.
Supplementary European Search Report for Application No. EP05753037, mailed on Aug. 21, 2009, 2 pages.
Supplementary Partial European Search Report for Application No. EP02709785.6, mailed Sep. 1, 2005, 5 pages.
Supplementary Partial European Search Report for Application No. EP05751872.2, mailed on Jan. 28, 2008, 8 pages.
Supplementary Partial European Search Report for Application No. EP05856582.1, mailed on Oct. 27, 2008, 10 pages.
Swaminathan B., et al., "PulseNet: The Molecular Subtyping Network for Foodborne Bacterial Disease Surveillance, United States," Emerging Infectious Diseases, 2001, vol. 7 (3), pp. 382-389.
Swanborg R.H., et al., "Human Herpesvirus 6 and Chlamydia Pneumoniae as Etiologic Agents in Multiplesclerosis—a Critical Review," Microbes and Infection / Institut Pasteur, 2002, vol. 4 (13), pp. 1327-1333.
Swenson J.M., et al., "Performance of Eight Methods, Including Two New Rapid Methods, for Detection of Oxacillin Resistance in a Challenge Set of *Staphylococcus aureus* Organisms," Journal of Clinical Microbiology, 2001, vol. 39 (10), pp. 3785-3788.
Takagaki Y., et al., "Four Factors are Required for 3"-End Cleavage of Pre-mRNAs," Genes and Development, 1989, vol. 3 (11), pp. 1711-1724.
Takahashi H., et al., "Characterization of gryA, gryB, grIA and grIB Mutations in Fluoroquinolone-Resistant Clinical Isolates of *Staphylococcus aureus*," The Journal of Antimicrobial Chemotherapy, 1998, vol. 41 (1), pp. 49-57.
Takahata M., et al., "Mutations in the GyrA and Grl A Genes of Quinolone-Resistant Clinical Isolates of Methicillin-Resistant Staphylococcus Aureus," The Journal of Antimicrobial Chemotherapy, 1996, vol. 38 (3), pp. 543-546.
Takayama R., et al., "Quantification of Adenovirus Species B and C Viremia by Real-Time PCR in Adults and Children Undergoing Stem Cell Transplantation," Journal of Medical Virology, 2007, vol. 79 (3), pp. 278-284.
Takeuchi S., et al., "Serotyping of Adenoviruses on Conjunctival Scrapings by PCR and Sequence Analysis," Journal of Clinical Microbiology, 1999, vol. 37 (6), pp. 1839-1845.
Talaat A.M., et al., "Genome-Directed Primers for Selective Labeling of Bacterial Transcripts for DNA Microarray Analysis," Nature Biotechnology, 2000, vol. 17, pp. 679-682.
Tan T.Y., "Use of Molecular Techniques for the Detection of Antibiotic Resistance in Bacteria," Expert Review of Molecular Diagnostics, 2003, vol. 3 (1), pp. 93-103.
Tanabe F., et al., "The Properties and Mec A Gene of the Methicillin-Resistant Staphylococcus Aureus Isolated in Fukushima Medical College Hospital," Fukushima Journal of Medical Science, 1993, vol. 39 (1), pp. 35-42.
Tang K., et al., "Detection of 500-Nucleotide DNA by Laser Desorption Mass Spectrometry," Rapid Communications in Mass Spectrometry, 1994, vol. 8 (9), pp. 727-730.
Tang K., et al., Double-Stranded DNA Analysis by Matrix Assisted Laser Desorption/Ionization, 42nd ASMS Conference on Mass Spectrometry, 1994.
Tang K., et al., "Matrix-Assisted Laser Desorption/lonization of Restriction Enzyme-Digested DNA," Rapid Communications in Mass Spectrometry, 1994, vol. 8 (2), pp. 183-186.
Tang K., et al., Matrix-Assisted Laser Desorption/Ionization Mass Spectrometry of Oligonucleotides, Dissertation submitted to the Faculty of Vanderbilt University, 1994.
Tarassishin L., et al., "Adenovirus Core Protein VII Displays a Linear Epitope Conserved in a Range of Human Adenoviruses," Journal of General Virology, 1999, vol. 80 (Pt 1), pp. 47-50.
Tarassishin L., et al., "An Epitope on the Adenovirus Fibre Tail is Common to all Human Subgroups," Archives of Virology, 2000, vol. 145 (4), pp. 805-811.
Tatuch Y., et al., "Heteroplasmic mtDNA Mutation (T-G) at 8993 Can Cause Leigh Disease When the Percentage of Abnormal mtDNA is High," The American Journal of Human Genetics, 1992, vol. 50 (4), pp. 852-858.
Taubenberger J.K., et al., "Characterization of the 1918 Influenza Virus Polymerase Genes," Nature, 2005, vol. 437 (7060), pp. 889-893.
Taylor L.H., et al., "Risk Factors for Human Disease Emergence," Philosophical Transactions of the Royal Society of London Series B, Biological Sciences, 2001, vol. 356 (1411), pp. 983-989.
Tenover F.C., et al., "Characterization of a Strain of Community-Associated Methicillin-ResistantSlaphylococcus Aureus Widely Disseminated in the United States," Journal of Clinical Microbiology, 2006, vol. 44 (1), pp. 108-118.
Teramura T., et al., "Quantitative Detection of Serum Adenovirus in a Transplant Recipient," Lancet, 2002, vol. 359 (9321), pp. 1945.
Thiel V., et al., "Infectious RNA Transcribed in Vitro from a cDNA Copy of the Human Coronavirus Genome Cloned in Vaccinia Virus," The Journal of General Virology, 2001, vol. 82 (Pt 6), pp. 1273-1281.
Thompson J.D., et al., "Clustal W: Improving the Sensitivity of Progressive Multiple Sequence Alignmen Through Sequence Weighting, Position-Specific Gap Penalties and Weight Matrix Choice," Nucleic Acids Research, 1994, vol. 22 (22), pp. 4673-4680.
Thompson W.W., et al., "Influenza-Associated Hospitalizations in the United States," The Journal of the American Medical Association, 2004, vol. 292 (11), pp. 1333-1340.
Tokue Y., et al., "Comparison of a Polymerase Chain Reaction Assay and a Conventional Microbiologic Method for Detection of Methicillin-Resistant *Slaphylococcus aureus*," Antimicrobial Agents and Chemotherapy, 1992, vol. 36 (1), pp. 6-9.

(56) References Cited

OTHER PUBLICATIONS

Tong J., et al., "Ligation Reaction Specificities of an NAD+-Dependent DNA Ligase from the Hyperthermophile Aquifex Aeolicus," Nucleic Acids Research, 2000, vol. 28 (6), pp. 1447-1454.

Top F.H Jr., "Control of Adenovirus Acute Respiratory Disease in U.S. Army Trainees," The Yale Journal of Biology and Medicine, 1975, vol. 48 (3), pp. 185-195.

Torroni A., et al., "Classification of European mtDNAs from an Analysis of Three European Populations," Genetics, 1996, vol. 144 (4), pp. 1835-1850.

Towner K.J., et al., "Development and Evaluation of a PCR-Based Immunoassay for the Rapid Detection of Methicillin-Resistant *Staphylococcus aureus*," Journal of Medical Microbiology, 1998, vol. 47 (7), pp. 607-613.

Tsuneyoshi T., et al., "Mass Spectrometric Gene Diagnosis of One-Base Substitution from Polymerase Chain Reaction Amplified Human DNA," Rapid Communications in Mass Spectomerty, 1997, vol. 11 (7), pp. 719-722.

Tsunoda T., et al., "Time and Memory Efficient Algorithm for Extracting Palindromic and RepetitiveSubsequences in Nucleic Acid Sequences," Pacific Symposium on Biocomputing, 1999, vol. 4, pp. 202-213.

Udo E.E., et al., "A Chromosomal Location of the MupA Gene in *Staphylococcus aureus* Expressing High-Level Mupirocin Resistance," The Journal of Antimicrobial Chemotherapy, 2003, vol. 51 (5), pp. 1283-1286.

Udo E.E., et al., "Genetic Analysis of Methicillin-Resistant *Staphylococcus aureus* Expressing High-and Low-Level Mupirocin Resistance," Journal of Medical Microbiology, 2001, vol. 50 (10), pp. 909-915.

Udo E.E., et al., "Rapid Detection of Methicillin Resistance in *Staphylococci* Using a Slide Latex Agglutination Kit," International Journal of Antimicrobial Agents, 2000, vol. 15 (1), pp. 19-24.

Unal S., et al., "Detection of Methicillin-Resistant *Staphylococci* by Using the Polymerase Chain Reaction," Journal of Clinical Microbiology, 1992, vol. 30 (7), pp. 1685-1691.

Upton A., et al., "Mupirocin and *Staphylococcus aureus*: A Recent Paradigm of Emerging Antibiotic Resistance," The Journal of Antimicrobial Chemotherapy, 2003, vol. 51 (3), pp. 613-617.

Vabret A., et al., "Development of a PCR-and Hybridization-Based Assay (PCR Adenovirus Consensus) for the Detection and the Species Identification of Adenoviruses in Respiratory Specimens," Journal of Clinical Virology, 2004, vol. 31 (2), pp. 116-122.

Van Aerschot A., et al., "In Search of Acyclic Analogues as Universal Nucleosides in Degenerate Probes," Nucleosides and Nucleotides, 1995, vol. 14 (3-5), pp. 1053-1056.

Van Baar B.L., "Characterisation of Bacteria by Matrix-Assisted Laser Desorption/Ionisation and Electrospray Mass Spectrometry," FEMS Microbiology Reviews, 2000, vol. 24 (2), pp. 193-219.

Van Camp G., et al., "Amplification and Sequencing of Variable Regions in Bacterial 23s Ribosomal RNA Genes with Conserved Primer Sequences," Current Microbiology, 1993, vol. 27 (3), pp. 147-151.

Van Der Vossen J.M., et al., "DNA Based Typing Identification and Detection Systems for Food Spoilage Microorganisms: Development and Implementation," International Journal of Food Microbiology, 1996, vol. 33 (1), pp. 35-49.

Van Der Zee H., et al., "Rapid and Alternative Screening Methods for Microbiological Analysis," Journal of AOAC International, 1997, vol. 80 (4), pp. 934-940.

Van Dinten L.C., et al., "Proteolytic Processing of the Open Reading Frame Ib-EncodedPart of Arterivirus Replicase Is Mediated by nsp4 Serine Protease and is Essential for Virus Replication," Journal of Virology, 1999, vol. 73 (3), pp. 2027-2037.

Van Elden L.J., et al., "Clinical Diagnosis of Influenza Virus Infection: Evaluation of Diagnostic Tools in General Practice," The British Journal of General Practice, 2001, vol. 51 (469), pp. 630-634.

Van Elden L.J., et al., "Simultaneous Detection of Influenza Viruses A and B Using Real-Time Quantitative PCR," Journal of Clinical Microbiology, 2001, vol. 39 (1), pp. 196-200.

Van Ert M.N., et al., "Mass Spectrometry Provides Accurate Characterization of Two Genetic Marker Types in Bacillus Anthracis," Bio Techniques, 2004, vol. 37 (4), pp. 642-651.

Van Leeuwen W.B., et al., "Multilocus Sequence Typing of *Staphylococcus aureus* with DNA Array Technology," Journal of Clinical Microbiology, 2003, vol. 41 (7), pp. 3323-3326.

Van Leeuwen W.B., et al., "Rapid Detection of Methicillin-Resistance in *Staphylococcus aureus* Isolates by the MRSA-Screen Latex Agglutination Test," Journal of Clinical Microbiology, 1999, vol. 37 (9), pp. 3029-3030.

Vanchiere J.A., et al., "Detection of BK Virus and Simian Virus 40 in the Urine of Healthy Children," Journal of Medical Virology, 2005, vol. 75 (3), pp. 447-454.

Vanderhallen H., et al. "Identification of Encephalomyocarditis Virus in Clinical Samples by ReverseTranscription-PCR Followed by Genetic Typing Using Sequence Analysis," Journal of Clinical Microbiology, 1998, vol. 36 (12), pp. 3463-3467.

Vannuffel P., et al., "Rapid and Specific Molecular Identification of Methicillin-Resistant *Staphylococcus aureus* in Endotracheal Aspirates from Mechanically Ventilated Patients," Journal of Clinical Microbiology, 1998, vol. 36 (8), pp. 2366-2368.

Vannuffel P., et al., "Specific Detection of Methicillin-Resistant *Staphylococcus* Species by Multiplex PCR," Journal of Clinical Microbiology, 1995, vol. 33 (11), pp. 2864-2867.

Verma S., et al., "Modified Oligonucleotides: Synthesis and Strategy for Users," Annual Review of Biochemistry, 1998, vol. 67, pp. 99-134.

Videla C., et al., "Genomic Analysis of Adenovirus Isolated from Argentinian Children with Acute Lower Respiratory Infections," Journal of Clinical Virology, 1999, vol. 14 (1), pp. 67-71.

Vilchez R.A. et al., "Detection of Polyomavirus Simian Virus 40 Tumor Antigen DNA in AIDS-Related Systemic Non-Hodgkin Lymphoma," Journal of Acquired Immune Deficiency Syndromes, 2002, vol. 29 (2), pp. 109-116.

Voelter C., et al., "Screening Human Tumor Samples with a Broad-Spectrum Polymerase Chain Reaction Method for the Detection of Polyomaviruses," Virology, 1997, vol. 237 (2), pp. 389-396.

Volokhov D., et al., "Microarray Analysis of Erythromycin Resistance Determinants," Journal of Applied Microbiology, 2003, vol. 95 (4), pp. 787-798.

Von Eiff C., et al., "Pathogenesis of Infections Due to Coagulase-Negative *Staphylococci*," The Lancet Infectious Diseases, 2002, vol. 2 (11), pp. 677-685.

Von Wintzingerode F., et al., "Base-Specific Fragmentation of Amplified 16S rRNA Genes Analyzed by Mass Spectrometry: A Tool for Rapid Bacterial Identification," Proceedings of the National Academy of Sciences, 2002, vol. 99 (10), pp. 7039-7044.

Walker E.S., et al., "A Decline in Mupirocin Resistance in Methicillin-Resistant Staphylococcus aureus Accompanied Administrative Control of Prescriptions," Journal of Clinical Microbiology, 2004, vol. 42 (6), pp. 2792-2795.

Wallace S.S., et al., "The Enigma of Endonuclease VIII," DNA Repair, 2003, vol. 2 (5), pp. 441-453.

Wallet F., et al., "Choice of a Routine Method for Detecting Methicillin-Resistance in *Staphylococci*," The Journal of Antimicrobial Chemotherapy, 1996, vol. 37 (5), pp. 901-909.

Walters J.J., et al., "Genotyping Single Nucleotide Polymorphisms Using Intact Polymerase Chain Reaction Products by Electrospray Quadrupole Mass Spectrometry," Rapid Communications in Mass Spectrometry, 2001, vol. 15 (18), pp. 1752-1759.

Wang G., et al., "Targeted Mutagenesis in Mammalian Cells Mediated by Intracellular Triple Helix Formation," Molecular and Cellular Biology, 1995, vol. 15 (3), pp. 1759-1768.

Ward C.L., et al., "Design and Performance Testing of Quantitative Real Time PCR Assays for Influenza A and B Viral Load Measurement," Journal of Clinical Virology, 2004, vol. 29 (3), pp. 179-188.

Watanabe K., et al., "ICB Database: The gyrB Database for Identification and Classification of Bacteria," Nucleic Acids Research, 2001, vol. 29 (1), pp. 344-345.

Weissenbacher M., et al., "Etiologic and Clinical Evaluation of Acute Lower Respiratory TractInfections in Young Argentinean Children: An Overview," Reviews of Infectious Diseases, 1990, vol. 12 (Suppl 8), pp. S889-S898.

(56) References Cited

OTHER PUBLICATIONS

Welham K.J., et al., "The Characterization of Micro-Organisms by Matrix-Assisted Laser Desorption/Lonization Time-of-Flight Mass Spectrometry," Rapid Communications in Mass Spectrometry, 1998, vol. 12 (4), pp. 176-180.
Wertheim H.F., et al., "Effect of Mupirocin Treatment on Nasal, Pharyngeal, and Perineal Carriage of Staphylococcus aureus in Healthy Adults," Antimicrobial Agents and Chemotherapy, 2005, vol. 49 (4), pp. 1465-1467.
Westermann P., et al., "Inhibition of Expression of SV40 Virus Large T-Antigen by Antisense Oligodeoxyribonucleotides," Biomedica Biochimica Acta, 1989, vol. 1, pp. 85-93.
Whiley D.M., et al., "Simultaneous Detection and Differentiation of Human Polyomaviruses JC and BK by a Rapid and Sensitive PCR-ELAHA Assay and a Survey of the JCV Subtypes within an Australian Population," Journal of Medical Virology, 2004, vol. 72 (3), pp. 467-472.
Wichelhaus T.A., et al., "Rapid Detection of Epidemic Strains of Methicillin-Resistant*Staphylococcus aureus*," Journal of Clinical Microbiology, 1999, vol. 37 (3), pp. 690-693.
Wickham T.J., "Targeting Adenovirus," Gene Therapy, 2000, vol. 7 (2), pp. 110-114.
Widjojoatmodjo M.N., et al., "Rapid Identification of Bacterial by PCR-Single-Strand Conformation Polymorphism," Journal of Clinical Microbiology, 1994, vol. 32 (12), pp. 3002-3007.
Widjojoatmodjo M.N., et al., "The Magnetic Immuno Polymerase Chain Reaction Assay for Direct Detection of Salmonellae in Fecal Samples," Journal of Clinical Microbiology, 1992, vol. 30 (12), pp. 3195-3199.
Winger B.E., et al., "High Resolution Accurate Mass Measurements of Biomolecules using a new Electrospray Ionization Ion Cyclotron Resonance Mass Spectrometer," Journal American Society for Mass Spectrometry, 1993, vol. 4 (7), pp. 566-577.
Wolter A., et al., "Negative Ion FAB Mass Spectrometric Analysis of Non-Charged Key Intermediates in Oligonucleotide Synthesis: Rapid Identification of Partially Protected Dinucleoside Monophosphates," Biomedical and Environmental Mass Spectrometry, 1987, vol. 14, pp. 111-116.
Woo T.H., et al., "Identification of Leptospira Inadai by Continuous Monitoring of Fluorescence during Rapid Cycle PCR," Systematic and Applied Microbiology, 1998, vol. 21 (1), pp. 89-96.
Wood S.R., et al., "Rapid Detection and Serotyping of Adenovirus by Direct Immunofluorescence," Journal of Medical Virology, 1997, vol. 51 (3), pp. 198-201.
Wright K.E., et al., "Typing and Subtyping of Influenza Viruses in Clinical Samples by PCR," Journal of Clinical Microbiology, 1995, vol. 33 (5), pp. 1180-1184.
Written Opinion for Application No. PCT/US2004/33742, mailed on May 15, 2006, 5 pages.
Wu S., et al., "Genetic Organization of the mecA Region in Methicillin-Susceptible and Methicillin-Resistant Strains of Staphylococcus sciuri," The Journal of Bacteriology, 1998, vol. 180 (2), pp. 236-242.
Wu X., et al., "Establishment of a Fluorescent Polymerase Chain Reaction Method for the Detection of SARS-Associated Coronavhus and its Clinical Application," Chinese Medical Journal, 2003, vol. 116 (7), pp. 988-990.
Wunschel D., et al., "Discrimination Among the B. Cereus Group, in Comparison to B. Subtilis, by Structural Carbohydrate Profiles and Ribosomal RNA Spacer Region Pcr," Systematic and Applied Microbiology, 1994, vol. 17, pp. 625-635.
Wunschel D.S., et al., "Analysis of Double-Stranded Polymerase Chain Reaction Products from the Bacilus Cereus Group by Electrospray Lonization Fourier Transform Lon Cyclotron Resonance Mass Spectrometry," Rapid Communications in Mass Spectrometry, 1996, vol. 10 (1), pp. 29-35.
Wunschel D.S., et al., "Heterogeneity in Bacillus Cereus PCR Products Detected by ESI-FTICR Mass Spectrometry," Analytical Chemistry, 1998, vol. 70 (6), pp. 1203-1207.
Wunschel D.S., et al., "Mass spectrometric characterization of DNA for molecular biological applications: advances using MALDI and ESI," Advances in Mass Spectrometry, 1998, vol. 14, Elsevier, pp. 377-406.
Xu L., et al., "Electrophore Mass Tag Dideoxy DNA Sequencing," Analytical Chemistry, 1997, vol. 69 (17), pp. 3595-3602.
Xu W., et al., "Species-Specific Identification of Human Adenoviruses by a Multiplex PCR Assay," Journal of Clinical Microbiology, 2000, vol. 38 (11), pp. 4114-4120.
Xu W., et al., "Type-Specific Identification of Human Adenovirus, 3, 7, and 21 by a Multiplex PCR Assay," Journal of Medical Virology, 2001, vol. 64 (4), pp. 537-542.
Xu X., et al., "Intercontinental Circulation of Human Influenza A(H1N2) Reassortant Viruses During the 2001-2002 Influenza Season," The Journal of Infectious Diseases, 2002, vol. 186 (10), pp. 1490-1493.
Yao Z.P., et al., "Mass Spectrometry Based Proteolytic Mapping for Rapid Virus Identification," Analytical Chemistry, 2002, vol. 74 (11), pp. 2529-2534.
Yasui T., et al., "A Specific Oligonucleotide Primer for the Rapid Detection of Lactobacillus Lindneri by Polymerase Chain Reaction," Canadian Journal of Microbiology, 1997, vol. 43 (2), pp. 157-163.
Ye K., et al., "Three Distinct Promoters Direct Transcription of Different 5" Untranslated Regions of the Human Interleukin 1 Type 1 Receptor. A Possible Mechanism for Control of Translation," Cytokine, 1996, vol. 8 (6), pp. 421-429.
Yun H.J., et al., "Increased Antibacterial Activity of OW286, a Novel Fluoronaphthyridone Antibiotic, Against Staphylococcus aureus Strains with Defined Mutations in DNA Gyrase and Toposiomerase IV," International Journal of Antimicrobial Agents, 2005, vol. 25 (4), pp. 334-337.
Zeng Z.B., "Precision Mapping of Quantitative Trait Loci," Genetics, 1994, vol. 136 (4), pp. 1457-1468.
Zhang J., et al., "PowerBLAST: A New Network BLAST Application for Interactive or Automated Sequence Analysis and Annotation," Genome Research, 1997, vol. 7 (6), pp. 649-656.
Zhang K., et al., "New Quadriplex PCR Assay for Detection of Methicillin and Mupirocin Resistance and Simultaneous Discrimination of Staphylococcus aureus from Coagulase-Negative Staphylococci," Journal of Clinical Microbiology, 2004, vol. 42 (11), pp. 4947-4955.
Zhang W.D., et al., "Detection and Identification of Human Influenza Viruses by the Polymerase Chain Reaction," Journal of Virological Methods, 1991, vol. 33 (1-2), pp. 165-189.
Zhang Y.Q., et al., "Genome-Based Analysis of Virulence Genes in a Non-Biofilm-Forming Staphylococcus epidemidis Strain (ATCC 12228)," Molecular Microbiology, 2003, vol. 49 (6), pp. 1577-1593.
Ecker Supporting Information [online], May 23, 2005 [retrieved on Jul. 31, 2011]. Retrieved from the Internet:<URL:http://www.pnas.org/content/102/22/8012/suppl/DC1>.
Office Action mailed Oct. 30, 2012 for Japanese Application No. 2009528314 filed Sep. 14, 2007.
Office Action mailed Mar. 26, 2013 for Japanese Application No. 2009528314 filed Sep. 14, 2007.
Office Action mailed Jun. 28, 2013 for Canadian Application No. 2663029 filed Sep. 14, 2007.

* cited by examiner

SEQUENCE LISTING

```
<160> NUMBER OF SEQ ID NOS: 742

<210> SEQ ID NO 1
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(15)
<223> OTHER INFORMATION: n is a, c, g, or t

<400> SEQUENCE: 1
cgactcgagn nnnnnatgtg g                                              21

<210> SEQ ID NO 2
<211> LENGTH: 13
<212> TYPE: DNA
<213> ORGANISM: Artificial Sequence
<220> FEATURE:
<223> OTHER INFORMATION: Synthetic

<400> SEQUENCE: 2
aaatttrccc ggg                                                       13

<210> SEQ ID NO 3
<211> LENGTH: 13
<212> TYPE: DNA
<213> ORGANISM: Artificial Sequence
<220> FEATURE:
<223> OTHER INFORMATION: Synthetic

<400> SEQUENCE: 3
aaatttaccc ggg                                                       13

<210> SEQ ID NO 4
<211> LENGTH: 13
<212> TYPE: DNA
<213> ORGANISM: Artificial Sequence
<220> FEATURE:
```

-continued

```
<223> OTHER INFORMATION: Synthetic

<400> SEQUENCE: 4
aaatttgccc ggg                                                           13

<210> SEQ ID NO 5
<211> LENGTH: 8
<212> TYPE: DNA
<213> ORGANISM: Artificial Sequence
<220> FEATURE:
<223> OTHER INFORMATION: Synthetic

<400> SEQUENCE: 5 aattccgg                                                                  8

<210> SEQ ID NO 6
<211> LENGTH: 5
<212> TYPE: DNA
<213> ORGANISM: Artificial Sequence
<220> FEATURE:
<223> OTHER INFORMATION: Synthetic

<400> SEQUENCE: 6 aattc                                                                     5

<210> SEQ ID NO 7
<211> LENGTH: 5
<212> TYPE: DNA
<213> ORGANISM: Artificial Sequence
<220> FEATURE:
<223> OTHER INFORMATION: Synthetic

<400> SEQUENCE: 7 attcc                                                                     5

<210> SEQ ID NO 8
<211> LENGTH: 5
<212> TYPE: DNA
<213> ORGANISM: Artificial Sequence
<220> FEATURE:
<223> OTHER INFORMATION: Synthetic

<400> SEQUENCE: 8 ttccg                                                                     5

<210> SEQ ID NO 9
<211> LENGTH: 5
<212> TYPE: DNA
<213> ORGANISM: Artificial Sequence
<220> FEATURE:
<223> OTHER INFORMATION: Synthetic

<400> SEQUENCE: 9 tccgg                                                                     5

<210> SEQ ID NO 10
<211> LENGTH: 6
<212> TYPE: DNA
<213> ORGANISM: Artificial Sequence
<220> FEATURE:
<223> OTHER INFORMATION: Synthetic

<400> SEQUENCE: 10 aattcc                                                                    6
```

```
<210> SEQ ID NO 11
<211> LENGTH: 6
<212> TYPE: DNA
<213> ORGANISM: Artificial Sequence
<220> FEATURE:
<223> OTHER INFORMATION: Synthetic

<400> SEQUENCE: 11 attccg                                                                    6

<210> SEQ ID NO 12
<211> LENGTH: 6
<212> TYPE: DNA
<213> ORGANISM: Artificial Sequence
<220> FEATURE:
<223> OTHER INFORMATION: Synthetic

<400> SEQUENCE: 12 ttccgg                                                                    6

<210> SEQ ID NO 13
<211> LENGTH: 7
<212> TYPE: DNA
<213> ORGANISM: Artificial Sequence
<220> FEATURE:
<223> OTHER INFORMATION: Synthetic

<400> SEQUENCE: 13 aattccg                                                                   7

<210> SEQ ID NO 14
<211> LENGTH: 7
<212> TYPE: DNA
<213> ORGANISM: Artificial Sequence
<220> FEATURE:
<223> OTHER INFORMATION: Synthetic

<400> SEQUENCE: 14 attccgg                                                                   7

<210> SEQ ID NO 15
<211> LENGTH: 8
<212> TYPE: DNA
<213> ORGANISM: Artificial Sequence
<220> FEATURE:
<223> OTHER INFORMATION: Synthetic

<400> SEQUENCE: 15 aaaaaaaa                                                                  8

<210> SEQ ID NO 16
<211> LENGTH: 40
<212> TYPE: DNA
<213> ORGANISM: Artificial Sequence
<220> FEATURE:
<223> OTHER INFORMATION: Synthetic

<400> SEQUENCE: 16
aaaaaaaaaa tttttttttt cccccccccc gggggggggg                              40

<210> SEQ ID NO 17
<211> LENGTH: 32
<212> TYPE: DNA
<213> ORGANISM: Artificial Sequence
<220> FEATURE:
<223> OTHER INFORMATION: Synthetic
```

-continued

```
<400> SEQUENCE: 17
aaaaaaaatt tttttccccc ccccgggggg gg                                    32

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
aaaaaaaaaa tttttttttt                                                  20

<210> SEQ ID NO 19
<211> LENGTH: 9
<212> TYPE: DNA
<213> ORGANISM: Artificial Sequence
<220> FEATURE:
<223> OTHER INFORMATION: Synthetic

<400> SEQUENCE: 19 ccccccccc                                                               9

<210> SEQ ID NO 20
<211> LENGTH: 9
<212> TYPE: DNA
<213> ORGANISM: Artificial Sequence
<220> FEATURE:
<223> OTHER INFORMATION: Synthetic

<400> SEQUENCE: 20 ggggggggg                                                               9

<210> SEQ ID NO 21
<211> LENGTH: 10
<212> TYPE: DNA
<213> ORGANISM: Artificial Sequence
<220> FEATURE:
<223> OTHER INFORMATION: Synthetic

<400> SEQUENCE: 21
cccccccccc                                                             10

<210> SEQ ID NO 22
<211> LENGTH: 10
<212> TYPE: DNA
<213> ORGANISM: Artificial Sequence
<220> FEATURE:
<223> OTHER INFORMATION: Synthetic

<400> SEQUENCE: 22
ccccccccg                                                              10

<210> SEQ ID NO 23
<211> LENGTH: 10
<212> TYPE: DNA
<213> ORGANISM: Artificial Sequence
<220> FEATURE:
<223> OTHER INFORMATION: Synthetic

<400> SEQUENCE: 23
cggggggggg                                                             10

<210> SEQ ID NO 24
<211> LENGTH: 10
```

```
<212> TYPE: DNA
<213> ORGANISM: Artificial Sequence
<220> FEATURE:
<223> OTHER INFORMATION: Synthetic

<400> SEQUENCE: 24
gggggggggg                                                          10

<210> SEQ ID NO 25
<211> LENGTH: 10
<212> TYPE: DNA
<213> ORGANISM: Artificial Sequence
<220> FEATURE:
<223> OTHER INFORMATION: Synthetic

<400> SEQUENCE: 25
tccccccccc                                                          10

<210> SEQ ID NO 26
<211> LENGTH: 10
<212> TYPE: DNA
<213> ORGANISM: Artificial Sequence
<220> FEATURE:
<223> OTHER INFORMATION: Synthetic

<400> SEQUENCE: 26
ttttttttc                                                           10

<210> SEQ ID NO 27
<211> LENGTH: 11
<212> TYPE: DNA
<213> ORGANISM: Artificial Sequence
<220> FEATURE:
<223> OTHER INFORMATION: Synthetic

<400> SEQUENCE: 27
cccccccccc g                                                        11

<210> SEQ ID NO 28
<211> LENGTH: 11
<212> TYPE: DNA
<213> ORGANISM: Artificial Sequence
<220> FEATURE:
<223> OTHER INFORMATION: Synthetic

<400> SEQUENCE: 28 ccccccccccg g                                                       11

<210> SEQ ID NO 29
<211> LENGTH: 11
<212> TYPE: DNA
<213> ORGANISM: Artificial Sequence
<220> FEATURE:
<223> OTHER INFORMATION: Synthetic

<400> SEQUENCE: 29 ccggggggggg g                                                       11

<210> SEQ ID NO 30
<211> LENGTH: 11
<212> TYPE: DNA
<213> ORGANISM: Artificial Sequence
<220> FEATURE:
<223> OTHER INFORMATION: Synthetic

<400> SEQUENCE: 30
```
cggggggggg g                                          11

<210> SEQ ID NO 31
<211> LENGTH: 11
<212> TYPE: DNA
<213> ORGANISM: Artificial Sequence
<220> FEATURE:
<223> OTHER INFORMATION: Synthetic

<400> SEQUENCE: 31
tccccccccc c                                          11

<210> SEQ ID NO 32
<211> LENGTH: 11
<212> TYPE: DNA
<213> ORGANISM: Artificial Sequence
<220> FEATURE:
<223> OTHER INFORMATION: Synthetic

<400> SEQUENCE: 32 ttccccccccc c                                         11

<210> SEQ ID NO 33
<211> LENGTH: 11
<212> TYPE: DNA
<213> ORGANISM: Artificial Sequence
<220> FEATURE:
<223> OTHER INFORMATION: Synthetic

<400> SEQUENCE: 33
tttttttttc c                                          11

<210> SEQ ID NO 34
<211> LENGTH: 11
<212> TYPE: DNA
<213> ORGANISM: Artificial Sequence
<220> FEATURE:
<223> OTHER INFORMATION: Synthetic

<400> SEQUENCE: 34
tttttttttt c                                          11

<210> SEQ ID NO 35
<211> LENGTH: 12
<212> TYPE: DNA
<213> ORGANISM: Artificial Sequence
<220> FEATURE:
<223> OTHER INFORMATION: Synthetic

<400> SEQUENCE: 35 atttttttttt tc                                        12

<210> SEQ ID NO 36
<211> LENGTH: 12
<212> TYPE: DNA
<213> ORGANISM: Artificial Sequence
<220> FEATURE:
<223> OTHER INFORMATION: Synthetic

<400> SEQUENCE: 36
cccccccccc gg                                         12

<210> SEQ ID NO 37
<211> LENGTH: 12
<212> TYPE: DNA
<213> ORGANISM: Artificial Sequence

```
<220> FEATURE:
<223> OTHER INFORMATION: Synthetic

<400> SEQUENCE: 37 ccccccccg gg                                                                12

<210> SEQ ID NO 38
<211> LENGTH: 12
<212> TYPE: DNA
<213> ORGANISM: Artificial Sequence
<220> FEATURE:
<223> OTHER INFORMATION: Synthetic

<400> SEQUENCE: 38
cccggggggg gg                                                               12

<210> SEQ ID NO 39
<211> LENGTH: 12
<212> TYPE: DNA
<213> ORGANISM: Artificial Sequence
<220> FEATURE:
<223> OTHER INFORMATION: Synthetic

<400> SEQUENCE: 39
ccgggggggg gg                                                               12

<210> SEQ ID NO 40
<211> LENGTH: 12
<212> TYPE: DNA
<213> ORGANISM: Artificial Sequence
<220> FEATURE:
<223> OTHER INFORMATION: Synthetic

<400> SEQUENCE: 40
tccccccccc cg                                                               12

<210> SEQ ID NO 41
<211> LENGTH: 12
<212> TYPE: DNA
<213> ORGANISM: Artificial Sequence
<220> FEATURE:
<223> OTHER INFORMATION: Synthetic

<400> SEQUENCE: 41 ttccccccccc cc                                                              12

<210> SEQ ID NO 42
<211> LENGTH: 12
<212> TYPE: DNA
<213> ORGANISM: Artificial Sequence
<220> FEATURE:
<223> OTHER INFORMATION: Synthetic

<400> SEQUENCE: 42
tttccccccc cc                                                               12

<210> SEQ ID NO 43
<211> LENGTH: 12
<212> TYPE: DNA
<213> ORGANISM: Artificial Sequence
<220> FEATURE:
<223> OTHER INFORMATION: Synthetic

<400> SEQUENCE: 43
tttttttttc cc                                                               12
```

```
<210> SEQ ID NO 44
<211> LENGTH: 12
<212> TYPE: DNA
<213> ORGANISM: Artificial Sequence
<220> FEATURE:
<223> OTHER INFORMATION: Synthetic

<400> SEQUENCE: 44
tttttttttt cc                                                              12

<210> SEQ ID NO 45
<211> LENGTH: 8
<212> TYPE: DNA
<213> ORGANISM: Artificial Sequence
<220> FEATURE:
<223> OTHER INFORMATION: Synthetic

<400> SEQUENCE: 45 cccccccc                                                                    8

<210> SEQ ID NO 46
<211> LENGTH: 8
<212> TYPE: DNA
<213> ORGANISM: Artificial Sequence
<220> FEATURE:
<223> OTHER INFORMATION: Synthetic

<400> SEQUENCE: 46 gggggggg                                                                    8

<210> SEQ ID NO 47
<211> LENGTH: 7
<212> TYPE: DNA
<213> ORGANISM: Artificial Sequence
<220> FEATURE:
<223> OTHER INFORMATION: Synthetic

<400> SEQUENCE: 47 ggggggg                                                                     7

<210> SEQ ID NO 48
<211> LENGTH: 6
<212> TYPE: DNA
<213> ORGANISM: Artificial Sequence
<220> FEATURE:
<223> OTHER INFORMATION: Synthetic

<400> SEQUENCE: 48 cccccc                                                                      6

<210> SEQ ID NO 49
<211> LENGTH: 6
<212> TYPE: DNA
<213> ORGANISM: Artificial Sequence
<220> FEATURE:
<223> OTHER INFORMATION: Synthetic

<400> SEQUENCE: 49 gggggg                                                                      6

<210> SEQ ID NO 50
<211> LENGTH: 6
<212> TYPE: DNA
<213> ORGANISM: Artificial Sequence
<220> FEATURE:
<223> OTHER INFORMATION: Synthetic
```

```
<400> SEQUENCE: 50 cccccg                                                                6

<210> SEQ ID NO 51
<211> LENGTH: 6
<212> TYPE: DNA
<213> ORGANISM: Artificial Sequence
<220> FEATURE:
<223> OTHER INFORMATION: Synthetic

<400> SEQUENCE: 51 ccccgg                                                                6

<210> SEQ ID NO 52
<211> LENGTH: 6
<212> TYPE: DNA
<213> ORGANISM: Artificial Sequence
<220> FEATURE:
<223> OTHER INFORMATION: Synthetic

<400> SEQUENCE: 52 cccggg                                                                6

<210> SEQ ID NO 53
<211> LENGTH: 6
<212> TYPE: DNA
<213> ORGANISM: Artificial Sequence
<220> FEATURE:
<223> OTHER INFORMATION: Synthetic

<400> SEQUENCE: 53 ccgggg                                                                6

<210> SEQ ID NO 54
<211> LENGTH: 6
<212> TYPE: DNA
<213> ORGANISM: Artificial Sequence
<220> FEATURE:
<223> OTHER INFORMATION: Synthetic

<400> SEQUENCE: 54 cggggg                                                                6

<210> SEQ ID NO 55
<211> LENGTH: 6
<212> TYPE: DNA
<213> ORGANISM: Artificial Sequence
<220> FEATURE:
<223> OTHER INFORMATION: Synthetic

<400> SEQUENCE: 55 tccccc                                                                6

<210> SEQ ID NO 56
<211> LENGTH: 6
<212> TYPE: DNA
<213> ORGANISM: Artificial Sequence
<220> FEATURE:
<223> OTHER INFORMATION: Synthetic

<400> SEQUENCE: 56 ttcccc                                                                6

<210> SEQ ID NO 57
```

```
<211> LENGTH: 6
<212> TYPE: DNA
<213> ORGANISM: Artificial Sequence
<220> FEATURE:
<223> OTHER INFORMATION: Synthetic

<400> SEQUENCE: 57 tttccc                                                                     6

<210> SEQ ID NO 58
<211> LENGTH: 6
<212> TYPE: DNA
<213> ORGANISM: Artificial Sequence
<220> FEATURE:
<223> OTHER INFORMATION: Synthetic

<400> SEQUENCE: 58 ttttcc                                                                     6

<210> SEQ ID NO 59
<211> LENGTH: 6
<212> TYPE: DNA
<213> ORGANISM: Artificial Sequence
<220> FEATURE:
<223> OTHER INFORMATION: Synthetic

<400> SEQUENCE: 59 tttttc                                                                     6

<210> SEQ ID NO 60
<211> LENGTH: 7
<212> TYPE: DNA
<213> ORGANISM: Artificial Sequence
<220> FEATURE:
<223> OTHER INFORMATION: Synthetic

<400> SEQUENCE: 60 cccccccg                                                                   7

<210> SEQ ID NO 61
<211> LENGTH: 7
<212> TYPE: DNA
<213> ORGANISM: Artificial Sequence
<220> FEATURE:
<223> OTHER INFORMATION: Synthetic

<400> SEQUENCE: 61 cccccgg                                                                    7

<210> SEQ ID NO 62
<211> LENGTH: 7
<212> TYPE: DNA
<213> ORGANISM: Artificial Sequence
<220> FEATURE:
<223> OTHER INFORMATION: Synthetic

<400> SEQUENCE: 62 ccccggg                                                                    7

<210> SEQ ID NO 63
<211> LENGTH: 7
<212> TYPE: DNA
<213> ORGANISM: Artificial Sequence
<220> FEATURE:
<223> OTHER INFORMATION: Synthetic

<400> SEQUENCE: 63
``` cccgggg                                                                        7

<210> SEQ ID NO 64
<211> LENGTH: 7
<212> TYPE: DNA
<213> ORGANISM: Artificial Sequence
<220> FEATURE:
<223> OTHER INFORMATION: Synthetic

<400> SEQUENCE: 64 ccggggg                                                                        7

<210> SEQ ID NO 65
<211> LENGTH: 7
<212> TYPE: DNA
<213> ORGANISM: Artificial Sequence
<220> FEATURE:
<223> OTHER INFORMATION: Synthetic

<400> SEQUENCE: 65 cgggggg                                                                        7

<210> SEQ ID NO 66
<211> LENGTH: 7
<212> TYPE: DNA
<213> ORGANISM: Artificial Sequence
<220> FEATURE:
<223> OTHER INFORMATION: Synthetic

<400> SEQUENCE: 66 tcccccc                                                                        7

<210> SEQ ID NO 67
<211> LENGTH: 7
<212> TYPE: DNA
<213> ORGANISM: Artificial Sequence
<220> FEATURE:
<223> OTHER INFORMATION: Synthetic

<400> SEQUENCE: 67 ttccccc                                                                        7

<210> SEQ ID NO 68
<211> LENGTH: 7
<212> TYPE: DNA
<213> ORGANISM: Artificial Sequence
<220> FEATURE:
<223> OTHER INFORMATION: Synthetic

<400> SEQUENCE: 68 tttcccc                                                                        7

<210> SEQ ID NO 69
<211> LENGTH: 7
<212> TYPE: DNA
<213> ORGANISM: Artificial Sequence
<220> FEATURE:
<223> OTHER INFORMATION: Synthetic

<400> SEQUENCE: 69 ttttccc                                                                        7

<210> SEQ ID NO 70
<211> LENGTH: 7
<212> TYPE: DNA

```
<213> ORGANISM: Artificial Sequence
<220> FEATURE:
<223> OTHER INFORMATION: Synthetic

<400> SEQUENCE: 70 tttttcc                                                              7

<210> SEQ ID NO 71
<211> LENGTH: 7
<212> TYPE: DNA
<213> ORGANISM: Artificial Sequence
<220> FEATURE:
<223> OTHER INFORMATION: Synthetic

<400> SEQUENCE: 71 tttttc                                                               7

<210> SEQ ID NO 72
<211> LENGTH: 8
<212> TYPE: DNA
<213> ORGANISM: Artificial Sequence
<220> FEATURE:
<223> OTHER INFORMATION: Synthetic

<400> SEQUENCE: 72 ccccccg                                                              8

<210> SEQ ID NO 73
<211> LENGTH: 8
<212> TYPE: DNA
<213> ORGANISM: Artificial Sequence
<220> FEATURE:
<223> OTHER INFORMATION: Synthetic

<400> SEQUENCE: 73 ccccccgg                                                             8

<210> SEQ ID NO 74
<211> LENGTH: 8
<212> TYPE: DNA
<213> ORGANISM: Artificial Sequence
<220> FEATURE:
<223> OTHER INFORMATION: Synthetic

<400> SEQUENCE: 74 cccccggg                                                             8

<210> SEQ ID NO 75
<211> LENGTH: 8
<212> TYPE: DNA
<213> ORGANISM: Artificial Sequence
<220> FEATURE:
<223> OTHER INFORMATION: Synthetic

<400> SEQUENCE: 75 ccccgggg                                                             8

<210> SEQ ID NO 76
<211> LENGTH: 8
<212> TYPE: DNA
<213> ORGANISM: Artificial Sequence
<220> FEATURE:
<223> OTHER INFORMATION: Synthetic

<400> SEQUENCE: 76 cccggggg                                                             8
```

<210> SEQ ID NO 77
<211> LENGTH: 8
<212> TYPE: DNA
<213> ORGANISM: Artificial Sequence
<220> FEATURE:
<223> OTHER INFORMATION: Synthetic

<400> SEQUENCE: 77 ccgggggg                                                                8

<210> SEQ ID NO 78
<211> LENGTH: 8
<212> TYPE: DNA
<213> ORGANISM: Artificial Sequence
<220> FEATURE:
<223> OTHER INFORMATION: Synthetic

<400> SEQUENCE: 78 cggggggg                                                                8

<210> SEQ ID NO 79
<211> LENGTH: 8
<212> TYPE: DNA
<213> ORGANISM: Artificial Sequence
<220> FEATURE:
<223> OTHER INFORMATION: Synthetic

<400> SEQUENCE: 79 tccccccc                                                                8

<210> SEQ ID NO 80
<211> LENGTH: 8
<212> TYPE: DNA
<213> ORGANISM: Artificial Sequence
<220> FEATURE:
<223> OTHER INFORMATION: Synthetic

<400> SEQUENCE: 80 ttcccccc                                                                8

<210> SEQ ID NO 81
<211> LENGTH: 8
<212> TYPE: DNA
<213> ORGANISM: Artificial Sequence
<220> FEATURE:
<223> OTHER INFORMATION: Synthetic

<400> SEQUENCE: 81 tttccccc                                                                8

<210> SEQ ID NO 82
<211> LENGTH: 8
<212> TYPE: DNA
<213> ORGANISM: Artificial Sequence
<220> FEATURE:
<223> OTHER INFORMATION: Synthetic

<400> SEQUENCE: 82 ttttcccc                                                                8

<210> SEQ ID NO 83
<211> LENGTH: 8
<212> TYPE: DNA
<213> ORGANISM: Artificial Sequence
<220> FEATURE:

```
<223> OTHER INFORMATION: Synthetic

<400> SEQUENCE: 83 tttttccc                                                                  8

<210> SEQ ID NO 84
<211> LENGTH: 8
<212> TYPE: DNA
<213> ORGANISM: Artificial Sequence
<220> FEATURE:
<223> OTHER INFORMATION: Synthetic

<400> SEQUENCE: 84 ttttttcc                                                                  8

<210> SEQ ID NO 85
<211> LENGTH: 8
<212> TYPE: DNA
<213> ORGANISM: Artificial Sequence
<220> FEATURE:
<223> OTHER INFORMATION: Synthetic

<400> SEQUENCE: 85 tttttttc                                                                  8

<210> SEQ ID NO 86
<211> LENGTH: 9
<212> TYPE: DNA
<213> ORGANISM: Artificial Sequence
<220> FEATURE:
<223> OTHER INFORMATION: Synthetic

<400> SEQUENCE: 86 aaaaaaaaa                                                                 9

<210> SEQ ID NO 87
<211> LENGTH: 9
<212> TYPE: DNA
<213> ORGANISM: Artificial Sequence
<220> FEATURE:
<223> OTHER INFORMATION: Synthetic

<400> SEQUENCE: 87 ccccccccg                                                                 9

<210> SEQ ID NO 88
<211> LENGTH: 9
<212> TYPE: DNA
<213> ORGANISM: Artificial Sequence
<220> FEATURE:
<223> OTHER INFORMATION: Synthetic

<400> SEQUENCE: 88 cccccccgg                                                                 9

<210> SEQ ID NO 89
<211> LENGTH: 9
<212> TYPE: DNA
<213> ORGANISM: Artificial Sequence
<220> FEATURE:
<223> OTHER INFORMATION: Synthetic

<400> SEQUENCE: 89 ccccccggg                                                                 9
```

```
<210> SEQ ID NO 90
<211> LENGTH: 9
<212> TYPE: DNA
<213> ORGANISM: Artificial Sequence
<220> FEATURE:
<223> OTHER INFORMATION: Synthetic

<400> SEQUENCE: 90 cccccgggg                                                                 9

<210> SEQ ID NO 91
<211> LENGTH: 9
<212> TYPE: DNA
<213> ORGANISM: Artificial Sequence
<220> FEATURE:
<223> OTHER INFORMATION: Synthetic

<400> SEQUENCE: 91 ccccggggg                                                                 9

<210> SEQ ID NO 92
<211> LENGTH: 9
<212> TYPE: DNA
<213> ORGANISM: Artificial Sequence
<220> FEATURE:
<223> OTHER INFORMATION: Synthetic

<400> SEQUENCE: 92 cccgggggg                                                                 9

<210> SEQ ID NO 93
<211> LENGTH: 9
<212> TYPE: DNA
<213> ORGANISM: Artificial Sequence
<220> FEATURE:
<223> OTHER INFORMATION: Synthetic

<400> SEQUENCE: 93 ccggggggg                                                                 9

<210> SEQ ID NO 94
<211> LENGTH: 9
<212> TYPE: DNA
<213> ORGANISM: Artificial Sequence
<220> FEATURE:
<223> OTHER INFORMATION: Synthetic

<400> SEQUENCE: 94 cgggggggg                                                                 9

<210> SEQ ID NO 95
<211> LENGTH: 9
<212> TYPE: DNA
<213> ORGANISM: Artificial Sequence
<220> FEATURE:
<223> OTHER INFORMATION: Synthetic

<400> SEQUENCE: 95 tcccccccc                                                                 9

<210> SEQ ID NO 96
<211> LENGTH: 9
<212> TYPE: DNA
<213> ORGANISM: Artificial Sequence
<220> FEATURE:
<223> OTHER INFORMATION: Synthetic
```

```
<400> SEQUENCE: 96 ttccccccc                                                            9

<210> SEQ ID NO 97
<211> LENGTH: 9
<212> TYPE: DNA
<213> ORGANISM: Artificial Sequence
<220> FEATURE:
<223> OTHER INFORMATION: Synthetic

<400> SEQUENCE: 97 tttcccccc                                                            9

<210> SEQ ID NO 98
<211> LENGTH: 9
<212> TYPE: DNA
<213> ORGANISM: Artificial Sequence
<220> FEATURE:
<223> OTHER INFORMATION: Synthetic

<400> SEQUENCE: 98 ttttccccc                                                            9

<210> SEQ ID NO 99
<211> LENGTH: 9
<212> TYPE: DNA
<213> ORGANISM: Artificial Sequence
<220> FEATURE:
<223> OTHER INFORMATION: Synthetic

<400> SEQUENCE: 99 tttttcccc                                                            9

<210> SEQ ID NO 100
<211> LENGTH: 9
<212> TYPE: DNA
<213> ORGANISM: Artificial Sequence
<220> FEATURE:
<223> OTHER INFORMATION: Synthetic

<400> SEQUENCE: 100 ttttttccc                                                            9

<210> SEQ ID NO 101
<211> LENGTH: 9
<212> TYPE: DNA
<213> ORGANISM: Artificial Sequence
<220> FEATURE:
<223> OTHER INFORMATION: Synthetic

<400> SEQUENCE: 101 tttttttcc                                                            9

<210> SEQ ID NO 102
<211> LENGTH: 9
<212> TYPE: DNA
<213> ORGANISM: Artificial Sequence
<220> FEATURE:
<223> OTHER INFORMATION: Synthetic

<400> SEQUENCE: 102 ttttttttc                                                            9

<210> SEQ ID NO 103
<211> LENGTH: 9
```

```
<212> TYPE: DNA
<213> ORGANISM: Artificial Sequence
<220> FEATURE:
<223> OTHER INFORMATION: Synthetic

<400> SEQUENCE: 103 ttttttttt                                                              9

<210> SEQ ID NO 104
<211> LENGTH: 10
<212> TYPE: DNA
<213> ORGANISM: Artificial Sequence
<220> FEATURE:
<223> OTHER INFORMATION: Synthetic

<400> SEQUENCE: 104
aaaaaaaaaa                                                            10

<210> SEQ ID NO 105
<211> LENGTH: 10
<212> TYPE: DNA
<213> ORGANISM: Artificial Sequence
<220> FEATURE:
<223> OTHER INFORMATION: Synthetic

<400> SEQUENCE: 105
aaaaaaaaat                                                            10

<210> SEQ ID NO 106
<211> LENGTH: 10
<212> TYPE: DNA
<213> ORGANISM: Artificial Sequence
<220> FEATURE:
<223> OTHER INFORMATION: Synthetic

<400> SEQUENCE: 106
attttttttt                                                            10

<210> SEQ ID NO 107
<211> LENGTH: 10
<212> TYPE: DNA
<213> ORGANISM: Artificial Sequence
<220> FEATURE:
<223> OTHER INFORMATION: Synthetic

<400> SEQUENCE: 107
ccccccccgg                                                            10

<210> SEQ ID NO 108
<211> LENGTH: 10
<212> TYPE: DNA
<213> ORGANISM: Artificial Sequence
<220> FEATURE:
<223> OTHER INFORMATION: Synthetic

<400> SEQUENCE: 108
cccccccggg                                                            10

<210> SEQ ID NO 109
<211> LENGTH: 10
<212> TYPE: DNA
<213> ORGANISM: Artificial Sequence
<220> FEATURE:
<223> OTHER INFORMATION: Synthetic

<400> SEQUENCE: 109
```
ccccccgggg                                                              10

<210> SEQ ID NO 110
<211> LENGTH: 10
<212> TYPE: DNA
<213> ORGANISM: Artificial Sequence
<220> FEATURE:
<223> OTHER INFORMATION: Synthetic

<400> SEQUENCE: 110
cccccggggg                                                              10

<210> SEQ ID NO 111
<211> LENGTH: 10
<212> TYPE: DNA
<213> ORGANISM: Artificial Sequence
<220> FEATURE:
<223> OTHER INFORMATION: Synthetic

<400> SEQUENCE: 111
ccccgggggg                                                              10

<210> SEQ ID NO 112
<211> LENGTH: 10
<212> TYPE: DNA
<213> ORGANISM: Artificial Sequence
<220> FEATURE:
<223> OTHER INFORMATION: Synthetic

<400> SEQUENCE: 112
cccggggggg                                                              10

<210> SEQ ID NO 113
<211> LENGTH: 10
<212> TYPE: DNA
<213> ORGANISM: Artificial Sequence
<220> FEATURE:
<223> OTHER INFORMATION: Synthetic

<400> SEQUENCE: 113
ccgggggggg                                                              10

<210> SEQ ID NO 114
<211> LENGTH: 10
<212> TYPE: DNA
<213> ORGANISM: Artificial Sequence
<220> FEATURE:
<223> OTHER INFORMATION: Synthetic

<400> SEQUENCE: 114
ttcccccccc                                                              10

<210> SEQ ID NO 115
<211> LENGTH: 10
<212> TYPE: DNA
<213> ORGANISM: Artificial Sequence
<220> FEATURE:
<223> OTHER INFORMATION: Synthetic

<400> SEQUENCE: 115
tttccccccc                                                              10

<210> SEQ ID NO 116
<211> LENGTH: 10
<212> TYPE: DNA
<213> ORGANISM: Artificial Sequence

```
-continued

<220> FEATURE:
<223> OTHER INFORMATION: Synthetic

<400> SEQUENCE: 116
ttttcccccc                                                              10

<210> SEQ ID NO 117
<211> LENGTH: 10
<212> TYPE: DNA
<213> ORGANISM: Artificial Sequence
<220> FEATURE:
<223> OTHER INFORMATION: Synthetic

<400> SEQUENCE: 117
tttttccccc                                                              10

<210> SEQ ID NO 118
<211> LENGTH: 10
<212> TYPE: DNA
<213> ORGANISM: Artificial Sequence
<220> FEATURE:
<223> OTHER INFORMATION: Synthetic

<400> SEQUENCE: 118
ttttttcccc                                                              10

<210> SEQ ID NO 119
<211> LENGTH: 10
<212> TYPE: DNA
<213> ORGANISM: Artificial Sequence
<220> FEATURE:
<223> OTHER INFORMATION: Synthetic

<400> SEQUENCE: 119
tttttttccc                                                              10

<210> SEQ ID NO 120
<211> LENGTH: 10
<212> TYPE: DNA
<213> ORGANISM: Artificial Sequence
<220> FEATURE:
<223> OTHER INFORMATION: Synthetic

<400> SEQUENCE: 120
ttttttttcc                                                              10

<210> SEQ ID NO 121
<211> LENGTH: 10
<212> TYPE: DNA
<213> ORGANISM: Artificial Sequence
<220> FEATURE:
<223> OTHER INFORMATION: Synthetic

<400> SEQUENCE: 121
tttttttttt                                                              10

<210> SEQ ID NO 122
<211> LENGTH: 11
<212> TYPE: DNA
<213> ORGANISM: Artificial Sequence
<220> FEATURE:
<223> OTHER INFORMATION: Synthetic

<400> SEQUENCE: 122
aaaaaaaaaa t                                                            11
```

<210> SEQ ID NO 123
<211> LENGTH: 11
<212> TYPE: DNA
<213> ORGANISM: Artificial Sequence
<220> FEATURE:
<223> OTHER INFORMATION: Synthetic

<400> SEQUENCE: 123
aaaaaaaaat t                                                              11

<210> SEQ ID NO 124
<211> LENGTH: 11
<212> TYPE: DNA
<213> ORGANISM: Artificial Sequence
<220> FEATURE:
<223> OTHER INFORMATION: Synthetic

<400> SEQUENCE: 124
aatttttttt t                                                              11

<210> SEQ ID NO 125
<211> LENGTH: 11
<212> TYPE: DNA
<213> ORGANISM: Artificial Sequence
<220> FEATURE:
<223> OTHER INFORMATION: Synthetic

<400> SEQUENCE: 125 atttttttttt t                                                             11

<210> SEQ ID NO 126
<211> LENGTH: 11
<212> TYPE: DNA
<213> ORGANISM: Artificial Sequence
<220> FEATURE:
<223> OTHER INFORMATION: Synthetic

<400> SEQUENCE: 126
ccccccccgg g                                                              11

<210> SEQ ID NO 127
<211> LENGTH: 11
<212> TYPE: DNA
<213> ORGANISM: Artificial Sequence
<220> FEATURE:
<223> OTHER INFORMATION: Synthetic

<400> SEQUENCE: 127 ccccccoggg g                                                              11

<210> SEQ ID NO 128
<211> LENGTH: 11
<212> TYPE: DNA
<213> ORGANISM: Artificial Sequence
<220> FEATURE:
<223> OTHER INFORMATION: Synthetic

<400> SEQUENCE: 128 cccccogggg g                                                              11

<210> SEQ ID NO 129
<211> LENGTH: 11
<212> TYPE: DNA
<213> ORGANISM: Artificial Sequence
<220> FEATURE:
<223> OTHER INFORMATION: Synthetic

```
<400> SEQUENCE: 129 ccccegggggg g                                                              11

<210> SEQ ID NO 130
<211> LENGTH: 11
<212> TYPE: DNA
<213> ORGANISM: Artificial Sequence
<220> FEATURE:
<223> OTHER INFORMATION: Synthetic

<400> SEQUENCE: 130 ccccggggggg g                                                              11

<210> SEQ ID NO 131
<211> LENGTH: 11
<212> TYPE: DNA
<213> ORGANISM: Artificial Sequence
<220> FEATURE:
<223> OTHER INFORMATION: Synthetic

<400> SEQUENCE: 131
cccggggggg g                                                               11

<210> SEQ ID NO 132
<211> LENGTH: 11
<212> TYPE: DNA
<213> ORGANISM: Artificial Sequence
<220> FEATURE:
<223> OTHER INFORMATION: Synthetic

<400> SEQUENCE: 132
tttccccccc c                                                               11

<210> SEQ ID NO 133
<211> LENGTH: 11
<212> TYPE: DNA
<213> ORGANISM: Artificial Sequence
<220> FEATURE:
<223> OTHER INFORMATION: Synthetic

<400> SEQUENCE: 133
ttttcccccc c                                                               11

<210> SEQ ID NO 134
<211> LENGTH: 11
<212> TYPE: DNA
<213> ORGANISM: Artificial Sequence
<220> FEATURE:
<223> OTHER INFORMATION: Synthetic

<400> SEQUENCE: 134
tttttccccc c                                                               11

<210> SEQ ID NO 135
<211> LENGTH: 11
<212> TYPE: DNA
<213> ORGANISM: Artificial Sequence
<220> FEATURE:
<223> OTHER INFORMATION: Synthetic

<400> SEQUENCE: 135
ttttttcccc c                                                               11

<210> SEQ ID NO 136
```

```
<211> LENGTH: 11
<212> TYPE: DNA
<213> ORGANISM: Artificial Sequence
<220> FEATURE:
<223> OTHER INFORMATION: Synthetic

<400> SEQUENCE: 136
tttttttccc c                                                          11

<210> SEQ ID NO 137
<211> LENGTH: 11
<212> TYPE: DNA
<213> ORGANISM: Artificial Sequence
<220> FEATURE:
<223> OTHER INFORMATION: Synthetic

<400> SEQUENCE: 137
ttttttttcc c                                                          11

<210> SEQ ID NO 138
<211> LENGTH: 12
<212> TYPE: DNA
<213> ORGANISM: Artificial Sequence
<220> FEATURE:
<223> OTHER INFORMATION: Synthetic

<400> SEQUENCE: 138
aaaaaaaaaa tt                                                         12

<210> SEQ ID NO 139
<211> LENGTH: 12
<212> TYPE: DNA
<213> ORGANISM: Artificial Sequence
<220> FEATURE:
<223> OTHER INFORMATION: Synthetic

<400> SEQUENCE: 139
aaaaaaaaat tt                                                         12

<210> SEQ ID NO 140
<211> LENGTH: 12
<212> TYPE: DNA
<213> ORGANISM: Artificial Sequence
<220> FEATURE:
<223> OTHER INFORMATION: Synthetic

<400> SEQUENCE: 140 aaatttttt tt                                                          12

<210> SEQ ID NO 141
<211> LENGTH: 12
<212> TYPE: DNA
<213> ORGANISM: Artificial Sequence
<220> FEATURE:
<223> OTHER INFORMATION: Synthetic

<400> SEQUENCE: 141 aattttttt tt                                                          12

<210> SEQ ID NO 142
<211> LENGTH: 12
<212> TYPE: DNA
<213> ORGANISM: Artificial Sequence
<220> FEATURE:
<223> OTHER INFORMATION: Synthetic

<400> SEQUENCE: 142
``` cccccccgg gg                                                                        12

<210> SEQ ID NO 143
<211> LENGTH: 12
<212> TYPE: DNA
<213> ORGANISM: Artificial Sequence
<220> FEATURE:
<223> OTHER INFORMATION: Synthetic

<400> SEQUENCE: 143
ccccccgggg gg                                                                       12

<210> SEQ ID NO 144
<211> LENGTH: 12
<212> TYPE: DNA
<213> ORGANISM: Artificial Sequence
<220> FEATURE:
<223> OTHER INFORMATION: Synthetic

<400> SEQUENCE: 144
cccccggggg gg                                                                       12

<210> SEQ ID NO 145
<211> LENGTH: 12
<212> TYPE: DNA
<213> ORGANISM: Artificial Sequence
<220> FEATURE:
<223> OTHER INFORMATION: Synthetic

<400> SEQUENCE: 145
ccccgggggg gg                                                                       12

<210> SEQ ID NO 146
<211> LENGTH: 12
<212> TYPE: DNA
<213> ORGANISM: Artificial Sequence
<220> FEATURE:
<223> OTHER INFORMATION: Synthetic

<400> SEQUENCE: 146
cccggggggg gg                                                                       12

<210> SEQ ID NO 147
<211> LENGTH: 12
<212> TYPE: DNA
<213> ORGANISM: Artificial Sequence
<220> FEATURE:
<223> OTHER INFORMATION: Synthetic

<400> SEQUENCE: 147 ttttccccc cc                                                                        12

<210> SEQ ID NO 148
<211> LENGTH: 12
<212> TYPE: DNA
<213> ORGANISM: Artificial Sequence
<220> FEATURE:
<223> OTHER INFORMATION: Synthetic

<400> SEQUENCE: 148 tttttcccc cc                                                                        12

<210> SEQ ID NO 149
<211> LENGTH: 12
<212> TYPE: DNA

```
<213> ORGANISM: Artificial Sequence
<220> FEATURE:
<223> OTHER INFORMATION: Synthetic

<400> SEQUENCE: 149
tttttccccc cc                                                           12

<210> SEQ ID NO 150
<211> LENGTH: 12
<212> TYPE: DNA
<213> ORGANISM: Artificial Sequence
<220> FEATURE:
<223> OTHER INFORMATION: Synthetic

<400> SEQUENCE: 150 ttttttccc cc                                                            12

<210> SEQ ID NO 151
<211> LENGTH: 12
<212> TYPE: DNA
<213> ORGANISM: Artificial Sequence
<220> FEATURE:
<223> OTHER INFORMATION: Synthetic

<400> SEQUENCE: 151 tttttttcc cc                                                            12

<210> SEQ ID NO 152
<211> LENGTH: 0
<212> TYPE: DNA
<213> ORGANISM: Artificial Sequence
<220> FEATURE:
<223> OTHER INFORMATION: Synthetic

<400> SEQUENCE: 152

000

<210> SEQ ID NO 153
<211> LENGTH: 8
<212> TYPE: DNA
<213> ORGANISM: Artificial Sequence
<220> FEATURE:
<223> OTHER INFORMATION: Synthetic

<400> SEQUENCE: 153 tttttttt                                                                8

<210> SEQ ID NO 154
<211> LENGTH: 7
<212> TYPE: DNA
<213> ORGANISM: Artificial Sequence
<220> FEATURE:
<223> OTHER INFORMATION: Synthetic

<400> SEQUENCE: 154 aaaaaaa                                                                 7

<210> SEQ ID NO 155
<211> LENGTH: 7
<212> TYPE: DNA
<213> ORGANISM: Artificial Sequence
<220> FEATURE:
<223> OTHER INFORMATION: Synthetic

<400> SEQUENCE: 155 ccccccc                                                                 7
```

<210> SEQ ID NO 156
<211> LENGTH: 7
<212> TYPE: DNA
<213> ORGANISM: Artificial Sequence
<220> FEATURE:
<223> OTHER INFORMATION: Synthetic

<400> SEQUENCE: 156 ttttttt                                                                 7

<210> SEQ ID NO 157
<211> LENGTH: 6
<212> TYPE: DNA
<213> ORGANISM: Artificial Sequence
<220> FEATURE:
<223> OTHER INFORMATION: Synthetic

<400> SEQUENCE: 157 aaaaaa                                                                  6

<210> SEQ ID NO 158
<211> LENGTH: 6
<212> TYPE: DNA
<213> ORGANISM: Artificial Sequence
<220> FEATURE:
<223> OTHER INFORMATION: Synthetic

<400> SEQUENCE: 158 tttttt                                                                  6

<210> SEQ ID NO 159
<211> LENGTH: 6
<212> TYPE: DNA
<213> ORGANISM: Artificial Sequence
<220> FEATURE:
<223> OTHER INFORMATION: Synthetic

<400> SEQUENCE: 159 aaaaat                                                                  6

<210> SEQ ID NO 160
<211> LENGTH: 6
<212> TYPE: DNA
<213> ORGANISM: Artificial Sequence
<220> FEATURE:
<223> OTHER INFORMATION: Synthetic

<400> SEQUENCE: 160 aaaatt                                                                  6

<210> SEQ ID NO 161
<211> LENGTH: 6
<212> TYPE: DNA
<213> ORGANISM: Artificial Sequence
<220> FEATURE:
<223> OTHER INFORMATION: Synthetic

<400> SEQUENCE: 161 aaattt                                                                  6

<210> SEQ ID NO 162
<211> LENGTH: 6
<212> TYPE: DNA
<213> ORGANISM: Artificial Sequence
<220> FEATURE:

<223> OTHER INFORMATION: Synthetic

<400> SEQUENCE: 162 aattt                                                                    6

<210> SEQ ID NO 163
<211> LENGTH: 6
<212> TYPE: DNA
<213> ORGANISM: Artificial Sequence
<220> FEATURE:
<223> OTHER INFORMATION: Synthetic

<400> SEQUENCE: 163 attttt                                                                   6

<210> SEQ ID NO 164
<211> LENGTH: 7
<212> TYPE: DNA
<213> ORGANISM: Artificial Sequence
<220> FEATURE:
<223> OTHER INFORMATION: Synthetic

<400> SEQUENCE: 164 aaaaaat                                                                  7

<210> SEQ ID NO 165
<211> LENGTH: 7
<212> TYPE: DNA
<213> ORGANISM: Artificial Sequence
<220> FEATURE:
<223> OTHER INFORMATION: Synthetic

<400> SEQUENCE: 165 aaaaatt                                                                  7

<210> SEQ ID NO 166
<211> LENGTH: 7
<212> TYPE: DNA
<213> ORGANISM: Artificial Sequence
<220> FEATURE:
<223> OTHER INFORMATION: Synthetic

<400> SEQUENCE: 166 aaaattt                                                                  7

<210> SEQ ID NO 167
<211> LENGTH: 7
<212> TYPE: DNA
<213> ORGANISM: Artificial Sequence
<220> FEATURE:
<223> OTHER INFORMATION: Synthetic

<400> SEQUENCE: 167 aaatttt                                                                  7

<210> SEQ ID NO 168
<211> LENGTH: 7
<212> TYPE: DNA
<213> ORGANISM: Artificial Sequence
<220> FEATURE:
<223> OTHER INFORMATION: Synthetic

<400> SEQUENCE: 168 aattttt                                                                  7

```
<210> SEQ ID NO 169
<211> LENGTH: 7
<212> TYPE: DNA
<213> ORGANISM: Artificial Sequence
<220> FEATURE:
<223> OTHER INFORMATION: Synthetic

<400> SEQUENCE: 169 atttttt                                                                    7

<210> SEQ ID NO 170
<211> LENGTH: 8
<212> TYPE: DNA
<213> ORGANISM: Artificial Sequence
<220> FEATURE:
<223> OTHER INFORMATION: Synthetic

<400> SEQUENCE: 170 aaaaaaat                                                                   8

<210> SEQ ID NO 171
<211> LENGTH: 8
<212> TYPE: DNA
<213> ORGANISM: Artificial Sequence
<220> FEATURE:
<223> OTHER INFORMATION: Synthetic

<400> SEQUENCE: 171 aaaaaatt                                                                   8

<210> SEQ ID NO 172
<211> LENGTH: 8
<212> TYPE: DNA
<213> ORGANISM: Artificial Sequence
<220> FEATURE:
<223> OTHER INFORMATION: Synthetic

<400> SEQUENCE: 172 aaaaattt                                                                   8

<210> SEQ ID NO 173
<211> LENGTH: 8
<212> TYPE: DNA
<213> ORGANISM: Artificial Sequence
<220> FEATURE:
<223> OTHER INFORMATION: Synthetic

<400> SEQUENCE: 173 aaaatttt                                                                   8

<210> SEQ ID NO 174
<211> LENGTH: 8
<212> TYPE: DNA
<213> ORGANISM: Artificial Sequence
<220> FEATURE:
<223> OTHER INFORMATION: Synthetic

<400> SEQUENCE: 174 aaattttt                                                                   8

<210> SEQ ID NO 175
<211> LENGTH: 8
<212> TYPE: DNA
<213> ORGANISM: Artificial Sequence
<220> FEATURE:
<223> OTHER INFORMATION: Synthetic
```

```
<400> SEQUENCE: 175 aattttt                                                              8

<210> SEQ ID NO 176
<211> LENGTH: 8
<212> TYPE: DNA
<213> ORGANISM: Artificial Sequence
<220> FEATURE:
<223> OTHER INFORMATION: Synthetic

<400> SEQUENCE: 176 attttttt                                                             8

<210> SEQ ID NO 177
<211> LENGTH: 9
<212> TYPE: DNA
<213> ORGANISM: Artificial Sequence
<220> FEATURE:
<223> OTHER INFORMATION: Synthetic

<400> SEQUENCE: 177 aaaaaaaat                                                            9

<210> SEQ ID NO 178
<211> LENGTH: 9
<212> TYPE: DNA
<213> ORGANISM: Artificial Sequence
<220> FEATURE:
<223> OTHER INFORMATION: Synthetic

<400> SEQUENCE: 178 aaaaaaatt                                                            9

<210> SEQ ID NO 179
<211> LENGTH: 9
<212> TYPE: DNA
<213> ORGANISM: Artificial Sequence
<220> FEATURE:
<223> OTHER INFORMATION: Synthetic

<400> SEQUENCE: 179 aaaaaattt                                                            9

<210> SEQ ID NO 180
<211> LENGTH: 9
<212> TYPE: DNA
<213> ORGANISM: Artificial Sequence
<220> FEATURE:
<223> OTHER INFORMATION: Synthetic

<400> SEQUENCE: 180 aaaaatttt                                                            9

<210> SEQ ID NO 181
<211> LENGTH: 9
<212> TYPE: DNA
<213> ORGANISM: Artificial Sequence
<220> FEATURE:
<223> OTHER INFORMATION: Synthetic

<400> SEQUENCE: 181 aaaattttt                                                            9

<210> SEQ ID NO 182
<211> LENGTH: 9
```

```
<212> TYPE: DNA
<213> ORGANISM: Artificial Sequence
<220> FEATURE:
<223> OTHER INFORMATION: Synthetic

<400> SEQUENCE: 182 aaatttttt                                                                9

<210> SEQ ID NO 183
<211> LENGTH: 9
<212> TYPE: DNA
<213> ORGANISM: Artificial Sequence
<220> FEATURE:
<223> OTHER INFORMATION: Synthetic

<400> SEQUENCE: 183 aattttttt                                                                9

<210> SEQ ID NO 184
<211> LENGTH: 9
<212> TYPE: DNA
<213> ORGANISM: Artificial Sequence
<220> FEATURE:
<223> OTHER INFORMATION: Synthetic

<400> SEQUENCE: 184 attttttttt                                                               9

<210> SEQ ID NO 185
<211> LENGTH: 10
<212> TYPE: DNA
<213> ORGANISM: Artificial Sequence
<220> FEATURE:
<223> OTHER INFORMATION: Synthetic

<400> SEQUENCE: 185
aaaaaaaatt                                                              10

<210> SEQ ID NO 186
<211> LENGTH: 10
<212> TYPE: DNA
<213> ORGANISM: Artificial Sequence
<220> FEATURE:
<223> OTHER INFORMATION: Synthetic

<400> SEQUENCE: 186
aaaaaaattt                                                              10

<210> SEQ ID NO 187
<211> LENGTH: 10
<212> TYPE: DNA
<213> ORGANISM: Artificial Sequence
<220> FEATURE:
<223> OTHER INFORMATION: Synthetic

<400> SEQUENCE: 187
aaaaaatttt                                                              10

<210> SEQ ID NO 188
<211> LENGTH: 10
<212> TYPE: DNA
<213> ORGANISM: Artificial Sequence
<220> FEATURE:
<223> OTHER INFORMATION: Synthetic

<400> SEQUENCE: 188
```

-continued aaaaattttt                                                      10

<210> SEQ ID NO 189
<211> LENGTH: 10
<212> TYPE: DNA
<213> ORGANISM: Artificial Sequence
<220> FEATURE:
<223> OTHER INFORMATION: Synthetic

<400> SEQUENCE: 189
aaaattttt                                                       10

<210> SEQ ID NO 190
<211> LENGTH: 10
<212> TYPE: DNA
<213> ORGANISM: Artificial Sequence
<220> FEATURE:
<223> OTHER INFORMATION: Synthetic

<400> SEQUENCE: 190
aaattttttt                                                      10

<210> SEQ ID NO 191
<211> LENGTH: 10
<212> TYPE: DNA
<213> ORGANISM: Artificial Sequence
<220> FEATURE:
<223> OTHER INFORMATION: Synthetic

<400> SEQUENCE: 191
aatttttttt                                                      10

<210> SEQ ID NO 192
<211> LENGTH: 11
<212> TYPE: DNA
<213> ORGANISM: Artificial Sequence
<220> FEATURE:
<223> OTHER INFORMATION: Synthetic

<400> SEQUENCE: 192
aaaaaaaatt t                                                    11

<210> SEQ ID NO 193
<211> LENGTH: 11
<212> TYPE: DNA
<213> ORGANISM: Artificial Sequence
<220> FEATURE:
<223> OTHER INFORMATION: Synthetic

<400> SEQUENCE: 193
aaaaaaattt t                                                    11

<210> SEQ ID NO 194
<211> LENGTH: 11
<212> TYPE: DNA
<213> ORGANISM: Artificial Sequence
<220> FEATURE:
<223> OTHER INFORMATION: Synthetic

<400> SEQUENCE: 194
aaaaaatttt t                                                    11

<210> SEQ ID NO 195
<211> LENGTH: 11
<212> TYPE: DNA
<213> ORGANISM: Artificial Sequence

```
<220> FEATURE:
<223> OTHER INFORMATION: Synthetic

<400> SEQUENCE: 195
aaaaattttt t                                                           11

<210> SEQ ID NO 196
<211> LENGTH: 11
<212> TYPE: DNA
<213> ORGANISM: Artificial Sequence
<220> FEATURE:
<223> OTHER INFORMATION: Synthetic

<400> SEQUENCE: 196 aaaattttt t                                                            11

<210> SEQ ID NO 197
<211> LENGTH: 11
<212> TYPE: DNA
<213> ORGANISM: Artificial Sequence
<220> FEATURE:
<223> OTHER INFORMATION: Synthetic

<400> SEQUENCE: 197 aaatttttt t                                                            11

<210> SEQ ID NO 198
<211> LENGTH: 12
<212> TYPE: DNA
<213> ORGANISM: Artificial Sequence
<220> FEATURE:
<223> OTHER INFORMATION: Synthetic

<400> SEQUENCE: 198
aaaaaaaatt tt                                                          12

<210> SEQ ID NO 199
<211> LENGTH: 12
<212> TYPE: DNA
<213> ORGANISM: Artificial Sequence
<220> FEATURE:
<223> OTHER INFORMATION: Synthetic

<400> SEQUENCE: 199
aaaaaaattt tt                                                          12

<210> SEQ ID NO 200
<211> LENGTH: 12
<212> TYPE: DNA
<213> ORGANISM: Artificial Sequence
<220> FEATURE:
<223> OTHER INFORMATION: Synthetic

<400> SEQUENCE: 200
aaaaaatttt tt                                                          12

<210> SEQ ID NO 201
<211> LENGTH: 12
<212> TYPE: DNA
<213> ORGANISM: Artificial Sequence
<220> FEATURE:
<223> OTHER INFORMATION: Synthetic

<400> SEQUENCE: 201
aaaaattttt tt                                                          12
```

```
<210> SEQ ID NO 202
<211> LENGTH: 12
<212> TYPE: DNA
<213> ORGANISM: Artificial Sequence
<220> FEATURE:
<223> OTHER INFORMATION: Synthetic

<400> SEQUENCE: 202 aaaattttt tt                                                          12

<210> SEQ ID NO 203
<211> LENGTH: 10
<212> TYPE: DNA
<213> ORGANISM: Artificial Sequence
<220> FEATURE:
<223> OTHER INFORMATION: Synthetic

<400> SEQUENCE: 203
aaaaaagcgg                                                            10

<210> SEQ ID NO 204
<211> LENGTH: 8
<212> TYPE: DNA
<213> ORGANISM: Artificial Sequence
<220> FEATURE:
<223> OTHER INFORMATION: Synthetic

<400> SEQUENCE: 204 aaaacgct                                                               8

<210> SEQ ID NO 205
<211> LENGTH: 12
<212> TYPE: DNA
<213> ORGANISM: Artificial Sequence
<220> FEATURE:
<223> OTHER INFORMATION: Synthetic

<400> SEQUENCE: 205
aaaagaagtt at                                                         12

<210> SEQ ID NO 206
<211> LENGTH: 9
<212> TYPE: DNA
<213> ORGANISM: Artificial Sequence
<220> FEATURE:
<223> OTHER INFORMATION: Synthetic

<400> SEQUENCE: 206 aaaaggcgg                                                              9

<210> SEQ ID NO 207
<211> LENGTH: 9
<212> TYPE: DNA
<213> ORGANISM: Artificial Sequence
<220> FEATURE:
<223> OTHER INFORMATION: Synthetic

<400> SEQUENCE: 207 aaaccgcca                                                              9

<210> SEQ ID NO 208
<211> LENGTH: 9
<212> TYPE: DNA
<213> ORGANISM: Artificial Sequence
<220> FEATURE:
<223> OTHER INFORMATION: Synthetic
```

-continued

<400> SEQUENCE: 208 aaaccgtat				9

<210> SEQ ID NO 209
<211> LENGTH: 9
<212> TYPE: DNA
<213> ORGANISM: Artificial Sequence
<220> FEATURE:
<223> OTHER INFORMATION: Synthetic

<400> SEQUENCE: 209 aaaccgtta				9

<210> SEQ ID NO 210
<211> LENGTH: 12
<212> TYPE: DNA
<213> ORGANISM: Artificial Sequence
<220> FEATURE:
<223> OTHER INFORMATION: Synthetic

<400> SEQUENCE: 210
aaagaagaag tt				12

<210> SEQ ID NO 211
<211> LENGTH: 12
<212> TYPE: DNA
<213> ORGANISM: Artificial Sequence
<220> FEATURE:
<223> OTHER INFORMATION: Synthetic

<400> SEQUENCE: 211
aaagaagctt ta				12

<210> SEQ ID NO 212
<211> LENGTH: 12
<212> TYPE: DNA
<213> ORGANISM: Artificial Sequence
<220> FEATURE:
<223> OTHER INFORMATION: Synthetic

<400> SEQUENCE: 212
aaagaagtat ta				12

<210> SEQ ID NO 213
<211> LENGTH: 9
<212> TYPE: DNA
<213> ORGANISM: Artificial Sequence
<220> FEATURE:
<223> OTHER INFORMATION: Synthetic

<400> SEQUENCE: 213 aaagccgat				9

<210> SEQ ID NO 214
<211> LENGTH: 12
<212> TYPE: DNA
<213> ORGANISM: Artificial Sequence
<220> FEATURE:
<223> OTHER INFORMATION: Synthetic

<400> SEQUENCE: 214
aaagcgtggg ga				12

<210> SEQ ID NO 215

```
<211> LENGTH: 12
<212> TYPE: DNA
<213> ORGANISM: Artificial Sequence
<220> FEATURE:
<223> OTHER INFORMATION: Synthetic

<400> SEQUENCE: 215
aaagtagaag aa                                                         12

<210> SEQ ID NO 216
<211> LENGTH: 10
<212> TYPE: DNA
<213> ORGANISM: Artificial Sequence
<220> FEATURE:
<223> OTHER INFORMATION: Synthetic

<400> SEQUENCE: 216
aaataacgat                                                            10

<210> SEQ ID NO 217
<211> LENGTH: 9
<212> TYPE: DNA
<213> ORGANISM: Artificial Sequence
<220> FEATURE:
<223> OTHER INFORMATION: Synthetic

<400> SEQUENCE: 217 aaatacgct                                                              9

<210> SEQ ID NO 218
<211> LENGTH: 12
<212> TYPE: DNA
<213> ORGANISM: Artificial Sequence
<220> FEATURE:
<223> OTHER INFORMATION: Synthetic

<400> SEQUENCE: 218
aaatcattaa ag                                                         12

<210> SEQ ID NO 219
<211> LENGTH: 9
<212> TYPE: DNA
<213> ORGANISM: Artificial Sequence
<220> FEATURE:
<223> OTHER INFORMATION: Synthetic

<400> SEQUENCE: 219 aaattagcg                                                              9

<210> SEQ ID NO 220
<211> LENGTH: 9
<212> TYPE: DNA
<213> ORGANISM: Artificial Sequence
<220> FEATURE:
<223> OTHER INFORMATION: Synthetic

<400> SEQUENCE: 220 aaccgcctt                                                              9

<210> SEQ ID NO 221
<211> LENGTH: 8
<212> TYPE: DNA
<213> ORGANISM: Artificial Sequence
<220> FEATURE:
<223> OTHER INFORMATION: Synthetic

<400> SEQUENCE: 221
``` aacgattg                                                          8

<210> SEQ ID NO 222
<211> LENGTH: 9
<212> TYPE: DNA
<213> ORGANISM: Artificial Sequence
<220> FEATURE:
<223> OTHER INFORMATION: Synthetic

<400> SEQUENCE: 222 aacgatatt                                                         9

<210> SEQ ID NO 223
<211> LENGTH: 9
<212> TYPE: DNA
<213> ORGANISM: Artificial Sequence
<220> FEATURE:
<223> OTHER INFORMATION: Synthetic

<400> SEQUENCE: 223 aacgcttcw                                                         9

<210> SEQ ID NO 224
<211> LENGTH: 9
<212> TYPE: DNA
<213> ORGANISM: Artificial Sequence
<220> FEATURE:
<223> OTHER INFORMATION: Synthetic

<400> SEQUENCE: 224 aacgtgaac                                                         9

<210> SEQ ID NO 225
<211> LENGTH: 12
<212> TYPE: DNA
<213> ORGANISM: Artificial Sequence
<220> FEATURE:
<223> OTHER INFORMATION: Synthetic

<400> SEQUENCE: 225
aacttctttt tc                                                    12

<210> SEQ ID NO 226
<211> LENGTH: 9
<212> TYPE: DNA
<213> ORGANISM: Artificial Sequence
<220> FEATURE:
<223> OTHER INFORMATION: Synthetic

<400> SEQUENCE: 226 aagaaacgc                                                         9

<210> SEQ ID NO 227
<211> LENGTH: 12
<212> TYPE: DNA
<213> ORGANISM: Artificial Sequence
<220> FEATURE:
<223> OTHER INFORMATION: Synthetic

<400> SEQUENCE: 227
aagarttaaa ag                                                    12

<210> SEQ ID NO 228
<211> LENGTH: 12
<212> TYPE: DNA

```
<213> ORGANISM: Artificial Sequence
<220> FEATURE:
<223> OTHER INFORMATION: Synthetic

<400> SEQUENCE: 228
aagataaaga tg                                                          12

<210> SEQ ID NO 229
<211> LENGTH: 12
<212> TYPE: DNA
<213> ORGANISM: Artificial Sequence
<220> FEATURE:
<223> OTHER INFORMATION: Synthetic

<400> SEQUENCE: 229
aagatgtaaa ag                                                          12

<210> SEQ ID NO 230
<211> LENGTH: 12
<212> TYPE: DNA
<213> ORGANISM: Artificial Sequence
<220> FEATURE:
<223> OTHER INFORMATION: Synthetic

<400> SEQUENCE: 230
aagcatctaa gc                                                          12

<210> SEQ ID NO 231
<211> LENGTH: 9
<212> TYPE: DNA
<213> ORGANISM: Artificial Sequence
<220> FEATURE:
<223> OTHER INFORMATION: Synthetic

<400> SEQUENCE: 231 aagcgatca                                                               9

<210> SEQ ID NO 232
<211> LENGTH: 9
<212> TYPE: DNA
<213> ORGANISM: Artificial Sequence
<220> FEATURE:
<223> OTHER INFORMATION: Synthetic

<400> SEQUENCE: 232 aagcggttc                                                               9

<210> SEQ ID NO 233
<211> LENGTH: 9
<212> TYPE: DNA
<213> ORGANISM: Artificial Sequence
<220> FEATURE:
<223> OTHER INFORMATION: Synthetic

<400> SEQUENCE: 233 aagtaacga                                                               9

<210> SEQ ID NO 234
<211> LENGTH: 9
<212> TYPE: DNA
<213> ORGANISM: Artificial Sequence
<220> FEATURE:
<223> OTHER INFORMATION: Synthetic

<400> SEQUENCE: 234 aataacgca                                                               9
```

<210> SEQ ID NO 235
<211> LENGTH: 12
<212> TYPE: DNA
<213> ORGANISM: Artificial Sequence
<220> FEATURE:
<223> OTHER INFORMATION: Synthetic

<400> SEQUENCE: 235
aatattggac aa                                                        12

<210> SEQ ID NO 236
<211> LENGTH: 12
<212> TYPE: DNA
<213> ORGANISM: Artificial Sequence
<220> FEATURE:
<223> OTHER INFORMATION: Synthetic

<400> SEQUENCE: 236
aatcattaat at                                                        12

<210> SEQ ID NO 237
<211> LENGTH: 9
<212> TYPE: DNA
<213> ORGANISM: Artificial Sequence
<220> FEATURE:
<223> OTHER INFORMATION: Synthetic

<400> SEQUENCE: 237 aatccagcg                                                             9

<210> SEQ ID NO 238
<211> LENGTH: 9
<212> TYPE: DNA
<213> ORGANISM: Artificial Sequence
<220> FEATURE:
<223> OTHER INFORMATION: Synthetic

<400> SEQUENCE: 238 aatcgccca                                                             9

<210> SEQ ID NO 239
<211> LENGTH: 9
<212> TYPE: DNA
<213> ORGANISM: Artificial Sequence
<220> FEATURE:
<223> OTHER INFORMATION: Synthetic

<400> SEQUENCE: 239 aatcgtatc                                                             9

<210> SEQ ID NO 240
<211> LENGTH: 9
<212> TYPE: DNA
<213> ORGANISM: Artificial Sequence
<220> FEATURE:
<223> OTHER INFORMATION: Synthetic

<400> SEQUENCE: 240 aatcgttaa                                                             9

<210> SEQ ID NO 241
<211> LENGTH: 9
<212> TYPE: DNA
<213> ORGANISM: Artificial Sequence
<220> FEATURE:

-continued

<223> OTHER INFORMATION: Synthetic

<400> SEQUENCE: 241 aatcgttgc                                                                9

<210> SEQ ID NO 242
<211> LENGTH: 12
<212> TYPE: DNA
<213> ORGANISM: Artificial Sequence
<220> FEATURE:
<223> OTHER INFORMATION: Synthetic

<400> SEQUENCE: 242
aatctggtgg ta                                                           12

<210> SEQ ID NO 243
<211> LENGTH: 8
<212> TYPE: DNA
<213> ORGANISM: Artificial Sequence
<220> FEATURE:
<223> OTHER INFORMATION: Synthetic

<400> SEQUENCE: 243 aatgcggt                                                                 8

<210> SEQ ID NO 244
<211> LENGTH: 8
<212> TYPE: DNA
<213> ORGANISM: Artificial Sequence
<220> FEATURE:
<223> OTHER INFORMATION: Synthetic

<400> SEQUENCE: 244 aattaacg                                                                 8

<210> SEQ ID NO 245
<211> LENGTH: 12
<212> TYPE: DNA
<213> ORGANISM: Artificial Sequence
<220> FEATURE:
<223> OTHER INFORMATION: Synthetic

<400> SEQUENCE: 245
aatttcatct aa                                                           12

<210> SEQ ID NO 246
<211> LENGTH: 9
<212> TYPE: DNA
<213> ORGANISM: Artificial Sequence
<220> FEATURE:
<223> OTHER INFORMATION: Synthetic

<400> SEQUENCE: 246 accgataat                                                                9

<210> SEQ ID NO 247
<211> LENGTH: 9
<212> TYPE: DNA
<213> ORGANISM: Artificial Sequence
<220> FEATURE:
<223> OTHER INFORMATION: Synthetic

<400> SEQUENCE: 247 accgcatca                                                                9

```
<210> SEQ ID NO 248
<211> LENGTH: 9
<212> TYPE: DNA
<213> ORGANISM: Artificial Sequence
<220> FEATURE:
<223> OTHER INFORMATION: Synthetic

<400> SEQUENCE: 248 acgaatgat                                                              9

<210> SEQ ID NO 249
<211> LENGTH: 9
<212> TYPE: DNA
<213> ORGANISM: Artificial Sequence
<220> FEATURE:
<223> OTHER INFORMATION: Synthetic

<400> SEQUENCE: 249 acgatgttg                                                              9

<210> SEQ ID NO 250
<211> LENGTH: 9
<212> TYPE: DNA
<213> ORGANISM: Artificial Sequence
<220> FEATURE:
<223> OTHER INFORMATION: Synthetic

<400> SEQUENCE: 250 acggttatc                                                              9

<210> SEQ ID NO 251
<211> LENGTH: 9
<212> TYPE: DNA
<213> ORGANISM: Artificial Sequence
<220> FEATURE:
<223> OTHER INFORMATION: Synthetic

<400> SEQUENCE: 251 acggtttta                                                              9

<210> SEQ ID NO 252
<211> LENGTH: 9
<212> TYPE: DNA
<213> ORGANISM: Artificial Sequence
<220> FEATURE:
<223> OTHER INFORMATION: Synthetic

<400> SEQUENCE: 252 acgrtaaaa                                                              9

<210> SEQ ID NO 253
<211> LENGTH: 8
<212> TYPE: DNA
<213> ORGANISM: Artificial Sequence
<220> FEATURE:
<223> OTHER INFORMATION: Synthetic

<400> SEQUENCE: 253 acgtttat                                                               8

<210> SEQ ID NO 254
<211> LENGTH: 12
<212> TYPE: DNA
<213> ORGANISM: Artificial Sequence
<220> FEATURE:
<223> OTHER INFORMATION: Synthetic
```

```
<400> SEQUENCE: 254 actttttat ct                                                    12

<210> SEQ ID NO 255
<211> LENGTH: 12
<212> TYPE: DNA
<213> ORGANISM: Artificial Sequence
<220> FEATURE:
<223> OTHER INFORMATION: Synthetic

<400> SEQUENCE: 255
agaattatta aa                                                   12

<210> SEQ ID NO 256
<211> LENGTH: 9
<212> TYPE: DNA
<213> ORGANISM: Artificial Sequence
<220> FEATURE:
<223> OTHER INFORMATION: Synthetic

<400> SEQUENCE: 256 agataaacg                                                        9

<210> SEQ ID NO 257
<211> LENGTH: 12
<212> TYPE: DNA
<213> ORGANISM: Artificial Sequence
<220> FEATURE:
<223> OTHER INFORMATION: Synthetic

<400> SEQUENCE: 257
agatgaaaat gg                                                   12

<210> SEQ ID NO 258
<211> LENGTH: 9
<212> TYPE: DNA
<213> ORGANISM: Artificial Sequence
<220> FEATURE:
<223> OTHER INFORMATION: Synthetic

<400> SEQUENCE: 258 agcaatcgc                                                        9

<210> SEQ ID NO 259
<211> LENGTH: 12
<212> TYPE: DNA
<213> ORGANISM: Artificial Sequence
<220> FEATURE:
<223> OTHER INFORMATION: Synthetic

<400> SEQUENCE: 259
agcagttgca gc                                                   12

<210> SEQ ID NO 260
<211> LENGTH: 9
<212> TYPE: DNA
<213> ORGANISM: Artificial Sequence
<220> FEATURE:
<223> OTHER INFORMATION: Synthetic

<400> SEQUENCE: 260 agcgcaatc                                                        9

<210> SEQ ID NO 261
<211> LENGTH: 9
```

```
<212> TYPE: DNA
<213> ORGANISM: Artificial Sequence
<220> FEATURE:
<223> OTHER INFORMATION: Synthetic

<400> SEQUENCE: 261 agcttgttg                                                                9

<210> SEQ ID NO 262
<211> LENGTH: 9
<212> TYPE: DNA
<213> ORGANISM: Artificial Sequence
<220> FEATURE:
<223> OTHER INFORMATION: Synthetic

<400> SEQUENCE: 262 agttgatcg                                                                9

<210> SEQ ID NO 263
<211> LENGTH: 12
<212> TYPE: DNA
<213> ORGANISM: Artificial Sequence
<220> FEATURE:
<223> OTHER INFORMATION: Synthetic

<400> SEQUENCE: 263
ataaaaaaag cg                                                           12

<210> SEQ ID NO 264
<211> LENGTH: 12
<212> TYPE: DNA
<213> ORGANISM: Artificial Sequence
<220> FEATURE:
<223> OTHER INFORMATION: Synthetic

<400> SEQUENCE: 264
ataaaaaagg ta                                                           12

<210> SEQ ID NO 265
<211> LENGTH: 12
<212> TYPE: DNA
<213> ORGANISM: Artificial Sequence
<220> FEATURE:
<223> OTHER INFORMATION: Synthetic

<400> SEQUENCE: 265
ataaagaaga tg                                                           12

<210> SEQ ID NO 266
<211> LENGTH: 12
<212> TYPE: DNA
<213> ORGANISM: Artificial Sequence
<220> FEATURE:
<223> OTHER INFORMATION: Synthetic

<400> SEQUENCE: 266
ataaagatat ta                                                           12

<210> SEQ ID NO 267
<211> LENGTH: 9
<212> TYPE: DNA
<213> ORGANISM: Artificial Sequence
<220> FEATURE:
<223> OTHER INFORMATION: Synthetic

<400> SEQUENCE: 267
``` ataacgaag                                                              9

<210> SEQ ID NO 268
<211> LENGTH: 12
<212> TYPE: DNA
<213> ORGANISM: Artificial Sequence
<220> FEATURE:
<223> OTHER INFORMATION: Synthetic

<400> SEQUENCE: 268
ataactaata aa                                                         12

<210> SEQ ID NO 269
<211> LENGTH: 12
<212> TYPE: DNA
<213> ORGANISM: Artificial Sequence
<220> FEATURE:
<223> OTHER INFORMATION: Synthetic

<400> SEQUENCE: 269
ataatagaag aa                                                         12

<210> SEQ ID NO 270
<211> LENGTH: 12
<212> TYPE: DNA
<213> ORGANISM: Artificial Sequence
<220> FEATURE:
<223> OTHER INFORMATION: Synthetic

<400> SEQUENCE: 270
ataccatttt ta                                                         12

<210> SEQ ID NO 271
<211> LENGTH: 9
<212> TYPE: DNA
<213> ORGANISM: Artificial Sequence
<220> FEATURE:
<223> OTHER INFORMATION: Synthetic

<400> SEQUENCE: 271 atacgataa                                                              9

<210> SEQ ID NO 272
<211> LENGTH: 12
<212> TYPE: DNA
<213> ORGANISM: Artificial Sequence
<220> FEATURE:
<223> OTHER INFORMATION: Synthetic

<400> SEQUENCE: 272
atagatgaaa at                                                         12

<210> SEQ ID NO 273
<211> LENGTH: 9
<212> TYPE: DNA
<213> ORGANISM: Artificial Sequence
<220> FEATURE:
<223> OTHER INFORMATION: Synthetic

<400> SEQUENCE: 273 atagcgata                                                              9

<210> SEQ ID NO 274
<211> LENGTH: 9
<212> TYPE: DNA
<213> ORGANISM: Artificial Sequence

```
<220> FEATURE:
<223> OTHER INFORMATION: Synthetic

<400> SEQUENCE: 274 atatcgtaa                                                          9

<210> SEQ ID NO 275
<211> LENGTH: 12
<212> TYPE: DNA
<213> ORGANISM: Artificial Sequence
<220> FEATURE:
<223> OTHER INFORMATION: Synthetic

<400> SEQUENCE: 275 atatctttt ca                                                      12

<210> SEQ ID NO 276
<211> LENGTH: 10
<212> TYPE: DNA
<213> ORGANISM: Artificial Sequence
<220> FEATURE:
<223> OTHER INFORMATION: Synthetic

<400> SEQUENCE: 276
atattaaagc                                                        10

<210> SEQ ID NO 277
<211> LENGTH: 12
<212> TYPE: DNA
<213> ORGANISM: Artificial Sequence
<220> FEATURE:
<223> OTHER INFORMATION: Synthetic

<400> SEQUENCE: 277
atattgaaga ag                                                     12

<210> SEQ ID NO 278
<211> LENGTH: 10
<212> TYPE: DNA
<213> ORGANISM: Artificial Sequence
<220> FEATURE:
<223> OTHER INFORMATION: Synthetic

<400> SEQUENCE: 278
atattgatac                                                        10

<210> SEQ ID NO 279
<211> LENGTH: 9
<212> TYPE: DNA
<213> ORGANISM: Artificial Sequence
<220> FEATURE:
<223> OTHER INFORMATION: Synthetic

<400> SEQUENCE: 279 atcagctac                                                          9

<210> SEQ ID NO 280
<211> LENGTH: 9
<212> TYPE: DNA
<213> ORGANISM: Artificial Sequence
<220> FEATURE:
<223> OTHER INFORMATION: Synthetic

<400> SEQUENCE: 280 atcatgccg                                                          9
```

<210> SEQ ID NO 281
<211> LENGTH: 9
<212> TYPE: DNA
<213> ORGANISM: Artificial Sequence
<220> FEATURE:
<223> OTHER INFORMATION: Synthetic

<400> SEQUENCE: 281 atcgcaccg                                                                  9

<210> SEQ ID NO 282
<211> LENGTH: 10
<212> TYPE: DNA
<213> ORGANISM: Artificial Sequence
<220> FEATURE:
<223> OTHER INFORMATION: Synthetic

<400> SEQUENCE: 282
atcgccttca                                                                10

<210> SEQ ID NO 283
<211> LENGTH: 9
<212> TYPE: DNA
<213> ORGANISM: Artificial Sequence
<220> FEATURE:
<223> OTHER INFORMATION: Synthetic

<400> SEQUENCE: 283 atcgtaata                                                                  9

<210> SEQ ID NO 284
<211> LENGTH: 9
<212> TYPE: DNA
<213> ORGANISM: Artificial Sequence
<220> FEATURE:
<223> OTHER INFORMATION: Synthetic

<400> SEQUENCE: 284 atcgtgaag                                                                  9

<210> SEQ ID NO 285
<211> LENGTH: 9
<212> TYPE: DNA
<213> ORGANISM: Artificial Sequence
<220> FEATURE:
<223> OTHER INFORMATION: Synthetic

<400> SEQUENCE: 285 atcgttaaa                                                                  9

<210> SEQ ID NO 286
<211> LENGTH: 9
<212> TYPE: DNA
<213> ORGANISM: Artificial Sequence
<220> FEATURE:
<223> OTHER INFORMATION: Synthetic

<400> SEQUENCE: 286 atcttcacg                                                                  9

<210> SEQ ID NO 287
<211> LENGTH: 12
<212> TYPE: DNA
<213> ORGANISM: Artificial Sequence
<220> FEATURE:
<223> OTHER INFORMATION: Synthetic

```
<400> SEQUENCE: 287
atcttcttta at                                                         12

<210> SEQ ID NO 288
<211> LENGTH: 9
<212> TYPE: DNA
<213> ORGANISM: Artificial Sequence
<220> FEATURE:
<223> OTHER INFORMATION: Synthetic

<400> SEQUENCE: 288 attaatacc                                                              9

<210> SEQ ID NO 289
<211> LENGTH: 9
<212> TYPE: DNA
<213> ORGANISM: Artificial Sequence
<220> FEATURE:
<223> OTHER INFORMATION: Synthetic

<400> SEQUENCE: 289 attacaacg                                                              9

<210> SEQ ID NO 290
<211> LENGTH: 10
<212> TYPE: DNA
<213> ORGANISM: Artificial Sequence
<220> FEATURE:
<223> OTHER INFORMATION: Synthetic

<400> SEQUENCE: 290
attacaacaa                                                            10

<210> SEQ ID NO 291
<211> LENGTH: 8
<212> TYPE: DNA
<213> ORGANISM: Artificial Sequence
<220> FEATURE:
<223> OTHER INFORMATION: Synthetic

<400> SEQUENCE: 291 attaccgc                                                               8

<210> SEQ ID NO 292
<211> LENGTH: 12
<212> TYPE: DNA
<213> ORGANISM: Artificial Sequence
<220> FEATURE:
<223> OTHER INFORMATION: Synthetic

<400> SEQUENCE: 292
attagaagaa at                                                         12

<210> SEQ ID NO 293
<211> LENGTH: 8
<212> TYPE: DNA
<213> ORGANISM: Artificial Sequence
<220> FEATURE:
<223> OTHER INFORMATION: Synthetic

<400> SEQUENCE: 293 attatcgg                                                               8

<210> SEQ ID NO 294
```

```
<211> LENGTH: 9
<212> TYPE: DNA
<213> ORGANISM: Artificial Sequence
<220> FEATURE:
<223> OTHER INFORMATION: Synthetic

<400> SEQUENCE: 294 attatcgta                                                                9

<210> SEQ ID NO 295
<211> LENGTH: 9
<212> TYPE: DNA
<213> ORGANISM: Artificial Sequence
<220> FEATURE:
<223> OTHER INFORMATION: Synthetic

<400> SEQUENCE: 295 attcatcgg                                                                9

<210> SEQ ID NO 296
<211> LENGTH: 10
<212> TYPE: DNA
<213> ORGANISM: Artificial Sequence
<220> FEATURE:
<223> OTHER INFORMATION: Synthetic

<400> SEQUENCE: 296
attgatatta                                                              10

<210> SEQ ID NO 297
<211> LENGTH: 12
<212> TYPE: DNA
<213> ORGANISM: Artificial Sequence
<220> FEATURE:
<223> OTHER INFORMATION: Synthetic

<400> SEQUENCE: 297
attgatataa at                                                           12

<210> SEQ ID NO 298
<211> LENGTH: 11
<212> TYPE: DNA
<213> ORGANISM: Artificial Sequence
<220> FEATURE:
<223> OTHER INFORMATION: Synthetic

<400> SEQUENCE: 298
attgatgaag c                                                            11

<210> SEQ ID NO 299
<211> LENGTH: 12
<212> TYPE: DNA
<213> ORGANISM: Artificial Sequence
<220> FEATURE:
<223> OTHER INFORMATION: Synthetic

<400> SEQUENCE: 299
attgatgatt ta                                                           12

<210> SEQ ID NO 300
<211> LENGTH: 10
<212> TYPE: DNA
<213> ORGANISM: Artificial Sequence
<220> FEATURE:
<223> OTHER INFORMATION: Synthetic

<400> SEQUENCE: 300
```
attgcagcaa 10

<210> SEQ ID NO 301
<211> LENGTH: 12
<212> TYPE: DNA
<213> ORGANISM: Artificial Sequence
<220> FEATURE:
<223> OTHER INFORMATION: Synthetic

<400> SEQUENCE: 301
atttagataa at 12

<210> SEQ ID NO 302
<211> LENGTH: 12
<212> TYPE: DNA
<213> ORGANISM: Artificial Sequence
<220> FEATURE:
<223> OTHER INFORMATION: Synthetic

<400> SEQUENCE: 302
atttagatga ag 12

<210> SEQ ID NO 303
<211> LENGTH: 10
<212> TYPE: DNA
<213> ORGANISM: Artificial Sequence
<220> FEATURE:
<223> OTHER INFORMATION: Synthetic

<400> SEQUENCE: 303
atttatcagc 10

<210> SEQ ID NO 304
<211> LENGTH: 12
<212> TYPE: DNA
<213> ORGANISM: Artificial Sequence
<220> FEATURE:
<223> OTHER INFORMATION: Synthetic

<400> SEQUENCE: 304
atttattatt ag 12

<210> SEQ ID NO 305
<211> LENGTH: 12
<212> TYPE: DNA
<213> ORGANISM: Artificial Sequence
<220> FEATURE:
<223> OTHER INFORMATION: Synthetic

<400> SEQUENCE: 305
atttctttat ca 12

<210> SEQ ID NO 306
<211> LENGTH: 9
<212> TYPE: DNA
<213> ORGANISM: Artificial Sequence
<220> FEATURE:
<223> OTHER INFORMATION: Synthetic

<400> SEQUENCE: 306 caatcggtg 9

<210> SEQ ID NO 307
<211> LENGTH: 9
<212> TYPE: DNA

```
<213> ORGANISM: Artificial Sequence
<220> FEATURE:
<223> OTHER INFORMATION: Synthetic

<400> SEQUENCE: 307 caatcgyta                                                                9

<210> SEQ ID NO 308
<211> LENGTH: 12
<212> TYPE: DNA
<213> ORGANISM: Artificial Sequence
<220> FEATURE:
<223> OTHER INFORMATION: Synthetic

<400> SEQUENCE: 308
cacctttttt aa                                                           12

<210> SEQ ID NO 309
<211> LENGTH: 9
<212> TYPE: DNA
<213> ORGANISM: Artificial Sequence
<220> FEATURE:
<223> OTHER INFORMATION: Synthetic

<400> SEQUENCE: 309 cagcgatta                                                                9

<210> SEQ ID NO 310
<211> LENGTH: 11
<212> TYPE: DNA
<213> ORGANISM: Artificial Sequence
<220> FEATURE:
<223> OTHER INFORMATION: Synthetic

<400> SEQUENCE: 310
cagctttttt a                                                            11

<210> SEQ ID NO 311
<211> LENGTH: 9
<212> TYPE: DNA
<213> ORGANISM: Artificial Sequence
<220> FEATURE:
<223> OTHER INFORMATION: Synthetic

<400> SEQUENCE: 311 catcgcttc                                                                9

<210> SEQ ID NO 312
<211> LENGTH: 12
<212> TYPE: DNA
<213> ORGANISM: Artificial Sequence
<220> FEATURE:
<223> OTHER INFORMATION: Synthetic

<400> SEQUENCE: 312
catctaaaat aa                                                           12

<210> SEQ ID NO 313
<211> LENGTH: 9
<212> TYPE: DNA
<213> ORGANISM: Artificial Sequence
<220> FEATURE:
<223> OTHER INFORMATION: Synthetic

<400> SEQUENCE: 313 catcttccg                                                                9
```

```
<210> SEQ ID NO 314
<211> LENGTH: 9
<212> TYPE: DNA
<213> ORGANISM: Artificial Sequence
<220> FEATURE:
<223> OTHER INFORMATION: Synthetic

<400> SEQUENCE: 314 ccaatcggc                                                                 9

<210> SEQ ID NO 315
<211> LENGTH: 9
<212> TYPE: DNA
<213> ORGANISM: Artificial Sequence
<220> FEATURE:
<223> OTHER INFORMATION: Synthetic

<400> SEQUENCE: 315 cccgcttca                                                                 9

<210> SEQ ID NO 316
<211> LENGTH: 9
<212> TYPE: DNA
<213> ORGANISM: Artificial Sequence
<220> FEATURE:
<223> OTHER INFORMATION: Synthetic

<400> SEQUENCE: 316 ccggtaata                                                                 9

<210> SEQ ID NO 317
<211> LENGTH: 9
<212> TYPE: DNA
<213> ORGANISM: Artificial Sequence
<220> FEATURE:
<223> OTHER INFORMATION: Synthetic

<400> SEQUENCE: 317 cgataatga                                                                 9

<210> SEQ ID NO 318
<211> LENGTH: 9
<212> TYPE: DNA
<213> ORGANISM: Artificial Sequence
<220> FEATURE:
<223> OTHER INFORMATION: Synthetic

<400> SEQUENCE: 318 cgattaaag                                                                 9

<210> SEQ ID NO 319
<211> LENGTH: 8
<212> TYPE: DNA
<213> ORGANISM: Artificial Sequence
<220> FEATURE:
<223> OTHER INFORMATION: Synthetic

<400> SEQUENCE: 319 cgattgcg                                                                  8

<210> SEQ ID NO 320
<211> LENGTH: 9
<212> TYPE: DNA
<213> ORGANISM: Artificial Sequence
<220> FEATURE:
```

```
<223> OTHER INFORMATION: Synthetic

<400> SEQUENCE: 320 cgcctcttc                                                                  9

<210> SEQ ID NO 321
<211> LENGTH: 9
<212> TYPE: DNA
<213> ORGANISM: Artificial Sequence
<220> FEATURE:
<223> OTHER INFORMATION: Synthetic

<400> SEQUENCE: 321 cgctaaata                                                                  9

<210> SEQ ID NO 322
<211> LENGTH: 9
<212> TYPE: DNA
<213> ORGANISM: Artificial Sequence
<220> FEATURE:
<223> OTHER INFORMATION: Synthetic

<400> SEQUENCE: 322 cgctttata                                                                  9

<210> SEQ ID NO 323
<211> LENGTH: 12
<212> TYPE: DNA
<213> ORGANISM: Artificial Sequence
<220> FEATURE:
<223> OTHER INFORMATION: Synthetic

<400> SEQUENCE: 323
cggcgcgctg aa                                                             12

<210> SEQ ID NO 324
<211> LENGTH: 9
<212> TYPE: DNA
<213> ORGANISM: Artificial Sequence
<220> FEATURE:
<223> OTHER INFORMATION: Synthetic

<400> SEQUENCE: 324 cggtattga                                                                  9

<210> SEQ ID NO 325
<211> LENGTH: 9
<212> TYPE: DNA
<213> ORGANISM: Artificial Sequence
<220> FEATURE:
<223> OTHER INFORMATION: Synthetic

<400> SEQUENCE: 325 cgtaaagaa                                                                  9

<210> SEQ ID NO 326
<211> LENGTH: 9
<212> TYPE: DNA
<213> ORGANISM: Artificial Sequence
<220> FEATURE:
<223> OTHER INFORMATION: Synthetic

<400> SEQUENCE: 326 cgtaaatac                                                                  9
```

```
<210> SEQ ID NO 327
<211> LENGTH: 9
<212> TYPE: DNA
<213> ORGANISM: Artificial Sequence
<220> FEATURE:
<223> OTHER INFORMATION: Synthetic

<400> SEQUENCE: 327 cgtgatcaa                                                                 9

<210> SEQ ID NO 328
<211> LENGTH: 9
<212> TYPE: DNA
<213> ORGANISM: Artificial Sequence
<220> FEATURE:
<223> OTHER INFORMATION: Synthetic

<400> SEQUENCE: 328 cgtttatta                                                                 9

<210> SEQ ID NO 329
<211> LENGTH: 9
<212> TYPE: DNA
<213> ORGANISM: Artificial Sequence
<220> FEATURE:
<223> OTHER INFORMATION: Synthetic

<400> SEQUENCE: 329 cgwtaataa                                                                 9

<210> SEQ ID NO 330
<211> LENGTH: 12
<212> TYPE: DNA
<213> ORGANISM: Artificial Sequence
<220> FEATURE:
<223> OTHER INFORMATION: Synthetic

<400> SEQUENCE: 330
ctaattcttc ta                                                            12

<210> SEQ ID NO 331
<211> LENGTH: 12
<212> TYPE: DNA
<213> ORGANISM: Artificial Sequence
<220> FEATURE:
<223> OTHER INFORMATION: Synthetic

<400> SEQUENCE: 331 ctacttttc ca                                                             12

<210> SEQ ID NO 332
<211> LENGTH: 12
<212> TYPE: DNA
<213> ORGANISM: Artificial Sequence
<220> FEATURE:
<223> OTHER INFORMATION: Synthetic

<400> SEQUENCE: 332
ctgtagaaga ag                                                            12

<210> SEQ ID NO 333
<211> LENGTH: 12
<212> TYPE: DNA
<213> ORGANISM: Artificial Sequence
<220> FEATURE:
<223> OTHER INFORMATION: Synthetic
```

<400> SEQUENCE: 333
ctgttttaga ag                                                         12

<210> SEQ ID NO 334
<211> LENGTH: 9
<212> TYPE: DNA
<213> ORGANISM: Artificial Sequence
<220> FEATURE:
<223> OTHER INFORMATION: Synthetic

<400> SEQUENCE: 334 cttcacgaa                                                              9

<210> SEQ ID NO 335
<211> LENGTH: 10
<212> TYPE: DNA
<213> ORGANISM: Artificial Sequence
<220> FEATURE:
<223> OTHER INFORMATION: Synthetic

<400> SEQUENCE: 335
cttcatcaac                                                            10

<210> SEQ ID NO 336
<211> LENGTH: 12
<212> TYPE: DNA
<213> ORGANISM: Artificial Sequence
<220> FEATURE:
<223> OTHER INFORMATION: Synthetic

<400> SEQUENCE: 336
cttcatctaa ta                                                         12

<210> SEQ ID NO 337
<211> LENGTH: 12
<212> TYPE: DNA
<213> ORGANISM: Artificial Sequence
<220> FEATURE:
<223> OTHER INFORMATION: Synthetic

<400> SEQUENCE: 337
cttcttctaa aa                                                         12

<210> SEQ ID NO 338
<211> LENGTH: 12
<212> TYPE: DNA
<213> ORGANISM: Artificial Sequence
<220> FEATURE:
<223> OTHER INFORMATION: Synthetic

<400> SEQUENCE: 338
cttcttcttt aa                                                         12

<210> SEQ ID NO 339
<211> LENGTH: 10
<212> TYPE: DNA
<213> ORGANISM: Artificial Sequence
<220> FEATURE:
<223> OTHER INFORMATION: Synthetic

<400> SEQUENCE: 339
cttctttcgc                                                            10

<210> SEQ ID NO 340
<211> LENGTH: 12

```
<212> TYPE: DNA
<213> ORGANISM: Artificial Sequence
<220> FEATURE:
<223> OTHER INFORMATION: Synthetic

<400> SEQUENCE: 340
ctttagaaaa ta                                                            12

<210> SEQ ID NO 341
<211> LENGTH: 12
<212> TYPE: DNA
<213> ORGANISM: Artificial Sequence
<220> FEATURE:
<223> OTHER INFORMATION: Synthetic

<400> SEQUENCE: 341
ctttatataa ar                                                            12

<210> SEQ ID NO 342
<211> LENGTH: 12
<212> TYPE: DNA
<213> ORGANISM: Artificial Sequence
<220> FEATURE:
<223> OTHER INFORMATION: Synthetic

<400> SEQUENCE: 342
ctttatcaat aa                                                            12

<210> SEQ ID NO 343
<211> LENGTH: 10
<212> TYPE: DNA
<213> ORGANISM: Artificial Sequence
<220> FEATURE:
<223> OTHER INFORMATION: Synthetic

<400> SEQUENCE: 343
ctttcgcttc                                                               10

<210> SEQ ID NO 344
<211> LENGTH: 12
<212> TYPE: DNA
<213> ORGANISM: Artificial Sequence
<220> FEATURE:
<223> OTHER INFORMATION: Synthetic

<400> SEQUENCE: 344
cttttatata aa                                                            12

<210> SEQ ID NO 345
<211> LENGTH: 12
<212> TYPE: DNA
<213> ORGANISM: Artificial Sequence
<220> FEATURE:
<223> OTHER INFORMATION: Synthetic

<400> SEQUENCE: 345 cttttttcwtc ta                                                           12

<210> SEQ ID NO 346
<211> LENGTH: 12
<212> TYPE: DNA
<213> ORGANISM: Artificial Sequence
<220> FEATURE:
<223> OTHER INFORMATION: Synthetic

<400> SEQUENCE: 346
```

-continued

```
gaaaaaggat ta                                                    12

<210> SEQ ID NO 347
<211> LENGTH: 9
<212> TYPE: DNA
<213> ORGANISM: Artificial Sequence
<220> FEATURE:
<223> OTHER INFORMATION: Synthetic

<400> SEQUENCE: 347 gaaacgatc                                                         9

<210> SEQ ID NO 348
<211> LENGTH: 9
<212> TYPE: DNA
<213> ORGANISM: Artificial Sequence
<220> FEATURE:
<223> OTHER INFORMATION: Synthetic

<400> SEQUENCE: 348 gaaacgtta                                                         9

<210> SEQ ID NO 349
<211> LENGTH: 12
<212> TYPE: DNA
<213> ORGANISM: Artificial Sequence
<220> FEATURE:
<223> OTHER INFORMATION: Synthetic

<400> SEQUENCE: 349
gaaattgctg ac                                                    12

<210> SEQ ID NO 350
<211> LENGTH: 12
<212> TYPE: DNA
<213> ORGANISM: Artificial Sequence
<220> FEATURE:
<223> OTHER INFORMATION: Synthetic

<400> SEQUENCE: 350
gaagaagyga aa                                                    12

<210> SEQ ID NO 351
<211> LENGTH: 12
<212> TYPE: DNA
<213> ORGANISM: Artificial Sequence
<220> FEATURE:
<223> OTHER INFORMATION: Synthetic

<400> SEQUENCE: 351
gaagatgaaa aa                                                    12

<210> SEQ ID NO 352
<211> LENGTH: 12
<212> TYPE: DNA
<213> ORGANISM: Artificial Sequence
<220> FEATURE:
<223> OTHER INFORMATION: Synthetic

<400> SEQUENCE: 352
gaagatttat ta                                                    12

<210> SEQ ID NO 353
<211> LENGTH: 12
<212> TYPE: DNA
<213> ORGANISM: Artificial Sequence
```

<220> FEATURE:
<223> OTHER INFORMATION: Synthetic

<400> SEQUENCE: 353
gaagtattaa aa    12

<210> SEQ ID NO 354
<211> LENGTH: 12
<212> TYPE: DNA
<213> ORGANISM: Artificial Sequence
<220> FEATURE:
<223> OTHER INFORMATION: Synthetic

<400> SEQUENCE: 354
gaatatgaag aa    12

<210> SEQ ID NO 355
<211> LENGTH: 12
<212> TYPE: DNA
<213> ORGANISM: Artificial Sequence
<220> FEATURE:
<223> OTHER INFORMATION: Synthetic

<400> SEQUENCE: 355
gatattgata aa    12

<210> SEQ ID NO 356
<211> LENGTH: 12
<212> TYPE: DNA
<213> ORGANISM: Artificial Sequence
<220> FEATURE:
<223> OTHER INFORMATION: Synthetic

<400> SEQUENCE: 356
gatgaagata aa    12

<210> SEQ ID NO 357
<211> LENGTH: 12
<212> TYPE: DNA
<213> ORGANISM: Artificial Sequence
<220> FEATURE:
<223> OTHER INFORMATION: Synthetic

<400> SEQUENCE: 357
gatttattat ta    12

<210> SEQ ID NO 358
<211> LENGTH: 12
<212> TYPE: DNA
<213> ORGANISM: Artificial Sequence
<220> FEATURE:
<223> OTHER INFORMATION: Synthetic

<400> SEQUENCE: 358
gatttcacga aa    12

<210> SEQ ID NO 359
<211> LENGTH: 8
<212> TYPE: DNA
<213> ORGANISM: Artificial Sequence
<220> FEATURE:
<223> OTHER INFORMATION: Synthetic

<400> SEQUENCE: 359 gcaataac    8

```
<210> SEQ ID NO 360
<211> LENGTH: 8
<212> TYPE: DNA
<213> ORGANISM: Artificial Sequence
<220> FEATURE:
<223> OTHER INFORMATION: Synthetic

<400> SEQUENCE: 360 gcctttac                                                              8

<210> SEQ ID NO 361
<211> LENGTH: 9
<212> TYPE: DNA
<213> ORGANISM: Artificial Sequence
<220> FEATURE:
<223> OTHER INFORMATION: Synthetic

<400> SEQUENCE: 361 gcgaaagaa                                                             9

<210> SEQ ID NO 362
<211> LENGTH: 9
<212> TYPE: DNA
<213> ORGANISM: Artificial Sequence
<220> FEATURE:
<223> OTHER INFORMATION: Synthetic

<400> SEQUENCE: 362 gcgatttta                                                             9

<210> SEQ ID NO 363
<211> LENGTH: 9
<212> TYPE: DNA
<213> ORGANISM: Artificial Sequence
<220> FEATURE:
<223> OTHER INFORMATION: Synthetic

<400> SEQUENCE: 363 gcggtatta                                                             9

<210> SEQ ID NO 364
<211> LENGTH: 9
<212> TYPE: DNA
<213> ORGANISM: Artificial Sequence
<220> FEATURE:
<223> OTHER INFORMATION: Synthetic

<400> SEQUENCE: 364 gcgttaata                                                             9

<210> SEQ ID NO 365
<211> LENGTH: 9
<212> TYPE: DNA
<213> ORGANISM: Artificial Sequence
<220> FEATURE:
<223> OTHER INFORMATION: Synthetic

<400> SEQUENCE: 365 gcgtttaaa                                                             9

<210> SEQ ID NO 366
<211> LENGTH: 9
<212> TYPE: DNA
<213> ORGANISM: Artificial Sequence
<220> FEATURE:
<223> OTHER INFORMATION: Synthetic
```

```
<400> SEQUENCE: 366 gcgttttga                                                            9

<210> SEQ ID NO 367
<211> LENGTH: 9
<212> TYPE: DNA
<213> ORGANISM: Artificial Sequence
<220> FEATURE:
<223> OTHER INFORMATION: Synthetic

<400> SEQUENCE: 367 gckgattta                                                            9

<210> SEQ ID NO 368
<211> LENGTH: 12
<212> TYPE: DNA
<213> ORGANISM: Artificial Sequence
<220> FEATURE:
<223> OTHER INFORMATION: Synthetic

<400> SEQUENCE: 368
gctaaaaaag aa                                                       12

<210> SEQ ID NO 369
<211> LENGTH: 12
<212> TYPE: DNA
<213> ORGANISM: Artificial Sequence
<220> FEATURE:
<223> OTHER INFORMATION: Synthetic

<400> SEQUENCE: 369
gctattttat ta                                                       12

<210> SEQ ID NO 370
<211> LENGTH: 12
<212> TYPE: DNA
<213> ORGANISM: Artificial Sequence
<220> FEATURE:
<223> OTHER INFORMATION: Synthetic

<400> SEQUENCE: 370
gctcgcgcga ca                                                       12

<210> SEQ ID NO 371
<211> LENGTH: 12
<212> TYPE: DNA
<213> ORGANISM: Artificial Sequence
<220> FEATURE:
<223> OTHER INFORMATION: Synthetic

<400> SEQUENCE: 371
gcttctttta ta                                                       12

<210> SEQ ID NO 372
<211> LENGTH: 12
<212> TYPE: DNA
<213> ORGANISM: Artificial Sequence
<220> FEATURE:
<223> OTHER INFORMATION: Synthetic

<400> SEQUENCE: 372
gctttttcat ca                                                       12

<210> SEQ ID NO 373
```

```
<211> LENGTH: 8
<212> TYPE: DNA
<213> ORGANISM: Artificial Sequence
<220> FEATURE:
<223> OTHER INFORMATION: Synthetic

<400> SEQUENCE: 373 ggcattac                                                                  8

<210> SEQ ID NO 374
<211> LENGTH: 9
<212> TYPE: DNA
<213> ORGANISM: Artificial Sequence
<220> FEATURE:
<223> OTHER INFORMATION: Synthetic

<400> SEQUENCE: 374 ggcggtaaa                                                                 9

<210> SEQ ID NO 375
<211> LENGTH: 9
<212> TYPE: DNA
<213> ORGANISM: Artificial Sequence
<220> FEATURE:
<223> OTHER INFORMATION: Synthetic

<400> SEQUENCE: 375 ggttgaaac                                                                 9

<210> SEQ ID NO 376
<211> LENGTH: 8
<212> TYPE: DNA
<213> ORGANISM: Artificial Sequence
<220> FEATURE:
<223> OTHER INFORMATION: Synthetic

<400> SEQUENCE: 376 ggtttaac                                                                  8

<210> SEQ ID NO 377
<211> LENGTH: 9
<212> TYPE: DNA
<213> ORGANISM: Artificial Sequence
<220> FEATURE:
<223> OTHER INFORMATION: Synthetic

<400> SEQUENCE: 377 gtaaaacga                                                                 9

<210> SEQ ID NO 378
<211> LENGTH: 12
<212> TYPE: DNA
<213> ORGANISM: Artificial Sequence
<220> FEATURE:
<223> OTHER INFORMATION: Synthetic

<400> SEQUENCE: 378
gtaaagcttt ca                                                            12

<210> SEQ ID NO 379
<211> LENGTH: 9
<212> TYPE: DNA
<213> ORGANISM: Artificial Sequence
<220> FEATURE:
<223> OTHER INFORMATION: Synthetic

<400> SEQUENCE: 379
```

```
gtgacgaaa                                                           9

<210> SEQ ID NO 380
<211> LENGTH: 9
<212> TYPE: DNA
<213> ORGANISM: Artificial Sequence
<220> FEATURE:
<223> OTHER INFORMATION: Synthetic

<400> SEQUENCE: 380 gttatcgca                                                           9

<210> SEQ ID NO 381
<211> LENGTH: 12
<212> TYPE: DNA
<213> ORGANISM: Artificial Sequence
<220> FEATURE:
<223> OTHER INFORMATION: Synthetic

<400> SEQUENCE: 381
gttgttttac ca                                                      12

<210> SEQ ID NO 382
<211> LENGTH: 9
<212> TYPE: DNA
<213> ORGANISM: Artificial Sequence
<220> FEATURE:
<223> OTHER INFORMATION: Synthetic

<400> SEQUENCE: 382 sttccgcaa                                                           9

<210> SEQ ID NO 383
<211> LENGTH: 12
<212> TYPE: DNA
<213> ORGANISM: Artificial Sequence
<220> FEATURE:
<223> OTHER INFORMATION: Synthetic

<400> SEQUENCE: 383
taaaatgggt ga                                                      12

<210> SEQ ID NO 384
<211> LENGTH: 12
<212> TYPE: DNA
<213> ORGANISM: Artificial Sequence
<220> FEATURE:
<223> OTHER INFORMATION: Synthetic

<400> SEQUENCE: 384
taaagcaatt aa                                                      12

<210> SEQ ID NO 385
<211> LENGTH: 12
<212> TYPE: DNA
<213> ORGANISM: Artificial Sequence
<220> FEATURE:
<223> OTHER INFORMATION: Synthetic

<400> SEQUENCE: 385
taaatcatct aa                                                      12

<210> SEQ ID NO 386
<211> LENGTH: 9
<212> TYPE: DNA
```

```
<213> ORGANISM: Artificial Sequence
<220> FEATURE:
<223> OTHER INFORMATION: Synthetic

<400> SEQUENCE: 386 taacgaaga                                                                  9

<210> SEQ ID NO 387
<211> LENGTH: 12
<212> TYPE: DNA
<213> ORGANISM: Artificial Sequence
<220> FEATURE:
<223> OTHER INFORMATION: Synthetic

<400> SEQUENCE: 387
taactcttct aa                                                             12

<210> SEQ ID NO 388
<211> LENGTH: 10
<212> TYPE: DNA
<213> ORGANISM: Artificial Sequence
<220> FEATURE:
<223> OTHER INFORMATION: Synthetic

<400> SEQUENCE: 388
taatgcttca                                                                10

<210> SEQ ID NO 389
<211> LENGTH: 10
<212> TYPE: DNA
<213> ORGANISM: Artificial Sequence
<220> FEATURE:
<223> OTHER INFORMATION: Synthetic

<400> SEQUENCE: 389
tacatcatca                                                                10

<210> SEQ ID NO 390
<211> LENGTH: 9
<212> TYPE: DNA
<213> ORGANISM: Artificial Sequence
<220> FEATURE:
<223> OTHER INFORMATION: Synthetic

<400> SEQUENCE: 390 tatcatcga                                                                  9

<210> SEQ ID NO 391
<211> LENGTH: 12
<212> TYPE: DNA
<213> ORGANISM: Artificial Sequence
<220> FEATURE:
<223> OTHER INFORMATION: Synthetic

<400> SEQUENCE: 391
tatcattaat aa                                                             12

<210> SEQ ID NO 392
<211> LENGTH: 12
<212> TYPE: DNA
<213> ORGANISM: Artificial Sequence
<220> FEATURE:
<223> OTHER INFORMATION: Synthetic

<400> SEQUENCE: 392
tatcctcttc ca                                                             12
```

```
<210> SEQ ID NO 393
<211> LENGTH: 12
<212> TYPE: DNA
<213> ORGANISM: Artificial Sequence
<220> FEATURE:
<223> OTHER INFORMATION: Synthetic

<400> SEQUENCE: 393
tcttctaata aa                                                         12

<210> SEQ ID NO 394
<211> LENGTH: 12
<212> TYPE: DNA
<213> ORGANISM: Artificial Sequence
<220> FEATURE:
<223> OTHER INFORMATION: Synthetic

<400> SEQUENCE: 394
tcttctaatt ca                                                         12

<210> SEQ ID NO 395
<211> LENGTH: 12
<212> TYPE: DNA
<213> ORGANISM: Artificial Sequence
<220> FEATURE:
<223> OTHER INFORMATION: Synthetic

<400> SEQUENCE: 395
tcttcttcta aa                                                         12

<210> SEQ ID NO 396
<211> LENGTH: 12
<212> TYPE: DNA
<213> ORGANISM: Artificial Sequence
<220> FEATURE:
<223> OTHER INFORMATION: Synthetic

<400> SEQUENCE: 396
tcttttttta ca                                                         12

<210> SEQ ID NO 397
<211> LENGTH: 9
<212> TYPE: DNA
<213> ORGANISM: Artificial Sequence
<220> FEATURE:
<223> OTHER INFORMATION: Synthetic

<400> SEQUENCE: 397 tgacgataa                                                              9

<210> SEQ ID NO 398
<211> LENGTH: 9
<212> TYPE: DNA
<213> ORGANISM: Artificial Sequence
<220> FEATURE:
<223> OTHER INFORMATION: Synthetic

<400> SEQUENCE: 398 tgatgcgaa                                                              9

<210> SEQ ID NO 399
<211> LENGTH: 12
<212> TYPE: DNA
<213> ORGANISM: Artificial Sequence
<220> FEATURE:
```

```
<223> OTHER INFORMATION: Synthetic

<400> SEQUENCE: 399
tgcttctttt aa                                                              12

<210> SEQ ID NO 400
<211> LENGTH: 12
<212> TYPE: DNA
<213> ORGANISM: Artificial Sequence
<220> FEATURE:
<223> OTHER INFORMATION: Synthetic

<400> SEQUENCE: 400
ttagatgaag aa                                                              12

<210> SEQ ID NO 401
<211> LENGTH: 12
<212> TYPE: DNA
<213> ORGANISM: Artificial Sequence
<220> FEATURE:
<223> OTHER INFORMATION: Synthetic

<400> SEQUENCE: 401
ttagctaaag aa                                                              12

<210> SEQ ID NO 402
<211> LENGTH: 12
<212> TYPE: DNA
<213> ORGANISM: Artificial Sequence
<220> FEATURE:
<223> OTHER INFORMATION: Synthetic

<400> SEQUENCE: 402
ttattagaag aa                                                              12

<210> SEQ ID NO 403
<211> LENGTH: 10
<212> TYPE: DNA
<213> ORGANISM: Artificial Sequence
<220> FEATURE:
<223> OTHER INFORMATION: Synthetic

<400> SEQUENCE: 403
aaaacaattg                                                                 10

<210> SEQ ID NO 404
<211> LENGTH: 10
<212> TYPE: DNA
<213> ORGANISM: Artificial Sequence
<220> FEATURE:
<223> OTHER INFORMATION: Synthetic

<400> SEQUENCE: 404
aaaacgttta                                                                 10

<210> SEQ ID NO 405
<211> LENGTH: 10
<212> TYPE: DNA
<213> ORGANISM: Artificial Sequence
<220> FEATURE:
<223> OTHER INFORMATION: Synthetic

<400> SEQUENCE: 405
aaaagaatta                                                                 10
```

```
<210> SEQ ID NO 406
<211> LENGTH: 10
<212> TYPE: DNA
<213> ORGANISM: Artificial Sequence
<220> FEATURE:
<223> OTHER INFORMATION: Synthetic

<400> SEQUENCE: 406
aaaaggtatt                                                              10

<210> SEQ ID NO 407
<211> LENGTH: 10
<212> TYPE: DNA
<213> ORGANISM: Artificial Sequence
<220> FEATURE:
<223> OTHER INFORMATION: Synthetic

<400> SEQUENCE: 407
aaaaggtgaa                                                              10

<210> SEQ ID NO 408
<211> LENGTH: 0
<212> TYPE: DNA
<213> ORGANISM: Artificial Sequence
<220> FEATURE:
<223> OTHER INFORMATION: Synthetic

<400> SEQUENCE: 408

000

<210> SEQ ID NO 409
<211> LENGTH: 12
<212> TYPE: DNA
<213> ORGANISM: Artificial Sequence
<220> FEATURE:
<223> OTHER INFORMATION: Synthetic

<400> SEQUENCE: 409
aaatcgttga ta                                                           12

<210> SEQ ID NO 410
<211> LENGTH: 11
<212> TYPE: DNA
<213> ORGANISM: Artificial Sequence
<220> FEATURE:
<223> OTHER INFORMATION: Synthetic

<400> SEQUENCE: 410
aaatggtgaa g                                                            11

<210> SEQ ID NO 411
<211> LENGTH: 10
<212> TYPE: DNA
<213> ORGANISM: Artificial Sequence
<220> FEATURE:
<223> OTHER INFORMATION: Synthetic

<400> SEQUENCE: 411
aacaccaatt                                                              10

<210> SEQ ID NO 412
<211> LENGTH: 10
<212> TYPE: DNA
<213> ORGANISM: Artificial Sequence
<220> FEATURE:
<223> OTHER INFORMATION: Synthetic
```

```
<400> SEQUENCE: 412
aacgaaagat                                                          10

<210> SEQ ID NO 413
<211> LENGTH: 12
<212> TYPE: DNA
<213> ORGANISM: Artificial Sequence
<220> FEATURE:
<223> OTHER INFORMATION: Synthetic

<400> SEQUENCE: 413
aacgaaagaa ga                                                       12

<210> SEQ ID NO 414
<211> LENGTH: 9
<212> TYPE: DNA
<213> ORGANISM: Artificial Sequence
<220> FEATURE:
<223> OTHER INFORMATION: Synthetic

<400> SEQUENCE: 414 aacgaataa                                                            9

<210> SEQ ID NO 415
<211> LENGTH: 11
<212> TYPE: DNA
<213> ORGANISM: Artificial Sequence
<220> FEATURE:
<223> OTHER INFORMATION: Synthetic

<400> SEQUENCE: 415
aagaagcgaa g                                                        11

<210> SEQ ID NO 416
<211> LENGTH: 12
<212> TYPE: DNA
<213> ORGANISM: Artificial Sequence
<220> FEATURE:
<223> OTHER INFORMATION: Synthetic

<400> SEQUENCE: 416
aagaagtaaa ag                                                       12

<210> SEQ ID NO 417
<211> LENGTH: 7
<212> TYPE: DNA
<213> ORGANISM: Artificial Sequence
<220> FEATURE:
<223> OTHER INFORMATION: Synthetic

<400> SEQUENCE: 417 aagcgga                                                              7

<210> SEQ ID NO 418
<211> LENGTH: 8
<212> TYPE: DNA
<213> ORGANISM: Artificial Sequence
<220> FEATURE:
<223> OTHER INFORMATION: Synthetic

<400> SEQUENCE: 418 aatcgcta                                                             8

<210> SEQ ID NO 419
<211> LENGTH: 10
```

```
<212> TYPE: DNA
<213> ORGANISM: Artificial Sequence
<220> FEATURE:
<223> OTHER INFORMATION: Synthetic

<400> SEQUENCE: 419
aatcgcaatt                                                              10

<210> SEQ ID NO 420
<211> LENGTH: 12
<212> TYPE: DNA
<213> ORGANISM: Artificial Sequence
<220> FEATURE:
<223> OTHER INFORMATION: Synthetic

<400> SEQUENCE: 420
aatcgcygat at                                                           12

<210> SEQ ID NO 421
<211> LENGTH: 10
<212> TYPE: DNA
<213> ORGANISM: Artificial Sequence
<220> FEATURE:
<223> OTHER INFORMATION: Synthetic

<400> SEQUENCE: 421
aatcgtttca                                                              10

<210> SEQ ID NO 422
<211> LENGTH: 9
<212> TYPE: DNA
<213> ORGANISM: Artificial Sequence
<220> FEATURE:
<223> OTHER INFORMATION: Synthetic

<400> SEQUENCE: 422 acaacgatt                                                                9

<210> SEQ ID NO 423
<211> LENGTH: 10
<212> TYPE: DNA
<213> ORGANISM: Artificial Sequence
<220> FEATURE:
<223> OTHER INFORMATION: Synthetic

<400> SEQUENCE: 423
accgataata                                                              10

<210> SEQ ID NO 424
<211> LENGTH: 9
<212> TYPE: DNA
<213> ORGANISM: Artificial Sequence
<220> FEATURE:
<223> OTHER INFORMATION: Synthetic

<400> SEQUENCE: 424 acgaagcaa                                                                9

<210> SEQ ID NO 425
<211> LENGTH: 11
<212> TYPE: DNA
<213> ORGANISM: Artificial Sequence
<220> FEATURE:
<223> OTHER INFORMATION: Synthetic

<400> SEQUENCE: 425
```
agaagcgatg a                                                                11

<210> SEQ ID NO 426
<211> LENGTH: 11
<212> TYPE: DNA
<213> ORGANISM: Artificial Sequence
<220> FEATURE:
<223> OTHER INFORMATION: Synthetic

<400> SEQUENCE: 426
agcgaaagaa g                                                                11

<210> SEQ ID NO 427
<211> LENGTH: 8
<212> TYPE: DNA
<213> ORGANISM: Artificial Sequence
<220> FEATURE:
<223> OTHER INFORMATION: Synthetic

<400> SEQUENCE: 427 atacgatg                                                                     8

<210> SEQ ID NO 428
<211> LENGTH: 8
<212> TYPE: DNA
<213> ORGANISM: Artificial Sequence
<220> FEATURE:
<223> OTHER INFORMATION: Synthetic

<400> SEQUENCE: 428 atacggaa                                                                     8

<210> SEQ ID NO 429
<211> LENGTH: 10
<212> TYPE: DNA
<213> ORGANISM: Artificial Sequence
<220> FEATURE:
<223> OTHER INFORMATION: Synthetic

<400> SEQUENCE: 429
atataaaaga                                                                  10

<210> SEQ ID NO 430
<211> LENGTH: 7
<212> TYPE: DNA
<213> ORGANISM: Artificial Sequence
<220> FEATURE:
<223> OTHER INFORMATION: Synthetic

<400> SEQUENCE: 430 atatgcg                                                                      7

<210> SEQ ID NO 431
<211> LENGTH: 10
<212> TYPE: DNA
<213> ORGANISM: Artificial Sequence
<220> FEATURE:
<223> OTHER INFORMATION: Synthetic

<400> SEQUENCE: 431
atattatcgt                                                                  10

<210> SEQ ID NO 432
<211> LENGTH: 12
<212> TYPE: DNA
<213> ORGANISM: Artificial Sequence

```
<220> FEATURE:
<223> OTHER INFORMATION: Synthetic

<400> SEQUENCE: 432
atcarcgatt tt                                                          12

<210> SEQ ID NO 433
<211> LENGTH: 8
<212> TYPE: DNA
<213> ORGANISM: Artificial Sequence
<220> FEATURE:
<223> OTHER INFORMATION: Synthetic

<400> SEQUENCE: 433 atcatacg                                                                8

<210> SEQ ID NO 434
<211> LENGTH: 8
<212> TYPE: DNA
<213> ORGANISM: Artificial Sequence
<220> FEATURE:
<223> OTHER INFORMATION: Synthetic

<400> SEQUENCE: 434 atccgtta                                                                8

<210> SEQ ID NO 435
<211> LENGTH: 8
<212> TYPE: DNA
<213> ORGANISM: Artificial Sequence
<220> FEATURE:
<223> OTHER INFORMATION: Synthetic

<400> SEQUENCE: 435 atgaagcg                                                                8

<210> SEQ ID NO 436
<211> LENGTH: 9
<212> TYPE: DNA
<213> ORGANISM: Artificial Sequence
<220> FEATURE:
<223> OTHER INFORMATION: Synthetic

<400> SEQUENCE: 436 atgtaacga                                                               9

<210> SEQ ID NO 437
<211> LENGTH: 11
<212> TYPE: DNA
<213> ORGANISM: Artificial Sequence
<220> FEATURE:
<223> OTHER INFORMATION: Synthetic

<400> SEQUENCE: 437
attaaagatg g                                                           11

<210> SEQ ID NO 438
<211> LENGTH: 8
<212> TYPE: DNA
<213> ORGANISM: Artificial Sequence
<220> FEATURE:
<223> OTHER INFORMATION: Synthetic

<400> SEQUENCE: 438 attaacgc                                                                8
```

```
<210> SEQ ID NO 439
<211> LENGTH: 10
<212> TYPE: DNA
<213> ORGANISM: Artificial Sequence
<220> FEATURE:
<223> OTHER INFORMATION: Synthetic

<400> SEQUENCE: 439
attacaaaag                                                                10

<210> SEQ ID NO 440
<211> LENGTH: 10
<212> TYPE: DNA
<213> ORGANISM: Artificial Sequence
<220> FEATURE:
<223> OTHER INFORMATION: Synthetic

<400> SEQUENCE: 440
attacgataa                                                                10

<210> SEQ ID NO 441
<211> LENGTH: 9
<212> TYPE: DNA
<213> ORGANISM: Artificial Sequence
<220> FEATURE:
<223> OTHER INFORMATION: Synthetic

<400> SEQUENCE: 441 attacgtta                                                                  9

<210> SEQ ID NO 442
<211> LENGTH: 10
<212> TYPE: DNA
<213> ORGANISM: Artificial Sequence
<220> FEATURE:
<223> OTHER INFORMATION: Synthetic

<400> SEQUENCE: 442
attacttgta                                                                10

<210> SEQ ID NO 443
<211> LENGTH: 10
<212> TYPE: DNA
<213> ORGANISM: Artificial Sequence
<220> FEATURE:
<223> OTHER INFORMATION: Synthetic

<400> SEQUENCE: 443
attatatgaa                                                                10

<210> SEQ ID NO 444
<211> LENGTH: 10
<212> TYPE: DNA
<213> ORGANISM: Artificial Sequence
<220> FEATURE:
<223> OTHER INFORMATION: Synthetic

<400> SEQUENCE: 444
attattatcg                                                                10

<210> SEQ ID NO 445
<211> LENGTH: 12
<212> TYPE: DNA
<213> ORGANISM: Artificial Sequence
<220> FEATURE:
<223> OTHER INFORMATION: Synthetic
```

```
<400> SEQUENCE: 445
attgaaaaag ca                                                        12

<210> SEQ ID NO 446
<211> LENGTH: 10
<212> TYPE: DNA
<213> ORGANISM: Artificial Sequence
<220> FEATURE:
<223> OTHER INFORMATION: Synthetic

<400> SEQUENCE: 446
attgaaacga                                                           10

<210> SEQ ID NO 447
<211> LENGTH: 10
<212> TYPE: DNA
<213> ORGANISM: Artificial Sequence
<220> FEATURE:
<223> OTHER INFORMATION: Synthetic

<400> SEQUENCE: 447
attgcttctt                                                           10

<210> SEQ ID NO 448
<211> LENGTH: 9
<212> TYPE: DNA
<213> ORGANISM: Artificial Sequence
<220> FEATURE:
<223> OTHER INFORMATION: Synthetic

<400> SEQUENCE: 448 attgtcgtt                                                             9

<210> SEQ ID NO 449
<211> LENGTH: 10
<212> TYPE: DNA
<213> ORGANISM: Artificial Sequence
<220> FEATURE:
<223> OTHER INFORMATION: Synthetic

<400> SEQUENCE: 449
atttatcgta                                                           10

<210> SEQ ID NO 450
<211> LENGTH: 10
<212> TYPE: DNA
<213> ORGANISM: Artificial Sequence
<220> FEATURE:
<223> OTHER INFORMATION: Synthetic

<400> SEQUENCE: 450
caacttcttt                                                           10

<210> SEQ ID NO 451
<211> LENGTH: 9
<212> TYPE: DNA
<213> ORGANISM: Artificial Sequence
<220> FEATURE:
<223> OTHER INFORMATION: Synthetic

<400> SEQUENCE: 451 caatcgtat                                                             9

<210> SEQ ID NO 452
```

```
<211> LENGTH: 10
<212> TYPE: DNA
<213> ORGANISM: Artificial Sequence
<220> FEATURE:
<223> OTHER INFORMATION: Synthetic

<400> SEQUENCE: 452
caattaatac                                                            10

<210> SEQ ID NO 453
<211> LENGTH: 10
<212> TYPE: DNA
<213> ORGANISM: Artificial Sequence
<220> FEATURE:
<223> OTHER INFORMATION: Synthetic

<400> SEQUENCE: 453
caattggaat                                                            10

<210> SEQ ID NO 454
<211> LENGTH: 10
<212> TYPE: DNA
<213> ORGANISM: Artificial Sequence
<220> FEATURE:
<223> OTHER INFORMATION: Synthetic

<400> SEQUENCE: 454
caccaattac                                                            10

<210> SEQ ID NO 455
<211> LENGTH: 10
<212> TYPE: DNA
<213> ORGANISM: Artificial Sequence
<220> FEATURE:
<223> OTHER INFORMATION: Synthetic

<400> SEQUENCE: 455
caccaattgt                                                            10

<210> SEQ ID NO 456
<211> LENGTH: 11
<212> TYPE: DNA
<213> ORGANISM: Artificial Sequence
<220> FEATURE:
<223> OTHER INFORMATION: Synthetic

<400> SEQUENCE: 456 cacctttac a                                                           11

<210> SEQ ID NO 457
<211> LENGTH: 8
<212> TYPE: DNA
<213> ORGANISM: Artificial Sequence
<220> FEATURE:
<223> OTHER INFORMATION: Synthetic

<400> SEQUENCE: 457 catacgaa                                                               8

<210> SEQ ID NO 458
<211> LENGTH: 9
<212> TYPE: DNA
<213> ORGANISM: Artificial Sequence
<220> FEATURE:
<223> OTHER INFORMATION: Synthetic

<400> SEQUENCE: 458
```

-continued

```
catataacg                                                          9

<210> SEQ ID NO 459
<211> LENGTH: 11
<212> TYPE: DNA
<213> ORGANISM: Artificial Sequence
<220> FEATURE:
<223> OTHER INFORMATION: Synthetic

<400> SEQUENCE: 459
catcaattgt t                                                       11

<210> SEQ ID NO 460
<211> LENGTH: 7
<212> TYPE: DNA
<213> ORGANISM: Artificial Sequence
<220> FEATURE:
<223> OTHER INFORMATION: Synthetic

<400> SEQUENCE: 460 ccgcttt                                                            7

<210> SEQ ID NO 461
<211> LENGTH: 12
<212> TYPE: DNA
<213> ORGANISM: Artificial Sequence
<220> FEATURE:
<223> OTHER INFORMATION: Synthetic

<400> SEQUENCE: 461
cgacttaccg ac                                                      12

<210> SEQ ID NO 462
<211> LENGTH: 7
<212> TYPE: DNA
<213> ORGANISM: Artificial Sequence
<220> FEATURE:
<223> OTHER INFORMATION: Synthetic

<400> SEQUENCE: 462 cgataac                                                            7

<210> SEQ ID NO 463
<211> LENGTH: 10
<212> TYPE: DNA
<213> ORGANISM: Artificial Sequence
<220> FEATURE:
<223> OTHER INFORMATION: Synthetic

<400> SEQUENCE: 463
cgataaagaa                                                         10

<210> SEQ ID NO 464
<211> LENGTH: 11
<212> TYPE: DNA
<213> ORGANISM: Artificial Sequence
<220> FEATURE:
<223> OTHER INFORMATION: Synthetic

<400> SEQUENCE: 464
cgatataatt t                                                       11

<210> SEQ ID NO 465
<211> LENGTH: 7
<212> TYPE: DNA
```

```
<213> ORGANISM: Artificial Sequence
<220> FEATURE:
<223> OTHER INFORMATION: Synthetic

<400> SEQUENCE: 465 cgatgta                                                                 7

<210> SEQ ID NO 466
<211> LENGTH: 9
<212> TYPE: DNA
<213> ORGANISM: Artificial Sequence
<220> FEATURE:
<223> OTHER INFORMATION: Synthetic

<400> SEQUENCE: 466 cgattgaag                                                               9

<210> SEQ ID NO 467
<211> LENGTH: 11
<212> TYPE: DNA
<213> ORGANISM: Artificial Sequence
<220> FEATURE:
<223> OTHER INFORMATION: Synthetic

<400> SEQUENCE: 467
cgatttttca a                                                           11

<210> SEQ ID NO 468
<211> LENGTH: 7
<212> TYPE: DNA
<213> ORGANISM: Artificial Sequence
<220> FEATURE:
<223> OTHER INFORMATION: Synthetic

<400> SEQUENCE: 468 cgcaata                                                                 7

<210> SEQ ID NO 469
<211> LENGTH: 11
<212> TYPE: DNA
<213> ORGANISM: Artificial Sequence
<220> FEATURE:
<223> OTHER INFORMATION: Synthetic

<400> SEQUENCE: 469 cgcttttat t                                                            11

<210> SEQ ID NO 470
<211> LENGTH: 7
<212> TYPE: DNA
<213> ORGANISM: Artificial Sequence
<220> FEATURE:
<223> OTHER INFORMATION: Synthetic

<400> SEQUENCE: 470 cggatat                                                                 7

<210> SEQ ID NO 471
<211> LENGTH: 8
<212> TYPE: DNA
<213> ORGANISM: Artificial Sequence
<220> FEATURE:
<223> OTHER INFORMATION: Synthetic

<400> SEQUENCE: 471 cggtaaat                                                                8
```

<210> SEQ ID NO 472
<211> LENGTH: 9
<212> TYPE: DNA
<213> ORGANISM: Artificial Sequence
<220> FEATURE:
<223> OTHER INFORMATION: Synthetic

<400> SEQUENCE: 472 cggtttaat                                                                  9

<210> SEQ ID NO 473
<211> LENGTH: 8
<212> TYPE: DNA
<213> ORGANISM: Artificial Sequence
<220> FEATURE:
<223> OTHER INFORMATION: Synthetic

<400> SEQUENCE: 473 cgtaatat                                                                   8

<210> SEQ ID NO 474
<211> LENGTH: 8
<212> TYPE: DNA
<213> ORGANISM: Artificial Sequence
<220> FEATURE:
<223> OTHER INFORMATION: Synthetic

<400> SEQUENCE: 474 cgtataac                                                                   8

<210> SEQ ID NO 475
<211> LENGTH: 9
<212> TYPE: DNA
<213> ORGANISM: Artificial Sequence
<220> FEATURE:
<223> OTHER INFORMATION: Synthetic

<400> SEQUENCE: 475 cgttaattg                                                                  9

<210> SEQ ID NO 476
<211> LENGTH: 9
<212> TYPE: DNA
<213> ORGANISM: Artificial Sequence
<220> FEATURE:
<223> OTHER INFORMATION: Synthetic

<400> SEQUENCE: 476 cgttatgaa                                                                  9

<210> SEQ ID NO 477
<211> LENGTH: 8
<212> TYPE: DNA
<213> ORGANISM: Artificial Sequence
<220> FEATURE:
<223> OTHER INFORMATION: Synthetic

<400> SEQUENCE: 477 ctatcgta                                                                   8

<210> SEQ ID NO 478
<211> LENGTH: 12
<212> TYPE: DNA
<213> ORGANISM: Artificial Sequence
<220> FEATURE:

<223> OTHER INFORMATION: Synthetic

<400> SEQUENCE: 478
ctgattaaag tt                                                           12

<210> SEQ ID NO 479
<211> LENGTH: 10
<212> TYPE: DNA
<213> ORGANISM: Artificial Sequence
<220> FEATURE:
<223> OTHER INFORMATION: Synthetic

<400> SEQUENCE: 479
cttccataat                                                              10

<210> SEQ ID NO 480
<211> LENGTH: 8
<212> TYPE: DNA
<213> ORGANISM: Artificial Sequence
<220> FEATURE:
<223> OTHER INFORMATION: Synthetic

<400> SEQUENCE: 480 cttcgtaa                                                                 8

<210> SEQ ID NO 481
<211> LENGTH: 10
<212> TYPE: DNA
<213> ORGANISM: Artificial Sequence
<220> FEATURE:
<223> OTHER INFORMATION: Synthetic

<400> SEQUENCE: 481
cttctatata                                                              10

<210> SEQ ID NO 482
<211> LENGTH: 10
<212> TYPE: DNA
<213> ORGANISM: Artificial Sequence
<220> FEATURE:
<223> OTHER INFORMATION: Synthetic

<400> SEQUENCE: 482
cttctgcaat                                                              10

<210> SEQ ID NO 483
<211> LENGTH: 10
<212> TYPE: DNA
<213> ORGANISM: Artificial Sequence
<220> FEATURE:
<223> OTHER INFORMATION: Synthetic

<400> SEQUENCE: 483
cttcttcacg                                                              10

<210> SEQ ID NO 484
<211> LENGTH: 12
<212> TYPE: DNA
<213> ORGANISM: Artificial Sequence
<220> FEATURE:
<223> OTHER INFORMATION: Synthetic

<400> SEQUENCE: 484
cttcttcttt cg                                                           12

```
<210> SEQ ID NO 485
<211> LENGTH: 10
<212> TYPE: DNA
<213> ORGANISM: Artificial Sequence
<220> FEATURE:
<223> OTHER INFORMATION: Synthetic

<400> SEQUENCE: 485
cttctttaat                                                              10

<210> SEQ ID NO 486
<211> LENGTH: 0
<212> TYPE: DNA
<213> ORGANISM: Artificial Sequence
<220> FEATURE:
<223> OTHER INFORMATION: Synthetic

<400> SEQUENCE: 486

000

<210> SEQ ID NO 487
<211> LENGTH: 11
<212> TYPE: DNA
<213> ORGANISM: Artificial Sequence
<220> FEATURE:
<223> OTHER INFORMATION: Synthetic

<400> SEQUENCE: 487
cttctttcgg a                                                            11

<210> SEQ ID NO 488
<211> LENGTH: 10
<212> TYPE: DNA
<213> ORGANISM: Artificial Sequence
<220> FEATURE:
<223> OTHER INFORMATION: Synthetic

<400> SEQUENCE: 488
ctttcgcttt                                                              10

<210> SEQ ID NO 489
<211> LENGTH: 12
<212> TYPE: DNA
<213> ORGANISM: Artificial Sequence
<220> FEATURE:
<223> OTHER INFORMATION: Synthetic

<400> SEQUENCE: 489
ctttcgcttc tt                                                           12

<210> SEQ ID NO 490
<211> LENGTH: 12
<212> TYPE: DNA
<213> ORGANISM: Artificial Sequence
<220> FEATURE:
<223> OTHER INFORMATION: Synthetic

<400> SEQUENCE: 490
cttttaattc tt                                                           12

<210> SEQ ID NO 491
<211> LENGTH: 11
<212> TYPE: DNA
<213> ORGANISM: Artificial Sequence
<220> FEATURE:
<223> OTHER INFORMATION: Synthetic
```

```
<400> SEQUENCE: 491
cttttgtaat a                                                    11

<210> SEQ ID NO 492
<211> LENGTH: 10
<212> TYPE: DNA
<213> ORGANISM: Artificial Sequence
<220> FEATURE:
<223> OTHER INFORMATION: Synthetic

<400> SEQUENCE: 492
cttttcgta                                                       10

<210> SEQ ID NO 493
<211> LENGTH: 10
<212> TYPE: DNA
<213> ORGANISM: Artificial Sequence
<220> FEATURE:
<223> OTHER INFORMATION: Synthetic

<400> SEQUENCE: 493
ctttttcat                                                       10

<210> SEQ ID NO 494
<211> LENGTH: 10
<212> TYPE: DNA
<213> ORGANISM: Artificial Sequence
<220> FEATURE:
<223> OTHER INFORMATION: Synthetic

<400> SEQUENCE: 494 cttttyatc                                                       10

<210> SEQ ID NO 495
<211> LENGTH: 10
<212> TYPE: DNA
<213> ORGANISM: Artificial Sequence
<220> FEATURE:
<223> OTHER INFORMATION: Synthetic

<400> SEQUENCE: 495
gaaacgattg                                                      10

<210> SEQ ID NO 496
<211> LENGTH: 12
<212> TYPE: DNA
<213> ORGANISM: Artificial Sequence
<220> FEATURE:
<223> OTHER INFORMATION: Synthetic

<400> SEQUENCE: 496
gaagaagcga aa                                                   12

<210> SEQ ID NO 497
<211> LENGTH: 10
<212> TYPE: DNA
<213> ORGANISM: Artificial Sequence
<220> FEATURE:
<223> OTHER INFORMATION: Synthetic

<400> SEQUENCE: 497
gaagaagtaa                                                      10

<210> SEQ ID NO 498
<211> LENGTH: 11
```

-continued

```
<212> TYPE: DNA
<213> ORGANISM: Artificial Sequence
<220> FEATURE:
<223> OTHER INFORMATION: Synthetic

<400> SEQUENCE: 498
gaagaagtag c                                                          11

<210> SEQ ID NO 499
<211> LENGTH: 10
<212> TYPE: DNA
<213> ORGANISM: Artificial Sequence
<220> FEATURE:
<223> OTHER INFORMATION: Synthetic

<400> SEQUENCE: 499
gatacgaaag                                                            10

<210> SEQ ID NO 500
<211> LENGTH: 10
<212> TYPE: DNA
<213> ORGANISM: Artificial Sequence
<220> FEATURE:
<223> OTHER INFORMATION: Synthetic

<400> SEQUENCE: 500
gatgaattag                                                            10

<210> SEQ ID NO 501
<211> LENGTH: 7
<212> TYPE: DNA
<213> ORGANISM: Artificial Sequence
<220> FEATURE:
<223> OTHER INFORMATION: Synthetic

<400> SEQUENCE: 501 gattacg                                                                7

<210> SEQ ID NO 502
<211> LENGTH: 12
<212> TYPE: DNA
<213> ORGANISM: Artificial Sequence
<220> FEATURE:
<223> OTHER INFORMATION: Synthetic

<400> SEQUENCE: 502
gattaaagtt tc                                                         12

<210> SEQ ID NO 503
<211> LENGTH: 12
<212> TYPE: DNA
<213> ORGANISM: Artificial Sequence
<220> FEATURE:
<223> OTHER INFORMATION: Synthetic

<400> SEQUENCE: 503
gcaattgaaa aa                                                         12

<210> SEQ ID NO 504
<211> LENGTH: 10
<212> TYPE: DNA
<213> ORGANISM: Artificial Sequence
<220> FEATURE:
<223> OTHER INFORMATION: Synthetic

<400> SEQUENCE: 504
```

```
gcaattgtat                                                              10

<210> SEQ ID NO 505
<211> LENGTH: 10
<212> TYPE: DNA
<213> ORGANISM: Artificial Sequence
<220> FEATURE:
<223> OTHER INFORMATION: Synthetic

<400> SEQUENCE: 505
gcaattgttg                                                              10

<210> SEQ ID NO 506
<211> LENGTH: 11
<212> TYPE: DNA
<213> ORGANISM: Artificial Sequence
<220> FEATURE:
<223> OTHER INFORMATION: Synthetic

<400> SEQUENCE: 506
gcgaaagaag c                                                            11

<210> SEQ ID NO 507
<211> LENGTH: 8
<212> TYPE: DNA
<213> ORGANISM: Artificial Sequence
<220> FEATURE:
<223> OTHER INFORMATION: Synthetic

<400> SEQUENCE: 507 gcgtaata                                                                 8

<210> SEQ ID NO 508
<211> LENGTH: 10
<212> TYPE: DNA
<213> ORGANISM: Artificial Sequence
<220> FEATURE:
<223> OTHER INFORMATION: Synthetic

<400> SEQUENCE: 508
gctactttat                                                              10

<210> SEQ ID NO 509
<211> LENGTH: 10
<212> TYPE: DNA
<213> ORGANISM: Artificial Sequence
<220> FEATURE:
<223> OTHER INFORMATION: Synthetic

<400> SEQUENCE: 509
gcttctttcg                                                              10

<210> SEQ ID NO 510
<211> LENGTH: 12
<212> TYPE: DNA
<213> ORGANISM: Artificial Sequence
<220> FEATURE:
<223> OTHER INFORMATION: Synthetic

<400> SEQUENCE: 510 gctttttta tt                                                            12

<210> SEQ ID NO 511
<211> LENGTH: 11
<212> TYPE: DNA
<213> ORGANISM: Artificial Sequence
```

```
<220> FEATURE:
<223> OTHER INFORMATION: Synthetic

<400> SEQUENCE: 511
gtattaaaag a                                                                11

<210> SEQ ID NO 512
<211> LENGTH: 10
<212> TYPE: DNA
<213> ORGANISM: Artificial Sequence
<220> FEATURE:
<223> OTHER INFORMATION: Synthetic

<400> SEQUENCE: 512
gttaattgaa                                                                  10

<210> SEQ ID NO 513
<211> LENGTH: 7
<212> TYPE: DNA
<213> ORGANISM: Artificial Sequence
<220> FEATURE:
<223> OTHER INFORMATION: Synthetic

<400> SEQUENCE: 513 gttcgta                                                                     7

<210> SEQ ID NO 514
<211> LENGTH: 7
<212> TYPE: DNA
<213> ORGANISM: Artificial Sequence
<220> FEATURE:
<223> OTHER INFORMATION: Synthetic

<400> SEQUENCE: 514 gttgcga                                                                     7

<210> SEQ ID NO 515
<211> LENGTH: 11
<212> TYPE: DNA
<213> ORGANISM: Artificial Sequence
<220> FEATURE:
<223> OTHER INFORMATION: Synthetic

<400> SEQUENCE: 515
taaagataat g                                                                11

<210> SEQ ID NO 516
<211> LENGTH: 9
<212> TYPE: DNA
<213> ORGANISM: Artificial Sequence
<220> FEATURE:
<223> OTHER INFORMATION: Synthetic

<400> SEQUENCE: 516 taaagcgtt                                                                   9

<210> SEQ ID NO 517
<211> LENGTH: 12
<212> TYPE: DNA
<213> ORGANISM: Artificial Sequence
<220> FEATURE:
<223> OTHER INFORMATION: Synthetic

<400> SEQUENCE: 517
taaagtgaaa ct                                                               12
```

```
<210> SEQ ID NO 518
<211> LENGTH: 11
<212> TYPE: DNA
<213> ORGANISM: Artificial Sequence
<220> FEATURE:
<223> OTHER INFORMATION: Synthetic

<400> SEQUENCE: 518
taaatcttct a                                                              11

<210> SEQ ID NO 519
<211> LENGTH: 10
<212> TYPE: DNA
<213> ORGANISM: Artificial Sequence
<220> FEATURE:
<223> OTHER INFORMATION: Synthetic

<400> SEQUENCE: 519
taacagaaga                                                                10

<210> SEQ ID NO 520
<211> LENGTH: 12
<212> TYPE: DNA
<213> ORGANISM: Artificial Sequence
<220> FEATURE:
<223> OTHER INFORMATION: Synthetic

<400> SEQUENCE: 520
taacgaaaga ag                                                             12

<210> SEQ ID NO 521
<211> LENGTH: 9
<212> TYPE: DNA
<213> ORGANISM: Artificial Sequence
<220> FEATURE:
<223> OTHER INFORMATION: Synthetic

<400> SEQUENCE: 521 taacggaaa                                                                  9

<210> SEQ ID NO 522
<211> LENGTH: 11
<212> TYPE: DNA
<213> ORGANISM: Artificial Sequence
<220> FEATURE:
<223> OTHER INFORMATION: Synthetic

<400> SEQUENCE: 522
taactcttct t                                                              11

<210> SEQ ID NO 523
<211> LENGTH: 8
<212> TYPE: DNA
<213> ORGANISM: Artificial Sequence
<220> FEATURE:
<223> OTHER INFORMATION: Synthetic

<400> SEQUENCE: 523 taatamcg                                                                   8

<210> SEQ ID NO 524
<211> LENGTH: 8
<212> TYPE: DNA
<213> ORGANISM: Artificial Sequence
<220> FEATURE:
<223> OTHER INFORMATION: Synthetic
```

```
<400> SEQUENCE: 524 taatcgya                                                               8

<210> SEQ ID NO 525
<211> LENGTH: 10
<212> TYPE: DNA
<213> ORGANISM: Artificial Sequence
<220> FEATURE:
<223> OTHER INFORMATION: Synthetic

<400> SEQUENCE: 525
taatgaagaa                                                            10

<210> SEQ ID NO 526
<211> LENGTH: 10
<212> TYPE: DNA
<213> ORGANISM: Artificial Sequence
<220> FEATURE:
<223> OTHER INFORMATION: Synthetic

<400> SEQUENCE: 526
taattgcttc                                                            10

<210> SEQ ID NO 527
<211> LENGTH: 10
<212> TYPE: DNA
<213> ORGANISM: Artificial Sequence
<220> FEATURE:
<223> OTHER INFORMATION: Synthetic

<400> SEQUENCE: 527
tacaatttca                                                            10

<210> SEQ ID NO 528
<211> LENGTH: 8
<212> TYPE: DNA
<213> ORGANISM: Artificial Sequence
<220> FEATURE:
<223> OTHER INFORMATION: Synthetic

<400> SEQUENCE: 528 taccgtta                                                               8

<210> SEQ ID NO 529
<211> LENGTH: 11
<212> TYPE: DNA
<213> ORGANISM: Artificial Sequence
<220> FEATURE:
<223> OTHER INFORMATION: Synthetic

<400> SEQUENCE: 529
tacgaaagaa g                                                          11

<210> SEQ ID NO 530
<211> LENGTH: 10
<212> TYPE: DNA
<213> ORGANISM: Artificial Sequence
<220> FEATURE:
<223> OTHER INFORMATION: Synthetic

<400> SEQUENCE: 530
tacgaatgat                                                            10

<210> SEQ ID NO 531
```

```
<211> LENGTH: 8
<212> TYPE: DNA
<213> ORGANISM: Artificial Sequence
<220> FEATURE:
<223> OTHER INFORMATION: Synthetic

<400> SEQUENCE: 531 tactcgtt                                                                  8

<210> SEQ ID NO 532
<211> LENGTH: 10
<212> TYPE: DNA
<213> ORGANISM: Artificial Sequence
<220> FEATURE:
<223> OTHER INFORMATION: Synthetic

<400> SEQUENCE: 532
tagaagaagt                                                               10

<210> SEQ ID NO 533
<211> LENGTH: 11
<212> TYPE: DNA
<213> ORGANISM: Artificial Sequence
<220> FEATURE:
<223> OTHER INFORMATION: Synthetic

<400> SEQUENCE: 533
tagaagaagc g                                                             11

<210> SEQ ID NO 534
<211> LENGTH: 9
<212> TYPE: DNA
<213> ORGANISM: Artificial Sequence
<220> FEATURE:
<223> OTHER INFORMATION: Synthetic

<400> SEQUENCE: 534 tagaagcga                                                                 9

<210> SEQ ID NO 535
<211> LENGTH: 12
<212> TYPE: DNA
<213> ORGANISM: Artificial Sequence
<220> FEATURE:
<223> OTHER INFORMATION: Synthetic

<400> SEQUENCE: 535
tatatcgact ta                                                            12

<210> SEQ ID NO 536
<211> LENGTH: 12
<212> TYPE: DNA
<213> ORGANISM: Artificial Sequence
<220> FEATURE:
<223> OTHER INFORMATION: Synthetic

<400> SEQUENCE: 536
tatatcrgcg at                                                            12

<210> SEQ ID NO 537
<211> LENGTH: 12
<212> TYPE: DNA
<213> ORGANISM: Artificial Sequence
<220> FEATURE:
<223> OTHER INFORMATION: Synthetic

<400> SEQUENCE: 537
```
tatcggcgat tt                                                           12

<210> SEQ ID NO 538
<211> LENGTH: 9
<212> TYPE: DNA
<213> ORGANISM: Artificial Sequence
<220> FEATURE:
<223> OTHER INFORMATION: Synthetic

<400> SEQUENCE: 538 tatgtaacg                                                                9

<210> SEQ ID NO 539
<211> LENGTH: 8
<212> TYPE: DNA
<213> ORGANISM: Artificial Sequence
<220> FEATURE:
<223> OTHER INFORMATION: Synthetic

<400> SEQUENCE: 539 tattagcg                                                                 8

<210> SEQ ID NO 540
<211> LENGTH: 8
<212> TYPE: DNA
<213> ORGANISM: Artificial Sequence
<220> FEATURE:
<223> OTHER INFORMATION: Synthetic

<400> SEQUENCE: 540 tattcgct                                                                 8

<210> SEQ ID NO 541
<211> LENGTH: 10
<212> TYPE: DNA
<213> ORGANISM: Artificial Sequence
<220> FEATURE:
<223> OTHER INFORMATION: Synthetic

<400> SEQUENCE: 541
tattgatgaa                                                              10

<210> SEQ ID NO 542
<211> LENGTH: 10
<212> TYPE: DNA
<213> ORGANISM: Artificial Sequence
<220> FEATURE:
<223> OTHER INFORMATION: Synthetic

<400> SEQUENCE: 542 tawtacgaaa                                                              10

<210> SEQ ID NO 543
<211> LENGTH: 10
<212> TYPE: DNA
<213> ORGANISM: Artificial Sequence
<220> FEATURE:
<223> OTHER INFORMATION: Synthetic

<400> SEQUENCE: 543
tcaattgcaa                                                              10

<210> SEQ ID NO 544
<211> LENGTH: 11
<212> TYPE: DNA

```
<213> ORGANISM: Artificial Sequence
<220> FEATURE:
<223> OTHER INFORMATION: Synthetic

<400> SEQUENCE: 544
tcaattgctt c                                                          11

<210> SEQ ID NO 545
<211> LENGTH: 9
<212> TYPE: DNA
<213> ORGANISM: Artificial Sequence
<220> FEATURE:
<223> OTHER INFORMATION: Synthetic

<400> SEQUENCE: 545 tcattacga                                                              9

<210> SEQ ID NO 546
<211> LENGTH: 10
<212> TYPE: DNA
<213> ORGANISM: Artificial Sequence
<220> FEATURE:
<223> OTHER INFORMATION: Synthetic

<400> SEQUENCE: 546
tccaattgaa                                                            10

<210> SEQ ID NO 547
<211> LENGTH: 10
<212> TYPE: DNA
<213> ORGANISM: Artificial Sequence
<220> FEATURE:
<223> OTHER INFORMATION: Synthetic

<400> SEQUENCE: 547
tccgaaagaa                                                            10

<210> SEQ ID NO 548
<211> LENGTH: 8
<212> TYPE: DNA
<213> ORGANISM: Artificial Sequence
<220> FEATURE:
<223> OTHER INFORMATION: Synthetic

<400> SEQUENCE: 548 tccgctaa                                                               8

<210> SEQ ID NO 549
<211> LENGTH: 7
<212> TYPE: DNA
<213> ORGANISM: Artificial Sequence
<220> FEATURE:
<223> OTHER INFORMATION: Synthetic

<400> SEQUENCE: 549 tccgtat                                                                7

<210> SEQ ID NO 550
<211> LENGTH: 10
<212> TYPE: DNA
<213> ORGANISM: Artificial Sequence
<220> FEATURE:
<223> OTHER INFORMATION: Synthetic

<400> SEQUENCE: 550
tcctgttaca                                                            10
```

<210> SEQ ID NO 551
<211> LENGTH: 7
<212> TYPE: DNA
<213> ORGANISM: Artificial Sequence
<220> FEATURE:
<223> OTHER INFORMATION: Synthetic

<400> SEQUENCE: 551 tcgcata                                                                 7

<210> SEQ ID NO 552
<211> LENGTH: 10
<212> TYPE: DNA
<213> ORGANISM: Artificial Sequence
<220> FEATURE:
<223> OTHER INFORMATION: Synthetic

<400> SEQUENCE: 552
tcgctttatt                                                             10

<210> SEQ ID NO 553
<211> LENGTH: 8
<212> TYPE: DNA
<213> ORGANISM: Artificial Sequence
<220> FEATURE:
<223> OTHER INFORMATION: Synthetic

<400> SEQUENCE: 553 tcgtattg                                                                8

<210> SEQ ID NO 554
<211> LENGTH: 10
<212> TYPE: DNA
<213> ORGANISM: Artificial Sequence
<220> FEATURE:
<223> OTHER INFORMATION: Synthetic

<400> SEQUENCE: 554
tcgttacaat                                                             10

<210> SEQ ID NO 555
<211> LENGTH: 10
<212> TYPE: DNA
<213> ORGANISM: Artificial Sequence
<220> FEATURE:
<223> OTHER INFORMATION: Synthetic

<400> SEQUENCE: 555
tctacaatta                                                             10

<210> SEQ ID NO 556
<211> LENGTH: 10
<212> TYPE: DNA
<213> ORGANISM: Artificial Sequence
<220> FEATURE:
<223> OTHER INFORMATION: Synthetic

<400> SEQUENCE: 556
tctactaatt                                                             10

<210> SEQ ID NO 557
<211> LENGTH: 10
<212> TYPE: DNA
<213> ORGANISM: Artificial Sequence
<220> FEATURE:

<223> OTHER INFORMATION: Synthetic

<400> SEQUENCE: 557
tcttcaatat                                                            10

<210> SEQ ID NO 558
<211> LENGTH: 10
<212> TYPE: DNA
<213> ORGANISM: Artificial Sequence
<220> FEATURE:
<223> OTHER INFORMATION: Synthetic

<400> SEQUENCE: 558
tcttctaacg                                                            10

<210> SEQ ID NO 559
<211> LENGTH: 10
<212> TYPE: DNA
<213> ORGANISM: Artificial Sequence
<220> FEATURE:
<223> OTHER INFORMATION: Synthetic

<400> SEQUENCE: 559
tctttatatg                                                            10

<210> SEQ ID NO 560
<211> LENGTH: 11
<212> TYPE: DNA
<213> ORGANISM: Artificial Sequence
<220> FEATURE:
<223> OTHER INFORMATION: Synthetic

<400> SEQUENCE: 560
tctttatatt c                                                          11

<210> SEQ ID NO 561
<211> LENGTH: 10
<212> TYPE: DNA
<213> ORGANISM: Artificial Sequence
<220> FEATURE:
<223> OTHER INFORMATION: Synthetic

<400> SEQUENCE: 561
tctttcgcta                                                            10

<210> SEQ ID NO 562
<211> LENGTH: 11
<212> TYPE: DNA
<213> ORGANISM: Artificial Sequence
<220> FEATURE:
<223> OTHER INFORMATION: Synthetic

<400> SEQUENCE: 562
tcttttttcg c                                                          11

<210> SEQ ID NO 563
<211> LENGTH: 10
<212> TYPE: DNA
<213> ORGANISM: Artificial Sequence
<220> FEATURE:
<223> OTHER INFORMATION: Synthetic

<400> SEQUENCE: 563
tgaaaaagcg                                                            10

```
<210> SEQ ID NO 564
<211> LENGTH: 11
<212> TYPE: DNA
<213> ORGANISM: Artificial Sequence
<220> FEATURE:
<223> OTHER INFORMATION: Synthetic

<400> SEQUENCE: 564
tgaaacaatt g                                                            11

<210> SEQ ID NO 565
<211> LENGTH: 10
<212> TYPE: DNA
<213> ORGANISM: Artificial Sequence
<220> FEATURE:
<223> OTHER INFORMATION: Synthetic

<400> SEQUENCE: 565
tgaaacgaat                                                              10

<210> SEQ ID NO 566
<211> LENGTH: 10
<212> TYPE: DNA
<213> ORGANISM: Artificial Sequence
<220> FEATURE:
<223> OTHER INFORMATION: Synthetic

<400> SEQUENCE: 566
tgaagcgatt                                                              10

<210> SEQ ID NO 567
<211> LENGTH: 7
<212> TYPE: DNA
<213> ORGANISM: Artificial Sequence
<220> FEATURE:
<223> OTHER INFORMATION: Synthetic

<400> SEQUENCE: 567 tgcaacg                                                                  7

<210> SEQ ID NO 568
<211> LENGTH: 11
<212> TYPE: DNA
<213> ORGANISM: Artificial Sequence
<220> FEATURE:
<223> OTHER INFORMATION: Synthetic

<400> SEQUENCE: 568
tgcgaaagaa a                                                            11

<210> SEQ ID NO 569
<211> LENGTH: 11
<212> TYPE: DNA
<213> ORGANISM: Artificial Sequence
<220> FEATURE:
<223> OTHER INFORMATION: Synthetic

<400> SEQUENCE: 569
tgcttcttct a                                                            11

<210> SEQ ID NO 570
<211> LENGTH: 10
<212> TYPE: DNA
<213> ORGANISM: Artificial Sequence
<220> FEATURE:
<223> OTHER INFORMATION: Synthetic
```

<400> SEQUENCE: 570
tgtaaaaggt                                                                    10

<210> SEQ ID NO 571
<211> LENGTH: 12
<212> TYPE: DNA
<213> ORGANISM: Artificial Sequence
<220> FEATURE:
<223> OTHER INFORMATION: Synthetic

<400> SEQUENCE: 571
tgtcggtaag tc                                                                 12

<210> SEQ ID NO 572
<211> LENGTH: 11
<212> TYPE: DNA
<213> ORGANISM: Artificial Sequence
<220> FEATURE:
<223> OTHER INFORMATION: Synthetic

<400> SEQUENCE: 572
tgttctttcg t                                                                  11

<210> SEQ ID NO 573
<211> LENGTH: 11
<212> TYPE: DNA
<213> ORGANISM: Artificial Sequence
<220> FEATURE:
<223> OTHER INFORMATION: Synthetic

<400> SEQUENCE: 573
ttaacgaaag a                                                                  11

<210> SEQ ID NO 574
<211> LENGTH: 9
<212> TYPE: DNA
<213> ORGANISM: Artificial Sequence
<220> FEATURE:
<223> OTHER INFORMATION: Synthetic

<400> SEQUENCE: 574 ttaacggaa                                                                      9

<210> SEQ ID NO 575
<211> LENGTH: 10
<212> TYPE: DNA
<213> ORGANISM: Artificial Sequence
<220> FEATURE:
<223> OTHER INFORMATION: Synthetic

<400> SEQUENCE: 575
ttacgaaaga                                                                    10

<210> SEQ ID NO 576
<211> LENGTH: 10
<212> TYPE: DNA
<213> ORGANISM: Artificial Sequence
<220> FEATURE:
<223> OTHER INFORMATION: Synthetic

<400> SEQUENCE: 576
ttagaagatg                                                                    10

<210> SEQ ID NO 577
<211> LENGTH: 10

```
<212> TYPE: DNA
<213> ORGANISM: Artificial Sequence
<220> FEATURE:
<223> OTHER INFORMATION: Synthetic

<400> SEQUENCE: 577
ttattatcgg                                                          10

<210> SEQ ID NO 578
<211> LENGTH: 9
<212> TYPE: DNA
<213> ORGANISM: Artificial Sequence
<220> FEATURE:
<223> OTHER INFORMATION: Synthetic

<400> SEQUENCE: 578 ttcaatacg                                                            9

<210> SEQ ID NO 579
<211> LENGTH: 10
<212> TYPE: DNA
<213> ORGANISM: Artificial Sequence
<220> FEATURE:
<223> OTHER INFORMATION: Synthetic

<400> SEQUENCE: 579
ttcacgaata                                                          10

<210> SEQ ID NO 580
<211> LENGTH: 8
<212> TYPE: DNA
<213> ORGANISM: Artificial Sequence
<220> FEATURE:
<223> OTHER INFORMATION: Synthetic

<400> SEQUENCE: 580 ttccgtaa                                                             8

<210> SEQ ID NO 581
<211> LENGTH: 10
<212> TYPE: DNA
<213> ORGANISM: Artificial Sequence
<220> FEATURE:
<223> OTHER INFORMATION: Synthetic

<400> SEQUENCE: 581
ttcgtaaatt                                                          10

<210> SEQ ID NO 582
<211> LENGTH: 9
<212> TYPE: DNA
<213> ORGANISM: Artificial Sequence
<220> FEATURE:
<223> OTHER INFORMATION: Synthetic

<400> SEQUENCE: 582 ttctttacg                                                            9

<210> SEQ ID NO 583
<211> LENGTH: 10
<212> TYPE: DNA
<213> ORGANISM: Artificial Sequence
<220> FEATURE:
<223> OTHER INFORMATION: Synthetic

<400> SEQUENCE: 583
```
ttctttcgca                                                              10

<210> SEQ ID NO 584
<211> LENGTH: 12
<212> TYPE: DNA
<213> ORGANISM: Artificial Sequence
<220> FEATURE:
<223> OTHER INFORMATION: Synthetic

<400> SEQUENCE: 584
ttctttcgtt aa                                                           12

<210> SEQ ID NO 585
<211> LENGTH: 10
<212> TYPE: DNA
<213> ORGANISM: Artificial Sequence
<220> FEATURE:
<223> OTHER INFORMATION: Synthetic

<400> SEQUENCE: 585
ttcttttata                                                              10

<210> SEQ ID NO 586
<211> LENGTH: 10
<212> TYPE: DNA
<213> ORGANISM: Artificial Sequence
<220> FEATURE:
<223> OTHER INFORMATION: Synthetic

<400> SEQUENCE: 586
ttgcaattgc                                                              10

<210> SEQ ID NO 587
<211> LENGTH: 10
<212> TYPE: DNA
<213> ORGANISM: Artificial Sequence
<220> FEATURE:
<223> OTHER INFORMATION: Synthetic

<400> SEQUENCE: 587
ttgtaattgg                                                              10

<210> SEQ ID NO 588
<211> LENGTH: 11
<212> TYPE: DNA
<213> ORGANISM: Artificial Sequence
<220> FEATURE:
<223> OTHER INFORMATION: Synthetic

<400> SEQUENCE: 588
ttgtcggtaa g                                                            11

<210> SEQ ID NO 589
<211> LENGTH: 11
<212> TYPE: DNA
<213> ORGANISM: Artificial Sequence
<220> FEATURE:
<223> OTHER INFORMATION: Synthetic

<400> SEQUENCE: 589
tttattagat g                                                            11

<210> SEQ ID NO 590
<211> LENGTH: 10
<212> TYPE: DNA
<213> ORGANISM: Artificial Sequence

```
<220> FEATURE:
<223> OTHER INFORMATION: Synthetic

<400> SEQUENCE: 590
tttcgtatat                                                              10

<210> SEQ ID NO 591
<211> LENGTH: 10
<212> TYPE: DNA
<213> ORGANISM: Artificial Sequence
<220> FEATURE:
<223> OTHER INFORMATION: Synthetic

<400> SEQUENCE: 591
tttcgttata                                                              10

<210> SEQ ID NO 592
<211> LENGTH: 10
<212> TYPE: DNA
<213> ORGANISM: Artificial Sequence
<220> FEATURE:
<223> OTHER INFORMATION: Synthetic

<400> SEQUENCE: 592 tttwtcgtaa                                                              10

<210> SEQ ID NO 593
<211> LENGTH: 9
<212> TYPE: DNA
<213> ORGANISM: Artificial Sequence
<220> FEATURE:
<223> OTHER INFORMATION: Synthetic

<400> SEQUENCE: 593 twacgattg                                                                9

<210> SEQ ID NO 594
<211> LENGTH: 21
<212> TYPE: DNA
<213> ORGANISM: Artificial Sequence
<220> FEATURE:
<223> OTHER INFORMATION: Synthetic

<400> SEQUENCE: 594
tagaacaccg atggcgaagg c                                                 21

<210> SEQ ID NO 595
<211> LENGTH: 23
<212> TYPE: DNA
<213> ORGANISM: Artificial Sequence
<220> FEATURE:
<223> OTHER INFORMATION: Synthetic

<400> SEQUENCE: 595
tttcgatgca acgcgaagaa cct                                               23

<210> SEQ ID NO 596
<211> LENGTH: 19
<212> TYPE: DNA
<213> ORGANISM: Artificial Sequence
<220> FEATURE:
<223> OTHER INFORMATION: Synthetic

<400> SEQUENCE: 596
tctgacacct gcccggtgc                                                    19
```

<210> SEQ ID NO 597
<211> LENGTH: 25
<212> TYPE: DNA
<213> ORGANISM: Artificial Sequence
<220> FEATURE:
<223> OTHER INFORMATION: Synthetic

<400> SEQUENCE: 597
tctggcaggt atgcgtggtc tgatg                                              25

<210> SEQ ID NO 598
<211> LENGTH: 21
<212> TYPE: DNA
<213> ORGANISM: Artificial Sequence
<220> FEATURE:
<223> OTHER INFORMATION: Synthetic

<400> SEQUENCE: 598
tcgtggcggc gtggttatcg a                                                  21

<210> SEQ ID NO 599
<211> LENGTH: 23
<212> TYPE: DNA
<213> ORGANISM: Artificial Sequence
<220> FEATURE:
<223> OTHER INFORMATION: Synthetic

<400> SEQUENCE: 599
ttatcgctca ggcgaactcc aac                                                23

<210> SEQ ID NO 600
<211> LENGTH: 21
<212> TYPE: DNA
<213> ORGANISM: Artificial Sequence
<220> FEATURE:
<223> OTHER INFORMATION: Synthetic

<400> SEQUENCE: 600
tccacacggt ggtggtgaag g                                                  21

<210> SEQ ID NO 601
<211> LENGTH: 30
<212> TYPE: DNA
<213> ORGANISM: Artificial Sequence
<220> FEATURE:
<223> OTHER INFORMATION: Synthetic

<400> SEQUENCE: 601
tgaacgtggt caaatcaaag ttggtgaaga                                         30

<210> SEQ ID NO 602
<211> LENGTH: 22
<212> TYPE: DNA
<213> ORGANISM: Artificial Sequence
<220> FEATURE:
<223> OTHER INFORMATION: Synthetic

<400> SEQUENCE: 602
tcgtggacta ccagggtatc ta                                                 22

<210> SEQ ID NO 603
<211> LENGTH: 21
<212> TYPE: DNA
<213> ORGANISM: Artificial Sequence
<220> FEATURE:
<223> OTHER INFORMATION: Synthetic

```
<400> SEQUENCE: 603
tacgagctga cgacagccat g                                              21

<210> SEQ ID NO 604
<211> LENGTH: 20
<212> TYPE: DNA
<213> ORGANISM: Artificial Sequence
<220> FEATURE:
<223> OTHER INFORMATION: Synthetic

<400> SEQUENCE: 604
tgaccgttat agttacggcc                                                20

<210> SEQ ID NO 605
<211> LENGTH: 26
<212> TYPE: DNA
<213> ORGANISM: Artificial Sequence
<220> FEATURE:
<223> OTHER INFORMATION: Synthetic

<400> SEQUENCE: 605
tcgcaccgtg ggttgagatg aagtac                                         26

<210> SEQ ID NO 606
<211> LENGTH: 25
<212> TYPE: DNA
<213> ORGANISM: Artificial Sequence
<220> FEATURE:
<223> OTHER INFORMATION: Synthetic

<400> SEQUENCE: 606
tcggtacgaa ctggatgtcg ccgtt                                          25

<210> SEQ ID NO 607
<211> LENGTH: 22
<212> TYPE: DNA
<213> ORGANISM: Artificial Sequence
<220> FEATURE:
<223> OTHER INFORMATION: Synthetic

<400> SEQUENCE: 607
tgctggattc gcctttgcta cg                                             22

<210> SEQ ID NO 608
<211> LENGTH: 22
<212> TYPE: DNA
<213> ORGANISM: Artificial Sequence
<220> FEATURE:
<223> OTHER INFORMATION: Synthetic

<400> SEQUENCE: 608
tgtgctggtt tacccatgg ag                                              22

<210> SEQ ID NO 609
<211> LENGTH: 28
<212> TYPE: DNA
<213> ORGANISM: Artificial Sequence
<220> FEATURE:
<223> OTHER INFORMATION: Synthetic

<400> SEQUENCE: 609
tgtcaccagc ttcagcgtag tctaataa                                       28

<210> SEQ ID NO 610
```

```
<211> LENGTH: 24
<212> TYPE: DNA
<213> ORGANISM: Artificial Sequence
<220> FEATURE:
<223> OTHER INFORMATION: Synthetic

<400> SEQUENCE: 610
tcagttcggt ggccagcgct tcgg                                              24

<210> SEQ ID NO 611
<211> LENGTH: 24
<212> TYPE: DNA
<213> ORGANISM: Artificial Sequence
<220> FEATURE:
<223> OTHER INFORMATION: Synthetic

<400> SEQUENCE: 611
tcagttcggt ggtcagcgct tcgg                                              24

<210> SEQ ID NO 612
<211> LENGTH: 28
<212> TYPE: DNA
<213> ORGANISM: Artificial Sequence
<220> FEATURE:
<223> OTHER INFORMATION: Synthetic

<400> SEQUENCE: 612
tcatactcat gaaggtggaa cgcatgaa                                          28

<210> SEQ ID NO 613
<211> LENGTH: 30
<212> TYPE: DNA
<213> ORGANISM: Artificial Sequence
<220> FEATURE:
<223> OTHER INFORMATION: Synthetic

<400> SEQUENCE: 613
tccaactgtt cgtggttctg taatgaaccc                                        30

<210> SEQ ID NO 614
<211> LENGTH: 21
<212> TYPE: DNA
<213> ORGANISM: Artificial Sequence
<220> FEATURE:
<223> OTHER INFORMATION: Synthetic

<400> SEQUENCE: 614
tccacacggt ggtggtgaag g                                                 21

<210> SEQ ID NO 615
<211> LENGTH: 23
<212> TYPE: DNA
<213> ORGANISM: Artificial Sequence
<220> FEATURE:
<223> OTHER INFORMATION: Synthetic

<400> SEQUENCE: 615
tccaccggtc cgtactccat gat                                               23

<210> SEQ ID NO 616
<211> LENGTH: 28
<212> TYPE: DNA
<213> ORGANISM: Artificial Sequence
<220> FEATURE:
<223> OTHER INFORMATION: Synthetic

<400> SEQUENCE: 616
```

-continued

```
<210> SEQ ID NO 617
<211> LENGTH: 25
<212> TYPE: DNA
<213> ORGANISM: Artificial Sequence
<220> FEATURE:
<223> OTHER INFORMATION: Synthetic

<400> SEQUENCE: 617
tgaaccctaa cgatcaccca cacgg                                          25

<210> SEQ ID NO 618
<211> LENGTH: 25
<212> TYPE: DNA
<213> ORGANISM: Artificial Sequence
<220> FEATURE:
<223> OTHER INFORMATION: Synthetic

<400> SEQUENCE: 618
tgaaccctaa tgatcaccca cacgg                                          25

<210> SEQ ID NO 619
<211> LENGTH: 21
<212> TYPE: DNA
<213> ORGANISM: Artificial Sequence
<220> FEATURE:
<223> OTHER INFORMATION: Synthetic

<400> SEQUENCE: 619
tgacaagatg cacgcgcgtt c                                              21

<210> SEQ ID NO 620
<211> LENGTH: 24
<212> TYPE: DNA
<213> ORGANISM: Artificial Sequence
<220> FEATURE:
<223> OTHER INFORMATION: Synthetic

<400> SEQUENCE: 620
tgatcactgg tgctgctcaa atgg                                           24

<210> SEQ ID NO 621
<211> LENGTH: 18
<212> TYPE: DNA
<213> ORGANISM: Artificial Sequence
<220> FEATURE:
<223> OTHER INFORMATION: Synthetic

<400> SEQUENCE: 621
tggcgaccgt ggcggcgt                                                  18

<210> SEQ ID NO 622
<211> LENGTH: 23
<212> TYPE: DNA
<213> ORGANISM: Artificial Sequence
<220> FEATURE:
<223> OTHER INFORMATION: Synthetic

<400> SEQUENCE: 622
tgtggcggcg tggttatcga acc                                            23

<210> SEQ ID NO 623
<211> LENGTH: 27
<212> TYPE: DNA
```
tgaaccactt ggttgacgac aagatgca                                       28

```
<213> ORGANISM: Artificial Sequence
<220> FEATURE:
<223> OTHER INFORMATION: Synthetic

<400> SEQUENCE: 623
tgttgatgac aagatgcacg cgcgttc                                              27

<210> SEQ ID NO 624
<211> LENGTH: 19
<212> TYPE: DNA
<213> ORGANISM: Artificial Sequence
<220> FEATURE:
<223> OTHER INFORMATION: Synthetic

<400> SEQUENCE: 624
ccgaagcgct ggccaccga                                                       19

<210> SEQ ID NO 625
<211> LENGTH: 27
<212> TYPE: DNA
<213> ORGANISM: Artificial Sequence
<220> FEATURE:
<223> OTHER INFORMATION: Synthetic

<400> SEQUENCE: 625
tacgtcgtcc gacttgaccg tcagcat                                              27

<210> SEQ ID NO 626
<211> LENGTH: 29
<212> TYPE: DNA
<213> ORGANISM: Artificial Sequence
<220> FEATURE:
<223> OTHER INFORMATION: Synthetic

<400> SEQUENCE: 626
tactgcttcg ggacgaactg gatgtcgcc                                            29

<210> SEQ ID NO 627
<211> LENGTH: 23
<212> TYPE: DNA
<213> ORGANISM: Artificial Sequence
<220> FEATURE:
<223> OTHER INFORMATION: Synthetic

<400> SEQUENCE: 627
tcaccgaaac gctgaccacc gaa                                                  23

<210> SEQ ID NO 628
<211> LENGTH: 21
<212> TYPE: DNA
<213> ORGANISM: Artificial Sequence
<220> FEATURE:
<223> OTHER INFORMATION: Synthetic

<400> SEQUENCE: 628
tccaagcgca ggtttacccc a                                                    21

<210> SEQ ID NO 629
<211> LENGTH: 21
<212> TYPE: DNA
<213> ORGANISM: Artificial Sequence
<220> FEATURE:
<223> OTHER INFORMATION: Synthetic

<400> SEQUENCE: 629
tccaagcgca ggtttacccc a                                                    21
```

<210> SEQ ID NO 630
<211> LENGTH: 24
<212> TYPE: DNA
<213> ORGANISM: Artificial Sequence
<220> FEATURE:
<223> OTHER INFORMATION: Synthetic

<400> SEQUENCE: 630
tccaagcgca ggtttacccc atgg                                          24

<210> SEQ ID NO 631
<211> LENGTH: 21
<212> TYPE: DNA
<213> ORGANISM: Artificial Sequence
<220> FEATURE:
<223> OTHER INFORMATION: Synthetic

<400> SEQUENCE: 631
tccaagcgct ggtttacccc a                                             21

<210> SEQ ID NO 632
<211> LENGTH: 26
<212> TYPE: DNA
<213> ORGANISM: Artificial Sequence
<220> FEATURE:
<223> OTHER INFORMATION: Synthetic

<400> SEQUENCE: 632
tccatctcac cgaaacgctg accacc                                        26

<210> SEQ ID NO 633
<211> LENGTH: 26
<212> TYPE: DNA
<213> ORGANISM: Artificial Sequence
<220> FEATURE:
<223> OTHER INFORMATION: Synthetic

<400> SEQUENCE: 633
tccgacttga ccgtcagcat ctcctg                                        26

<210> SEQ ID NO 634
<211> LENGTH: 23
<212> TYPE: DNA
<213> ORGANISM: Artificial Sequence
<220> FEATURE:
<223> OTHER INFORMATION: Synthetic

<400> SEQUENCE: 634
tcgtactgct tcgggacgaa ctg                                           23

<210> SEQ ID NO 635
<211> LENGTH: 29
<212> TYPE: DNA
<213> ORGANISM: Artificial Sequence
<220> FEATURE:
<223> OTHER INFORMATION: Synthetic

<400> SEQUENCE: 635
tcgtcggact tgatggtcag cagctcctg                                     29

<210> SEQ ID NO 636
<211> LENGTH: 22
<212> TYPE: DNA
<213> ORGANISM: Artificial Sequence
<220> FEATURE:

<223> OTHER INFORMATION: Synthetic

<400> SEQUENCE: 636
tctcaccgaa acgctgacca cc                                              22

<210> SEQ ID NO 637
<211> LENGTH: 24
<212> TYPE: DNA
<213> ORGANISM: Artificial Sequence
<220> FEATURE:
<223> OTHER INFORMATION: Synthetic

<400> SEQUENCE: 637
tgcagtcaag ccttcacgaa catc                                            24

<210> SEQ ID NO 638
<211> LENGTH: 26
<212> TYPE: DNA
<213> ORGANISM: Artificial Sequence
<220> FEATURE:
<223> OTHER INFORMATION: Synthetic

<400> SEQUENCE: 638
tggatgtgtt cacgagtttg aggcat                                          26

<210> SEQ ID NO 639
<211> LENGTH: 27
<212> TYPE: DNA
<213> ORGANISM: Artificial Sequence
<220> FEATURE:
<223> OTHER INFORMATION: Synthetic

<400> SEQUENCE: 639
tcccattgta ctggcataca tgcttga                                         27

<210> SEQ ID NO 640
<211> LENGTH: 31
<212> TYPE: DNA
<213> ORGANISM: Artificial Sequence
<220> FEATURE:
<223> OTHER INFORMATION: Synthetic

<400> SEQUENCE: 640
tacatccaga tgtgcactga actcaaactc a                                    31

<210> SEQ ID NO 641
<211> LENGTH: 27
<212> TYPE: DNA
<213> ORGANISM: Artificial Sequence
<220> FEATURE:
<223> OTHER INFORMATION: Synthetic

<400> SEQUENCE: 641
tccaatcatc agaccagcaa cccttgc                                         27

<210> SEQ ID NO 642
<211> LENGTH: 28
<212> TYPE: DNA
<213> ORGANISM: Artificial Sequence
<220> FEATURE:
<223> OTHER INFORMATION: Synthetic

<400> SEQUENCE: 642
tcttgccagt tgtatgggcc tcatatac                                        28

-continued

```
<210> SEQ ID NO 643
<211> LENGTH: 23
<212> TYPE: DNA
<213> ORGANISM: Artificial Sequence
<220> FEATURE:
<223> OTHER INFORMATION: Synthetic

<400> SEQUENCE: 643
tgggattcct ttcgtcagtc cga                                              23

<210> SEQ ID NO 644
<211> LENGTH: 34
<212> TYPE: DNA
<213> ORGANISM: Artificial Sequence
<220> FEATURE:
<223> OTHER INFORMATION: Synthetic

<400> SEQUENCE: 644
tccaggacat actgatgagg atgtcaaaaa tgca                                  34

<210> SEQ ID NO 645
<211> LENGTH: 28
<212> TYPE: DNA
<213> ORGANISM: Artificial Sequence
<220> FEATURE:
<223> OTHER INFORMATION: Synthetic

<400> SEQUENCE: 645
tgtcaaaaat gcaattgggg tcctcatc                                         28

<210> SEQ ID NO 646
<211> LENGTH: 26
<212> TYPE: DNA
<213> ORGANISM: Artificial Sequence
<220> FEATURE:
<223> OTHER INFORMATION: Synthetic

<400> SEQUENCE: 646
tgtcctggaa tgatgatggg catgtt                                           26

<210> SEQ ID NO 647
<211> LENGTH: 27
<212> TYPE: DNA
<213> ORGANISM: Artificial Sequence
<220> FEATURE:
<223> OTHER INFORMATION: Synthetic

<400> SEQUENCE: 647
tatgaactca gctgatgttg ctcctgc                                          27

<210> SEQ ID NO 648
<211> LENGTH: 31
<212> TYPE: DNA
<213> ORGANISM: Artificial Sequence
<220> FEATURE:
<223> OTHER INFORMATION: Synthetic

<400> SEQUENCE: 648
tcgtcaaatg cagagagcac cattctctct a                                     31

<210> SEQ ID NO 649
<211> LENGTH: 26
<212> TYPE: DNA
<213> ORGANISM: Artificial Sequence
<220> FEATURE:
<223> OTHER INFORMATION: Synthetic
```

```
<400> SEQUENCE: 649
tccgatatca gcttcactgc ttgtgg                                      26

<210> SEQ ID NO 650
<211> LENGTH: 23
<212> TYPE: DNA
<213> ORGANISM: Artificial Sequence
<220> FEATURE:
<223> OTHER INFORMATION: Synthetic

<400> SEQUENCE: 650
tgggagtcag caatctgctc aca                                         23

<210> SEQ ID NO 651
<211> LENGTH: 27
<212> TYPE: DNA
<213> ORGANISM: Artificial Sequence
<220> FEATURE:
<223> OTHER INFORMATION: Synthetic

<400> SEQUENCE: 651
tggagaagtt cggtgggaga ctttggt                                     27

<210> SEQ ID NO 652
<211> LENGTH: 24
<212> TYPE: DNA
<213> ORGANISM: Artificial Sequence
<220> FEATURE:
<223> OTHER INFORMATION: Synthetic

<400> SEQUENCE: 652
tgcttcccca agcgaatctc tgta                                        24

<210> SEQ ID NO 653
<211> LENGTH: 31
<212> TYPE: DNA
<213> ORGANISM: Artificial Sequence
<220> FEATURE:
<223> OTHER INFORMATION: Synthetic

<400> SEQUENCE: 653
tcattactgc ttctccaagc gaatctctgt a                                31

<210> SEQ ID NO 654
<211> LENGTH: 25
<212> TYPE: DNA
<213> ORGANISM: Artificial Sequence
<220> FEATURE:
<223> OTHER INFORMATION: Synthetic

<400> SEQUENCE: 654
tcatcagagg attggagtcc atccc                                       25

<210> SEQ ID NO 655
<211> LENGTH: 24
<212> TYPE: DNA
<213> ORGANISM: Artificial Sequence
<220> FEATURE:
<223> OTHER INFORMATION: Synthetic

<400> SEQUENCE: 655
tcagcggagg tgacatgtat caca                                        24

<210> SEQ ID NO 656
<211> LENGTH: 24
```

<212> TYPE: DNA
<213> ORGANISM: Artificial Sequence
<220> FEATURE:
<223> OTHER INFORMATION: Synthetic

<400> SEQUENCE: 656
tcgaccaacc ttaaacgcac tcca                                          24

<210> SEQ ID NO 657
<211> LENGTH: 19
<212> TYPE: DNA
<213> ORGANISM: Artificial Sequence
<220> FEATURE:
<223> OTHER INFORMATION: Synthetic

<400> SEQUENCE: 657
ttagcacctc gacggctgg                                                19

<210> SEQ ID NO 658
<211> LENGTH: 24
<212> TYPE: DNA
<213> ORGANISM: Artificial Sequence
<220> FEATURE:
<223> OTHER INFORMATION: Synthetic

<400> SEQUENCE: 658
tgctcggacc tttacttggt cacg                                          24

<210> SEQ ID NO 659
<211> LENGTH: 22
<212> TYPE: DNA
<213> ORGANISM: Artificial Sequence
<220> FEATURE:
<223> OTHER INFORMATION: Synthetic

<400> SEQUENCE: 659
tgcccgtctc ctacttgaag gg                                            22

<210> SEQ ID NO 660
<211> LENGTH: 18
<212> TYPE: DNA
<213> ORGANISM: Artificial Sequence
<220> FEATURE:
<223> OTHER INFORMATION: Synthetic

<400> SEQUENCE: 660
tttgcgggca ccttccgg                                                 18

<210> SEQ ID NO 661
<211> LENGTH: 23
<212> TYPE: DNA
<213> ORGANISM: Artificial Sequence
<220> FEATURE:
<223> OTHER INFORMATION: Synthetic

<400> SEQUENCE: 661
tggctcggtt gtacagggat gaa                                           23

<210> SEQ ID NO 662
<211> LENGTH: 25
<212> TYPE: DNA
<213> ORGANISM: Artificial Sequence
<220> FEATURE:
<223> OTHER INFORMATION: Synthetic

<400> SEQUENCE: 662

-continued

```
tactcctcct ttcggtagcg gtaga                                              25

<210> SEQ ID NO 663
<211> LENGTH: 25
<212> TYPE: DNA
<213> ORGANISM: Artificial Sequence
<220> FEATURE:
<223> OTHER INFORMATION: Synthetic

<400> SEQUENCE: 663
gacatgtatc acaacctgtc gcaca                                              25

<210> SEQ ID NO 664
<211> LENGTH: 22
<212> TYPE: DNA
<213> ORGANISM: Artificial Sequence
<220> FEATURE:
<223> OTHER INFORMATION: Synthetic

<400> SEQUENCE: 664
catgctaatg tcgttccggc ga                                                 22

<210> SEQ ID NO 665
<211> LENGTH: 23
<212> TYPE: DNA
<213> ORGANISM: Artificial Sequence
<220> FEATURE:
<223> OTHER INFORMATION: Synthetic

<400> SEQUENCE: 665
catgctgatg tcattccggt gca                                                23

<210> SEQ ID NO 666
<211> LENGTH: 19
<212> TYPE: DNA
<213> ORGANISM: Artificial Sequence
<220> FEATURE:
<223> OTHER INFORMATION: Synthetic

<400> SEQUENCE: 666
tcgggtggtc cactgctca                                                     19

<210> SEQ ID NO 667
<211> LENGTH: 18
<212> TYPE: DNA
<213> ORGANISM: Artificial Sequence
<220> FEATURE:
<223> OTHER INFORMATION: Synthetic

<400> SEQUENCE: 667
gctgtgtaca cccggcga                                                      18

<210> SEQ ID NO 668
<211> LENGTH: 21
<212> TYPE: DNA
<213> ORGANISM: Artificial Sequence
<220> FEATURE:
<223> OTHER INFORMATION: Synthetic

<400> SEQUENCE: 668
atgcggtatc cggtcctcac a                                                  21

<210> SEQ ID NO 669
<211> LENGTH: 22
<212> TYPE: DNA
<213> ORGANISM: Artificial Sequence
```

```
<220> FEATURE:
<223> OTHER INFORMATION: Synthetic

<400> SEQUENCE: 669
tgcccaacgg actacttcct ga                                        22

<210> SEQ ID NO 670
<211> LENGTH: 19
<212> TYPE: DNA
<213> ORGANISM: Artificial Sequence
<220> FEATURE:
<223> OTHER INFORMATION: Synthetic

<400> SEQUENCE: 670
tgtggccgcg atcaaggag                                            19

<210> SEQ ID NO 671
<211> LENGTH: 23
<212> TYPE: DNA
<213> ORGANISM: Artificial Sequence
<220> FEATURE:
<223> OTHER INFORMATION: Synthetic

<400> SEQUENCE: 671
tcagccagct gagccaattc atg                                       23

<210> SEQ ID NO 672
<211> LENGTH: 18
<212> TYPE: DNA
<213> ORGANISM: Artificial Sequence
<220> FEATURE:
<223> OTHER INFORMATION: Synthetic

<400> SEQUENCE: 672
tcgctgtcgg ggttgacc                                             18

<210> SEQ ID NO 673
<211> LENGTH: 20
<212> TYPE: DNA
<213> ORGANISM: Artificial Sequence
<220> FEATURE:
<223> OTHER INFORMATION: Synthetic

<400> SEQUENCE: 673
tgctctggca tgtcatcggc                                           20

<210> SEQ ID NO 674
<211> LENGTH: 19
<212> TYPE: DNA
<213> ORGANISM: Artificial Sequence
<220> FEATURE:
<223> OTHER INFORMATION: Synthetic

<400> SEQUENCE: 674
tgacggctac atcctgggc                                            19

<210> SEQ ID NO 675
<211> LENGTH: 23
<212> TYPE: DNA
<213> ORGANISM: Artificial Sequence
<220> FEATURE:
<223> OTHER INFORMATION: Synthetic

<400> SEQUENCE: 675
tgctcgtgga cataccgatt tcg                                       23
```

```
<210> SEQ ID NO 676
<211> LENGTH: 20
<212> TYPE: DNA
<213> ORGANISM: Artificial Sequence
<220> FEATURE:
<223> OTHER INFORMATION: Synthetic

<400> SEQUENCE: 676
tcggtaagga cgcgatcacc                                                   20

<210> SEQ ID NO 677
<211> LENGTH: 22
<212> TYPE: DNA
<213> ORGANISM: Artificial Sequence
<220> FEATURE:
<223> OTHER INFORMATION: Synthetic

<400> SEQUENCE: 677
tgccagcctt aagagccaga tc                                                22

<210> SEQ ID NO 678
<211> LENGTH: 16
<212> TYPE: DNA
<213> ORGANISM: Artificial Sequence
<220> FEATURE:
<223> OTHER INFORMATION: Synthetic

<400> SEQUENCE: 678
tcacccgcac ggcgac                                                       16

<210> SEQ ID NO 679
<211> LENGTH: 20
<212> TYPE: DNA
<213> ORGANISM: Artificial Sequence
<220> FEATURE:
<223> OTHER INFORMATION: Synthetic

<400> SEQUENCE: 679
tcgacgcgtc gatctacgac                                                   20

<210> SEQ ID NO 680
<211> LENGTH: 18
<212> TYPE: DNA
<213> ORGANISM: Artificial Sequence
<220> FEATURE:
<223> OTHER INFORMATION: Synthetic

<400> SEQUENCE: 680
tggctctgaa gggcagcc                                                     18

<210> SEQ ID NO 681
<211> LENGTH: 17
<212> TYPE: DNA
<213> ORGANISM: Artificial Sequence
<220> FEATURE:
<223> OTHER INFORMATION: Synthetic

<400> SEQUENCE: 681
tctgtggctg ccgcgtc                                                      17

<210> SEQ ID NO 682
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 682
tcatcacgtc gtggcaacca                                              20

<210> SEQ ID NO 683
<211> LENGTH: 18
<212> TYPE: DNA
<213> ORGANISM: Artificial Sequence
<220> FEATURE:
<223> OTHER INFORMATION: Synthetic

<400> SEQUENCE: 683
tgtgcctaca ccggagcg                                                18

<210> SEQ ID NO 684
<211> LENGTH: 20
<212> TYPE: DNA
<213> ORGANISM: Artificial Sequence
<220> FEATURE:
<223> OTHER INFORMATION: Synthetic

<400> SEQUENCE: 684
tccgatcatt gtgtgcgcca                                              20

<210> SEQ ID NO 685
<211> LENGTH: 26
<212> TYPE: DNA
<213> ORGANISM: Artificial Sequence
<220> FEATURE:
<223> OTHER INFORMATION: Synthetic

<400> SEQUENCE: 685
tcgacccgtc gtaggtaata cgatac                                       26

<210> SEQ ID NO 686
<211> LENGTH: 25
<212> TYPE: DNA
<213> ORGANISM: Artificial Sequence
<220> FEATURE:
<223> OTHER INFORMATION: Synthetic

<400> SEQUENCE: 686
tgcctgtttg aaactgccca catac                                        25

<210> SEQ ID NO 687
<211> LENGTH: 20
<212> TYPE: DNA
<213> ORGANISM: Artificial Sequence
<220> FEATURE:
<223> OTHER INFORMATION: Synthetic

<400> SEQUENCE: 687
tgccttggtc gggcacattc                                              20

<210> SEQ ID NO 688
<211> LENGTH: 19
<212> TYPE: DNA
<213> ORGANISM: Artificial Sequence
<220> FEATURE:
<223> OTHER INFORMATION: Synthetic

<400> SEQUENCE: 688
tctgcccgcc gagcaatac                                               19

<210> SEQ ID NO 689
```

```
<210> SEQ ID NO 689
<211> LENGTH: 24
<212> TYPE: DNA
<213> ORGANISM: Artificial Sequence
<220> FEATURE:
<223> OTHER INFORMATION: Synthetic

<400> SEQUENCE: 689
tccgtaagtc ggtgttgacc aaac                                          24

<210> SEQ ID NO 690
<211> LENGTH: 19
<212> TYPE: DNA
<213> ORGANISM: Artificial Sequence
<220> FEATURE:
<223> OTHER INFORMATION: Synthetic

<400> SEQUENCE: 690
tcgggtccac cacggaatg                                                19

<210> SEQ ID NO 691
<211> LENGTH: 19
<212> TYPE: DNA
<213> ORGANISM: Artificial Sequence
<220> FEATURE:
<223> OTHER INFORMATION: Synthetic

<400> SEQUENCE: 691
tgccgacgcg atcgaacag                                                19

<210> SEQ ID NO 692
<211> LENGTH: 21
<212> TYPE: DNA
<213> ORGANISM: Artificial Sequence
<220> FEATURE:
<223> OTHER INFORMATION: Synthetic

<400> SEQUENCE: 692
tgaccaagac caagttgggc a                                             21

<210> SEQ ID NO 693
<211> LENGTH: 17
<212> TYPE: DNA
<213> ORGANISM: Artificial Sequence
<220> FEATURE:
<223> OTHER INFORMATION: Synthetic

<400> SEQUENCE: 693
tgcccagagc cgttcgt                                                  17

<210> SEQ ID NO 694
<211> LENGTH: 17
<212> TYPE: DNA
<213> ORGANISM: Artificial Sequence
<220> FEATURE:
<223> OTHER INFORMATION: Synthetic

<400> SEQUENCE: 694
tagcccggca cgctcac                                                  17

<210> SEQ ID NO 695
<211> LENGTH: 20
<212> TYPE: DNA
<213> ORGANISM: Artificial Sequence
<220> FEATURE:
<223> OTHER INFORMATION: Synthetic

<400> SEQUENCE: 695
```
tccgacagcg ggttgttctg                                                    20

<210> SEQ ID NO 696
<211> LENGTH: 17
<212> TYPE: DNA
<213> ORGANISM: Artificial Sequence
<220> FEATURE:
<223> OTHER INFORMATION: Synthetic

<400> SEQUENCE: 696
tccgacagtc ggcgctt                                                       17

<210> SEQ ID NO 697
<211> LENGTH: 20
<212> TYPE: DNA
<213> ORGANISM: Artificial Sequence
<220> FEATURE:
<223> OTHER INFORMATION: Synthetic

<400> SEQUENCE: 697
tgaagggatc ctccgggctg                                                    20

<210> SEQ ID NO 698
<211> LENGTH: 17
<212> TYPE: DNA
<213> ORGANISM: Artificial Sequence
<220> FEATURE:
<223> OTHER INFORMATION: Synthetic

<400> SEQUENCE: 698
tgcgtggtcg gcgactc                                                       17

<210> SEQ ID NO 699
<211> LENGTH: 20
<212> TYPE: DNA
<213> ORGANISM: Artificial Sequence
<220> FEATURE:
<223> OTHER INFORMATION: Synthetic

<400> SEQUENCE: 699
tcagtggctg tggcagtcac                                                    20

<210> SEQ ID NO 700
<211> LENGTH: 21
<212> TYPE: DNA
<213> ORGANISM: Artificial Sequence
<220> FEATURE:
<223> OTHER INFORMATION: Synthetic

<400> SEQUENCE: 700
tgtccatacg acctcgatgc c                                                  21

<210> SEQ ID NO 701
<211> LENGTH: 23
<212> TYPE: DNA
<213> ORGANISM: Artificial Sequence
<220> FEATURE:
<223> OTHER INFORMATION: Synthetic

<400> SEQUENCE: 701
tgtgagacag tcaatcccga tgc                                                23

<210> SEQ ID NO 702
<211> LENGTH: 17
<212> TYPE: DNA

```
<213> ORGANISM: Artificial Sequence
<220> FEATURE:
<223> OTHER INFORMATION: Synthetic

<400> SEQUENCE: 702
tgggccatgc gcaccag                                                    17

<210> SEQ ID NO 703
<211> LENGTH: 19
<212> TYPE: DNA
<213> ORGANISM: Artificial Sequence
<220> FEATURE:
<223> OTHER INFORMATION: Synthetic

<400> SEQUENCE: 703
tgccgtgacc tcgacctga                                                  19

<210> SEQ ID NO 704
<211> LENGTH: 17
<212> TYPE: DNA
<213> ORGANISM: Artificial Sequence
<220> FEATURE:
<223> OTHER INFORMATION: Synthetic

<400> SEQUENCE: 704
tcggcgccac cggttac                                                    17

<210> SEQ ID NO 705
<211> LENGTH: 22
<212> TYPE: DNA
<213> ORGANISM: Artificial Sequence
<220> FEATURE:
<223> OTHER INFORMATION: Synthetic

<400> SEQUENCE: 705
tacgtgtcca gactgggatg ga                                              22

<210> SEQ ID NO 706
<211> LENGTH: 21
<212> TYPE: DNA
<213> ORGANISM: Artificial Sequence
<220> FEATURE:
<223> OTHER INFORMATION: Synthetic

<400> SEQUENCE: 706
tcgtctggcg cacacaatga t                                               21

<210> SEQ ID NO 707
<211> LENGTH: 19
<212> TYPE: DNA
<213> ORGANISM: Artificial Sequence
<220> FEATURE:
<223> OTHER INFORMATION: Synthetic

<400> SEQUENCE: 707
tggtgcgcat ctcctccag                                                  19

<210> SEQ ID NO 708
<211> LENGTH: 17
<212> TYPE: DNA
<213> ORGANISM: Artificial Sequence
<220> FEATURE:
<223> OTHER INFORMATION: Synthetic

<400> SEQUENCE: 708
tgccgaggtg gcgcatt                                                    17
```

<210> SEQ ID NO 709
<211> LENGTH: 21
<212> TYPE: DNA
<213> ORGANISM: Artificial Sequence
<220> FEATURE:
<223> OTHER INFORMATION: Synthetic

<400> SEQUENCE: 709
tcgggctcaa cgacacttcc t                                        21

<210> SEQ ID NO 710
<211> LENGTH: 19
<212> TYPE: DNA
<213> ORGANISM: Artificial Sequence
<220> FEATURE:
<223> OTHER INFORMATION: Synthetic

<400> SEQUENCE: 710
tccaccggaa cccggatca                                           19

<210> SEQ ID NO 711
<211> LENGTH: 17
<212> TYPE: DNA
<213> ORGANISM: Artificial Sequence
<220> FEATURE:
<223> OTHER INFORMATION: Synthetic

<400> SEQUENCE: 711
tggtccgggt acgcgga                                             17

<210> SEQ ID NO 712
<211> LENGTH: 23
<212> TYPE: DNA
<213> ORGANISM: Artificial Sequence
<220> FEATURE:
<223> OTHER INFORMATION: Synthetic

<400> SEQUENCE: 712
tggcgggtag ataaagctgg aca                                      23

<210> SEQ ID NO 713
<211> LENGTH: 23
<212> TYPE: DNA
<213> ORGANISM: Artificial Sequence
<220> FEATURE:
<223> OTHER INFORMATION: Synthetic

<400> SEQUENCE: 713
tggatgccgc catagttctt gtc                                      23

<210> SEQ ID NO 714
<211> LENGTH: 19
<212> TYPE: DNA
<213> ORGANISM: Artificial Sequence
<220> FEATURE:
<223> OTHER INFORMATION: Synthetic

<400> SEQUENCE: 714
taacagctcg gccatggcg                                           19

<210> SEQ ID NO 715
<211> LENGTH: 22
<212> TYPE: DNA
<213> ORGANISM: Artificial Sequence
<220> FEATURE:

<223> OTHER INFORMATION: Synthetic

<400> SEQUENCE: 715
tgaggacaca gccttgttca ca                                              22

<210> SEQ ID NO 716
<211> LENGTH: 17
<212> TYPE: DNA
<213> ORGANISM: Artificial Sequence
<220> FEATURE:
<223> OTHER INFORMATION: Synthetic

<400> SEQUENCE: 716
tacacccacg ccgtgga                                                    17

<210> SEQ ID NO 717
<211> LENGTH: 24
<212> TYPE: DNA
<213> ORGANISM: Artificial Sequence
<220> FEATURE:
<223> OTHER INFORMATION: Synthetic

<400> SEQUENCE: 717
tcaggtactg ctatccaccc tcaa                                            24

<210> SEQ ID NO 718
<211> LENGTH: 28
<212> TYPE: DNA
<213> ORGANISM: Artificial Sequence
<220> FEATURE:
<223> OTHER INFORMATION: Synthetic

<400> SEQUENCE: 718
tttacacata tcgtgagcaa tgaactga                                        28

<210> SEQ ID NO 719
<211> LENGTH: 30
<212> TYPE: DNA
<213> ORGANISM: Artificial Sequence
<220> FEATURE:
<223> OTHER INFORMATION: Synthetic

<400> SEQUENCE: 719
tagctatctt atcgttgaga agggatttgc                                      30

<210> SEQ ID NO 720
<211> LENGTH: 32
<212> TYPE: DNA
<213> ORGANISM: Artificial Sequence
<220> FEATURE:
<223> OTHER INFORMATION: Synthetic

<400> SEQUENCE: 720
tctgaacatg ataatatctt tgaaatcggc tc                                   32

<210> SEQ ID NO 721
<211> LENGTH: 26
<212> TYPE: DNA
<213> ORGANISM: Artificial Sequence
<220> FEATURE:
<223> OTHER INFORMATION: Synthetic

<400> SEQUENCE: 721
tgagctgcat caactgtatt ggatag                                          26

```
<210> SEQ ID NO 722
<211> LENGTH: 30
<212> TYPE: DNA
<213> ORGANISM: Artificial Sequence
<220> FEATURE:
<223> OTHER INFORMATION: Synthetic

<400> SEQUENCE: 722
tacaaaggtc aaccaatgac attcagacta                                    30

<210> SEQ ID NO 723
<211> LENGTH: 31
<212> TYPE: DNA
<213> ORGANISM: Artificial Sequence
<220> FEATURE:
<223> OTHER INFORMATION: Synthetic

<400> SEQUENCE: 723
taattgggct ctttctcgct taaacacctt a                                  31

<210> SEQ ID NO 724
<211> LENGTH: 23
<212> TYPE: DNA
<213> ORGANISM: Artificial Sequence
<220> FEATURE:
<223> OTHER INFORMATION: Synthetic

<400> SEQUENCE: 724
tgccgtgttg aacgtggtca aat                                           23

<210> SEQ ID NO 725
<211> LENGTH: 29
<212> TYPE: DNA
<213> ORGANISM: Artificial Sequence
<220> FEATURE:
<223> OTHER INFORMATION: Synthetic

<400> SEQUENCE: 725
tagataattg ggctctttct cgcttaaac                                     29

<210> SEQ ID NO 726
<211> LENGTH: 28
<212> TYPE: DNA
<213> ORGANISM: Artificial Sequence
<220> FEATURE:
<223> OTHER INFORMATION: Synthetic

<400> SEQUENCE: 726
tcgtcatcag ctaactcaaa tacatgga                                      28

<210> SEQ ID NO 727
<211> LENGTH: 27
<212> TYPE: DNA
<213> ORGANISM: Artificial Sequence
<220> FEATURE:
<223> OTHER INFORMATION: Synthetic

<400> SEQUENCE: 727
tggatagacg tcatatgaag gtgtgct                                       27

<210> SEQ ID NO 728
<211> LENGTH: 28
<212> TYPE: DNA
<213> ORGANISM: Artificial Sequence
<220> FEATURE:
<223> OTHER INFORMATION: Synthetic
```

<400> SEQUENCE: 728
ttgtgatatg gaggtgtaga aggtgtta                                28

<210> SEQ ID NO 729
<211> LENGTH: 28
<212> TYPE: DNA
<213> ORGANISM: Artificial Sequence
<220> FEATURE:
<223> OTHER INFORMATION: Synthetic

<400> SEQUENCE: 729
tgagcatttt tatatccatc tccaccat                                28

<210> SEQ ID NO 730
<211> LENGTH: 34
<212> TYPE: DNA
<213> ORGANISM: Artificial Sequence
<220> FEATURE:
<223> OTHER INFORMATION: Synthetic

<400> SEQUENCE: 730
tccgtagttt tgcataattt atggtctatt tcaa                         34

<210> SEQ ID NO 731
<211> LENGTH: 30
<212> TYPE: DNA
<213> ORGANISM: Artificial Sequence
<220> FEATURE:
<223> OTHER INFORMATION: Synthetic

<400> SEQUENCE: 731
tggaaaactc atgaaattaa agtgaaagga                              30

<210> SEQ ID NO 732
<211> LENGTH: 26
<212> TYPE: DNA
<213> ORGANISM: Artificial Sequence
<220> FEATURE:
<223> OTHER INFORMATION: Synthetic

<400> SEQUENCE: 732
taaatgcact tgcttcaggg ccatat                                  26

<210> SEQ ID NO 733
<211> LENGTH: 27
<212> TYPE: DNA
<213> ORGANISM: Artificial Sequence
<220> FEATURE:
<223> OTHER INFORMATION: Synthetic

<400> SEQUENCE: 733
ttaatctggc tgcggaagtg aaatcgt                                 27

<210> SEQ ID NO 734
<211> LENGTH: 31
<212> TYPE: DNA
<213> ORGANISM: Artificial Sequence
<220> FEATURE:
<223> OTHER INFORMATION: Synthetic

<400> SEQUENCE: 734
tgcttcagcg tagtctaata atttacggaa c                            31

<210> SEQ ID NO 735
<211> LENGTH: 23

<210> SEQ ID NO 736
<211> LENGTH: 28
<212> TYPE: DNA
<213> ORGANISM: Artificial Sequence
<220> FEATURE:
<223> OTHER INFORMATION: Synthetic

<400> SEQUENCE: 735
taatctggct gcggaagtga aat                                              23

<210> SEQ ID NO 736
<211> LENGTH: 28
<212> TYPE: DNA
<213> ORGANISM: Artificial Sequence
<220> FEATURE:
<223> OTHER INFORMATION: Synthetic

<400> SEQUENCE: 736
tcactttgat atgtggatcc gtcattca                                         28

<210> SEQ ID NO 737
<211> LENGTH: 30
<212> TYPE: DNA
<213> ORGANISM: Artificial Sequence
<220> FEATURE:
<223> OTHER INFORMATION: Synthetic

<400> SEQUENCE: 737
taaggtatga caccggataa atcatataaa                                       30

<210> SEQ ID NO 738
<211> LENGTH: 29
<212> TYPE: DNA
<213> ORGANISM: Artificial Sequence
<220> FEATURE:
<223> OTHER INFORMATION: Synthetic

<400> SEQUENCE: 738
taatgggtaa atatcaccct catggtgac                                        29

<210> SEQ ID NO 739
<211> LENGTH: 28
<212> TYPE: DNA
<213> ORGANISM: Artificial Sequence
<220> FEATURE:
<223> OTHER INFORMATION: Synthetic

<400> SEQUENCE: 739
tcaccctcat ggtgactcat ctatttat                                         28

<210> SEQ ID NO 740
<211> LENGTH: 23
<212> TYPE: DNA
<213> ORGANISM: Artificial Sequence
<220> FEATURE:
<223> OTHER INFORMATION: Synthetic

<400> SEQUENCE: 740
tcttgagcca tacgtaccat tgc                                              23

<210> SEQ ID NO 741
<211> LENGTH: 28
<212> TYPE: DNA
<213> ORGANISM: Artificial Sequence
<220> FEATURE:
<223> OTHER INFORMATION: Synthetic

<400> SEQUENCE: 741

-continued

```
tatccattga accaaagtta ccttggcc                                28

<210> SEQ ID NO 742
<211> LENGTH: 31
<212> TYPE: DNA
<213> ORGANISM: Artificial Sequence
<220> FEATURE:
<223> OTHER INFORMATION: Synthetic

<400> SEQUENCE: 742
tagccatacg taccattgct tcataaatag a                             31
```

TARGETED WHOLE GENOME AMPLIFICATION METHOD FOR IDENTIFICATION OF PATHOGENS

This application is a §371 national stage entry of PCT International Patent Application No. PCT/US2007/020045, filed Sep. 14, 2007, which claims priority to expired U.S. Provisional Application Ser. No. 60/825,703, filed Sep. 14, 2006 and 60/946,367, filed Jun. 26, 2007, the disclosures of each of which are herein incorporated by reference in their entireties.

GOVERNMENT SUPPORT STATEMENT

This invention was made with United States Government support under HSARPA W81XWH-05-C-0116. The United States Government has certain rights in the invention.

CROSS REFERENCE TO RELATED APPLICATIONS

This application is a 371 national stage entry of PCT International Patent Application No. PCT/US2007/020045, filed Sep. 14, 2007, which claims priority to U. S. Provisional Application Ser. No. 60/825,703, filed Sep. 14, 2006 and Ser. No. 60/946,367, filed Jun. 26, 2007, the disclosures of each of which are herein incorporated by reference in their entireties.

FIELD OF THE INVENTION

The methods disclosed herein relate to methods and compositions for amplifying nucleic acid sequences, more specifically, from specific nucleic acid sequences of pathogens.

BACKGROUND OF THE INVENTION

In many fields of research such as genetic diagnosis, cancer research or forensic medicine, the scarcity of genomic DNA can be a severely limiting factor on the type and quantity of genetic tests that can be performed on a sample. One approach designed to overcome this problem is whole genome amplification. The objective is to amplify a limited DNA sample in a non-specific manner in order to generate a new sample that is indistinguishable from the original but with a higher DNA concentration. The aim of a typical whole genome amplification technique would be to amplify a sample up to a microgram level while respecting the original sequence representation.

The first whole genome amplification methods were described in 1992, and were based on the principles of the polymerase chain reaction. Zhang and coworkers (Zhang, L., et al. Proc. Natl. Acad. Sci. USA, 1992, 89: 5847-5851) developed the primer extension PCR technique (PEP) and Telenius and collaborators (Telenius et al., Genomics. 1992, 13(3):718-25) designed the degenerate oligonucleotide-primed PCR method (DOP-PCR) Zhang et al., 1992).

PEP involves a high number of PCR cycles; using Taq polymerase and 15 base random primers that anneal at a low stringency temperature. Although the PEP protocol has been improved in different ways, it still results in incomplete genome coverage, failing to amplify certain sequences such as repeats. Failure to prime and amplify regions containing repeats may lead to incomplete representation of a whole genome because consistent primer coverage across the length of the genome provides for optimal representation of the genome. This method also has limited efficiency on very small samples (such as single cells). Moreover, the use of Taq polymerase implies that the maximal product length is about 3 kb.

DOP-PCR is a method which uses Taq polymerase and semi-degenerate oligonucleotides (such as CGACTC-GAGNNNNATGTGG (SEQ ID NO: 1), for example, where N=A, T, C or G) that bind at a low annealing temperature at approximately one million sites within the human genome. The first cycles are followed by a large number of cycles with a higher annealing temperature, allowing only for the amplification of the fragments that were tagged in the first step. This leads to incomplete representation of a whole genome. DOP-PCR generates, like PEP, fragments that are in average 400-500 bp, with a maximum size of 3 kb, although fragments up to 10 kb have been reported. On the other hand, as noted for PEP, a low input of genomic DNA (less than 1 ng) decreases the fidelity and the genome coverage (Kittler et al., Anal. Biochem. 2002, 300(2), 237-44).

Multiple displacement amplification (MDA, also known as strand displacement amplification; SDA) is a non-PCR-based isothermal method based on the annealing of random hexamers to denatured DNA, followed by strand-displacement synthesis at constant temperature (Blanco et al., 1989, J. Biol. Chem. 264:8935-40). It has been applied to small genomic DNA samples, leading to the synthesis of high molecular weight DNA with limited sequence representation bias (Lizardi et al., Nature Genetics 1998, 19, 225-232; Dean et al., Proc. Natl. Acad. Sci. U.S.A. 2002, 99, 5261-5266). As DNA is synthesized by strand displacement, a gradually increasing number of priming events occur, forming a network of hyper-branched DNA structures. The reaction can be catalyzed by the Phi29 DNA polymerase or by the large fragment of the Bst DNA polymerase. The Phi29 DNA polymerase possesses a proofreading activity resulting in error rates 100 times lower than the Taq polymerase.

The methods described above generally produce amplification of whole genomes wherein all of the nucleic acid in a given sample is indiscriminately amplified. These methods cannot selectively amplify target genomes in the presence of background or contaminating genomes. Therefore, the results obtained from these methods have a problematically high amount of contaminating background nucleic acid. Purifying collected samples to isolate target genome(s) and remove background genome(s) will result in a further reduction in the amount of already scarce target genome.

There is a long felt need for a method of targeted amplification of a whole genome relative to background or contaminating genomes. In certain cases where only small quantities of a nucleic acid sample to be tested for the presence of a given target nucleic acid sequence, it would be advantageous to introduce specificity into amplification of whole genomes so that a particular target genome is selectively amplified relative to other genomes present within a given sample. For example, in cases of microbial forensics or clinical diagnostics, it would be useful to selectively amplify a genome of a pathogen, or a class of pathogens relative to the genomes of organisms which are also present in the sample which contains a small quantity of total nucleic acid. This would provide the quantities of nucleic acid of the pathogen that are necessary to identify the pathogen. The methods disclosed herein satisfy this long felt need.

SUMMARY OF THE INVENTION

The methods disclosed herein include methods of designing targeted whole genome amplification primers and using the targeted whole genome amplification primers in selective whole genome amplification reactions of a sample to elevate the quantity of nucleic acid representing a pathogen genome in a given sample which may be a common diagnostic sample such as blood and fractions or components thereof, sputum, urine, cerebrals spinal fluid, hepatic cells, and tissue biopsies.

Design of targeted whole genome amplification primers is accomplished by identifying at least one pathogen genome of interest and identifying at least one background genome of a bioagent suspected of being present in a sample that would contain the pathogen genome of interest. The next step is to identify all unique genome sequence segments of specified lengths within the pathogen genome sequence and to determine the frequency of occurrence of these genome sequence segments in the pathogen genome(s) and in the background genome(s). The next step is to calculate a selectivity ratio for the genome sequence segments by dividing the frequency of occurrence within the pathogen genome sequence by the frequency of occurrence of the plurality of genome sequence segments within the background genome sequences. A selectivity ratio threshold is chosen to a first subset of genome sequence segments that have selectivity ratios equal to or above the selectivity ratio threshold. This first sub-set of genome sequence segments is analyzed with respect to the pathogen genome(s) to determine the lengths of separation of the genome sequence segments along the pathogen genome. A second sub-set of genome sequence segments is chosen from the first sub-set such that the genome sequence segments of the second sub-set have a mean separation distance of less than a selected length of nucleobases. Next, targeted whole genome amplification primers are selected to hybridize to the genome sequence segments of the second sub-set such that the pathogen genome will be amplified selectively over the background genomes when subjected to whole genome amplification conditions.

The elevated quantity of nucleic acid representing a pathogen genome obtained with the targeted whole genome amplification primers may then be used as template DNA for subsequent detailed analyses to identify the pathogen by producing amplification products corresponding to bioagent identifying amplicons. The molecular masses of the bioagent identifying amplicons are measured by mass spectrometry methods such as electrospray time-of-flight mass spectrometry for example. Base compositions of the bioagent identifying amplicons are calculated from the molecular masses. The molecular masses and/or base compositions are then compared with a database of molecular masses and/or base compositions of bioagent identifying amplicons of known bioagents which are defined by specifically designed primer pair, in order to identify the pathogen in the sample. In certain embodiments, the amplification products corresponding to bioagent identifying amplicons are carried out in multiplexing reactions where more than one primer pair is included in a single reaction mixture.

Also disclosed are diagnostic kits that include any or all of the following components: targeted whole genome amplification primers, a highly processive polymerase suitable for catalyzing a whole genome amplification reaction, deoxynucleotide triphosphates and primer pairs for producing amplification products corresponding to bioagent identifying amplicons. The kits may also include buffer components or additives and instructions for carrying out the amplification reactions such as for example, indications of specific combinations of primer pairs for multiplexing reactions.

Disclosed herein are methods and related kits used for identification of pathogens implicated in septicemia and sepsis. Such methods and kits may include any of primer pairs of primer pair numbers 346 (SEQ ID NOs: 594:602), 348 (SEQ ID NOs: 595:603), 349 (SEQ ID NOs: 596:604), 354 (SEQ ID NOs: 597:605), 358 (SEQ ID NOs: 598:606), 359 (SEQ ID NOs: 599:607), 3346 (SEQ ID NOs: 616:631), 449 (SEQ ID NOs: 600:608), 3350 (SEQ ID NOs: 614:629), 2249 (SEQ ID NOs: 601:609), 3361 (SEQ ID NOs: 620:635), and 3360 (SEQ ID NOs: 612:627). These primer pairs are useful for obtaining amplification products corresponding to bioagent identifying amplicons which are used to identify pathogens causing septicemia or sepsis. These pathogens are bacteria that include, but are not limited to the following: *Escherichia coli, Klebsiella pneumoniae, Klebsiella oxytoca, Serratia marcescens, Enterobacter cloacae, Enterobacter aerogenes, Proteus mirabilis, Pseudomonas aeruginosa, Acinetobacter baumannii, Stenotrophomonas maltophilia, Staphylococcus aureus, Staphylococcus epidermidis, Staphylococcus haemolyticus, Streptococcus pneumoniae, Streptococcus pyogenes, Streptococcus agalactiae, Streptococcus mitis, Enterococcus faecium, Enterococcus faecalis, Candida albicans, Candida tropicalis, Candida parapsilosis, Candida krusei, Candida glabrata, Mycobacterium tuberculosis*, and *Aspergillus fumigatus*. After selection of appropriate targeted whole genome amplification primers to a reference sequence of any of the genomes of the bacteria including, but not limited to those listed above, which are implicated in sepsis and septicemia, targeted whole genome amplification reactions can be performed to obtain sufficient quantities of nucleic acid such that identification of a bacterium implicated in sepsis or septicemia at the genus, species or sub-species level can be rapidly confirmed using an appropriate combination of the primer pairs listed above, which are appropriate for identification of bacteria implicated in sepsis or septicemia. In some cases, a single primer pair selected from those listed above may be sufficient for identification of a bacterium implicated in sepsis or septicemia at the genus, species or sub-species level.

Also disclosed herein are methods and kits for identification of *Mycobacterium tuberculosis* and drug-resistant strains thereof. Such methods and kits may include any of primer pair numbers 3600 (SEQ ID NOs: 692:715), 3546 (SEQ ID NOs: 670:694), 3547 (SEQ ID NOs: 671:695), 3548 (SEQ ID NOs: 672:696), 3550 (SEQ ID NOs: 673:697), 3551 (SEQ ID NOs: 674:698), 3552 (SEQ ID NOs: 675:699), 3553 (SEQ ID NOs: 676:700), 3554 (SEQ ID NOs: 677:701), 3555 (SEQ ID NOs: 678:702), 3556 (SEQ ID NOs: 679:702), 3557 (SEQ ID NOs: 680:703), 3558 (SEQ ID NOs: 681:704), 3559 (SEQ ID NOs: 682:705), 3560 (SEQ ID NOs: 683:706), 3561 (SEQ ID NOs: 684:707), 3581 (SEQ ID NOs: 685:708), 3582 (SEQ ID NOs: 686:709), 3583 (SEQ ID NOs: 687:710), 3584 (SEQ ID NOs: 688:711), 3586 (SEQ ID NOs: 689:712), 3587 (SEQ ID NOs: 690:713), 3599 (SEQ ID NOs: 691:714), and 3601 (SEQ ID NOs: 692:715). After selection of appropriate targeted whole genome amplification primers to a reference sequence of *Mycobacterium tuberculosis*, targeted whole genome amplification reactions can be performed to obtain sufficient quantities of nucleic acid such that identification of individual strains or sub-species of *Mycobacterium tuberculosis*, such as drug-resistant strains, for example, can be rapidly confirmed using an appropriate combination of the primer pairs listed above. In some cases, a single primer pair selected from those listed above may be appropriate for identification of individual strains or sub-species of *Mycobacterium tuberculosis*.

Also disclosed herein are methods and kits for identification of *Staphylococcus aureus*, and drug-resistant strains thereof. Such methods and kits may include any of primer pair numbers 879 (SEQ ID NOs: 717:727), 2056 (SEQ ID NOs: 718:728), 2081 (SEQ ID NOs: 719:729), 2086 (SEQ ID NOs: 720:730), 2095 (SEQ ID NOs: 721:731), 2256 (SEQ ID NOs: 722:732), 2313 (SEQ ID NOs: 723:733), 3005 (SEQ ID NOs: 724:734), 3016 (SEQ ID NOs: 725:735), 3106 (SEQ ID NOs: 726:736), 2738 (SEQ ID NOs: 737:740), 2739 (SEQ ID NOs: 738:741), 2740 (SEQ ID NOs: 738:742) and 2741 (SEQ ID NOs: 739:740). After selection of appropriate targeted whole genome amplification primers to a reference sequence of *Mycobacterium tuberculosis*, targeted whole genome amplification reactions can be performed to obtain sufficient quantities of nucleic acid such that identification of individual strains or sub-species of *Staphylococcus aureus*, such as drug-resistant strains, for example, can be rapidly confirmed using an appropriate combination of the primer pairs listed above. In some cases, a single primer pair selected from those listed above may be appropriate for identification of individual strains or sub-species of *Staphylococcus aureus*.

Also disclosed herein are methods and kits for identification of influenza viruses, and drug-resistant strains thereof. Such methods and kits may include any of primer pair numbers 1261 (SEQ ID NOs: 639:647), 1266 (SEQ ID NOs: 640:648), 1275 (SEQ ID NOs: 641:649), 1279 (SEQ ID NOs: 642:650), 1287 (SEQ ID NOs: 643:651), 2775 (SEQ ID NOs: 644:652), 2777 (SEQ ID NOs: 645:653), and 2798 (SEQ ID NOs: 646:654). After selection of appropriate targeted whole genome amplification primers to a reference sequence for an influenza virus, targeted whole genome amplification reactions can be performed to obtain sufficient quantities of nucleic acid such that identification of individual strains or sub-species of influenza viruses, such as drug-resistant strains, for example, can be rapidly confirmed using an appropriate combination of the primer pairs listed above. In some cases, a single primer pair selected from those listed above may be appropriate for identification of individual strains or sub-species of influenza viruses.

Also disclosed herein are methods and kits for identification of hepatitis C viruses, and drug-resistant strains thereof. Such methods and kits may include any of primer pair numbers 3682 (SEQ ID NOs: 655:662), 3683 (SEQ ID NOs: 656:663), 3684 (SEQ ID NOs: 657:664), 3685 (SEQ ID NOs: 658:665), 3686 (SEQ ID NOs: 658:666), 3687 (SEQ ID NOs: 659:667), 3688 (SEQ ID NOs: 660:667), 3689 (SEQ ID NOs: 660:668) and 3691 (SEQ ID NOs: 661:669). After selection of appropriate targeted whole genome amplification primers to a reference sequence for a hepatitis C virus, targeted whole genome amplification reactions can be performed to obtain sufficient quantities of nucleic acid such that identification of individual strains or sub-species of hepatitis C viruses, such as drug-resistant strains, for example, can be rapidly confirmed using an appropriate combination of the primer pairs listed above. In some cases, a single primer pair selected from those listed above may be appropriate for identification of individual strains or sub-species of hepatitis C viruses.

For example, in some embodiments, the present invention provides a method comprising: amplifying at least one pathogen genome from a sample suspected of comprising at least one pathogen genome and at least one background genome using a plurality of targeted whole genome amplification primers, thereby elevating the quantity of nucleic acid representing said at least one pathogen genome relative to the quantity of nucleic acid representing said at least one background genome, wherein said plurality of targeted whole genome amplification primers is selected by one or more or each of the steps of:

i. identifying at least one pathogen genome;

ii. identifying at least one background genome;

iii. identifying a plurality of genome sequence segments having unique sequences within said pathogen genome sequence;

iv. determining frequency of occurrence of members of said plurality of genome sequence segments within said pathogen genome sequence and determining frequency of occurrence of said plurality of genome sequence segments within said background genome sequences;

v. calculating a selectivity ratio for said members by dividing said frequency of occurrence within said pathogen genome sequence by said frequency of occurrence of said plurality of genome sequence segments within said background genome sequences;

vi. selecting a selectivity ratio threshold value, thereby defining a first sub-set of said plurality of genome sequence segments having selectivity ratios equal to or greater than said selectivity ratio threshold value;

vii. determining the lengths of pathogen genome sequence occurring between genome sequence segments of said first sub-set;

viii. selecting a second sub-set of genome sequence segments from said first sub-set wherein members of said second sub-set have a mean separation distance of less than a selected length of nucleobases; and ix. selecting targeted whole genome amplification primers that hybridize to members of said second sub-set of genome sequence segments such that, under whole genome amplification conditions, said at least one pathogen genome is amplified selectively over said at least one background genomes.

In some embodiments, the method further comprises the step of producing one or more amplification products representing bioagent identifying amplicons from said amplified pathogen genome using one or more primer pairs. In some embodiments, the method further comprises the step of measuring molecular masses of said amplification products by mass spectrometry. In some embodiments, the mass spectrometry is electrospray time-of-flight mass spectrometry. In some embodiments, the method further comprises the step of comparing said molecular masses with a database comprising molecular masses of bioagent identifying amplicons of pathogens produced with said primer pairs, thereby identifying said pathogen in said sample. In some embodiments, the method further comprising the step of calculating base compositions of said amplification products from said molecular masses. In some embodiments, the method further comprises the step of comparing said base compositions with a database comprising base compositions of bioagent identifying amplicons of pathogens produced with said primer pairs, thereby identifying said pathogen in said sample.

In some embodiments, the amplification products are generated using a plurality of primer pairs that define bioagent identifying amplicons. In some embodiments, the plurality of primer pairs are used in a multiplex reaction to generate a plurality of amplification products. In some embodiments, the plurality of primer pairs comprises at least two primer pairs from the group consisting of primer pair numbers: 346 (SEQ ID NOs: 594:602), 348 (SEQ ID NOs: 595:603), 349 (SEQ ID NOs: 596:604), 354 (SEQ ID NOs: 597:605), 358 (SEQ ID NOs: 598:606), 359 (SEQ ID NOs: 599:607), 3346 (SEQ ID NOs: 616:631), 449 (SEQ ID NOs: 600:608), 3350 (SEQ ID NOs: 614:629), 2249 (SEQ ID NOs: 601:609), 3361 (SEQ ID NOs: 620:635), and 3360 (SEQ ID NOs: 612:627). In some embodiments, the plurality of primer pairs comprises primer pair numbers: 346 (SEQ ID NOs: 594:602), 348 (SEQ ID NOs: 595:603), 349 (SEQ ID NOs: 596:604), 3346 (SEQ ID NOs: 616:631). In some embodiments, the plurality of primer pairs comprises primer pair numbers: 346 (SEQ ID NOs: 594:602), 348 (SEQ ID NOs: 595:603), 349 (SEQ ID NOs: 596:604), and 3361 (SEQ ID NOs: 620:635). In some embodiments, the plurality of primer pairs comprises primer pair numbers 346 (SEQ ID NOs: 594:602), 348 (SEQ ID NOs: 595:603), 349 (SEQ ID NOs: 596:604) and at least one of the primer pairs selected from the group consisting of 354 358 (SEQ ID NOs: 598:606), 359 (SEQ ID NOs: 599:607), 3346 (SEQ ID NOs: 616:631), 449 (SEQ ID NOs: 600:608), 3350 (SEQ ID NOs: 614:629), 3361 (SEQ ID NOs: 620:635), and 3360 (SEQ ID NOs: 612:627).

In some embodiments, a high processivity polymerase enzyme is used at said amplification step. In some embodiments, the high processivity polymerase enzyme is a recombinant polymerase enzyme. In some embodiments, the high processivity polymerase enzyme is a genetically engineered polymerase enzyme. In some embodiments, the high processivity polymerase enzyme is phi29.

In some embodiments, the sample comprises human whole blood. In some embodiments, the method further comprises the step of extracting total nucleic acid from said sample before carrying out said amplifying step. In some embodiments, the sample comprises human buffy coat. In some embodiments, the method comprises the step of extracting total nucleic acid from said sample before carrying out said amplifying step. In some embodiments, the sample comprises human serum. In some embodiments, the method further comprises the step of extracting total nucleic acid from said sample before carrying out said amplifying step. In some embodiments, the sample comprises human hepatic cells. In some embodiments, the method further comprises the step of extracting total nucleic acid from sample before carrying out said amplifying step. In some embodiments, the sample comprises sputum. In some embodiments, the method further comprises the step of extracting total nucleic acid from sample before carrying out said amplifying step. In some embodiments, the sample comprises urine. In some embodiments, the method further comprises the step of extracting total nucleic acid from sample before carrying out said amplifying step. In some embodiments, the sample comprises biopsy tissue. In some embodiments, the method further comprises the step of extracting total nucleic acid from sample before carrying out said amplifying step.

In some embodiments, the at least one pathogen is a bacterium. In some embodiments, the bacterium is one or more of (e.g., is selected from the group consisting of): *Escherichia coli, Klebsiella pneumoniae, Klebsiella oxytoca, Serratia marcescens, Enterobacter cloacae, Enterobacter aerogenes, Proteus mirabilis, Pseudomonas aeruginosa, Acinetobacter baumannii, Stenotrophomonas maltophilia, Staphylococcus aureus, Staphylococcus epidermidis, Staphylococcus haemolyticus, Streptococcus pneumoniae, Streptococcus pyogenes, Streptococcus agalactiae, Streptococcus mitis, Enterococcus faecium, Enterococcus faecalis, Candida albicans, Candida tropicalis, Candida parapsilosis, Candida krusei, Candida glabrata, Mycobacterium tuberculosis,* and *Aspergillus fumigatus.*

In some embodiments, the at least one background genome comprises a human nucleic acid. In some embodiments, the said identifying step indicates the presence of bacterial sepsis in a human patient. In some embodiments, the said identifying step indicates the presence of bacteremia in a human patient.

In some embodiments, the at least one pathogen is a virus. In some embodiments, the virus is HIV. In some embodiments, the virus is HCV. In some embodiments, the virus is influenza virus.

The present invention also provides a method comprising one or more of, or each of, the steps of:
a. extracting nucleic acids from a sample; and
b. mixing said nucleic acids with a plurality of targeted whole genome amplification primers, a high processivity polymerase enzyme to produce an amplification mixture, wherein said plurality of targeted whole genome amplification primers is selected by:
   i. identifying at least one target genome suspected of being present in said sample;
   ii. identifying at least one background genome suspected of being present in said sample;
   iii. identifying a plurality of genome sequence segments having unique sequences within said target genome sequence;
   iv. determining frequency of occurrence of members of said plurality of genome sequence segments within said target genome sequence and within said background genome sequences;
   v. calculating a selectivity ratio for said members by dividing said frequency of occurrence within said target genome by said frequency of occurrence of said plurality of genome sequence segments within said background genome sequences;
   vi. selecting a selectivity ratio threshold value, thereby defining a first sub-set of said plurality of genome sequence segments having selectivity ratios equal to or greater than said selectivity ratio threshold value;
   vii. determining the lengths of target genome sequence occurring between genome sequence segments of said first sub-set;
   viii. selecting a second sub-set of genome sequence segments from said first sub-set wherein members of said second sub-set have a mean separation of less than a selected length of nucleobases; and
   ix. selecting targeted whole genome amplification primers that hybridize to members of said second sub-set of genome sequence segments such that said at least one target genome is amplified selectively over said at least one background genome.

In some embodiments, the method further comprises the step of amplifying one or more of said extracted nucleic acids in said mixture of step b. In some embodiments, the amplifying step is a targeted whole genome amplification reaction. In some embodiments, the method further comprises the step of performing a second amplification step using at least one primer pair that defines a bioagent identifying amplicon to obtain at least a second amplification product. In some embodiments, the method further comprises the step of measuring the molecular mass of said second amplification product by mass spectrometry. In some embodiments, the mass spectrometry is electrospray time-of-flight mass spectrometry.

In some embodiments, the method further comprises the step of comparing said molecular mass with a database comprising molecular masses of bioagent identifying amplicons of pathogens produced with said primer pairs, thereby identifying said pathogen in said sample. In some embodiments, the method further comprises the step of calculating a base composition of said amplification products from said molecular mass. In some embodiments, the method further comprises the step of comparing said base compositions with a database comprising base compositions of bioagent identifying amplicons of pathogens produced with said primer pairs, thereby identifying said pathogen in said sample.

In some embodiments, the second amplification step comprises obtaining a plurality of amplification products generated using a plurality of primer pairs that define bioagent identifying amplicons. In some embodiments, the plurality of primer pairs is used in one or more multiplex reactions to generate a plurality of amplification products. In some embodiments, the plurality of primer pairs comprises at least two primer pairs from the group consisting of primer pair numbers: 346 (SEQ ID NOs: 594:602), 348 (SEQ ID NOs: 595:603), 349 (SEQ ID NOs: 596:604), 354 (SEQ ID NOs: 597:605), 358 (SEQ ID NOs: 598:606), 359 (SEQ ID NOs: 599:607), 3346 (SEQ ID NOs: 616:631), 449 (SEQ ID NOs: 600:608), 3350 (SEQ ID NOs: 614:629), 2249 (SEQ ID NOs: 601:609), 3361 (SEQ ID NOs: 620:635), and 3360 (SEQ ID NOs: 612:627). In some embodiments, the plurality of primer pairs comprises primer pair numbers: 346 (SEQ ID NOs: 594:602), 348 (SEQ ID NOs: 595:603), 349 (SEQ ID NOs: 596:604), 3346 (SEQ ID NOs: 616:631). In some embodiments, the plurality of primer pairs comprises primer pair numbers: 346 (SEQ ID NOs: 594:602), 348 (SEQ ID NOs: 595:603), 349 (SEQ ID NOs: 596:604), and 3361 (SEQ ID NOs: 620:635). In some embodiments, the plurality of primer pairs comprises primer pair numbers 346 (SEQ ID NOs: 594:602), 348 (SEQ ID NOs: 595:603), 349 (SEQ ID NOs: 596:604) and at least one of the primer pairs selected from the group consisting of 354 358 (SEQ ID NOs: 598:606), 359 (SEQ ID NOs: 599:607), 3346 (SEQ ID NOs: 616:631), 449 (SEQ ID NOs: 600:608), 3350 (SEQ ID NOs: 614:629), 3361 (SEQ ID NOs: 620:635), and 3360 (SEQ ID NOs: 612:627).

In some embodiments, a high processivity polymerase enzyme is used at said amplification step. In some embodiments, the high processivity polymerase enzyme is a recombinant polymerase enzyme. In some embodiments, the high processivity polymerase enzyme is a genetically engineered polymerase enzyme. In some embodiments, the high processivity polymerase enzyme is phi29.

In some embodiments, the sample comprises human whole blood. In some embodiments, the method further comprises the step of extracting total nucleic acid from said sample before carrying out said amplifying step. In some embodiments, the sample comprises human buffy coat. In some embodiments, the method comprises the step of extracting total nucleic acid from said sample before carrying out said amplifying step. In some embodiments, the sample comprises human serum. In some embodiments, the method further comprises the step of extracting total nucleic acid from said sample before carrying out said amplifying step. In some embodiments, the sample comprises human hepatic cells. In some embodiments, the method further comprises the step of extracting total nucleic acid from sample before carrying out said amplifying step. In some embodiments, the sample comprises sputum. In some embodiments, the method further comprises the step of extracting total nucleic acid from sample before carrying out said amplifying step. In some embodiments, the sample comprises urine. In some embodiments, the method further comprises the step of extracting total nucleic acid from sample before carrying out said amplifying step. In some embodiments, the sample comprises biopsy tissue. In some embodiments, the method further comprises the step of extracting total nucleic acid from sample before carrying out said amplifying step.

In some embodiments, the at least one pathogen is a bacterium. In some embodiments, the bacterium is one or more of (e.g., is selected from the group consisting of): *Escherichia coli, Klebsiella pneumoniae, Klebsiella oxytoca, Serratia marcescens, Enterobacter cloacae, Enterobacter aerogenes, Proteus mirabilis, Pseudomonas aeruginosa, Acinetobacter baumannii, Stenotrophomonas maltophilia, Staphylococcus aureus, Staphylococcus epidermidis, Staphylococcus haemolyticus, Streptococcus pneumoniae, Streptococcus pyogenes, Streptococcus agalactiae, Streptococcus mitis, Enterococcus faecium, Enterococcus faecalis, Candida albicans, Candida tropicalis, Candida parapsilosis, Candida krusei, Candida glabrata, Mycobacterium tuberculosis*, and *Aspergillus fumigatus*.

In some embodiments, the at least one background genome comprises a human nucleic acid. In some embodiments, the said identifying step indicates the presence of bacterial sepsis in a human patient. In some embodiments, the said identifying step indicates the presence of bacteremia in a human patient.

In some embodiments, the at least one pathogen is a virus. In some embodiments, the virus is HIV. In some embodiments, the virus is HCV. In some embodiments, the virus is influenza virus.

The present invention also provides kits containing one or more components necessary for, useful for, or sufficient for performing any of the methods described above or elsewhere herein. In some embodiments, the kit comprises a high processivity polymerase enzyme and a plurality of purified targeted whole genome amplification primers. In some embodiments, the kit further comprises at least one primer pair that defines a bioagent identifying amplicon. In some embodiments, the plurality of primer pairs comprises at least two primer pairs from the group consisting of primer pair numbers: 346 (SEQ ID NOs: 594:602), 348 (SEQ ID NOs: 595:603), 349 (SEQ ID NOs: 596:604), 354 (SEQ ID NOs: 597:605), 358 (SEQ ID NOs: 598:606), 359 (SEQ ID NOs: 599:607), 3346 (SEQ ID NOs: 616:631), 449 (SEQ ID NOs: 600:608), 3350 (SEQ ID NOs: 614:629), 2249 (SEQ ID NOs: 601:609), 3361 (SEQ ID NOs: 620:635), and 3360 (SEQ ID NOs: 612:627). In some embodiments, the plurality of primer pairs comprises primer pair numbers: 346 (SEQ ID NOs: 594:602), 348 (SEQ ID NOs: 595:603), 349 (SEQ ID NOs: 596:604), 3346 (SEQ ID NOs: 616:631). In some embodiments, the plurality of primer pairs comprises primer pair numbers: 346 (SEQ ID NOs: 594:602), 348 (SEQ ID NOs: 595:603), 349 (SEQ ID NOs: 596:604), and 3361 (SEQ ID NOs: 620:635). In some embodiments, the plurality of primer pairs comprises primer pair numbers 346 (SEQ ID NOs: 594:602), 348 (SEQ ID NOs: 595:603), 349 (SEQ ID NOs: 596:604) and at least one of the primer pairs selected from the group consisting of 354 358 (SEQ ID NOs: 598:606), 359 (SEQ ID NOs: 599:607), 3346 (SEQ ID NOs: 616:631), 449 (SEQ ID NOs: 600:608), 3350 (SEQ ID NOs: 614:629), 3361 (SEQ ID NOs: 620:635), and 3360 (SEQ ID NOs: 612:627). In some embodiments, the high processivity enzyme is phi29.

BRIEF DESCRIPTION OF THE DRAWINGS

FIG. 1 is a plot indicating the relationships between sensitivity, selectivity and length of the genome sequence segments and primers hybridizing thereto.

FIG. 2 is a process diagram indicating the process steps for selection of genome sequence segments and primers hybridizing thereto.

FIG. 3A is a plot indicating the quantities of human DNA obtained from whole genome amplification (WGA) reactions performed with random hexamer primers (solid diamond) and the targeted whole genome amplification (TWGA) method using the primers of Table 3 (clear circle).

FIG. 3B is a plot indicating the quantity of *Bacillus anthracis* DNA obtained from whole genome amplification (WGA) reactions performed with random hexamer primers (solid diamond) and targeted whole genome amplification (TWGA) method using the primers of Table 3 (clear circle).

FIG. 4A is a plot indicating the quantities of human DNA obtained from whole genome amplification (WGA) reactions performed with random hexamer primers (solid diamond) and the targeted whole genome amplification (TWGA) method using the first generation primers of Table 3 (clear circle) and the second generation primers of Table 4 (clear square).

Figure 7:
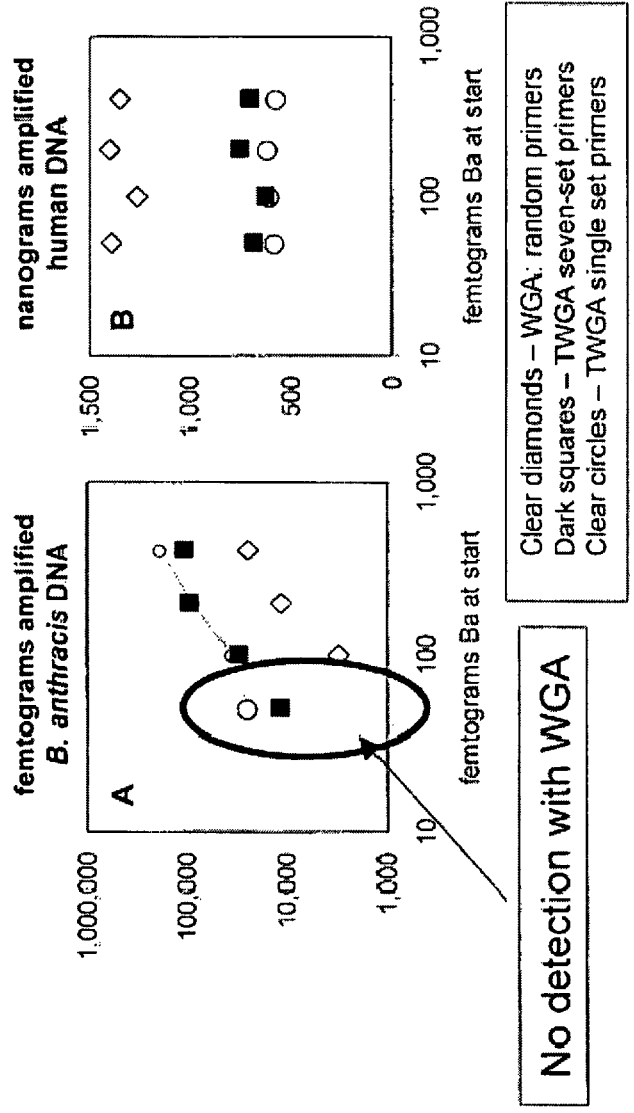

FIGS. 7A and 7B are plots of quantity of amplified DNA obtained in a range of concentrations of *Bacillus anthracis* DNA (target genome) with a constant concentration of *Homo sapiens* DNA (background genome). FIG. 7A indicates the quantities of *Bacillus anthracis* DNA obtained in two different targeted whole genome amplification reactions and in a conventional whole genome amplification reaction. FIG. 7B indicates the quantities of *Homo sapiens* DNA in the same three reactions.

Figure 8:
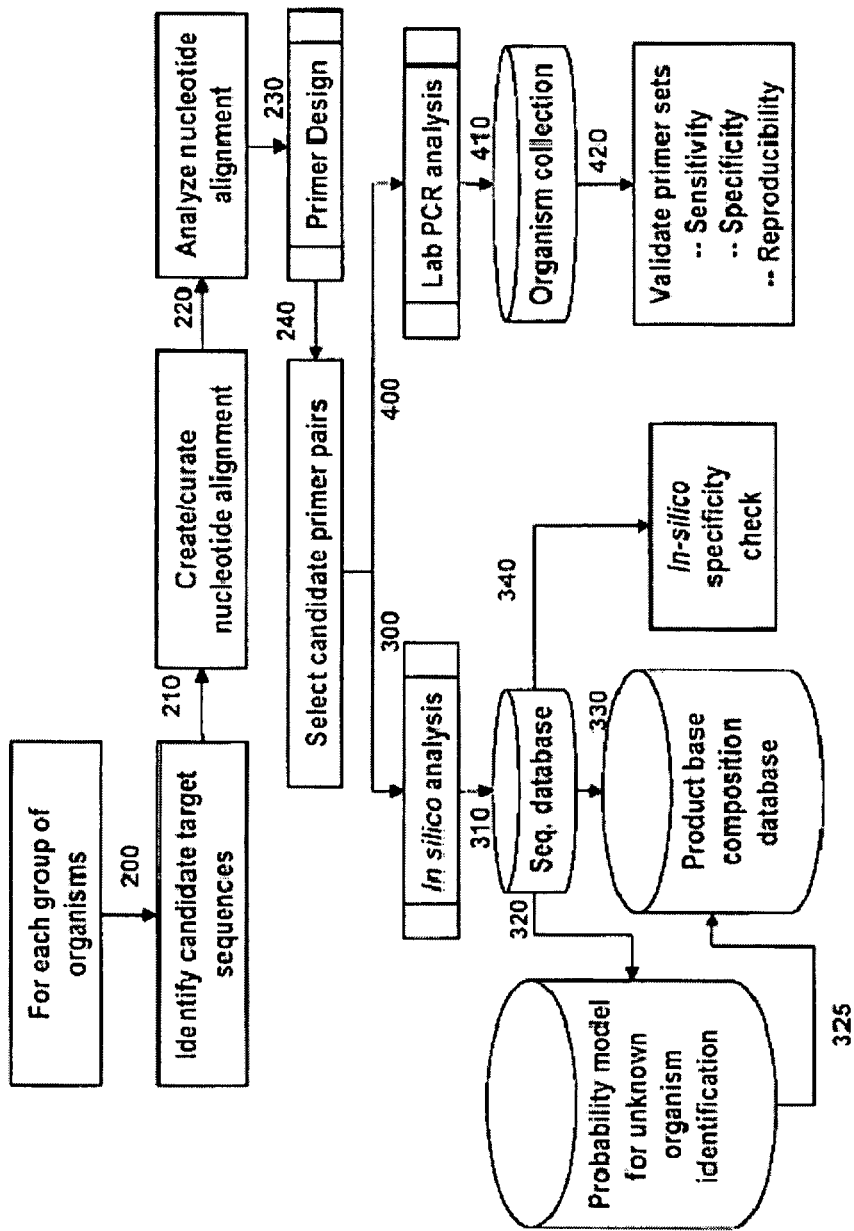

FIG. 8 is a process diagram illustrating a representative primer pair selection process.

Figure 9:
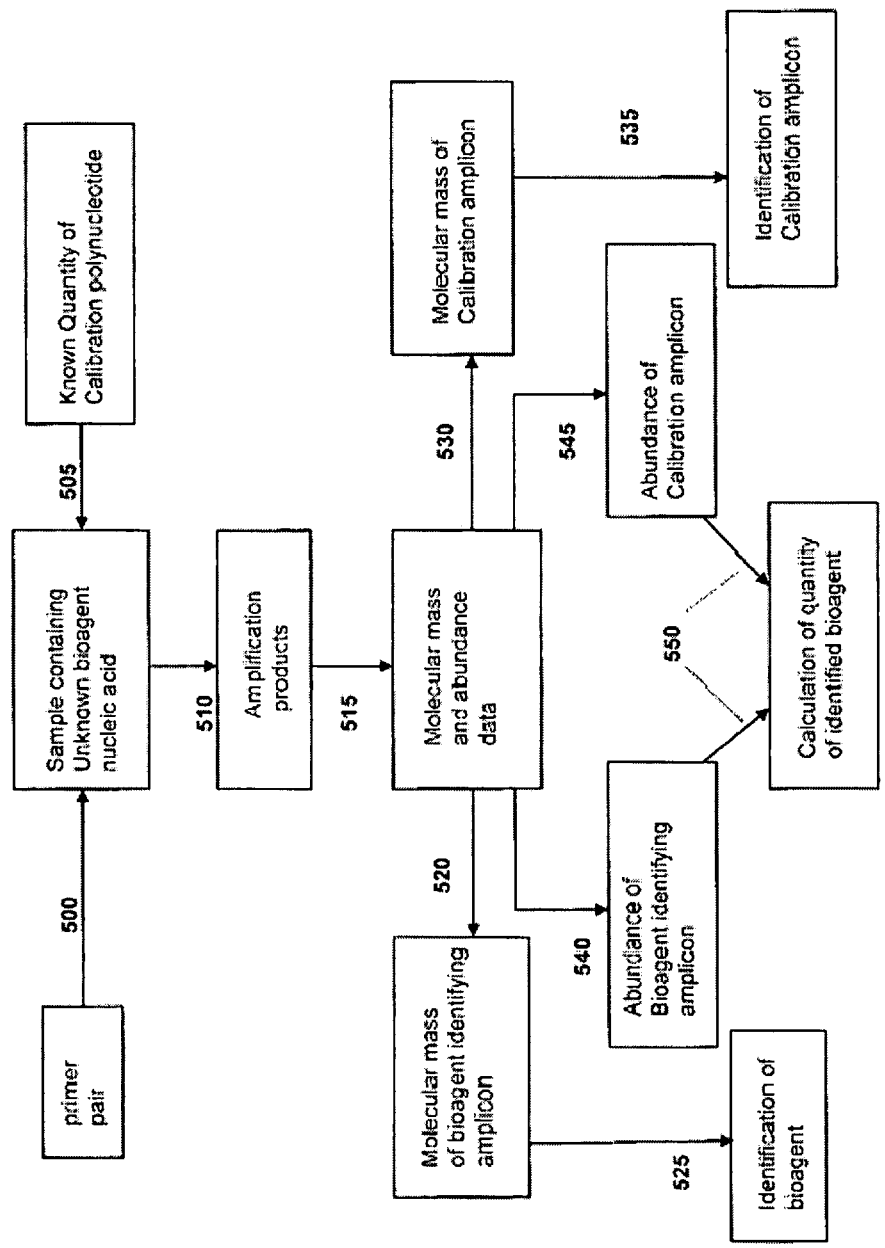

FIG. 9 is a process diagram illustrating an embodiment of the calibration method.

DEFINITIONS

To facilitate an understanding of the methods disclosed herein, a number of terms and phrases are defined below:

As used herein, the term "abundance" refers to an amount. The amount may be described in terms of concentration which are common in molecular biology such as "copy number" "pfu or plate-forming unit" which are well known to those with ordinary skill. Concentration may be relative to a known standard or may be absolute.

The term "amplification," as used herein, refers to a process of multiplying an original quantity of a nucleic acid template in order to obtain greater quantities of the original nucleic acid.

As used herein, the term "amplifiable nucleic acid" is used in reference to nucleic acids that may be amplified by any amplification method. It is contemplated that "amplifiable nucleic acid" also applies to the term "sample template."

As used herein, the term "amplification reagents" refers to those reagents (deoxyribonucleotide triphosphates, buffer, etc.), needed for amplification, excluding primers, nucleic acid template, and the amplification enzyme. Typically, amplification reagents along with other reaction components are placed and contained in a reaction vessel (test tube, microwell, or other vessel).

As used herein, the term "analogous" when used in context of comparison of bioagent identifying amplicons indicates that the bioagent identifying amplicons being compared are produced with the same pair of primers. For example, bioagent identifying amplicon "A" and bioagent identifying amplicon "B", produced with the same pair of primers are analogous with respect to each other. Bioagent identifying amplicon "C", produced with a different pair of primers is not analogous to either bioagent identifying amplicon "A" or bioagent identifying amplicon "B".

As used herein, the term "anion exchange functional group" refers to a positively charged functional group capable of binding an anion through an electrostatic interaction. The most well known anion exchange functional groups are the amines, including primary, secondary, tertiary and quaternary amines.

The term "background organisms," as used herein, refers to organisms typically present in a given sample which are not of interest and are thus considered to be contaminants.

The term "background genome," as used herein refers to the genome of a background organism. Background organisms will vary according to the sample source. In a non-limiting example, for targeted whole genome amplification of a soil bioremediation bacterium in a soil sample, it would be advantageous to define the genomes of organisms native to soil such as *C. elegans*, as background genomes. In another non-limiting example, for whole genome amplification of a genome belonging to a target pathogen in a human tissue sample, it would be advantageous to define human DNA as a background genome.

The term "bacteria" or "bacterium" refers to any member of the groups of eubacteria and archaebacteria.

The term "bacteremia" refers to the presence of bacteria in the bloodstream. It is also known by the related terms "blood poisoning" or "toxemia." In the hospital, indwelling catheters are a frequent cause of bacteremia and subsequent nosocomial infections, because they provide a means by which bacteria normally found on the skin can enter the bloodstream. Other causes of bacteremia include dental procedures (occasionally including simple tooth brushing), herpes (including herpetic whitlow), urinary tract infections, intravenous drug use, and colorectal cancer. Bacteremia may also be seen in oropharyngeal, gastrointestinal or genitourinary surgery or exploration.

As used herein, a "base composition" is the exact number of each nucleobase (for example, A, T, C and G) in a segment of nucleic acid. For example, amplification of nucleic acid of strain 5170 of *Mycobacterium tuberculosis* using primer pair number 3550 (SEQ ID NOs: 673:697) produces an amplification product 129 nucleobases in length from nucleic acid of the embB gene that has a base composition of A21 G37 C44 T27 (by convention—with reference to the sense strand of the amplification product). Because the molecular masses of each of the four natural nucleotides and chemical modifications thereof are known (if applicable), a measured molecular mass can be deconvoluted to a list of possible base compositions. Identification of a base composition of a sense strand which is complementary to the corresponding antisense strand in terms of base composition provides a confirmation of the true base composition of an unknown amplification product. For example, the base composition of the antisense strand of the 129 nucleobase amplification product described above is A27 G44 C37 T21.

As used herein, a "base composition probability cloud" is a representation of the diversity in base composition resulting from a variation in sequence that occurs among different isolates of a given species. The "base composition probability cloud" represents the base composition constraints for each species and is typically visualized using a pseudo four-dimensional plot.

As used herein, a "bioagent" is any organism, cell, or virus, living or dead, or a nucleic acid derived from such an organism, cell or virus. Examples of bioagents include, but are not limited to, cells, (including but not limited to human clinical samples, bacterial cells and other pathogens), viruses, fungi, protists, parasites, and pathogenicity markers (including but not limited to: pathogenicity islands, antibiotic resistance genes, virulence factors, toxin genes and other bioregulating compounds). Samples may be alive or dead or in a vegetative state (for example, vegetative bacteria or spores) and may be encapsulated or bioengineered. As used herein, a "pathogen" is a bioagent which causes a disease or disorder. A pathogen that infects a human is known as a "human pathogen." Non-human pathogens may infect specific animals but not humans. Human pathogens are of interest for clinical reasons and non-human pathogen identification is of interest in veterinary applications of the methods disclosed herein.

As used herein, a "bioagent division" is defined as group of bioagents above the species level and includes but is not limited to, orders, families, classes, clades, genera or other such groupings of bioagents above the species level.

As used herein, the term "bioagent identifying amplicon" refers to a polynucleotide that is amplified from nucleic acid of a bioagent in an amplification reaction and which 1) provides sufficient variability to distinguish among bioagents from whose nucleic acid the bioagent identifying amplicon is produced and 2) whose molecular mass is amenable to a rapid and convenient molecular mass determination modality such as mass spectrometry, for example. In silico representations of bioagent identifying amplicons are particularly useful for inclusion in databases used for identification of bioagents. Bioagent identifying amplicons are defined by a pair of primers that hybridize to regions of nucleic acid of a given bioagent.

As used herein, the term "biological product" refers to any product originating from an organism. Biological products are often products of processes of biotechnology. Examples of biological products include, but are not limited to: cultured cell lines, cellular components, antibodies, proteins and other cell-derived biomolecules, growth media, growth harvest fluids, natural products and bio-pharmaceutical products.

The terms "biowarfare agent" and "bioweapon" are synonymous and refer to a bacterium, virus, fungus or protozoan that could be deployed as a weapon to cause bodily harm to individuals. Military or terrorist groups may be implicated in deployment of biowarfare agents.

As used herein, the term "broad range survey primer pair" refers to a primer pair designed to produce bioagent identifying amplicons across different broad groupings of bioagents. For example, the ribosomal RNA-targeted primer pairs are broad range survey primer pairs which have the capability of producing bacterial bioagent identifying amplicons for essentially all known bacteria. With respect to broad range primer pairs employed for identification of bacteria, a broad range survey primer pair for bacteria such as 16S rRNA primer pair number 346 (SEQ ID NOs: 594:602) for example, will produce an bacterial bioagent identifying amplicon for essentially all known bacteria.

The term "calibration amplicon" refers to a nucleic acid segment representing an amplification product obtained by amplification of a calibration sequence with a pair of primers designed to produce a bioagent identifying amplicon.

The term "calibration sequence" refers to a polynucleotide sequence to which a given pair of primers hybridizes for the purpose of producing an internal (i.e.: included in the reaction) calibration standard amplification product for use in determining the quantity of a bioagent in a sample. The calibration sequence may be expressly added to an amplification reaction, or may already be present in the sample prior to analysis.

The term "clade primer pair" refers to a primer pair designed to produce bioagent identifying amplicons for species belonging to a clade group. A clade primer pair may also be considered as a "speciating" primer pair which is useful for distinguishing among closely related species.

The term "codon" refers to a set of three adjoined nucleotides (triplet) that codes for an amino acid or a termination signal.

As used herein, the term "codon base composition analysis," refers to determination of the base composition of an individual codon by obtaining a bioagent identifying amplicon that includes the codon. The bioagent identifying amplicon will at least include regions of the target nucleic acid sequence to which the primers hybridize for generation of the bioagent identifying amplicon as well as the codon being analyzed, located between the two primer hybridization regions.

As used herein, the terms "complementary" or "complementarity" are used in reference to polynucleotides (i.e., a sequence of nucleotides such as an oligonucleotide or a target nucleic acid) related by the base-pairing rules. For example, the sequence 5'-A-G-T-3', is complementary to the sequence 3'-T-C-A-5'. Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids. Either term may also be used in reference to individual nucleotides, especially within the context of polynucleotides. For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand. But in this sense, complementarity either exists or does not exist i.e.: there is no partial complementarity.

The term "complement of a nucleic acid sequence" as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids disclosed herein and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. Where a first oligonucleotide is complementary to a region of a target nucleic acid and a second oligonucleotide has complementary to the same region (or a portion of this region) a "region of overlap" exists along the target nucleic acid. The degree of overlap will vary depending upon the extent of the complementarity.

The term "degenerate primers," as used herein refers to a mixture of similar, but not identical, primers having one or more residues substituted relative to the other primer(s) in the mixture. Degenerate nucleotide codes include R, K, S, Y, M, W, B, H, N, D, V and I. The corresponding combinations are listed in 37 CFR §1.821. For example, the sequence AAATTT RCCCGGG (SEQ ID NO: 2) actually refers to a combination of primers having the following sequences: AAATTT ACCCGGG (SEQ ID NO: 3), and AAATTTGCCCGGG (SEQ ID NO: 4) because R=A or G.

As used herein, the term "division-wide primer pair" refers to a primer pair designed to produce bioagent identifying amplicons within sections of a broader spectrum of bioagents For example, primer pair number 354 (SEQ ID NOs: 597: 605), a division-wide primer pair, is designed to produce bacterial bioagent identifying amplicons for members of the *Bacillus* group of bacteria which comprises, for example, members of the genera *Streptococcus, Enterococcus*, and *Staphylococcus*. Other division-wide primer pairs may be used to produce bacterial bioagent identifying amplicons for other groups of bacterial bioagents.

As used herein, the term "concurrently amplifying" used with respect to more than one amplification reaction refers to the act of simultaneously amplifying more than one nucleic acid in a single reaction mixture.

As used herein, the term "drill-down primer pair" refers to a primer pair designed to produce bioagent identifying amplicons for identification of sub-species characteristics or confirmation of a species assignment. For example, primer pair number 897 (SEQ ID NOs: 717:727), a drill-down *Staphylococcus aureus* genotyping primer pair, is designed to produce *Staphylococcus aureus* genotyping amplicons. Other drill-down primer pairs may be used to produce bioagent identifying amplicons for *Staphylococcus aureus* and other bacterial species.

The term "duplex" refers to the state of nucleic acids in which the base portions of the nucleotides on one strand are bound through hydrogen bonding the their complementary bases arrayed on a second strand. The condition of being in a duplex form reflects on the state of the bases of a nucleic acid. By virtue of base pairing, the strands of nucleic acid also generally assume the tertiary structure of a double helix, having a major and a minor groove. The assumption of the helical form is implicit in the act of becoming duplexed.

As used herein, the term "etiology" refers to the causes or origins, of diseases or abnormal physiological conditions.

The term "frequency of occurrence" as used herein, refers to the number of different coordinates where a given genome sequence segment occurs within a given genome. The frequency of occurrence of a given genome sequence segment provides a means of defining the sensitivity of a primer designed to hybridize to the genome sequence segment. The frequency of occurrence of a given genome sequence segment is also used in the calculation of selectivity ratios.

The term "gene" refers to a DNA sequence that comprises control and coding sequences necessary for the production of an RNA having a non-coding function (e.g., a ribosomal or transfer RNA), a polypeptide or a precursor. The RNA or polypeptide can be encoded by a full length coding sequence or by any portion of the coding sequence so long as the desired activity or function is retained.

The term "genome," as used herein, generally refers to the complete set of genetic information in the form of one or more nucleic acid sequences, including text or in silico representations thereof. A genome may include either DNA or RNA, depending upon its organism of origin. Most organisms have DNA genomes while some viruses have RNA genomes. As used herein, the term "genome" need not comprise the complete set of genetic information. The term may also refer to at least a majority portion of a genome such as at least 50% to 100% of an entire genome or any whole or fractional percentage therebetween.

The term "genome sequence segment," as used herein, refers to a portion of a genome sequence which is initially defined as a primer hybridization candidate for the purpose of the targeted whole genome amplification methods disclosed herein. The related term "unique genome sequence segment" refers to a genome sequence segment that occurs at least once in a given genome. For example, a simplified hypothetical 8 nucleobase genome consisting of the following sequence: aattccgg (SEQ ID NO: 5) has four unique genome sequence segments of five nucleobase lengths (aattc (SEQ ID NO: 6); attcc (SEQ ID NO: 7); ttccg (SEQ ID NO: 8); and tccgg (SEQ ID NO: 9)). This same simplified hypothetical 8 nucleobase genome also has three unique genome sequence segments of six nucleobase lengths: (aattcc (SEQ ID NO: 10); attccg (SEQ ID NO: 11); and ttccgg (SEQ ID NO: 12)). This same simplified hypothetical 8 nucleobase genome also has two unique genome sequence segments of seven nucleobase lengths: (aattccg (SEQ ID NO: 13); and attccgg (SEQ ID NO: 14)). This same simplified hypothetical 8 nucleobase genome also has one unique genome sequence segment which is 8 nucleobases in length: (aattccgg (SEQ ID NO: 5). In another example, a simplified hypothetical 8 nucleobase genome consisting of the following sequence: aaaaaaaa (SEQ ID NO: 15) obviously only has a single unique genome sequence segment which is five nucleobases in length (occurring 4 times), as well as a single unique genome sequence segment which is six nucleobases in length (occurring 3 times), a single unique genome sequence segment which is seven nucleobases in length (occurring twice) and a single unique genome sequence segment which is eight nucleobases in length (occurring once).

The term "genotype," as used herein, refers to the genetic makeup of an organism. Members of the same species of organism having genetic differences are said to have different genotypes.

The terms "homology," "homologous" and "sequence identity" refer to a degree of identity. There may be partial homology or complete homology. A partially homologous sequence is one that is less than 100% identical to another sequence. Determination of sequence identity is described in the following example: a primer 20 nucleobases in length which is otherwise identical to another 20 nucleobase primer but having two non-identical residues has 18 of 20 identical residues (18/20=0.9 or 90% sequence identity). In another example, a primer 15 nucleobases in length having all residues identical to a 15 nucleobase segment of a primer 20 nucleobases in length would have 15/20=0.75 or 75% sequence identity with the 20 nucleobase primer. As used herein, sequence identity is meant to be properly determined when the query sequence and the subject sequence are both described and aligned in the 5' to 3' direction. Sequence alignment algorithms such as BLAST, will return results in two different alignment orientations. In the Plus/Plus orientation, both the query sequence and the subject sequence are aligned in the 5' to 3' direction. On the other hand, in the Plus/Minus orientation, the query sequence is in the 5' to 3' direction while the subject sequence is in the 3' to 5' direction. It should be understood that with respect to the primers disclosed herein, sequence identity is properly determined when the alignment is designated as Plus/Plus. Sequence identity may also encompass alternate or modified nucleobases that perform in a functionally similar manner to the regular nucleobases adenine, thymine, guanine and cytosine with respect to hybridization and primer extension in amplification reactions. In a non-limiting example, if the 5-propynyl pyrimidines propyne C and/or propyne T replace one or more C or T residues in one primer which is otherwise identical to another primer in sequence and length, the two primers will have 100% sequence identity with each other. In another non-limiting example, Inosine (I) may be used as a replacement for G or T and effectively hybridize to C, A or U (uracil). Thus, if inosine replaces one or more C, A or U residues in one primer which is otherwise identical to another primer in sequence and length, the two primers will have 100% sequence identity with each other. Other such modified or universal bases may exist which would perform in a functionally similar manner for hybridization and amplification reactions and will be understood to fall within this definition of sequence identity.

As used herein, "housekeeping gene" refers to a gene encoding a protein or RNA involved in basic functions required for survival and reproduction of a bioagent. Housekeeping genes include, but are not limited to genes encoding RNA or proteins involved in translation, replication, recombination and repair, transcription, nucleotide metabolism, amino acid metabolism, lipid metabolism, energy generation, uptake, secretion and the like.

The term "hybridization," as used herein refers to the process of joining two complementary strands of DNA or one each of DNA and RNA to form a double-stranded molecule.

The term "in silico" refers to processes taking place via computer calculations. For example, electronic PCR (ePCR) is a process analogous to ordinary PCR except that it is carried out using nucleic acid sequences and primer pair sequences stored on a computer formatted medium.

The term "in vitro method," as used herein, describes a biochemical process performed in a test-tube or other laboratory apparatus. An amplification reaction performed on a nucleic acid sample in a microtube or a well of a multi-well plate is an example of an in vitro method.

The "ligase chain reaction" (LCR; sometimes referred to as "Ligase Amplification Reaction" (LAR) described by Barany, Proc. Natl. Acad. Sci., 88:189 (1991); Barany, PCR Methods and Applic., 1:5 (1991); and Wu and Wallace, Genomics 4:560 (1989) has developed into a well-recognized alternative method for amplifying nucleic acids. In LCR, four oligonucleotides, two adjacent oligonucleotides which uniquely hybridize to one strand of target DNA, and a complementary set of adjacent oligonucleotides, that hybridize to the opposite strand are mixed and DNA ligase is added to the mixture. Provided that there is complete complementarity at the junction, ligase will covalently link each set of hybridized molecules. Importantly, in LCR, two probes are ligated together only when they base-pair with sequences in the target sample, without gaps or mismatches. Repeated cycles of denaturation, hybridization and ligation amplify a short segment of DNA. LCR has also been used in combination with PCR to achieve enhanced detection of single-base changes. However, because the four oligonucleotides used in this assay can pair to form two short ligatable fragments, there is the potential for the generation of target-independent background signal. The use of LCR for mutant screening is limited to the examination of specific nucleic acid positions.

The term "locked nucleic acid" or "LNA" refers to a nucleic acid analogue containing one or more 2'-O, 4'-C-methylene-β-D-ribofuranosyl nucleotide monomers in an RNA mimicking sugar conformation. LNA oligonucleotides display unprecedented hybridization affinity toward complementary single-stranded RNA and complementary single- or double-stranded DNA. LNA oligonucleotides induce A-type (RNA-like) duplex conformations. The primers disclosed herein may contain LNA modifications.

As used herein, the term "mass-modifying tag" refers to any modification to a given nucleotide which results in an increase in mass relative to the analogous non-mass modified nucleotide. Mass-modifying tags can include heavy isotopes of one or more elements included in the nucleotide such as carbon-13 for example. Other possible modifications include addition of substituents such as iodine or bromine at the 5 position of the nucleobase for example.

The term "mass spectrometry" refers to measurement of the mass of atoms or molecules. The molecules are first converted to ions, which are separated using electric or magnetic fields according to the ratio of their mass to electric charge. The measured masses are used to identity the molecules.

The term "mean" as used herein refers to the arithmetic average; the sum of the data divided by the sample size.

The term "microorganism" as used herein means an organism too small to be observed with the unaided eye and includes, but is not limited to bacteria, virus, protozoans, fungi; and ciliates.

The term "multi-drug resistant" or multiple-drug resistant" refers to a microorganism which is resistant to more than one of the antibiotics or antimicrobial agents used in the treatment of said microorganism.

The term "multiplex PCR" refers to a PCR reaction where more than one primer set is included in the reaction pool allowing 2 or more different DNA targets to be amplified by PCR in a single reaction tube.

The term "non-template tag" refers to a stretch of at least three guanine or cytosine nucleobases of a primer used to produce a bioagent identifying amplicon which are not complementary to the template. A non-template tag is incorporated into a primer for the purpose of increasing the primer-duplex stability of later cycles of amplification by incorporation of extra G-C pairs which each have one additional hydrogen bond relative to an A-T pair.

The term "nucleic acid sequence" as used herein refers to the linear composition of the nucleic acid residues A, T, C or G or any modifications thereof, within an oligonucleotide, nucleotide or polynucleotide, and fragments or portions thereof, and to DNA or RNA of genomic or synthetic origin which may be single or double stranded, and represent the sense or antisense strand As used herein, the term "nucleobase" is synonymous with other terms in use in the art including "nucleotide," "deoxynucleotide," "nucleotide residue," "deoxynucleotide residue," "nucleotide triphosphate (NTP)," or deoxynucleotide triphosphate (dNTP).

The term "nucleotide analog" as used herein refers to modified or non-naturally occurring nucleotides such as 5-propynyl pyrimidines (i.e., 5-propynyl-dTTP and 5-propynyl-dTCP), 7-deaza purines (i.e., 7-deaza-dATP and 7-deaza-dGTP). Nucleotide analogs include base analogs and comprise modified forms of deoxyribonucleotides as well as ribonucleotides.

The term "oligonucleotide" as used herein is defined as a molecule comprising two or more deoxyribonucleotides or ribonucleotides, preferably at least 5 nucleotides, more preferably at least about 13 to 35 nucleotides. The exact size will depend on many factors, which in turn depend on the ultimate function or use of the oligonucleotide. The oligonucleotide may be generated in any manner, including chemical synthesis, DNA replication, reverse transcription, PCR, or a combination thereof. Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5'-end" if its 5' phosphate is not linked to the 3' oxygen of a mononucleotide pentose ring and as the "3'-end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. A first region along a nucleic acid strand is said to be upstream of another region if the 3' end of the first region is before the 5' end of the second region when moving along a strand of nucleic acid in a 5' to 3' direction. All oligonucleotide primers disclosed herein are understood to be presented in the 5' to 3' direction when reading left to right. When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide. Similarly, when two overlapping oligonucleotides are hybridized to the same linear complementary nucleic acid sequence, with the first oligonucleotide positioned such that its 5' end is upstream of the 5' end of the second oligonucleotide, and the 3' end of the first oligonucleotide is upstream of the 3' end of the second oligonucleotide, the first oligonucleotide may be called the "upstream" oligonucleotide and the second oligonucleotide may be called the "downstream" oligonucleotide.

The term "organism," as used herein, refers to humans, animals, plants, protozoa, bacteria, fungi and viruses.

As used herein, a "pathogen" is a bioagent which causes a disease or disorder.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

The term "peptide nucleic acid" ("PNA") as used herein refers to a molecule comprising bases or base analogs such as would be found in natural nucleic acid, but attached to a peptide backbone rather than the sugar-phosphate backbone typical of nucleic acids. The attachment of the bases to the peptide is such as to allow the bases to base pair with complementary bases of nucleic acid in a manner similar to that of an oligonucleotide. These small molecules, also designated anti gene agents, stop transcript elongation by binding to their complementary strand of nucleic acid (Nielsen, et al. Anticancer Drug Des. 1993, 8, 53-63). The primers disclosed herein may comprise PNAs.

The term "polymerase" refers to an enzyme having the ability to synthesize a complementary strand of nucleic acid from a starting template nucleic acid strand and free dNTPs.

As used herein, the term "polymerase chain reaction" ("PCR") refers to the method of K. B. Mullis U.S. Pat. Nos. 4,683,195, 4,683,202, and 4,965,188, hereby incorporated by reference, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified." With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of 32P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

The term "polymerization means" or "polymerization agent" refers to any agent capable of facilitating the addition of nucleoside triphosphates to an oligonucleotide. Preferred polymerization means comprise DNA and RNA polymerases.

The term "primer," as used herein refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, use of the method, and the parameters used for primer design, as disclosed herein. Primers disclosed herein fall into two general categories; (i) primer pairs, generally ranging in length from about 12 to about 35 nucleobases in length, that define bioagent identifying amplicons which are useful for preparing amplification products corresponding to bioagent identifying amplicons; and (ii) targeted whole genome amplification primers which are designed to hybridize at positions across essentially the entire genome of a bioagent of interest. Targeted whole genome amplification primers are not matched up in pairs and are typically of lengths ranging from about 5 to about 13 nucleobases in length.

As used herein, the terms "pair of primers," or "primer pair" are synonymous. A primer pair is used for amplification of a nucleic acid sequence. A pair of primers comprises a forward primer and a reverse primer. The forward primer hybridizes to a sense strand of a target gene sequence to be amplified and primes synthesis of an antisense strand (complementary to the sense strand) using the target sequence as a template. A reverse primer hybridizes to the antisense strand of a target gene sequence to be amplified and primes synthesis of a sense strand (complementary to the antisense strand) using the target sequence as a template.

The primer pairs are designed to bind to highly conserved sequence regions of a bioagent identifying amplicon that flank an intervening variable region and yield amplification products which ideally provide enough variability to distinguish each individual bioagent, and which are amenable to molecular mass analysis. In some embodiments, the highly conserved sequence regions exhibit between about 80-100%, or between about 90-100%, or between about 95-100% identity, or between about 99-100% identity. The molecular mass of a given amplification product provides a means of identifying the bioagent from which it was obtained, due to the variability of the variable region. Thus design of the primers requires selection of a variable region with appropriate variability to resolve the identity of a given bioagent. Bioagent identifying amplicons are ideally specific to the identity of the bioagent.

Properties of the primers may include any number of properties related to structure including, but not limited to: nucleobase length which may be contiguous (linked together) or non-contiguous (for example, two or more contiguous segments which are joined by a linker or loop moiety), modified or universal nucleobases (used for specific purposes such as for example, increasing hybridization affinity, preventing non-templated adenylation and modifying molecular mass) percent complementarity to a given target sequences.

Properties of the primers also include functional features including, but not limited to, orientation of hybridization (forward or reverse) relative to a nucleic acid template. The coding or sense strand is the strand to which the forward priming primer hybridizes (forward priming orientation) while the reverse priming primer hybridizes to the non-coding or antisense strand (reverse priming orientation). The functional properties of a given primer pair also include the generic template nucleic acid to which the primer pair hybridizes. For example, in the case of primer pairs, identification of bioagents can be accomplished at different levels using primers suited to resolution of each individual level of identification. Broad range survey primers are designed with the objective of identifying a bioagent as a member of a particular division (e.g., an order, family, genus or other such grouping of bioagents above the species level of bioagents). In some embodiments, broad range survey intelligent primers are capable of identification of bioagents at the species or subspecies level. Other primers may have the functionality of producing bioagent identifying amplicons for members of a given taxonomic genus, lade, species, sub-species or genotype (including genetic variants which may include presence of virulence genes or antibiotic resistance genes or mutations). Additional functional properties of primer pairs include the functionality of performing amplification either singly (single primer pair per amplification reaction vessel) or in a multiplex fashion (multiple primer pairs and multiple amplification reactions within a single reaction vessel).

The term "processivity," as used herein, refers to the ability of an enzyme to repetitively continue its catalytic function without dissociating from its substrate. For example, Phi29 polymerase is a highly processive polymerase due to its tight binding of the template DNA substrate.

As used herein, the terms "purified" or "substantially purified" refer to molecules, either nucleic or amino acid sequences, that are removed from their natural environment, isolated or separated, and are at least 60% free, preferably 75% free, and most preferably 90% free from other components with which they are naturally associated. An "isolated polynucleotide" or "isolated oligonucleotide" is therefore a substantially purified polynucleotide.

The term "reverse transcriptase" refers to an enzyme having the ability to transcribe DNA from an RNA template. This enzymatic activity is known as reverse transcriptase activity. Reverse transcriptase activity is desirable in order to obtain DNA from RNA viruses which can then be amplified and analyzed by the methods disclosed herein.

The term "ribosomal RNA" or "rRNA" refers to the primary ribonucleic acid constituent of ribosomes. Ribosomes are the protein-manufacturing organelles of cells and exist in the cytoplasm. Ribosomal RNAs are transcribed from the DNA genes encoding them.

The term "sample" in the present specification and claims is used in its broadest sense. On the one hand it is meant to include a specimen or culture (e.g., microbiological cultures). On the other hand, it is meant to include both biological and environmental samples. A sample may include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as ungulates, bear, fish, lagamorphs, rodents, etc. Environmental samples include environmental material such as surface matter, soil, water, air and industrial samples, as well as samples obtained from food and dairy processing instruments, apparatus, equipment, utensils, disposable and non-disposable items. These examples are not to be construed as limiting the sample types applicable to the methods disclosed herein. The term "source of target nucleic acid" refers to any sample that contains nucleic acids (RNA or DNA). Particularly preferred sources of nucleic acids are biological samples including, but not limited to blood, saliva, urine, cerebral spinal fluid, pleural fluid, milk, lymph, sputum and semen. In particular, different fractions of blood samples exist such as serum or plasma (the liquid component of blood which contains various vital proteins), and buffy coat (a centrifuged fraction of blood that contains white blood cells and platelets). Other preferred sources of nucleic acids are specific cell types such as, hepatic cells for example. Other preferred sources of nucleic acids are tissue biopsies. Methods of handing such samples are well within the technical skill of an ordinary practitioner in the art.

As used herein, the term "sample template" refers to nucleic acid originating from a sample that is analyzed for the presence of "target" (defined below). In contrast, "background template" is used in reference to nucleic acid other than sample template that may or may not be present in a sample. Background template is often a contaminant. It may be the result of carryover, or it may be due to the presence of nucleic acid contaminants sought to be purified away from the sample. For example, nucleic acids from organisms other than those to be detected may be present as background in a test sample.

A "segment" is defined herein as a region of nucleic acid within a nucleic acid sequence.

The term "selectivity," as used herein, is a measure which indicates the frequency of occurrence of a given genome sequence segment in a target relative to the frequency of occurrence of the same genome sequence segment in background genomes. The related term "selectivity ratio," as used herein, is a number calculated by dividing the frequency of occurrence of a given genome sequence segment in a target genome by its frequency of occurrence in background genomes.

The "self-sustained sequence replication reaction" (3 SR) (Guatelli et al., Proc. Natl. Acad. Sci. 1990, 87:1874-1878, with an erratum at Proc. Natl. Acad. Sci. 1990, 87:7797) is a transcription-based in vitro amplification system (Kwok et al., Proc. Natl. Acad. Sci. 1989, 86:1173-1177) that can exponentially amplify RNA sequences at a uniform temperature. The amplified RNA can then be utilized for mutation detection (Fahy et al., 1991, PCR Meth. Appl., 1:25-33). In this method, an oligonucleotide primer is used to add a phage RNA polymerase promoter to the 5' end of the sequence of interest. In a cocktail of enzymes and substrates that includes a second primer, reverse transcriptase, RNase H, RNA polymerase and ribo- and deoxyribonucleoside triphosphates, the target sequence undergoes repeated rounds of transcription, cDNA synthesis and second-strand synthesis to amplify the area of interest. The use of 3SR to detect mutations is kinetically limited to screening small segments of DNA (e.g., 200-300 base pairs).

As used herein, the term "sequence alignment" refers to a listing of multiple DNA or amino acid sequences and aligns them to highlight their similarities. The listings can be made using bioinformatics computer programs.

The term "sensitivity," as used herein, is a measure which indicates the frequency of occurrence of a given genome sequence segment within a target genome.

The term "separation distance," as used herein, refers to the intervening distance along a given genome sequence between two genome sequence segments chosen as primer hybridization sites. For example, a first genome sequence segment having genome coordinates 100-107 and a second genome sequence segment having genome coordinates of 200-207 have a separation distance of 92 nucleobases (genome coordinates 108 to 199).

The term "sepsis," as used herein, refers to a serious medical condition resulting from the immune response to a severe infection. The related term "septicemia" is a sepsis of the bloodstream caused by bacteremia (the presence of bacteria in the bloodstream). The associated term "sepsis-causing organisms" refers to organisms that are frequently found in the blood when in the state of sepsis. Although the majority of sepsis-causing organisms are bacteria, fungi have also been identified in the blood of individuals with sepsis.

As used herein, the term "speciating primer pair" refers to a primer pair designed to produce a bioagent identifying amplicon with the diagnostic capability of identifying species members of a group of genera or a particular genus of bioagents. Primer pair number 2249 (SEQ ID NOs: 601:609), for example, is a speciating primer pair used to distinguish *Staphylococcus aureus* from other species of the genus *Staphylococcus*.

The terms "stopping criterion" and "stopping criteria" refer to a chosen minimal acceptable criterion or criteria of collections of genome sequence segments for inclusion in the set of selected genome sequence segments to which primers will be designed. Examples of stopping criteria include, but are not limited to values reflecting mean separation distance or maximum separation distance. These stopping criteria can be chosen to act as the final step in a method for primer design of primers useful with targeted whole genome amplification.

As used herein, a "sub-species characteristic" is a genetic characteristic that provides the means to distinguish two members of the same bioagent species. For example, one viral strain could be distinguished from another viral strain of the same species by possessing a genetic change (e.g., for example, a nucleotide deletion, addition or substitution) in one of the viral genes, such as the RNA-dependent RNA polymerase. Sub-species characteristics such as virulence genes and drug-are responsible for the phenotypic differences among the different strains of bacteria.

The term "target genome," as used herein, refers to a genome of interest acting as the subject of analysis of the methods disclosed herein. For example, it is desirable to produce large quantities of a "target genome" while minimizing production of "background genomes."

The terms "threshold criterion" and "threshold criteria," as used herein refer to values reflecting characteristics of genome sequence segments at which selections of sub-sets of genome sequence segments are made. For example, sub-sets of genome sequence segments can be chosen using a threshold criterion of a selectivity ratio at or above the mean selectivity ratio.

As used herein, the term "targeted whole genome amplification primers" refers to primers collected in a set which are useful for selectively amplifying one or more target genome relative to one or more background genomes. Targeted whole genome amplification primers are designed according methods disclosed herein.

As used herein, the term "target genome sequence segment" refers to a portion of specified length (typically about six to about twelve nucleobases in length) of a genome which is desired to be selectively amplified relative to one or more background genomes. Primers are selected to hybridize as selectively as possible to target genome sequence segments while minimizing hybridization to one or more background genomes.

The term "template" refers to a strand of nucleic acid on which a complementary copy is built from nucleoside triphosphates through the activity of a template-dependent nucleic acid polymerase. Within a duplex the template strand is, by convention, depicted and described as the "bottom" strand. Similarly, the non-template strand is often depicted and described as the "top" strand.

The term "triangulation genotyping analysis" refers to a method of genotyping a bioagent by measurement of molecular masses or base compositions of amplification products, corresponding to bioagent identifying amplicons, obtained by amplification of regions of more than one gene. In this sense, the term "triangulation" refers to a method of establishing the accuracy of information by comparing three or more types of independent points of view bearing on the same findings. Triangulation genotyping analysis carried out with a plurality of triangulation genotyping analysis primers yields a plurality of base compositions that then provide a pattern or "barcode" from which a species type can be assigned. The species type may represent a previously known sub-species or strain, or may be a previously unknown strain having a specific and previously unobserved base composition barcode indicating the existence of a previously unknown genotype.

As used herein, the term "triangulation genotyping analysis primer pair" is a primer pair designed to produce bioagent identifying amplicons for determining species types in a triangulation genotyping analysis.

The employment of more than one bioagent identifying amplicon for identification of a bioagent is herein referred to as "triangulation identification." Triangulation identification is pursued by analyzing a plurality of bioagent identifying amplicons produced with different primer pairs. This process is used to reduce false negative and false positive signals, and enable reconstruction of the origin of hybrid or otherwise engineered bioagents. For example, identification of the three part toxin genes typical of *B. anthracis* (Bowen et al., J. Appl.

Microbiol., 1999, 87, 270-278) in the absence of the expected signatures from the *B. anthracis* genome would suggest a genetic engineering event.

As used herein, the term "unknown bioagent" may mean either: (i) a bioagent whose existence is known (such as the well known bacterial species *Staphylococcus aureus* for example) but which is not known to be in a sample to be analyzed, or (ii) a bioagent whose existence is not known (for example, the SARS coronavirus was unknown prior to April 2003). For example, if the method for identification of coronaviruses disclosed in commonly owned U.S. patent Ser. No. 10/829,826 (incorporated herein by reference in its entirety) was to be employed prior to April 2003 to identify the SARS coronavirus in a clinical sample, both meanings of "unknown" bioagent are applicable since the SARS coronavirus was unknown to science prior to April, 2003 and since it was not known what bioagent (in this case a coronavirus) was present in the sample. On the other hand, if the method of U.S. patent Ser. No. 10/829,826 was to be employed subsequent to April 2003 to identify the SARS coronavirus in a clinical sample, only the first meaning (i) of "unknown" bioagent would apply since the SARS coronavirus became known to science subsequent to April 2003 and since it was not known what bioagent was present in the sample.

The term "variable sequence" as used herein refers to differences in nucleic acid sequence between two nucleic acids. For example, the genes of two different bacterial species may vary in sequence by the presence of single base substitutions and/or deletions or insertions of one or more nucleotides. These two forms of the structural gene are said to vary in sequence from one another. As used herein, the term "viral nucleic acid" includes, but is not limited to, DNA, RNA, or DNA that has been obtained from viral RNA, such as, for example, by performing a reverse transcription reaction. Viral RNA can either be single-stranded (of positive or negative polarity) or double-stranded.

The term "virus" refers to obligate, ultramicroscopic, parasites that are incapable of autonomous replication (i.e., replication requires the use of the host cell's machinery). Viruses can survive outside of a host cell but cannot replicate.

The term "viremia" refers to a condition where viruses enter the bloodstream. It is similar to bacteremia, a condition where bacteria enter the bloodstream, and septicemia. Active viremia refers to the capability of the virus to replicate in blood. There are two types of viremia: primary viremia, which is the initial spread of virus in the blood; and secondary viremia, where the primary viremia has resulted in infection of additional tissues, in which the virus has replicated and once more entered the circulation.

The term "wild-type" refers to a gene or a gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified", "mutant" or "polymorphic" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, a "wobble base" is a variation in a codon found at the third nucleotide position of a DNA triplet. Variations in conserved regions of sequence are often found at the third nucleotide position due to redundancy in the amino acid code.

DESCRIPTION OF EMBODIMENTS

Overview

Disclosed herein are methods and compositions for amplifying a target genome of interest in the presence of background genomes. In the sense that one or more target genomes is selected to be amplified from a sample containing background genomes, the method may be considered as a method for "targeted whole genome amplification." The problem being solved using the disclosed compositions and methods is the production of larger quantities of genomic nucleic acid of an organism of interest than of the genomic or other nucleic acid originating from the background organisms.

The greater quantities of nucleic acid representing the organism of interest are then available for further analyses, such as analyses conducted toward determining the genotype of a given microorganism, for example. Such analyses may encompass any type of nucleic acid characterization such as probe detection analysis by real time PCR, microarray analysis, sequencing analysis or analysis by methods disclosed herein which include determination of molecular mass and/or base composition of amplification products corresponding to bioagent identifying amplicons. The methods are particularly useful for obtaining increased quantities of nucleic acid of pathogens existing in human samples such as blood and fractions thereof, including serum and buffy coat, hepatic cells, sputum, urine and tissue biopsies. Pathogens that may be identified in such samples are implicated in bacteremia, septicemia and sepsis as well as viremia.

Target Genomes for Design of Targeted Whole Genome Amplification Primers

In some preferred embodiments, one or more target genomes are chosen. The choice of target genomes is dictated by the objective of the analysis. For example, if the desired outcome of the targeted whole genome amplification process is to obtain nucleic acid representing the genome of a biowarfare organism such as *Bacillus anthracis*, which is suspected of being present in a soil sample at the scene of a biowarfare attack, one may choose to select the genome of *Bacillus anthracis* as the one and only target genome. If, on the other hand, the desired outcome of the targeted whole genome amplification process is to obtain nucleic acid representing a group of bacteria, such as, a group of potential biowarfare agents, more than one target genome may be selected such as, a group comprising any or all of the following bacteria: *Bacillus anthracis, Francisella tularensis, Yersinia pestis, Brucella* sp., *Burkholderia mallei, Rickettsia prowazekii*, and *Escherichia coli* 0157. Likewise, a different genome or group of genomes could be selected as the target genome(s) for other purposes. For example, a human genome or mitochondrial DNA may be the target over common genomes found in a soil sample or other sample environments where a crime may have taken place. Thus, the current methods and compositions can be applied and the human genome (target) selectively amplified over the background genomes. Other examples could include the genomes of group of viruses that cause respiratory illness, pathogens that cause sepsis, or a group of fungi known to contaminate households.

Background Genomes for Design of Targeted Whole Genome Amplification Primers

Background genomes may be selected based on the likelihood of the nucleic acid of certain organisms being present. For example, a soil sample which was handled by a human would be expected to contain nucleic acid representing the genomes of organisms including, but not limited to: *Homo sapiens, Gallus gallus, Guillardia theta, Oryza sativa, Ara-*

*bidopsis thaliana, Yarrowia lipolytica, Saccharomyces cerevisiae, Debaryomyces hansenii, Kluyveromyces lactis, Schizosaccharmyces pom, Aspergillus fumigatus, Cryptococcus neoformans, Encephalitozoon cuniculi, Eremothecium gossypii, Candida glabrata, Apis mellifera, Drosophila melanogaster, Tribolium castaneum, Anopheles gambiae,* and *Caenorhabditis elegans.* Any or all of these genomes are appropriate to estimate as background genomes in the sample. The organisms actually in any particular sample will vary for each sample based upon the source and/or environment. Therefore, background genomes may be selected based upon the identities of organisms actually present in the sample. The composition of a sample can be determined using any of a number of techniques known to those ordinarily skilled in the art. In a further embodiment, the primers can be designed based upon actual identification of one or more background organisms in the sample, and based upon likelihood of any further one or more background organisms being in the sample.

Identification of Unique Genome Sequence Segments as Primer Hybridization Sites

Once the target and background genomes of a sample are determined, the next step is to identify genome sequence segments within the target genome which are useful as primer hybridization sites. The efficiency of a given targeted whole genome amplification is dependent on effective use of primers. To produce an amplification product representative of a whole genome, the primer hybridization sites should have appropriate separation across the length of the genome. Preferably the mean separation distance between the primer hybridization sites is about 1000 nucleobases or less. More preferably the mean separation is about 800 nucleobases in length or less. Even more preferably, the mean separation is about 600 nucleobases in length or less. Most preferably, the mean separation between primer hybridization sites is about 500 nucleobases in length or less.

One with ordinary skill in the art will recognize that effective priming for whole genome amplification depends upon several factors such as the fidelity and processivity of the polymerase enzyme used for primer extension. A longer mean separation distance between primer hybridization sites becomes more acceptable if the polymerase enzyme has high processivity. This indicates that the polymerase binds tightly to the nucleic acid template. This is a desirable characteristic for targeted whole genome amplification because it enables the polymerase to remain bound to the template nucleic acid and continue to extend the complementary nucleic acid strand being synthesized. Examples of polymerase enzymes having high processivity include, but are not limited to Phi29 polymerase and Taq polymerase. Protein engineering strategies have been used to produce high processivity polymerase enzymes, for example, by covalent linkage of a polymerase to a DNA-binding protein (Wang et al., Nucl. Acids Res., 2004, 32(3) 1197-1207). As polymerases with improved processivity become available, longer mean separation distances, even greatly exceeding 1000 nucleobases may be acceptable for targeted whole genome amplification.

Hybridization Sensitivity and Selectivity

Figure 1:
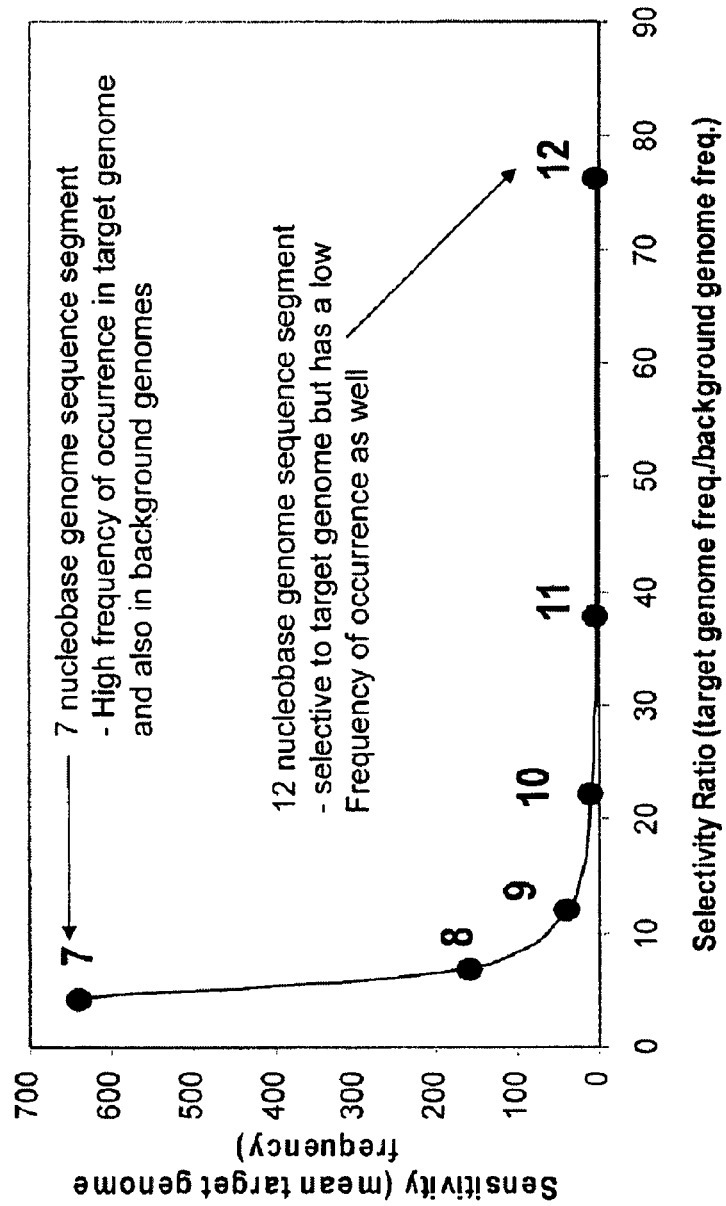

For the purpose of targeted whole genome amplification, the choice of length of the primer hybridization sites (genome sequence segments) and the lengths of the corresponding primers hybridizing thereto, preferably will balance two factors; (1) sensitivity, which indicates the frequency of binding of a given primer to the target genome, and (2) selectivity, which indicates the extent to which a given primer hybridizes to the target genome with greater frequency than it hybridizes to background genomes. Generally, longer primers tend toward greater selectivity and lesser sensitivity while the converse holds for shorter primers. The relationship between primer length, selectivity and sensitivity is graphically represented in FIG. 1. Preferably primers of about 5 to about 13 nucleobases in length are useful for targeted whole genome amplification; however, primer lengths falling outside of this range can be used as well. One will recognize that this range comprises primers having lengths of 5, 6, 7, 8, 9, 10, 11, 12 and 13 nucleobases. Primer size affects the balance between selectivity of the primer and sensitivity of the primer. Optimal primer length is determined for each sample with this balance in mind. Primers with lengths less than 5 nucleobases or greater than 13 nucleobases are also useful if the selectivity and sensitivity can be optimally maintained for that sample. Choosing a plurality of primers having various lengths provide broad priming across the target genome sequence(s) while also providing preferential binding of the primers to the target genome sequence(s) relative to the background genome sequences.

Selection Threshold Criteria

In some embodiments, it is preferable to determine a suitable sub-set of the total unique genome sequence segments in order to reduce the total number of primers in the targeted whole genome amplification set in order to reduce the costs and complexity of the primer set. In some embodiments, determination of the suitable sub-set of unique genome sequence segments entails choosing one or more threshold criteria which indicate a useful and practical cut-off point for sensitivity and/or selectivity of a given genome sequence segment. Examples of such criteria include, but are not limited to, a selected threshold frequency of occurrence (a frequency of occurrence threshold value), and a selected selectivity ratio (a selectivity ratio threshold value).

In some embodiments, it is useful to rank the total unique genome sequence segments according to the criteria. For example, the total unique genome sequence segments are ranked according to frequency of occurrence with the #1 rank indicating the greatest frequency of occurrence and the lowest rank indicating the lowest frequency of occurrence. A threshold frequency of occurrence can then be chosen from the ranks. The threshold frequency of occurrence serves as the dividing line between members of the sub-set chosen for further analysis and the members that will not be further analyzed.

In a non-limiting example, the mean "frequency of occurrence" can be calculated from the frequency of occurrence of the total genome sequence segments and this mean frequency of occurrence can be selected as a threshold criterion. The "frequency of occurrence" is defined in the "Definitions" section and also described in detail in Example 1. In one embodiment, genome sequence segments having a frequency of occurrence equal to or greater than the mean frequency of occurrence for all genome sequences being analyzed are chosen as a sub-set for further analysis. In other examples, the frequency of occurrence threshold criterion can be chosen above the mean frequency of occurrence or below the mean frequency of occurrence. In other examples, the sub-set is chosen with a frequency of occurrence threshold criterion that defines the sub-set as consisting of 80%, 70%, 60% or 50% of the total unique genome sequence segments or any whole or fractional number therebetween.

In another non-limiting example, a "selectivity ratio" is chosen as the threshold criterion. The selectivity ratio is defined in the "Definitions" section and also described in detail in Example 1. In one embodiment, all genome sequence segments having a selectivity ratio equal to or greater than the mean selectivity ratio are chosen as a sub-set for further analysis. In other examples, the selectivity ratio threshold criterion can be chosen above the mean selectivity ratio or below the mean selectivity ratio. In other examples, the sub-set is chosen with a selectivity ratio threshold criterion that defines the sub-set as consisting of 80%, 70%, 60% or 50% of the total unique genome sequence segments or any whole or fractional number therebetween.

In some embodiments, choosing the target genome sequence segments that are useful as primer hybridization sites is facilitated by the identification of most, if not all, of the unique genome sequence segments with lengths of 5, 6, 7, 8, 9, 10, 11, 12 and 13 nucleobases from which the primer hybridization sites will be chosen. Identification of unique sequence segments within genome sequences itself is a procedure that is well known to those with ordinary skill in bioinformatics. Furthermore, determination of the frequency of occurrence of a given genome sequence segment can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656). One with ordinary skill will recognize that improvements in polymerase processivity through, for example, protein engineering, discovery of new polymerases or improvements in amplification reagents and methods will allow for a shift in the balance between selectivity and sensitivity toward selectivity because a polymerase with improved processivity can synthesize longer stretches of primer extension products without the need for high frequency of occurrence of shorter genome sequence segments acting as hybridization sites for shorter primers. Thus, primer lengths above 13 nucleobases are also practical for use in targeted whole genome amplification.

Example 1 provides a demonstration of identification of unique genome sequence segments within a target genome, determination of the frequencies of occurrence of the genome sequence segments within the target genome sequence and determination of the frequencies of occurrence of the genome sequence segments within the background genome sequences. The example further describes calculation and ranking of selectivity ratios using the frequencies of occurrence of genome sequence segments within the target genomes and within the background genomes. In brief, selectivity ratios provide a description of the selectivity of a given genome sequence segment towards the target genome(s) with respect to the background genomes. A selectivity ratio is calculated for a given genome sequence segment simply by dividing the frequency of occurrence of the genome sequence segment within the target genome(s) by the frequency of occurrence of the genome sequence segment in the background genomes. A high selectivity ratio for a given genome sequence segment is favorable because it indicates that a primer designed to hybridize to the genome sequence segment will hybridize to the target genome(s) more frequently than it will hybridize to the background genomes, thus, accomplishing one objective for selective priming of the target genome. Selectivity ratios can be calculated either for a single target genome or for a plurality of target genomes. It is advantageous to consider the frequency of occurrence of all genome sequence segments in all of the chosen background genome segments to obtain useful selectivity ratios but, depending on the objective of the targeted whole genome amplification, it is not typically necessary to consider all possible target genomes in calculation of selectivity ratios. For example, in a simplified system consisting of two target genomes (target genome A and target genome B) and three background genomes (background genomes C, D and E), the selectivity ratio for genome sequence segment X which occurs once (frequency of occurrence=1) in A, B, C, D and E, the target genome A selectivity ratio would be calculated as follows:

$$1(A)/(1(C)+1(D)+1(E))=0.333$$

In contrast, the total target genome (A+B) selectivity ratio would be calculated as follows:

$$1(A)+1(B)/(1(C)+1(D)+1(E))=0.667$$

Design of Primers

The primers that are designed to hybridize to the selected genome sequence segments are preferably 100% complementary to the genome sequence segments. In other embodiments, the primers that are designed to hybridize to the selected genome sequence segments are at least about 70% to about 100% complementary to the genome sequence segments, or any whole or fractional number therebetween. In general terms, design of primers for hybridization to selected nucleic acid sequences is well known to those with skill in the art and can be aided by commercially available computer programs. It is generally preferable to design a given primer such that it is the same length as the genome sequence segment which was analyzed and chosen as a primer hybridization site. However, in some cases it may be advantageous to alter the length of the primer relative to the primer hybridization site. For example, if the primer is analyzed and found to have an unfavorable melting temperature and would benefit from elongation at the 5' or 3' end to produce a primer having an improved affinity for the target genome sequence. The length of the primer can be either increased or decreased. One with ordinary skill will recognize that alteration of the primer length also alters the primer hybridization site so that it no longer identical to the originally selected genome sequence segment. In some cases, it may be beneficial to analyze the genome sequence segment which corresponds to the hybridization site of a given length-altered primer. This analysis may be done by examination of data including but not limited to: frequency of occurrence and selectivity ratio and may also be done by actual in vitro testing of the length-altered primer.

In some embodiments, in cases where it may be advantageous to design a primer to be less than 100% complementary to its corresponding genome sequence segment, it is also advantageous to examine the complement of the re-calculate selection criteria (such as frequency of occurrence and selectivity ratio) for a hypothetical genome sequence segment that is 100% complementary to the primer which is less than 100% complementary to its corresponding original genome sequence segment. If the selection criteria are unfavorable, it would be advantageous to consider design of an alternate primer sequence having improved selection criteria.

In some embodiments, degenerate primers are designed in cases where there is ambiguity in the genome sequence or there is the possibility of occurrence of a single nucleotide polymorphism.

In some embodiments, one or more phosphorothioate linkages are incorporated into the primers at the 3' end for the purpose of making the primers more resistant to nuclease activity.

In some embodiments, the primers comprise chemically modified nucleobases which enhance affinity of hybridization and promote amplification efficiency. Such chemical modifications include, but are not limited to: 5-propynyl pyrimidines, phenoxazines, G-clamps, 2,6-diaminopurines and the like. One with ordinary skill in the art of making nucleotide modifications is capable of producing appropriate modifications to enhance the affinity of primers designed by the methods disclosed herein.

In some embodiments, the primers are designed based upon the methods disclosed herein, synthesized and tested in targeted whole genome amplification under in vitro conditions where the efficiency of the targeted whole genome amplification can be assessed with respect to efficiency and/or bias toward the target genome(s) with respect to the background genomes. If the efficiency and/or bias is found to be sub-optimal, redesign of selected primers may then be made by modifying them to correct potential defects such as poor affinity for template nucleic acid, occurrence of secondary structure and formation of primer dimers. In some embodiments, the redesigned primers are subjected to one or more additional rounds of in vitro testing in targeted whole genome amplification reactions to confirm their collective efficiency and/or bias toward the target genome(s) with respect to the background genomes. In some embodiments, if the efficiency and/or bias is found to be sub-optimal after a round of in vitro testing, the process of selection of primers is repeated using altered selection criteria which may include a higher selectivity ratio threshold value or one or more altered stopping criteria values which may include altered values for mean separation distance or maximum separation distance. One with ordinary skill will recognize that alteration of the selectivity ratio threshold value and the stopping criteria will result in a different set of primers being selected. The different sets of primers selected as a result of alteration of the selectivity ratio threshold value and/or stopping criteria may then be subjected to in vitro testing and additional rounds of alterations of the selection criteria for selection of an improved set of primers as needed.

Targeted Whole Genome Amplification Primer Kits

Some embodiments also comprise kits that include targeted whole genome amplification primers designed according to the methods disclosed herein. In some embodiments, the kits comprise primers designed for general targeted whole genome amplification of bacteria from one or more collections of background genomes. For example, a targeted whole genome amplification kit for identification of bacteria in soil will have primers selected based on the genomes of typical background organisms found in soil. In another example, a targeted whole genome amplification kit for genotyping of viruses causing respiratory illness might be assembled with primers selected based on the target genomes of the respiratory pathogens and background genomes including the human genome and the genomes of commensal organisms found in human mucus, or other fluids. In another example, a targeted whole genome amplification kit for genotyping of sepsis-causing bacteria might be assembled with primers selected based on the target genomes of the sepsis-causing bacteria and background genomes including the human genome. Since human blood generally does not contain significant quantities of bacteria under non-sepsis conditions, bacterial genomes generally not be included in the primer selection process for this kit.

In some embodiments, the kits comprise a sufficient quantity of a polymerase enzyme having high processivity. In some embodiments, the high processivity polymerase is Phi29 polymerase or Taq polymerase. In other embodiments, the high processivity polymerase is a genetically engineered polymerase whose processivity is increased relative to the native polymerase from which it was constructed.

In some embodiments, the kits further comprise deoxynucleotide triphosphates, buffers, buffer additives such as magnesium salts, trehalose and betaine at concentrations optimized for targeted whole genome amplification.

In some embodiments, the kits further comprise instructions for carrying out targeted whole genome amplification reactions.

In one embodiment, the kits comprise at least a majority of the primers of the group consisting of SEQ ID NOs: 203-402 (see Table 3) or preferably at least a majority of the primers of the group consisting of SEQ ID NOs: 204:593 (see Table 4).

Bioagent Identifying Amplicons

Disclosed herein are methods for detection and identification of unknown bioagents using bioagent identifying amplicons. Primers are selected to hybridize to conserved sequence regions of nucleic acids derived from a bioagent, and which bracket variable sequence regions to yield a bioagent identifying amplicon, which can be amplified and which is amenable to molecular mass determination. The molecular mass then provides a means to uniquely identify the bioagent without a requirement for prior knowledge of the possible identity of the bioagent. The molecular mass or corresponding base composition signature of the amplification product is then matched against a database of molecular masses or base composition signatures. A match is obtained when an experimentally-determined molecular mass or base composition of an analyzed amplification product is compared with known molecular masses or base compositions of known bioagent identifying amplicons and the experimentally determined molecular mass or base composition is the same as the molecular mass or base composition of one of the known bioagent identifying amplicons. Alternatively, the experimentally-determined molecular mass or base composition may be within experimental error of the molecular mass or base composition of a known bioagent identifying amplicon and still be classified as a match. In some cases, the match may also be classified using a probability of match model such as the models described in U.S. Ser. No. 11/073,362, which is commonly owned and incorporated herein by reference in entirety. Furthermore, the method can be applied to rapid parallel multiplex analyses, the results of which can be employed in a triangulation identification strategy. The present method provides rapid throughput and does not require nucleic acid sequencing of the amplified target sequence for bioagent detection and identification.

Despite enormous biological diversity, all forms of life on earth share sets of essential, common features in their genomes. Since genetic data provide the underlying basis for identification of bioagents by the methods disclosed herein, it is necessary to select segments of nucleic acids which ideally provide enough variability to distinguish each individual bioagent and whose molecular mass is amenable to molecular mass determination.

Unlike bacterial genomes, which exhibit conservation of numerous genes (i.e. housekeeping genes) across all organisms, viruses do not share a gene that is essential and conserved among all virus families. Therefore, viral identification is achieved within smaller groups of related viruses, such as members of a particular virus family or genus. For example, RNA-dependent RNA polymerase is present in all single-stranded RNA viruses and can be used for broad priming as well as resolution within the virus family.

In some embodiments, at least one bacterial nucleic acid segment is amplified in the process of identifying the bacterial bioagent. Thus, the nucleic acid segments that can be amplified by the primers disclosed herein and that provide enough variability to distinguish each individual bioagent and whose molecular masses are amenable to molecular mass determination are herein described as bioagent identifying amplicons.

In some embodiments, bioagent identifying amplicons comprise from about 27 to about 200 nucleobases (i.e. from about 39 to about 200 linked nucleosides), although both longer and short regions may be used. One of ordinary skill in the art will appreciate that these embodiments include compounds of 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199 or 200 nucleobases in length, or any range therewithin.

It is the combination of the portions of the bioagent nucleic acid segment to which the primers hybridize (hybridization sites) and the variable region between the primer hybridization sites that comprises the bioagent identifying amplicon. Thus, it can be said that a given bioagent identifying amplicon is "defined by" a given pair of primers.

In some embodiments, bioagent identifying amplicons amenable to molecular mass determination which are produced by the primers described herein are either of a length, size or mass compatible with the particular mode of molecular mass determination or compatible with a means of providing a predictable fragmentation pattern in order to obtain predictable fragments of a length compatible with the particular mode of molecular mass determination. Such means of providing a predictable fragmentation pattern of an amplification product include, but are not limited to, cleavage with chemical reagents, restriction enzymes or cleavage primers, for example. Thus, in some embodiments, bioagent identifying amplicons are larger than 200 nucleobases and are amenable to molecular mass determination following restriction digestion. Methods of using restriction enzymes and cleavage primers are well known to those with ordinary skill in the art.

In some embodiments, amplification products corresponding to bioagent identifying amplicons are obtained using the polymerase chain reaction (PCR) that is a routine method to those with ordinary skill in the molecular biology arts. Other amplification methods may be used such as ligase chain reaction (LCR), low-stringency single primer PCR, and multiple strand displacement amplification (MDA). These methods are also known to those with ordinary skill.

Primer Pairs that Define Bioagent Identifying Amplicons

In some embodiments, the primers are designed to bind to conserved sequence regions of a bioagent identifying amplicon that flank an intervening variable region and yield amplification products which provide variability sufficient to distinguish each individual bioagent, and which are amenable to molecular mass analysis. In some embodiments, the highly conserved sequence regions exhibit between about 80-100%, or between about 90-100%, or between about 95-100% identity, or between about 99-100% identity. The molecular mass of a given amplification product provides a means of identifying the bioagent from which it was obtained, due to the variability of the variable region. Thus, design of the primers involves selection of a variable region with sufficient variability to resolve the identity of a given bioagent. In some embodiments, bioagent identifying amplicons are specific to the identity of the bioagent.

In some embodiments, identification of bioagents is accomplished at different levels using primers suited to resolution of each individual level of identification. Broad range survey primers are designed with the objective of identifying a bioagent as a member of a particular division (e.g., an order, family, genus or other such grouping of bioagents above the species level of bioagents). In some embodiments, broad range survey intelligent primers are capable of identification of bioagents at the species or sub-species level. Examples of broad range survey primers include, but are not limited to: primer pair numbers: 346 (SEQ ID NOs: 594:602), and 348 (SEQ ID NOs: 595:603) which target DNA encoding 16S rRNA, and primer pair number 349 (SEQ ID NOs: 596:604) which targets DNA encoding 23S rRNA. Additional broad range survey primer pairs are disclosed in U.S. Ser. No. 11/409,535 which is incorporated herein by reference in entirety.

In some embodiments, drill-down primers are designed with the objective of identifying a bioagent at the sub-species level (including strains, subtypes, variants and isolates) based on sub-species characteristics which may, for example, include single nucleotide polymorphisms (SNPs), variable number tandem repeats (VNTRs), deletions, drug resistance mutations or any other modification of a nucleic acid sequence of a bioagent relative to other members of a species having different sub-species characteristics. Drill-down intelligent primers are not always required for identification at the sub-species level because broad range survey intelligent primers may, in some cases provide sufficient identification resolution to accomplishing this identification objective. Examples of drill-down primers are disclosed in U.S. patent application Ser. No. 11/409,535 which is incorporated herein by reference in entirety.

A representative process flow diagram used for primer selection and validation process is outlined in FIG. 8. For each group of organisms, candidate target sequences are identified (200) from which nucleotide alignments are created (210) and analyzed (220). Primers are then designed by selecting appropriate priming regions (230) to facilitate the selection of candidate primer pairs (240). The primer pairs are then subjected to in silico analysis by electronic PCR (ePCR) (300) wherein bioagent identifying amplicons are obtained from sequence databases such as GenBank or other sequence collections (310) and checked for specificity in silico (320). Bioagent identifying amplicons obtained from GenBank sequences (310) can also be analyzed by a probability model which predicts the capability of a given amplicon to identify unknown bioagents such that the base compositions of amplicons with favorable probability scores are then stored in a base composition database (325). Alternatively, base compositions of the bioagent identifying amplicons obtained from the primers and GenBank sequences can be directly entered into the base composition database (330). Candidate primer pairs (240) are validated by testing their ability to hybridize to target nucleic acid by an in vitro amplification by a method such as PCR analysis (400) of nucleic acid from a collection of organisms (410). Amplification products thus obtained are analyzed by gel electrophoresis or by mass spectrometry to confirm the sensitivity, specificity and reproducibility of the primers used to obtain the amplification products (420).

Many important pathogens, including the organisms of greatest concern as biowarfare agents, have been completely sequenced. This effort has greatly facilitated the design of primers for the detection of unknown bioagents. The combination of broad-range priming with division-wide and drill-down priming has been used very successfully in several applications of the technology, including environmental surveillance for biowarfare threat agents and clinical sample analysis for medically important pathogens.

Synthesis of primers is well known and routine in the art. The primers may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. However, it should be noted that "synthesis" of primers does not equate with "design" of primers. The primers disclosed herein have been designed by the methods disclosed herein and then synthesized by the known methods.

In some embodiments, primers are employed as compositions for use in methods for identification of bacterial bioagents as follows: a primer pair composition is contacted with nucleic acid (such as, for example, bacterial DNA or DNA reverse transcribed from the rRNA) of an unknown bacterial bioagent. The nucleic acid is then amplified by a nucleic acid amplification technique, such as PCR for example, to obtain an amplification product that represents a bioagent identifying amplicon. The molecular mass of each strand of the double-stranded amplification product is determined by a molecular mass measurement technique such as mass spectrometry for example, wherein the two strands of the double-stranded amplification product are separated during the ionization process. In some embodiments, the mass spectrometry is electrospray Fourier transform ion cyclotron resonance mass spectrometry (ESI-FTICR-MS) or electrospray time of flight mass spectrometry (ESI-TOF-MS). A list of possible base compositions can be generated for the molecular mass value obtained for each strand and the choice of the correct base composition from the list is facilitated by matching the base composition of one strand with a complementary base composition of the other strand. The molecular mass or base composition thus determined is then compared with a database of molecular masses or base compositions of analogous bioagent identifying amplicons for known bacterial bioagents. A match between the molecular mass or base composition of the amplification product and the molecular mass or base composition of an analogous bioagent identifying amplicon for a known viral bioagent indicates the identity of the unknown bacterial bioagent. In some embodiments, the method is repeated using one or more different primer pairs to resolve possible ambiguities in the identification process or to improve the confidence level for the identification assignment.

In some embodiments, a bioagent identifying amplicon may be produced using only a single primer (either the forward or reverse primer of any given primer pair), provided an appropriate amplification method is chosen, such as, for example, low stringency single primer PCR (LSSP-PCR). Adaptation of this amplification method in order to produce bioagent identifying amplicons can be accomplished by one with ordinary skill in the art without undue experimentation.

In some cases, the molecular mass or base composition of a bacterial bioagent identifying amplicon defined by a broad range survey primer pair does not provide enough resolution to unambiguously identify a bacterial bioagent at or below the species level. These cases benefit from further analysis of one or more bacterial bioagent identifying amplicons generated from at least one additional broad range survey primer pair or from at least one additional division-wide primer pair. The employment of more than one bioagent identifying amplicon for identification of a bioagent is herein referred to as triangulation identification.

In other embodiments, the oligonucleotide primers are division-wide primers which hybridize to nucleic acid encoding genes of species within a genus of bacteria. In other embodiments, the oligonucleotide primers are drill-down primers which enable the identification of sub-species characteristics. Drill down primers provide the functionality of producing bioagent identifying amplicons for drill-down analyses such as strain typing when contacted with nucleic acid under amplification conditions. Identification of such sub-species characteristics is often critical for determining proper clinical treatment of viral infections. In some embodiments, sub-species characteristics are identified using only broad range survey primers and division-wide and drill-down primers are not used.

In some embodiments, the primers used for amplification hybridize to and amplify genomic DNA, and DNA of bacterial plasmids.

In some embodiments, various computer software programs may be used to aid in design of primers for amplification reactions such as Primer Premier 5 (Premier Biosoft, Palo Alto, Calif.) or OLIGO Primer Analysis Software (Molecular Biology Insights, Cascade, Colo.). These programs allow the user to input desired hybridization conditions such as melting temperature of a primer-template duplex for example. In some embodiments, an in silico PCR search algorithm, such as (ePCR) is used to analyze primer specificity across a plurality of template sequences which can be readily obtained from public sequence databases such as GenBank for example. An existing RNA structure search algorithm (Macke et al., Nucl. Acids Res., 2001, 29, 4724-4735, which is incorporated herein by reference in its entirety) has been modified to include PCR parameters such as hybridization conditions, mismatches, and thermodynamic calculations (SantaLucia, Proc. Natl. Acad. Sci. U.S.A., 1998, 95, 1460-1465, which is incorporated herein by reference in its entirety). This also provides information on primer specificity of the selected primer pairs. In some embodiments, the hybridization conditions applied to the algorithm can limit the results of primer specificity obtained from the algorithm. In some embodiments, the melting temperature threshold for the primer template duplex is specified to be 35° C. or a higher temperature. In some embodiments the number of acceptable mismatches is specified to be seven mismatches or less. In some embodiments, the buffer components and concentrations and primer concentrations may be specified and incorporated into the algorithm, for example, an appropriate primer concentration is about 250 nM and appropriate buffer components are 50 mM sodium or potassium and 1.5 mM $Mg^{2+}$.

One with ordinary skill in the art of design of amplification primers will recognize that a given primer need not hybridize with 100% complementarity in order to effectively prime the synthesis of a complementary nucleic acid strand in an amplification reaction. Moreover, a primer may hybridize over one or more segments such that intervening or adjacent segments are not involved in the hybridization event. (e.g., for example, a loop structure or a hairpin structure). The primers may comprise at least 70%, at least 75%, at least 80%, at least 85%, at least 90%, at least 95% or at least 99% sequence identity with any of the primers listed in Table 2 of U.S. Ser. No. 11/409,535, which is incorporated herein by reference in entirety. Thus, in some embodiments, an extent of variation of 70% to 100%, or any range therewithin, of the sequence identity is possible relative to the specific primer sequences disclosed herein. Determination of sequence identity is described in the following example: a primer 20 nucleobases in length which is identical to another 20 nucleobase primer having two non-identical residues has 18 of 20 identical residues (18/20=0.9 or 90% sequence identity). In another example, a primer 15 nucleobases in length having all residues identical to a 15 nucleobase segment of primer 20 nucleobases in length would have 15/20=0.75 or 75% sequence identity with the 20 nucleobase primer.

Percent homology, sequence identity or complementarity, can be determined by, for example, the Gap program (Wisconsin Sequence Analysis Package, Version 8 for UNIX, Genetics Computer Group, University Research Park, Madison Wis.), using default settings, which uses the algorithm of Smith and Waterman (Adv. Appl. Math., 1981, 2, 482-489). In some embodiments, complementarity of primers with respect to the conserved priming regions of viral nucleic acid is between about 70% and about 75% 80%. In other embodiments, homology, sequence identity or complementarity, is between about 75% and about 80%. In yet other embodiments, homology, sequence identity or complementarity, is at least 85%, at least 90%, at least 92%, at least 94%, at least 95%, at least 96%, at least 97%, at least 98%, at least 99% or is 100%.

In some embodiments, the primers described herein comprise at least 70%, at least 75%, at least 80%, at least 85%, at least 90%, at least 92%, at least 94%, at least 95%, at least 96%, at least 98%, at least 99%, or 100% (or any range therewithin) sequence identity with the primer sequences specifically disclosed herein.

One with ordinary skill is able to calculate percent sequence identity or percent sequence homology and able to determine, without undue experimentation, the effects of variation of primer sequence identity on the function of the primer in its role in priming synthesis of a complementary strand of nucleic acid for production of an amplification product of a corresponding bioagent identifying amplicon.

In one embodiment, the primers are at least 13 nucleobases in length. In another embodiment, the primers are less than 36 nucleobases in length.

In some embodiments, the oligonucleotide primers are 13 to 35 nucleobases in length (13 to 35 linked nucleotide residues). These embodiments comprise oligonucleotide primers 13, 14, 15, 16, 17, 18, 19, 20, 21, 22, 23, 24, 25, 26, 27, 28, 29, 30, 31, 32, 33, 34 or 35 nucleobases in length, or any range therewithin. The methods disclosed herein contemplate use of both longer and shorter primers. Furthermore, the primers may also be linked to one or more other desired moieties, including, but not limited to, affinity groups, ligands, regions of nucleic acid that are not complementary to the nucleic acid to be amplified, labels, etc. Primers may also form hairpin structures. For example, hairpin primers may be used to amplify short target nucleic acid molecules. The presence of the hairpin may stabilize the amplification complex (see e.g., TAQMAN MicroRNA Assays, Applied Biosystems, Foster City, Calif.).

In some embodiments, any oligonucleotide primer pair may have one or both primers with less then 70% sequence homology with a corresponding member of any of the primer pairs of Table 2 of U.S. Ser. No. 11/409,535, if the primer pair has the capability of producing an amplification product corresponding to a bioagent identifying amplicon. In other embodiments, any oligonucleotide primer pair may have one or both primers with a length greater than 35 nucleobases if the primer pair has the capability of producing an amplification product corresponding to a bioagent identifying amplicon.

In some embodiments, the function of a given primer may be substituted by a combination of two or more primers segments that hybridize adjacent to each other or that are linked by a nucleic acid loop structure or linker which allows a polymerase to extend the two or more primers in an amplification reaction.

In some embodiments, the primer pairs used for obtaining bioagent identifying amplicons are the primer pairs of Table 2 of U.S. Ser. No. 11/409,535. In other embodiments, other combinations of primer pairs are possible by combining certain members of the forward primers with certain members of the reverse primers. An example can be seen in Table 2 of U.S. Ser. No. 11/409,535, for two primer pair combinations of forward primer 16S_EC_789_810_F with the reverse primers 16S_EC_880_894_R or 16S_EC_882_899_R. Arriving at a favorable alternate combination of primers in a primer pair depends upon the properties of the primer pair, most notably the size of the bioagent identifying amplicon that is defined by the primer pair, which preferably is between about 39 to about 200 nucleobases in length. Alternatively, a bioagent identifying amplicon longer than 200 nucleobases in length could be cleaved into smaller segments by cleavage reagents such as chemical reagents, or restriction enzymes, for example.

In some embodiments, the primers are configured to amplify nucleic acid of a bioagent to produce amplification products that can be measured by mass spectrometry and from whose molecular masses candidate base compositions can be readily calculated.

In some embodiments, any given primer comprises a modification comprising the addition of a non-templated T residue to the 5' end of the primer (i.e., the added T residue does not necessarily hybridize to the nucleic acid being amplified). The addition of a non-templated T residue has an effect of minimizing the addition of non-templated adenosine residues as a result of the non-specific enzyme activity of Taq polymerase (Magnuson et al., Biotechniques, 1996, 21, 700-709), an occurrence which may lead to ambiguous results arising from molecular mass analysis.

In some embodiments, primers may contain one or more universal bases. Because any variation (due to codon wobble in the 3rd position) in the conserved regions among species is likely to occur in the third position of a DNA (or RNA) triplet, oligonucleotide primers can be designed such that the nucleotide corresponding to this position is a base which can bind to more than one nucleotide, referred to herein as a "universal nucleobase." For example, under this "wobble" pairing, inosine (I) binds to U, C or A; guanine (G) binds to U or C, and uridine (U) binds to U or C. Other examples of universal nucleobases include nitroindoles such as 5-nitroindole or 3-nitropyrrole (Loakes et al., Nucleosides and Nucleotides, 1995, 14, 1001-1003), the degenerate nucleotides dP or dK (Hill et al.), an acyclic nucleoside analog containing 5-nitroindazole (Van Aerschot et al., Nucleosides and Nucleotides, 1995, 14, 1053-1056) or the purine analog 1-(2-deoxy-β-D-ribofuranosyl)-imidazole-4-carboxamide (Sala et al., Nucl. Acids Res., 1996, 24, 3302-3306).

In some embodiments, to compensate for the somewhat weaker binding by the wobble base, the oligonucleotide primers are designed such that the first and second positions of each triplet are occupied by nucleotide analogs that bind with greater affinity than the unmodified nucleotide. Examples of these analogs include, but are not limited to, 2,6-diaminopurine which binds to thymine, 5-propynyluracil (also known as propynylated thymine) which binds to adenine and 5-propynylcytosine and phenoxazines, including G-clamp, which binds to G. Propynylated pyrimidines are described in U.S. Pat. Nos. 5,645,985, 5,830,653 and 5,484,908, each of which is commonly owned and incorporated herein by reference in its entirety. Propynylated primers are described in U.S. Pre- Grant Publication No. 2003-0170682, which is also commonly owned and incorporated herein by reference in its entirety. Phenoxazines are described in U.S. Pat. Nos. 5,502,177, 5,763,588, and 6,005,096, each of which is incorporated herein by reference in its entirety. G-clamps are described in U.S. Pat. Nos. 6,007,992 and 6,028,183, each of which is incorporated herein by reference in its entirety.

In some embodiments, primer hybridization is enhanced using primers containing 5-propynyl deoxycytidine and deoxythymidine nucleotides. These modified primers offer increased affinity and base pairing selectivity.

In some embodiments, non-template primer tags are used to increase the melting temperature (Tm) of a primer-template duplex in order to improve amplification efficiency. A non-template tag is at least three consecutive A or T nucleotide residues on a primer which are not complementary to the template. In any given non-template tag, A can be replaced by C or G and T can also be replaced by C or G. Although Watson-Crick hybridization is not expected to occur for a non-template tag relative to the template, the extra hydrogen bond in a G-C pair relative to an A-T pair confers increased stability of the primer-template duplex and improves amplification efficiency for subsequent cycles of amplification when the primers hybridize to strands synthesized in previous cycles.

In other embodiments, propynylated tags may be used in a manner similar to that of the non-template tag, wherein two or more 5-propynylcytidine or 5-propynyluridine residues replace template matching residues on a primer. In other embodiments, a primer contains a modified internucleoside linkage such as a phosphorothioate linkage, for example.

In some embodiments, the primers contain mass-modifying tags. Reducing the total number of possible base compositions of a nucleic acid of specific molecular weight provides a means of avoiding a persistent source of ambiguity in determination of base composition of amplification products. Addition of mass-modifying tags to certain nucleobases of a given primer will result in simplification of de novo determination of base composition of a given bioagent identifying amplicon from its molecular mass.

In some embodiments, the mass modified nucleobase comprises one or more of the following: for example, 7-deaza-2'-deoxyadenosine-5-triphosphate, 5-iodo-2'-deoxyuridine-5'-triphosphate, 5-bromo-2'-deoxyuridine-5'-triphosphate, 5-bromo-2'-deoxycytidine-5'-triphosphate, 5-iodo-2'-deoxycytidine-5'-triphosphate, 5-hydroxy-2'-deoxyuridine-5'-triphosphate, 4-thiothymidine-5'-triphosphate, 5-aza-2'-deoxyuridine-5'-triphosphate, 5-fluoro-2'-deoxyuridine-5'-triphosphate, O6-methyl-2'-deoxyguanosine-5'-triphosphate, N2-methyl-2'-deoxyguanosine-5'-triphosphate, 8-oxo-2'-deoxyguanosine-5'-triphosphate or thiothymidine-5'-triphosphate. In some embodiments, the mass-modified nucleobase comprises 15N or 13C or both 15N and 13C.

In some embodiments, multiplex amplification is performed where multiple bioagent identifying amplicons are amplified with a plurality of primer pairs. The advantages of multiplexing are that fewer reaction containers (for example, wells of a 96- or 384-well plate) are needed for each molecular mass measurement, providing time, resource and cost savings because additional bioagent identification data can be obtained within a single analysis. Multiplex amplification methods are well known to those with ordinary skill and can be developed without undue experimentation. However, in some embodiments, one useful and non-obvious step in selecting a plurality candidate bioagent identifying amplicons for multiplex amplification is to ensure that each strand of each amplification product will be sufficiently different in molecular mass that mass spectral signals will not overlap and lead to ambiguous analysis results. In some embodiments, a 10 Da difference in mass of two strands of one or more amplification products is sufficient to avoid overlap of mass spectral peaks.

In some embodiments, as an alternative to multiplex amplification, single amplification reactions can be pooled before analysis by mass spectrometry. In these embodiments, as for multiplex amplification embodiments, it is useful to select a plurality of candidate bioagent identifying amplicons to ensure that each strand of each amplification product will be sufficiently different in molecular mass that mass spectral signals will not overlap and lead to ambiguous analysis results.

Determination of Molecular Mass of Bioagent Identifying Amplicons

In some embodiments, the molecular mass of a given bioagent identifying amplicon is determined by mass spectrometry. Mass spectrometry has several advantages, not the least of which is high bandwidth characterized by the ability to separate (and isolate) many molecular peaks across a broad range of mass to charge ratio (m/z). Thus mass spectrometry is intrinsically a parallel detection scheme without the need for radioactive or fluorescent labels, since every amplification product is identified by its molecular mass. The current state of the art in mass spectrometry is such that less than femtomole quantities of material can be readily analyzed to afford information about the molecular contents of the sample. An accurate assessment of the molecular mass of the material can be quickly obtained, irrespective of whether the molecular weight of the sample is several hundred, or in excess of one hundred thousand atomic mass units (amu) or Daltons.

In some embodiments, intact molecular ions are generated from amplification products using one of a variety of ionization techniques to convert the sample to gas phase. These ionization methods include, but are not limited to, electrospray ionization (ES), matrix-assisted laser desorption ionization (MALDI) and fast atom bombardment (FAB). Upon ionization, several peaks are observed from one sample due to the formation of ions with different charges. Averaging the multiple readings of molecular mass obtained from a single mass spectrum affords an estimate of molecular mass of the bioagent identifying amplicon. Electrospray ionization mass spectrometry (ESI-MS) is particularly useful for very high molecular weight polymers such as proteins and nucleic acids having molecular weights greater than 10 kDa, since it yields a distribution of multiply-charged molecules of the sample without causing a significant amount of fragmentation.

The mass detectors used in the methods described herein include, but are not limited to, Fourier transform ion cyclotron resonance mass spectrometry (FT-ICR-MS), time of flight (TOF), ion trap, quadrupole, magnetic sector, Q-TOF, and triple quadrupole.

Base Compositions of Bioagent Identifying Amplicons

Although the molecular mass of amplification products obtained using intelligent primers provides a means for identification of bioagents, conversion of molecular mass data to a base composition signature is useful for certain analyses. As used herein, "base composition" is the exact number of each nucleobase (A, T, C and G) determined from the molecular mass of a bioagent identifying amplicon. In some embodiments, a base composition provides an index of a specific organism. Base compositions can be calculated from known sequences of known bioagent identifying amplicons and can be experimentally determined by measuring the molecular mass of a given bioagent identifying amplicon, followed by determination of all possible base compositions which are consistent with the measured molecular mass within acceptable experimental error. The following example illustrates determination of base composition from an experimentally obtained molecular mass of a 46-mer amplification product originating at position 1337 of the 16S rRNA of *Bacillus anthracis*. The forward and reverse strands of the amplification product have measured molecular masses of 14208 and 14079 Da, respectively. The possible base compositions derived from the molecular masses of the forward and reverse strands for the *Bacillus anthracis* products are listed in Table 1.

sification, a problem which is overcome by a triangulation identification process using bioagent identifying amplicons not affected by overlap of base composition probability clouds.

In some embodiments, base composition probability clouds provide the means for screening potential primer pairs in order to avoid potential misclassifications of base compositions. In other embodiments, base composition probability clouds provide the means for predicting the identity of a bioagent whose assigned base composition was not previously observed and/or indexed in a bioagent identifying amplicon base composition database due to evolutionary

TABLE 1

Possible Base Compositions for *B. anthracis* 46mer Amplification Product

| Calc. Mass Forward Strand | Mass Error Forward Strand | Base Composition of Forward Strand | Calc. Mass Reverse Strand | Mass Error Reverse Strand | Base Composition of Reverse Strand |
|---|---|---|---|---|---|
| 14208.2935 | 0.079520 | A1 G17 C10 T18 | 14079.2624 | 0.080600 | A0 G14 C13 T19 |
| 14208.3160 | 0.056980 | A1 G20 C15 T10 | 14079.2849 | 0.058600 | A0 G17 C18 T11 |
| 14208.3386 | 0.034440 | A1 G23 C20 T2 | 14079.3075 | 0.035520 | A0 G20 C23 T3 |
| 14208.3074 | 0.065560 | A6 G11 C3 T26 | 14079.2538 | 0.089180 | A5 G5 C1 T35 |
| 14208.3300 | 0.043020 | A6 G14 C8 T18 | 14079.2764 | 0.066640 | A5 G8 C6 T27 |
| 14208.3525 | 0.020480 | A6 G17 C13 T10 | 14079.2989 | 0.044100 | A5 G11 C11 T19 |
| 14208.3751 | 0.002060 | A6 G20 C18 T2 | 14079.3214 | 0.021560 | A5 G14 C16 T11 |
| 14208.3439 | 0.029060 | A11 G8 C1 T26 | 14079.3440 | 0.000980 | A5 G17 C21 T3 |
| 14208.3665 | 0.006520 | A11 G11 C6 T18 | 14079.3129 | 0.030140 | A10 G5 C4 T27 |
| 14208.3890 | 0.016020 | A11 G14 C11 T10 | 14079.3354 | 0.007600 | A10 G8 C9 T19 |
| 14208.4116 | 0.038560 | A11 G17 C16 T2 | 14079.3579 | 0.014940 | A10 G11 C14 T11 |
| 14208.4030 | 0.029980 | A16 G8 C4 T18 | 14079.3805 | 0.037480 | A10 G14 C19 T3 |
| 14208.4255 | 0.052520 | A16 G11 C9 T10 | 14079.3494 | 0.006360 | A15 G2 C2 T27 |
| 14208.4481 | 0.075060 | A16 G14 C14 T2 | 14079.3719 | 0.028900 | A15 G5 C7 T19 |
| 14208.4395 | 0.066480 | A21 G5 C2 T18 | 14079.3944 | 0.051440 | A15 G8 C12 T11 |
| 14208.4620 | 0.089020 | A21 G8 C7 T10 | 14079.4170 | 0.073980 | A15 G11 C17 T3 |
| — | — | — | 14079.4084 | 0.065400 | A20 G2 C5 T19 |
| — | — | — | 14079.4309 | 0.087940 | A20 G5 C10 T13 |

Among the 16 possible base compositions for the forward strand and the 18 possible base compositions for the reverse strand that were calculated, only one pair (shown in bold) are complementary base compositions, which indicates the true base composition of the amplification product. It should be recognized that this logic is applicable for determination of base compositions of any bioagent identifying amplicon, regardless of the class of bioagent from which the corresponding amplification product was obtained.

In some embodiments, assignment of previously unobserved base compositions (also known as "true unknown base compositions") to a given phylogeny can be accomplished via the use of pattern classifier model algorithms. Base compositions, like sequences, vary slightly from strain to strain within species, for example. In some embodiments, the pattern classifier model is the mutational probability model. On other embodiments, the pattern classifier is the polytope model. The mutational probability model and polytope model are both commonly owned and described in U.S. patent application Ser. No. 11/073,362 which is incorporated herein by reference in entirety.

In one embodiment, it is possible to manage this diversity by building "base composition probability clouds" around the composition constraints for each species. This permits identification of organisms in a fashion similar to sequence analysis. A "pseudo four-dimensional plot" can be used to visualize the concept of base composition probability clouds. Optimal primer design requires optimal choice of bioagent identifying amplicons and maximizes the separation between the base composition signatures of individual bioagents. Areas where clouds overlap indicate regions that may result in a misclastransitions in its nucleic acid sequence. Thus, in contrast to probe-based techniques, mass spectrometry determination of base composition does not require prior knowledge of the composition or sequence in order to make the measurement.

The methods disclosed herein provide bioagent classifying information similar to DNA sequencing and phylogenetic analysis at a level sufficient to identify a given bioagent. Furthermore, the process of determination of a previously unknown base composition for a given bioagent (for example, in a case where sequence information is unavailable) has downstream utility by providing additional bioagent indexing information with which to populate base composition databases. The process of future bioagent identification is thus greatly improved as more base composition indexes become available in base composition databases.

Triangulation Identification

In some cases, a molecular mass of a single bioagent identifying amplicon alone does not provide enough resolution to unambiguously identify a given bioagent. The employment of more than one bioagent identifying amplicon for identification of a bioagent is herein referred to as "triangulation identification." Triangulation identification is pursued by determining the molecular masses of a plurality of bioagent identifying amplicons selected within a plurality of housekeeping genes. This process is used to reduce false negative and false positive signals, and enable reconstruction of the origin of hybrid or otherwise engineered bioagents. For example, identification of the three part toxin genes typical of *B. anthracis* (Bowen et al., J. Appl. Microbiol., 1999, 87, 270-278) in the absence of the expected signatures from the *B. anthracis* genome would suggest a genetic engineering event.

In some embodiments, the triangulation identification process can be pursued by characterization of bioagent identifying amplicons in a massively parallel fashion using the polymerase chain reaction (PCR), such as multiplex PCR where multiple primers are employed in the same amplification reaction mixture, or PCR in multi-well plate format wherein a different and unique pair of primers is used in multiple wells containing otherwise identical reaction mixtures. Such multiplex and multi-well PCR methods are well known to those with ordinary skill in the arts of rapid throughput amplification of nucleic acids. In other related embodiments, one PCR reaction per well or container may be carried out, followed by an amplicon pooling step wherein the amplification products of different wells are combined in a single well or container which is then subjected to molecular mass analysis. The combination of pooled amplicons can be chosen such that the expected ranges of molecular masses of individual amplicons are not overlapping and thus will not complicate identification of signals.

Codon Base Composition Analysis

In some embodiments, one or more nucleotide substitutions within a codon of a gene of an infectious organism confer drug resistance upon an organism which can be determined by codon base composition analysis. The organism can be a bacterium, virus, fungus or protozoan.

In some embodiments, the amplification product containing the codon being analyzed is of a length of about 39 to about 200 nucleobases. The primers employed in obtaining the amplification product can hybridize to upstream and downstream sequences directly adjacent to the codon, or can hybridize to upstream and downstream sequences one or more sequence positions away from the codon. The primers may have between about 70% to 100% sequence complementarity with the sequence of the gene containing the codon being analyzed.

In some embodiments, the codon analysis is undertaken for the purpose of investigating genetic disease in an individual. In other embodiments, the codon analysis is undertaken for the purpose of investigating a drug resistance mutation or any other deleterious mutation in an infectious organism such as a bacterium, virus, fungus or protozoan. In some embodiments, the bioagent is a bacterium identified in a biological product.

In some embodiments, the molecular mass of an amplification product containing the codon being analyzed is measured by mass spectrometry. The mass spectrometry can be either electrospray (ESI) mass spectrometry or matrix-assisted laser desorption ionization (MALDI) mass spectrometry. Time-of-flight (TOF) is an example of one mode of mass spectrometry compatible with the methods disclosed herein.

The methods disclosed herein can also be employed to determine the relative abundance of drug resistant strains of the organism being analyzed. Relative abundances can be calculated from amplitudes of mass spectral signals with relation to internal calibrants. In some embodiments, known quantities of internal amplification calibrants can be included in the amplification reactions and abundances of analyte amplification product estimated in relation to the known quantities of the calibrants.

In some embodiments, upon identification of one or more drug-resistant strains of an infectious organism infecting an individual, one or more alternative treatments can be devised to treat the individual.

Determination of the Quantity of a Bioagent Using a Calibration Amplicon

In some embodiments, the identity and quantity of an unknown bioagent can be determined using the process illustrated in FIG. 9. Primers (500) and a known quantity of a calibration polynucleotide (505) are added to a sample containing nucleic acid of an unknown bioagent. The total nucleic acid in the sample is then subjected to an amplification reaction (510) to obtain amplification products. The molecular masses of amplification products are determined (515) from which are obtained molecular mass and abundance data. The molecular mass of the bioagent identifying amplicon (520) provides the means for its identification (525) and the molecular mass of the calibration amplicon obtained from the calibration polynucleotide (530) provides the means for its identification (535). The abundance data of the bioagent identifying amplicon is recorded (540) and the abundance data for the calibration data is recorded (545), both of which are used in a calculation (550) which determines the quantity of unknown bioagent in the sample.

A sample comprising an unknown bioagent is contacted with a pair of primers that provide the means for amplification of nucleic acid from the bioagent, and a known quantity of a polynucleotide that comprises a calibration sequence. The nucleic acids of the bioagent and of the calibration sequence are amplified and the rate of amplification is reasonably assumed to be similar for the nucleic acid of the bioagent and of the calibration sequence. The amplification reaction then produces two amplification products: a bioagent identifying amplicon and a calibration amplicon. The bioagent identifying amplicon and the calibration amplicon should be distinguishable by molecular mass while being amplified at essentially the same rate. Effecting differential molecular masses can be accomplished by choosing as a calibration sequence, a representative bioagent identifying amplicon (from a specific species of bioagent) and performing, for example, a 2-8 nucleobase deletion or insertion within the variable region between the two priming sites. The amplified sample containing the bioagent identifying amplicon and the calibration amplicon is then subjected to molecular mass analysis by mass spectrometry, for example. The resulting molecular mass analysis of the nucleic acid of the bioagent and of the calibration sequence provides molecular mass data and abundance data for the nucleic acid of the bioagent and of the calibration sequence. The molecular mass data obtained for the nucleic acid of the bioagent enables identification of the unknown bioagent and the abundance data enables calculation of the quantity of the bioagent, based on the knowledge of the quantity of calibration polynucleotide contacted with the sample.

In some embodiments, construction of a standard curve where the amount of calibration polynucleotide spiked into the sample is varied provides additional resolution and improved confidence for the determination of the quantity of bioagent in the sample. The use of standard curves for analytical determination of molecular quantities is well known to one with ordinary skill and can be performed without undue experimentation.

In some embodiments, multiplex amplification is performed where multiple bioagent identifying amplicons are amplified with multiple primer pairs which also amplify the corresponding standard calibration sequences. In this or other embodiments, the standard calibration sequences are optionally included within a single vector which functions as the calibration polynucleotide. Multiplex amplification methods are well known to those with ordinary skill and can be performed without undue experimentation.

In some embodiments, the calibrant polynucleotide is used as an internal positive control to confirm that amplification conditions and subsequent analysis steps are successful in producing a measurable amplicon. Even in the absence of copies of the genome of a bioagent, the calibration polynucleotide should give rise to a calibration amplicon. Failure to produce a measurable calibration amplicon indicates a failure of amplification or subsequent analysis step such as amplicon purification or molecular mass determination. Reaching a conclusion that such failures have occurred is in itself, a useful event.

In some embodiments, the calibration sequence is comprised of DNA. In some embodiments, the calibration sequence is comprised of RNA.

In some embodiments, the calibration sequence is inserted into a vector that itself functions as the calibration polynucleotide. In some embodiments, more than one calibration sequence is inserted into the vector that functions as the calibration polynucleotide. Such a calibration polynucleotide is herein termed a "combination calibration polynucleotide." The process of inserting polynucleotides into vectors is routine to those skilled in the art and can be accomplished without undue experimentation. Thus, it should be recognized that the calibration method should not be limited to the embodiments described herein. The calibration method can be applied for determination of the quantity of any bioagent identifying amplicon when an appropriate standard calibrant polynucleotide sequence is designed and used. The process of choosing an appropriate vector for insertion of a calibrant is also a routine operation that can be accomplished by one with ordinary skill without undue experimentation.

Identification of Bacteria Using Bioagent Identifying Amplicons

In other embodiments, the primer pairs produce bioagent identifying amplicons defined by priming regions at stable and highly conserved regions of nucleic acid of bacteria. The advantage to characterization of an amplicon defined by priming regions that fall within a highly conserved region is that there is a low probability that the region will evolve past the point of primer recognition, in which case, the primer hybridization of the amplification step would fail. Such a primer pair is thus useful as a broad range survey-type primer pair. In another embodiment, the intelligent primers produce bioagent identifying amplicons including a region which evolves more quickly than the stable region described above. The advantage of characterization bioagent identifying amplicon corresponding to an evolving genomic region is that it is useful for distinguishing emerging strain variants or the presence of virulence genes, drug resistance genes, or codon mutations that induce drug resistance.

The methods disclosed herein have significant advantages as a platform for identification of diseases caused by emerging bacterial strains such as, for example, drug-resistant strains of *Staphylococcus aureus*. The methods disclosed herein eliminate the need for prior knowledge of bioagent sequence to generate hybridization probes. This is possible because the methods are not confounded by naturally occurring evolutionary variations occurring in the sequence acting as the template for production of the bioagent identifying amplicon. Measurement of molecular mass and determination of base composition is accomplished in an unbiased manner without sequence prejudice.

Another embodiment also provides a means of tracking the spread of a bacterium, such as a particular drug-resistant strain when a plurality of samples obtained from different locations are analyzed by the methods described above in an epidemiological setting. In one embodiment, a plurality of samples from a plurality of different locations is analyzed with primer pairs which produce bioagent identifying amplicons, a subset of which contains a specific drug-resistant bacterial strain. The corresponding locations of the members of the drug-resistant strain subset indicate the spread of the specific drug-resistant strain to the corresponding locations.

Another embodiment provides the means of identifying a sepsis-causing bacterium. The sepsis-causing bacterium is identified in samples including, but not limited to blood and fractions thereof (including but not limited to serum and buffy coat), sputum, urine, specific cell types including but not limited to hepatic cells, and various tissue biopsies.

Sepsis-causing bacteria include, but are not limited to the following bacteria: *Prevotella denticola, Porphyromonas gingivalis, Borrelia burgdorferi, Mycobacterium tuberculosis, Mycobacterium fortuitum, Corynebacterium jeikeium, Propionibacterium acnes, Mycoplasma pneumoniae, Streptococcus agalactiae, Streptococcus pneumoniae, Streptococcus mitis, Streptococcus pyogenes, Listeria monocytogenes, Enterococcus faecalis, Enterococcus faecium, Staphylococcus aureus, Staphylococcus coagulase*-negative, *Staphylococcus epidermis, Staphylococcus hemolyticus, Campylobacter jejuni, Bordatella pertussis, Burkholderia cepacia, Legionella pneumophila, Acinetobacter baumannii, Acinetobacter calcoaceticus, Pseudomonas aeruginosa, Aeromonas hydrophila, Enterobacter aerogenes, Enterobacter cloacae, Klebsiella pneumoniae, Moxarella catarrhalis, Morganella morganii, Proteus mirabilis, Proteus vulgaris, Pantoea agglomerans, Bartonella henselae, Stenotrophomonas maltophila, Actinobacillus actinomycetemcomitans, Haemophilus influenzae, Escherichia coli, Klebsiella oxytoca, Serratia marcescens,* and *Yersinia enterocolitica*.

In some embodiments, identification of a sepsis-causing bacterium provides the information required to choose an antibiotic with which to treat an individual infected with the sepsis-causing bacterium and treating the individual with the antibiotic. Treatment of humans with antibiotics is well known to medical practitioners with ordinary skill.

Kits for Producing Bioagent Identifying Amplicons

Also provided are kits for carrying out the methods described herein. In some embodiments, the kit may comprise a sufficient quantity of one or more primer pairs to perform an amplification reaction on a target polynucleotide from a bioagent to form a bioagent identifying amplicon. In some embodiments, the kit may comprise from one to fifty primer pairs, from one to twenty primer pairs, from one to ten primer pairs, or from two to five primer pairs. In some embodiments, the kit may comprise one or more primer pairs recited in Table 2 of U.S. Ser. No. 11/409,535.

In some embodiments, the kit comprises one or more broad range survey primer(s), division wide primer(s), or drill-down primer(s), or any combination thereof. If a given problem involves identification of a specific bioagent, the solution to the problem may require the selection of a particular combination of primers to provide the solution to the problem. A kit may be designed so as to comprise particular primer pairs for identification of a particular bioagent. A drill-down kit may be used, for example, to distinguish different genotypes or strains, drug-resistant, or otherwise. In some embodiments, the primer pair components of any of these kits may be additionally combined to comprise additional combinations of broad range survey primers and division-wide primers so as to be able to identify a bacterium.

In some embodiments, the kit contains standardized calibration polynucleotides for use as internal amplification calibrants. Internal calibrants are described in commonly owned PCT Publication Number WO 2005/098047 which is incorporated herein by reference in its entirety.

In some embodiments, the kit comprises a sufficient quantity of reverse transcriptase (if RNA is to be analyzed for example), a DNA polymerase, suitable nucleoside triphosphates (including alternative dNTPs such as inosine or modified dNTPs such as the 5-propynyl pyrimidines or any dNTP containing molecular mass-modifying tags such as those described above), a DNA ligase, and/or reaction buffer, or any combination thereof, for the amplification processes described above. A kit may further include instructions pertinent for the particular embodiment of the kit, such instructions describing the primer pairs and amplification conditions for operation of the method. A kit may also comprise amplification reaction containers such as microcentrifuge tubes and the like. A kit may also comprise reagents or other materials for isolating bioagent nucleic acid or bioagent identifying amplicons from amplification, including, for example, detergents, solvents, or ion exchange resins which may be linked to magnetic beads. A kit may also comprise a table of measured or calculated molecular masses and/or base compositions of bioagents using the primer pairs of the kit.

Some embodiments are kits that contain one or more survey bacterial primer pairs represented by primer pair compositions wherein each member of each pair of primers has 70% to 100% sequence identity with the corresponding member from the group of primer pairs represented by any of the primer pairs of Table 2 of U.S. Ser. No. 11/409,535. The survey primer pairs may include broad range primer pairs which hybridize to ribosomal RNA, and may also include division-wide primer pairs which hybridize to housekeeping genes such as rplB, tufB, rpoB, rpoC, valS, and infB, for example.

In some embodiments, a kit may contain one or more survey bacterial primer pairs and one or more triangulation genotyping analysis primer pairs such as the primer pairs of Tables 8, 12, 14, 19, 21, 23, or 24 of U.S. Ser. No. 11/409,535. In some embodiments, the kit may represent a less expansive genotyping analysis but include triangulation genotyping analysis primer pairs for more than one genus or species of bacteria. For example, a kit for surveying nosocomial infections at a health care facility may include, for example, one or more broad range survey primer pairs, one or more division wide primer pairs, one or more *Acinetobacter baumannii* triangulation genotyping analysis primer pairs and one or more *Staphylococcus aureus* triangulation genotyping analysis primer pairs. One with ordinary skill will be capable of analyzing in silico amplification data to determine which primer pairs will be able to provide optimal identification resolution for the bacterial bioagents of interest.

In some embodiments, a kit may be assembled for identification of sepsis-causing bacteria. An example of such a kit embodiment is a kit comprising one or more of the primer pairs of Table 25 of U.S. Ser. No. 11/409,535, which provide for a broad survey of sepsis-causing bacteria.

Some embodiments of the kits are 96-well or 384-well plates with a plurality of wells containing any or all of the following components: dNTPs, buffer salts, $Mg^{2+}$, betaine, and primer pairs. In some embodiments, a polymerase is also included in the plurality of wells of the 96-well or 384-well plates.

Some embodiments of the kit contain instructions for PCR and mass spectrometry analysis of amplification products obtained using the primer pairs of the kits.

Some embodiments of the kit include a barcode which uniquely identifies the kit and the components contained therein according to production lots and may also include any other information relative to the components such as concentrations, storage temperatures, etc. The barcode may also include analysis information to be read by optical barcode readers and sent to a computer controlling amplification, purification and mass spectrometric measurements. In some embodiments, the barcode provides access to a subset of base compositions in a base composition database which is in digital communication with base composition analysis software such that a base composition measured with primer pairs from a given kit can be compared with known base compositions of bioagent identifying amplicons defined by the primer pairs of that kit.

In some embodiments, the kit contains a database of base compositions of bioagent identifying amplicons defined by the primer pairs of the kit. The database is stored on a convenient computer readable medium such as a compact disk or USB drive, for example.

In some embodiments, the kit includes a computer program stored on a computer formatted medium (such as a compact disk or portable USB disk drive, for example) comprising instructions which direct a processor to analyze data obtained from the use of the primer pairs disclosed herein. The instructions of the software transform data related to amplification products into a molecular mass or base composition which is a useful concrete and tangible result used in identification and/or classification of bioagents. In some embodiments, the kits contain all of the reagents sufficient to carry out one or more of the methods described herein.

Combination Kits Including Targeted Whole Genome Amplification Primers and Primer Pairs for Obtaining Bioagent Identifying Amplicons In some embodiments, kits are provided that include targeted whole genome amplification primers and primer pairs for production of bioagent identifying amplicons. These kits are for use in applications where a bioagent such as a human pathogen for example, is present only in small quantities in a human clinical sample. An example of such a kit could include a set of targeted whole genome amplification primers for selective amplification of a bacterium implicated in septicemia. The targeted whole genome amplification primers are designed with human genomic DNA chosen as a background genome, for the purpose of detection of an infection of an individual with *Bacillus anthracis*. The kit would also include one or more broad range survey primer pairs and/or division-wide primer pairs for production of amplification products corresponding to bioagent identifying amplicons for identification of the bacterium. Optionally one or more drill-down primer pairs are included in the kit for determining sub-species characteristics of the septicemia by analysis of additional bioagent identifying amplicons.

These combination kits may also include a plurality of polymerase enzymes whose members are specialized for a PCR type amplification reaction, such as Taq polymerase, for example, to obtain amplification products corresponding to bioagent identifying amplicons, and such as Phi29 polymerase which is a high processivity polymerase suitable for catalysis of multiple displacement amplification reactions for targeted whole genome amplification reactions carried out for elevating the quantity of a target genome of interest.

The combination kits may also include amplification reagents including but not limited to: deoxynucleotide triphosphates, compatible solutes such as betaine and trehalose, buffer components, and salts such as magnesium chloride.

While the present invention has been described with specificity in accordance with certain of its embodiments, the following examples serve only to illustrate the invention and are not intended to limit the same. In order that the invention disclosed herein may be more efficiently understood, examples are provided below. It should be understood that these examples are for illustrative purposes only and are not to be construed as limiting the invention in any manner.

Example 1

Identification and Ranking of Genome Sequence Segments

This example illustrates the process of identification of unique genome sequence segments of 6 to 12 nucleobases in length, as well as determination of frequency of occurrence and selectivity ratio values for a simplified hypothetical genome model system consisting of a single target genome having the sequence: aaaaaaaaaatttttttttc-ccccccccggggggggggg ((SEQ ID NO: 16) base composition of A10 T10 C10 and G10) with two background genomes having the following sequences aaaaaaaatttttttc-cccccccggggggg (SEQ ID NO: 17) Bkg 1: base composition of A8 T8 C8 G8) and aaaaaaaaaatttttttttt (SEQ ID NO: 18) Bkg 2: base composition of A10 T10 C0 G0). Table 2 provides a list of all unique genome sequence segments for the target genome and indicates the frequency of occurrence of each genome sequence segment in the target genome and in the background genomes. For example, the genome sequence segment having the sequence of eight consecutive c residues cccccccc (SEQ ID NO:445) occurs 3 times (bold) within the 10 nucleobase stretch of c residues in the simplified hypothetical target genome:

(SEQ ID NO: 16)
aaaaaaaaaattttttttttcccccccccggggggggggg;

(SEQ ID NO: 16)
aaaaaaaaaatttttttttccccccccccggggggggggg;

(SEQ ID NO: 16)
aaaaaaaaaatttttttttcccccccccggggggggggg;

(c residue stretch underlined) but only once in the background genomes (the genome sequence segment appears once in Bkg 1 and does not appear in Bkg 2). The selectivity ratio for this genome sequence segment is 3.00 as determined by dividing the frequency of occurrence in the target genome by the frequency of occurrence in the background genomes. The data in Table 2 are sorted according to the selectivity ratio rank. A selectivity ratio of infinity (∞) indicates that the genome sequence segment does not occur in the background genomes (Bkg 1 and Bkg 2). The mean frequency of occurrence of the genome sequence segments in the target genome was calculated to be 1.22 and the mean selectivity ratio was calculated to be 0.76. If desired, these values could be used as threshold values for selection of one or more sub-sets of genome sequence segments for further characterization by processes such as the process shown in FIG. 2 for example. Alternatively, threshold values greater than or less than the mean frequency of occurrence or the mean selectivity ratio could be chosen.

TABLE 2

Frequency of Occurrence of Genome Sequence Segments in a
Hypothetical Target Genome and Two Hypothetical Background Genomes

| Genome Sequence Segment | SEQ ID NO: | Frequency in Target | Frequency in Bkg 1 | Frequency in Bkg 2 | Total Background | Selectivity Ratio | Selectivity Ratio Rank |
|---|---|---|---|---|---|---|---|
| cccccccc | 19 | 2 | 0 | 0 | 0 | Infinity | 1 |
| gggggggg | 20 | 2 | 0 | 0 | 0 | Infinity | 1 |
| ccccccccc | 21 | 1 | 0 | 0 | 0 | Infinity | 1 |
| ccccccccg | 22 | 1 | 0 | 0 | 0 | Infinity | 1 |
| cggggggggg | 23 | 1 | 0 | 0 | 0 | Infinity | 1 |
| ggggggggg | 24 | 1 | 0 | 0 | 0 | Infinity | 1 |
| tccccccccc | 25 | 1 | 0 | 0 | 0 | Infinity | 1 |
| tttttttttc | 26 | 1 | 0 | 0 | 0 | Infinity | 1 |
| ccccccccccg | 27 | 1 | 0 | 0 | 0 | Infinity | 1 |
| cccccccccgg | 28 | 1 | 0 | 0 | 0 | Infinity | 1 |
| ccgggggggggg | 29 | 1 | 0 | 0 | 0 | Infinity | 1 |
| cggggggggg | 30 | 1 | 0 | 0 | 0 | Infinity | 1 |
| tcccccccccc | 31 | 1 | 0 | 0 | 0 | Infinity | 1 |
| ttccccccccc | 32 | 1 | 0 | 0 | 0 | Infinity | 1 |
| ttttttttttcc | 33 | 1 | 0 | 0 | 0 | Infinity | 1 |
| tttttttttttc | 34 | 1 | 0 | 0 | 0 | Infinity | 1 |
| attttttttttc | 35 | 1 | 0 | 0 | 0 | Infinity | 1 |
| cccccccccgg | 36 | 1 | 0 | 0 | 0 | Infinity | 1 |
| cccccccccggg | 37 | 1 | 0 | 0 | 0 | Infinity | 1 |

TABLE 2-continued

Frequency of Occurrence of Genome Sequence Segments in a Hypothetical Target Genome and Two Hypothetical Background Genomes

| Genome Sequence Segment | SEQ ID NO: | Frequency in Target | Frequency in Bkg 1 | Frequency in Bkg 2 | Total Background | Selectivity Ratio | Selectivity Ratio Rank |
|---|---|---|---|---|---|---|---|
| cccggggggggg | 38 | 1 | 0 | 0 | 0 | Infinity | 1 |
| ccgggggggggg | 39 | 1 | 0 | 0 | 0 | Infinity | 1 |
| tccccccccccg | 40 | 1 | 0 | 0 | 0 | Infinity | 1 |
| ttccccccccccc | 41 | 1 | 0 | 0 | 0 | Infinity | 1 |
| tttccccccccc | 42 | 1 | 0 | 0 | 0 | Infinity | 1 |
| ttttttttttccc | 43 | 1 | 0 | 0 | 0 | Infinity | 1 |
| tttttttttttcc | 44 | 1 | 0 | 0 | 0 | Infinity | 1 |
| cccccccc | 45 | 3 | 1 | 0 | 1 | 3.00 | 2 |
| gggggggg | 46 | 3 | 1 | 0 | 1 | 3.00 | 2 |
| ggggggg | 47 | 4 | 2 | 0 | 2 | 2.00 | 3 |
| cccccc | 48 | 5 | 3 | 0 | 3 | 1.67 | 4 |
| gggggg | 49 | 5 | 3 | 0 | 3 | 1.67 | 4 |
| cccccg | 50 | 1 | 1 | 0 | 1 | 1.00 | 5 |
| ccccgg | 51 | 1 | 1 | 0 | 1 | 1.00 | 5 |
| cccggg | 52 | 1 | 1 | 0 | 1 | 1.00 | 5 |
| ccgggg | 53 | 1 | 1 | 0 | 1 | 1.00 | 5 |
| cggggg | 54 | 1 | 1 | 0 | 1 | 1.00 | 5 |
| tccccc | 55 | 1 | 1 | 0 | 1 | 1.00 | 5 |
| ttcccc | 56 | 1 | 1 | 0 | 1 | 1.00 | 5 |
| tttccc | 57 | 1 | 1 | 0 | 1 | 1.00 | 5 |
| ttttcc | 58 | 1 | 1 | 0 | 1 | 1.00 | 5 |
| tttttc | 59 | 1 | 1 | 0 | 1 | 1.00 | 5 |
| ccccccg | 60 | 1 | 1 | 0 | 1 | 1.00 | 5 |
| cccccgg | 61 | 1 | 1 | 0 | 1 | 1.00 | 5 |
| ccccggg | 62 | 1 | 1 | 0 | 1 | 1.00 | 5 |
| cccgggg | 63 | 1 | 1 | 0 | 1 | 1.00 | 5 |
| ccggggg | 64 | 1 | 1 | 0 | 1 | 1.00 | 5 |
| cgggggg | 65 | 1 | 1 | 0 | 1 | 1.00 | 5 |
| tcccccc | 66 | 1 | 1 | 0 | 1 | 1.00 | 5 |
| ttccccc | 67 | 1 | 1 | 0 | 1 | 1.00 | 5 |
| tttcccc | 68 | 1 | 1 | 0 | 1 | 1.00 | 5 |
| ttttccc | 69 | 1 | 1 | 0 | 1 | 1.00 | 5 |
| tttttcc | 70 | 1 | 1 | 0 | 1 | 1.00 | 5 |
| ttttttc | 71 | 1 | 1 | 0 | 1 | 1.00 | 5 |
| ccccccccg | 72 | 1 | 1 | 0 | 1 | 1.00 | 5 |
| ccccccgg | 73 | 1 | 1 | 0 | 1 | 1.00 | 5 |

TABLE 2-continued

Frequency of Occurrence of Genome Sequence Segments in a
Hypothetical Target Genome and Two Hypothetical Background Genomes

| Genome Sequence Segment | SEQ ID NO: | Frequency in Target | Frequency in Bkg 1 | Frequency in Bkg 2 | Total Background | Selectivity Ratio | Selectivity Ratio Rank |
|---|---|---|---|---|---|---|---|
| cccccggg | 74 | 1 | 1 | 0 | 1 | 1.00 | 5 |
| ccccgggg | 75 | 1 | 1 | 0 | 1 | 1.00 | 5 |
| cccggggg | 76 | 1 | 1 | 0 | 1 | 1.00 | 5 |
| ccgggggg | 77 | 1 | 1 | 0 | 1 | 1.00 | 5 |
| cggggggg | 78 | 1 | 1 | 0 | 1 | 1.00 | 5 |
| tccccccc | 79 | 1 | 1 | 0 | 1 | 1.00 | 5 |
| ttcccccc | 80 | 1 | 1 | 0 | 1 | 1.00 | 5 |
| tttccccc | 81 | 1 | 1 | 0 | 1 | 1.00 | 5 |
| ttttcccc | 82 | 1 | 1 | 0 | 1 | 1.00 | 5 |
| tttttccc | 83 | 1 | 1 | 0 | 1 | 1.00 | 5 |
| ttttttcc | 84 | 1 | 1 | 0 | 1 | 1.00 | 5 |
| tttttttc | 85 | 1 | 1 | 0 | 1 | 1.00 | 5 |
| aaaaaaaaa | 86 | 2 | 0 | 2 | 2 | 1.00 | 5 |
| ccccccccg | 87 | 1 | 1 | 0 | 1 | 1.00 | 5 |
| cccccccgg | 88 | 1 | 1 | 0 | 1 | 1.00 | 5 |
| ccccccggg | 89 | 1 | 1 | 0 | 1 | 1.00 | 5 |
| cccccgggg | 90 | 1 | 1 | 0 | 1 | 1.00 | 5 |
| ccccggggg | 91 | 1 | 1 | 0 | 1 | 1.00 | 5 |
| cccgggggg | 92 | 1 | 1 | 0 | 1 | 1.00 | 5 |
| ccggggggg | 93 | 1 | 1 | 0 | 1 | 1.00 | 5 |
| cgggggggg | 94 | 1 | 1 | 0 | 1 | 1.00 | 5 |
| tcccccccc | 95 | 1 | 1 | 0 | 1 | 1.00 | 5 |
| ttccccccc | 96 | 1 | 1 | 0 | 1 | 1.00 | 5 |
| tttcccccc | 97 | 1 | 1 | 0 | 1 | 1.00 | 5 |
| ttttccccc | 98 | 1 | 1 | 0 | 1 | 1.00 | 5 |
| tttttcccc | 99 | 1 | 1 | 0 | 1 | 1.00 | 5 |
| ttttttccc | 100 | 1 | 1 | 0 | 1 | 1.00 | 5 |
| tttttttcc | 101 | 1 | 1 | 0 | 1 | 1.00 | 5 |
| ttttttttc | 102 | 1 | 1 | 0 | 1 | 1.00 | 5 |
| ttttttttt | 103 | 2 | 0 | 2 | 2 | 1.00 | 5 |
| aaaaaaaaaa | 104 | 1 | 0 | 1 | 1 | 1.00 | 5 |
| aaaaaaaaat | 105 | 1 | 0 | 1 | 1 | 1.00 | 5 |
| attttttttt | 106 | 1 | 0 | 1 | 1 | 1.00 | 5 |
| ccccccccgg | 107 | 1 | 1 | 0 | 1 | 1.00 | 5 |
| cccccccggg | 108 | 1 | 1 | 0 | 1 | 1.00 | 5 |
| ccccccgggg | 109 | 1 | 1 | 0 | 1 | 1.00 | 5 |
| cccccggggg | 110 | 1 | 1 | 0 | 1 | 1.00 | 5 |

TABLE 2-continued

Frequency of Occurrence of Genome Sequence Segments in a
Hypothetical Target Genome and Two Hypothetical Background Genomes

| Genome Sequence Segment | SEQ ID NO: | Frequency in Target | Frequency in Bkg 1 | Frequency in Bkg 2 | Total Background | Selectivity Ratio | Selectivity Ratio Rank |
|---|---|---|---|---|---|---|---|
| ccccgggggg | 111 | 1 | 1 | 0 | 1 | 1.00 | 5 |
| cccgggggggg | 112 | 1 | 1 | 0 | 1 | 1.00 | 5 |
| ccggggggggg | 113 | 1 | 1 | 0 | 1 | 1.00 | 5 |
| ttccccccccc | 114 | 1 | 1 | 0 | 1 | 1.00 | 5 |
| tttcccccccc | 115 | 1 | 1 | 0 | 1 | 1.00 | 5 |
| ttttccccccc | 116 | 1 | 1 | 0 | 1 | 1.00 | 5 |
| tttttcccccc | 117 | 1 | 1 | 0 | 1 | 1.00 | 5 |
| ttttttccccc | 118 | 1 | 1 | 0 | 1 | 1.00 | 5 |
| tttttttcccc | 119 | 1 | 1 | 0 | 1 | 1.00 | 5 |
| ttttttttccc | 120 | 1 | 1 | 0 | 1 | 1.00 | 5 |
| ttttttttttt | 121 | 1 | 0 | 1 | 1 | 1.00 | 5 |
| aaaaaaaaaat | 122 | 1 | 0 | 1 | 1 | 1.00 | 5 |
| aaaaaaaaatt | 123 | 1 | 0 | 1 | 1 | 1.00 | 5 |
| aattttttttt | 124 | 1 | 0 | 1 | 1 | 1.00 | 5 |
| attttttttttt | 125 | 1 | 0 | 1 | 1 | 1.00 | 5 |
| ccccccccggg | 126 | 1 | 1 | 0 | 1 | 1.00 | 5 |
| cccccccgggg | 127 | 1 | 1 | 0 | 1 | 1.00 | 5 |
| ccccccggggg | 128 | 1 | 1 | 0 | 1 | 1.00 | 5 |
| cccccgggggg | 129 | 1 | 1 | 0 | 1 | 1.00 | 5 |
| ccccggggggg | 130 | 1 | 1 | 0 | 1 | 1.00 | 5 |
| cccgggggggg | 131 | 1 | 1 | 0 | 1 | 1.00 | 5 |
| tttccccccccc | 132 | 1 | 1 | 0 | 1 | 1.00 | 5 |
| ttttcccccccc | 133 | 1 | 1 | 0 | 1 | 1.00 | 5 |
| tttttccccccc | 134 | 1 | 1 | 0 | 1 | 1.00 | 5 |
| ttttttcccccc | 135 | 1 | 1 | 0 | 1 | 1.00 | 5 |
| tttttttccccc | 136 | 1 | 1 | 0 | 1 | 1.00 | 5 |
| ttttttttcccc | 137 | 1 | 1 | 0 | 1 | 1.00 | 5 |
| aaaaaaaaaatt | 138 | 1 | 0 | 1 | 1 | 1.00 | 5 |
| aaaaaaaaattt | 139 | 1 | 0 | 1 | 1 | 1.00 | 5 |
| aaattttttttt | 140 | 1 | 0 | 1 | 1 | 1.00 | 5 |
| aattttttttttt | 141 | 1 | 0 | 1 | 1 | 1.00 | 5 |
| ccccccccgggg | 142 | 1 | 1 | 0 | 1 | 1.00 | 5 |
| cccccccggggg | 143 | 1 | 1 | 0 | 1 | 1.00 | 5 |
| ccccccgggggg | 144 | 1 | 1 | 0 | 1 | 1.00 | 5 |
| cccccggggggg | 145 | 1 | 1 | 0 | 1 | 1.00 | 5 |
| ccccgggggggg | 146 | 1 | 1 | 0 | 1 | 1.00 | 5 |

TABLE 2-continued

Frequency of Occurrence of Genome Sequence Segments in a
Hypothetical Target Genome and Two Hypothetical Background Genomes

| Genome Sequence Segment | SEQ ID NO: | Frequency in Target | Frequency in Bkg 1 | Frequency in Bkg 2 | Total Background | Selectivity Ratio | Selectivity Ratio Rank |
|---|---|---|---|---|---|---|---|
| ttttcccccccc | 147 | 1 | 1 | 0 | 1 | 1.00 | 5 |
| tttttccccccc | 148 | 1 | 1 | 0 | 1 | 1.00 | 5 |
| ttttttcccccc | 149 | 1 | 1 | 0 | 1 | 1.00 | 5 |
| tttttttccccc | 150 | 1 | 1 | 0 | 1 | 1.00 | 5 |
| ttttttttcccc | 151 | 1 | 1 | 0 | 1 | 1.00 | 5 |
| aaaaaaaa | 15 | 3 | 1 | 3 | 4 | 0.75 | 6 |
| tttttttt | 153 | 3 | 1 | 3 | 4 | 0.75 | 6 |
| aaaaaaa | 154 | 4 | 2 | 4 | 6 | 0.67 | 7 |
| ccccccc | 155 | 4 | 2 | 4 | 6 | 0.67 | 7 |
| ttttttt | 156 | 4 | 2 | 4 | 6 | 0.67 | 7 |
| aaaaaa | 157 | 5 | 3 | 5 | 8 | 0.63 | 8 |
| tttttt | 158 | 5 | 3 | 5 | 8 | 0.63 | 8 |
| aaaaat | 159 | 1 | 1 | 1 | 2 | 0.50 | 9 |
| aaaatt | 160 | 1 | 1 | 1 | 2 | 0.50 | 9 |
| aaattt | 161 | 1 | 1 | 1 | 2 | 0.50 | 9 |
| aatttt | 162 | 1 | 1 | 1 | 2 | 0.50 | 9 |
| attttt | 163 | 1 | 1 | 1 | 2 | 0.50 | 9 |
| aaaaaat | 164 | 1 | 1 | 1 | 2 | 0.50 | 9 |
| aaaaatt | 165 | 1 | 1 | 1 | 2 | 0.50 | 9 |
| aaaattt | 166 | 1 | 1 | 1 | 2 | 0.50 | 9 |
| aaatttt | 167 | 1 | 1 | 1 | 2 | 0.50 | 9 |
| aattttt | 168 | 1 | 1 | 1 | 2 | 0.50 | 9 |
| atttttt | 169 | 1 | 1 | 1 | 2 | 0.50 | 9 |
| aaaaaaat | 170 | 1 | 1 | 1 | 2 | 0.50 | 9 |
| aaaaaatt | 171 | 1 | 1 | 1 | 2 | 0.50 | 9 |
| aaaaattt | 172 | 1 | 1 | 1 | 2 | 0.50 | 9 |
| aaaatttt | 173 | 1 | 1 | 1 | 2 | 0.50 | 9 |
| aaattttt | 174 | 1 | 1 | 1 | 2 | 0.50 | 9 |
| aattttttt | 175 | 1 | 1 | 1 | 2 | 0.50 | 9 |
| attttttt | 176 | 1 | 1 | 1 | 2 | 0.50 | 9 |
| aaaaaaaat | 177 | 1 | 1 | 1 | 2 | 0.50 | 9 |
| aaaaaaatt | 178 | 1 | 1 | 1 | 2 | 0.50 | 9 |
| aaaaaattt | 179 | 1 | 1 | 1 | 2 | 0.50 | 9 |
| aaaaatttt | 180 | 1 | 1 | 1 | 2 | 0.50 | 9 |
| aaaattttt | 181 | 1 | 1 | 1 | 2 | 0.50 | 9 |
| aaatttttt | 182 | 1 | 1 | 1 | 2 | 0.50 | 9 |
| aattttttt | 183 | 1 | 1 | 1 | 2 | 0.50 | 9 |

TABLE 2-continued

Frequency of Occurrence of Genome Sequence Segments in a
Hypothetical Target Genome and Two Hypothetical Background Genomes

| Genome Sequence Segment | SEQ ID NO: | Frequency in Target | Frequency in Bkg 1 | Frequency in Bkg 2 | Total Background | Selectivity Ratio | Selectivity Ratio Rank |
|---|---|---|---|---|---|---|---|
| attttttt | 184 | 1 | 1 | 1 | 2 | 0.50 | 9 |
| aaaaaaatt | 185 | 1 | 1 | 1 | 2 | 0.50 | 9 |
| aaaaaattt | 186 | 1 | 1 | 1 | 2 | 0.50 | 9 |
| aaaaatttt | 187 | 1 | 1 | 1 | 2 | 0.50 | 9 |
| aaaattttt | 188 | 1 | 1 | 1 | 2 | 0.50 | 9 |
| aaatttttt | 189 | 1 | 1 | 1 | 2 | 0.50 | 9 |
| aattttttt | 190 | 1 | 1 | 1 | 2 | 0.50 | 9 |
| atttttttt | 191 | 1 | 1 | 1 | 2 | 0.50 | 9 |
| aaaaaaattt | 192 | 1 | 1 | 1 | 2 | 0.50 | 9 |
| aaaaaatttt | 193 | 1 | 1 | 1 | 2 | 0.50 | 9 |
| aaaaattttt | 194 | 1 | 1 | 1 | 2 | 0.50 | 9 |
| aaaatttttt | 195 | 1 | 1 | 1 | 2 | 0.50 | 9 |
| aaattttttt | 196 | 1 | 1 | 1 | 2 | 0.50 | 9 |
| aatttttttt | 197 | 1 | 1 | 1 | 2 | 0.50 | 9 |
| aaaaaaatttt | 198 | 1 | 1 | 1 | 2 | 0.50 | 9 |
| aaaaaattttt | 199 | 1 | 1 | 1 | 2 | 0.50 | 9 |
| aaaaatttttt | 200 | 1 | 1 | 1 | 2 | 0.50 | 9 |
| aaaattttttt | 201 | 1 | 1 | 1 | 2 | 0.50 | 9 |
| aaatttttttt | 202 | 1 | 1 | 1 | 2 | 0.50 | 9 |

Example 2

In Silico Method for Design of Primers for Targeted Whole Genome Amplification

Some embodiments of the methods disclosed herein are in silico methods for selecting primers for targeted whole genome amplification. The primers are selected by first defining the target genome(s) and background genome(s). For the target genome(s), all unique genome sequence segments of lengths of about 5 to about 13 nucleobases in length are determined by a set of computer executable instructions stored on a computer-readable medium.

In some embodiments, the target and background genome segments are obtained from public databases such as GenBank, for example. The frequency of occurrence values of members of the genome sequence segments in the target genome(s) and background genome(s) are determined by computer executable instructions such as a BLAST algorithm for example. The selectivity ratio values of members of the genome sequence segments are determined by computer executable mathematical instructions. In some embodiments, the in silico method ranks the genome sequence segments according to frequency of occurrence and/or selectivity ratio. In some embodiments, a frequency of occurrence threshold value is chosen to define a sub-set of genome sequence segments to carry forward.

In some embodiments, a selectivity ratio threshold value is chosen to define a sub-set of genome sequence segments to carry forward. In some embodiments, the selectivity ratio threshold value is any whole or fractional percentage between about 25% above or about 25% below the mean selectivity ratio. For example, if the mean selectivity ratio is 55, the chosen selectivity ratio threshold value may be any whole or fractional number between about 41.25 and about 68.75. In other embodiments, both a frequency of occurrence threshold value and a selectivity ratio threshold value are chosen and both of these threshold values are used to define the sub-set of genome sequence segments to carry forward. The genome sequence segments are ranked according to the chosen threshold value.

Figure 2:
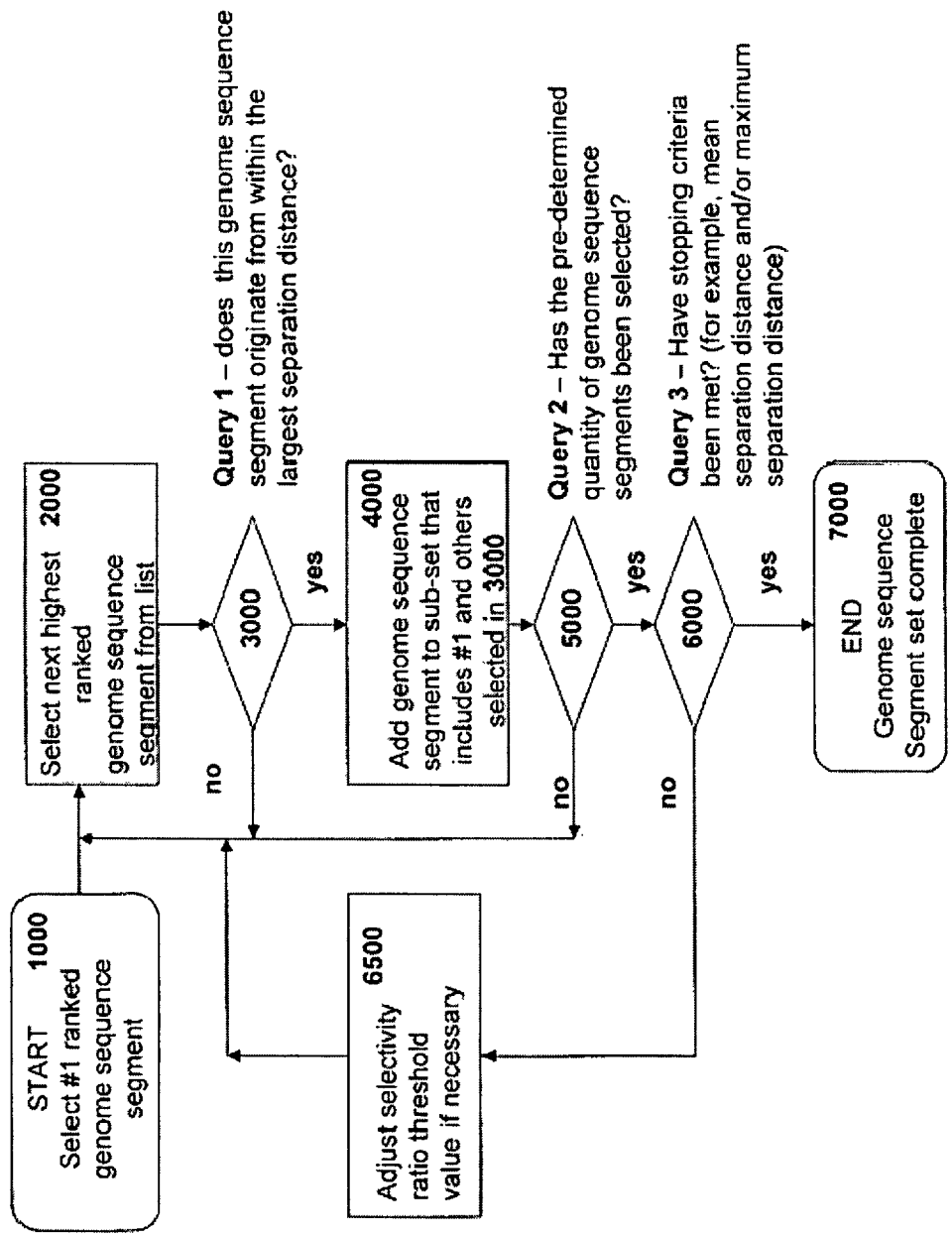

At this point, a process such as the process outlined in FIG. 2 may be followed wherein the top ranked genome sequence segment is selected and added to the sub-set of genome sequence segments (1000). Then the next highest ranking genome sequence segment is selected (2000) and subjected to a first computer executable query (3000) which determines whether or not the next ranked genome sequence segment originates from within the largest remaining separation distance (remaining portion of the genome which has not had a genome sequence segment selected). If the next highest ranking genome sequence segment does not originate within the largest separation distance, it is skipped (but remains in with the same rank in the group of unselected genome sequence segments) and the process reverts to step 2000. If the next highest ranking genome sequence segment does originate from within the largest separation distance it is selected and added to the set of genome sequence segments to which primers will be designed (4000). An example of operation of steps 1000 to 5000 (including cycling between steps 2000 and 5000) of FIG. 2 follows: the top ranked genome sequence segment (#1) is selected by default in step 1000. As a result of selection of genome sequence segment #1, only two separation distances remain on the target genome. One of the two separation distances stretches from the 5' end of the #1 genome sequence segment to the 5' end of the genome and the other of the two separation distances stretches from the 3' end of the #1 genome sequence segment to the 5' end of the genome. It is assumed in this example that the 5' end of the genome to the 5' end of the #1 genome sequence segment has the longest separation distance. In step 2000, the next highest ranked genome sequence segment (#2 in this case) is selected. At step 3000 (query 1) it is determined whether or not the #2 ranked genome sequence segment is located within this longest separation distance between the 5' end of the genome and the 5' end of the #1 genome sequence segment. If the #2 ranked genome sequence segment is not located within this longest separation distance, it is not selected and remains in the unselected group while the process reverts to step 2000 where the next highest ranked genome sequence segment (#3) is selected from the list of ranked genome sequence segments. In performing step 3000 on genome sequence segment #3, it is determined that this genome sequence segment is located within the largest separation distance. Thus genome sequence segment #3 is added to the sub-set in step 4000. At this point, only genome sequence segments #1 and #3 have been added to the sub-set. In step 5000, it is confirmed that the predetermined quantity of genome sequence segments (for example 200 genome sequence segments) has not been obtained (because only 2 genome sequence segments have been selected thus far). The answer to query 2 (5000) is "no" and the process cycles back to step 2000 where the next ranked genome sequence segment is selected. In this example, the next ranked genome sequence segment is #2 because it was skipped in the previous cycle. In step 3000 query 1 determines that genome sequence segment now does fall within the largest separation distance (because the largest separation distance in the previous cycle is no longer the largest in the current cycle due to the appearance of genome sequence segment #3). Thus genome sequence segment #2 is added to the sub-set in step 4000. Step 5000 is then performed and the answer to query 2 is "no" because only 3 genome sequence segments have been selected thus far. Again the process cycles back to step 2000 and continues cycling between steps 2000 and 5000, selecting the next highest ranked genome sequence segments in each cycle and performing the queries of step 3000 and step 5000 until the predetermined quantity of genome sequence segments is obtained.

In some embodiments, the predetermined number of genome sequence segments is sufficient to provide consistently dispersed coverage of the genome by primers hybridizing to the selected genome sequence segments. In some embodiments, this predetermined number of genome sequence segments is between about 100 to about 300 genome sequence segments, including any number therebetween.

The predetermined number will depend upon the length of the target genome(s). For example, longer genomes may require additional primer coverage and thus selecting a larger predetermined number of genome sequence segments to serve as primer hybridization sites may be advantageous. In some embodiments, after a group of genome sequence segments have been selected, statistical measures such as those presented in Table 5 may be used to evaluate the likelihood that a group of primers designed to hybridize to the genome sequence segments will produce efficient and biased amplification of the target genome(s) of interest. If the statistics are deemed inefficient, it may be advantageous to consider revising the predetermined number of genome sequence segments to a larger number to provide greater coverage of the target genome(s). This statistical evaluation process is useful because it avoids the unnecessary expense of in vitro testing of entire groups of primers.

Continuing now in the process of FIG. 2, when the answer to the second query (5000) is "yes," the predetermined quantity of genome sequence segments has been obtained. At that point, a third computer executable query (6000) is performed to determine whether or not the "stopping criterion/criteria" has or have been met. The "stopping criterion/criteria" represent the final threshold value(s) relating to genome sequence segment coverage over which the in silico method must pass before the method instructions and queries of the in silico end (7000). If the stopping criteria have not been met, the process cycles back to step 2000 with an adjustment of the selectivity threshold value if necessary (6500).

In some embodiments, a single stopping criterion used. In other embodiments, more than one stopping criteria are used. In one embodiment one stopping criterion is a value reflecting the mean separation distance between genome sequence segments within the target genome sequence(s). For example, a mean distance between genome sequence segments is a whole or fractional number less or equal to about 500, 600, 700, 900, or 1000 nucleobases or any whole or fractional number therebetween. In other embodiments, the stopping criterion is the mean distance between genome sequence segments within the target genome sequence(s) or a value above or below the mean distance between genome sequence segments within the target genome sequence(s).

In other embodiments, a stopping criterion is the maximum distance between any two of the selected genome sequence segments within the target genome sequence(s). For example, an appropriate maximum distance between any two genome sequence segments might be less than or equal to about 5,000, 6,000, 7,000, 8,000, 9,000 or 10,000 nucleobases or any number therebetween.

In some embodiments, after the stopping criterion or criteria have been met and the computer executable instructions are complete, the in silico method produces an output report comprising a list of genome sequence segments. The report may be a print-out or a display on a graphical interface or any other means for displaying the results of the selection process. The in silico method may also provide a means for designing primers that hybridize to the genome sequence segments.

Example 3

Selection of Primer Sets for Targeted Whole Genome Amplification

In a first example for targeted whole genome amplification, *Bacillus anthracis* Ames was chosen as a single target genome. The set of background genomes included the genomes of: *Homo sapiens, Gallus gallus, Guillardia theta, Oryza sativa, Arabidopsis thaliana, Yarrowia lipolytica, Saccharomyces cerevisiae, Debaryomyces hansenii, Kluyveromyces lactis, Schizosaccharoyces pom, Aspergillus fumigatus, Cryptococcus neoformans, Encephalitozoon cuniculi,*

Eremothecium gossypii, Candida glabrata, Apis mellifera, Drosophila melanogaster, Tribolium castaneum, Anopheles gambiae, and Caenorhabditis elegans. These background genomes were chosen because they would be expected to be present in a typical soil sample handled by a human.

Unique genome sequence segments 7 to 12 nucleobases in length were identified. Frequency of occurrence and selectivity ratio values were determined. As a result, 200 genome sequence segments were identified. In most cases, the primers designed to hybridize with 100% complementarity to its corresponding genome sequence segment. In a few other cases, degenerate primers were prepared. The degenerate bases of the primers occur at positions complementary to positions having ambiguity within the target Bacillus anthracis genome or complementary to positions known or thought to be susceptible to single nucleotide polymorphisms. The 200 primers (Table 3) designed to hybridize to the genome sequence segments were found to have a combined total of 12822 hybridization sites. The mean separation distance of the genome sequence segments and the primers hybridizing thereto was found to be 815 nucleobases in length. The maximum distance between the genome sequence segments and the primers hybridizing thereto was found to be 5420 nucleobases in length. The mean "frequency bias" of hybridization of a primer to the target genome relative to the background genomes was calculated to be 3.31, indicating that the average primer hybridizes at 3.31 different positions on the target genome sequence for each single position it hybridizes to a background genome sequence.

In an experiment designed to test the efficiency of the targeted whole genome amplification reaction vs. traditional whole genome amplification, reactions were carried out using 50, 100, 200, and 400 femtograms of Bacillus anthracis Sterne genomic DNA in the presence of 100 nanograms of human genomic DNA. Amplified quantities of DNA were determined and it was found that the targeted whole genome amplification reactions resulted in much greater specificity toward amplification of Bacillus anthracis Sterne genomic DNA than human genomic DNA. FIG. 3A indicates that ordinary whole genome amplification using random primers 6 nucleobases in length under the conditions listed above results in production of larger quantities of human genomic DNA, as would be expected. FIG. 3B, on the other hand indicates that the 200 primers described above selectively amplify the Bacillus anthracis Sterne genomic DNA relative to the human DNA, even though the quantity of Bacillus anthracis Sterne genomic DNA was much lower than the human genomic DNA.

A second experiment was conducted where additional target genomes were selected for the primer design process. The group of total target genomes included the genomes of the following potential biowarfare agents: Bacillus anthracis, Francisella tularensis, Yersinia pestis, Brucella sp., Burkholderia mallei, Rickettsia prowazekii, and Escherichia coli 0157. The group of background genomes was expanded. An exact match BLAST was used to determine the frequency of occurrence of genome sequence segments in the background genomes. A larger number of genome sequence segments was analyzed and query 3 (FIG. 2—6000) was automated.

The 200 primers designed in the first experiment are shown in Table 3 and the 191 primers designed in the second experiment are shown in Table 4. In Tables 3 and 4, an asterisk (*) indicates a phosphorothioate linkage and degenerate nucleobases codes are as follows: r=a or g; k=g or t; s=g or c; y=c or t; m=a or c, and w=a or t.

TABLE 3

First Generation Targeted Whole Genome Amplification Primer Set

| Sequence | SEQ ID NO: |
|---|---|
| aaaaaagc*g*g | 203 |
| aaaacg*c*t | 204 |
| aaaagaagtt*a*t | 205 |
| aaaaggc*g*g | 206 |
| aaaccgc*c*a | 207 |
| aaaccgt*a*t | 208 |
| aaaccgt*t*a | 209 |
| aaagaagaag*t*t | 210 |
| aaagaagctt*t*a | 211 |
| aaagaagtat*t*a | 212 |
| aaagccg*a*t | 213 |
| aaagcgtggg*g*a | 214 |
| aaagtagaag*a*a | 215 |
| aaataacg*a*t | 216 |
| aaatacg*c*t | 217 |
| aaatcattaa*a*g | 218 |
| aaattag*c*g | 219 |
| aaccgcc*t*t | 220 |
| aacgat*t*g | 221 |
| aacgata*t*t | 222 |
| aacgctt*c*w | 223 |
| aacgtga*a*c | 224 |
| aacttctttt*t*c | 225 |
| aagaaac*g*c | 226 |
| aagarttaaa*a*g | 227 |
| aagataaaga*t*g | 228 |
| aagatgtaaa*a*g | 229 |
| aagcatctaa*g*c | 230 |
| aagcgat*c*a | 231 |
| aagcggt*t*c | 232 |
| aagtaac*g*a | 233 |
| aataacg*c*a | 234 |
| aatattggac*a*a | 235 |
| aatcattaat*a*t | 236 |
| aatccag*c*g | 237 |
| aatcgcc*c*a | 238 |
| aatcgta*t*c | 239 |
| aatcgtt*a*a | 240 |

TABLE 3-continued

First Generation Targeted Whole Genome Amplification Primer Set

| Sequence | SEQ ID NO: |
|---|---|
| aatcgtt*g*c | 241 |
| aatctggtgg*t*a | 242 |
| aatgcg*g*t | 243 |
| aattaa*c*g | 244 |
| aatttcatct*a*a | 245 |
| accgata*a*t | 246 |
| accgcat*c*a | 247 |
| acgaatg*a*t | 248 |
| acgatgt*t*g | 249 |
| acggtta*t*c | 250 |
| acggttt*t*a | 251 |
| acgrtaa*a*a | 252 |
| acgttt*a*t | 253 |
| acttttttat*c*t | 254 |
| agaattatta*a*a | 255 |
| agataaa*c*g | 256 |
| agatgaaaat*g*g | 257 |
| agcaatc*g*c | 258 |
| agcagttgca*g*c | 259 |
| agcgcaa*t*c | 260 |
| agcttgt*t*g | 261 |
| agttgat*c*g | 262 |
| ataaaaaag*c*g | 263 |
| ataaaaagg*t*a | 264 |
| ataagaaga*t*g | 265 |
| ataaagatat*t*a | 266 |
| ataacga*a*g | 267 |
| ataactaata*a*a | 268 |
| ataatagaag*a*a | 269 |
| ataccatttt*t*a | 270 |
| atacgat*a*a | 271 |
| atagatgaaa*a*t | 272 |
| atagcga*t*a | 273 |
| atatcgt*a*a | 274 |
| atatcttttt*c*a | 275 |
| atattaaa*g*c | 276 |
| atattgaaga*a*g | 277 |

TABLE 3-continued

First Generation Targeted Whole Genome Amplification Primer Set

| Sequence | SEQ ID NO: |
|---|---|
| atattgat*a*c | 278 |
| atcagct*a*c | 279 |
| atcatgc*c*g | 280 |
| atcgcac*c*g | 281 |
| atcgcctt*c*a | 282 |
| atcgtaa*t*a | 283 |
| atcgtga*a*g | 284 |
| atcgtta*a*a | 285 |
| atcttca*c*g | 286 |
| atcttcttta*a*t | 287 |
| attaata*c*c | 288 |
| attacaa*c*g | 289 |
| attacaac*a*a | 290 |
| attacc*g*c | 291 |
| attagaagaa*a*t | 292 |
| attatc*g*g | 293 |
| attatcg*t*a | 294 |
| attcatc*g*g | 295 |
| attgatat*t*a | 296 |
| attgatataa*a*t | 297 |
| attgatgaa*g*c | 298 |
| attgatgatt*t*a | 299 |
| attgcagc*a*a | 300 |
| atttagataa*a*t | 301 |
| atttagatga*a*g | 302 |
| atttatca*g*c | 303 |
| atttattatt*a*g | 304 |
| atttctttat*c*a | 305 |
| caatcgg*t*g | 306 |
| caatcgy*t*a | 307 |
| caccttttt*a*a | 308 |
| cagcgat*t*a | 309 |
| cagctttt*t*a | 310 |
| catcgct*t*c | 311 |
| catctaaaat*a*a | 312 |
| catcttc*c*g | 313 |
| ccaatcg*g*c | 314 |
| cccgctt*c*a | 315 |

TABLE 3-continued

First Generation Targeted Whole Genome Amplification Primer Set

| Sequence | SEQ ID NO: |
|---|---|
| ccggtaa*t*a | 316 |
| cgataat*g*a | 317 |
| cgattaa*a*g | 318 |
| cgattg*c*g | 319 |
| cgcctct*t*c | 320 |
| cgctaaa*t*a | 321 |
| cgcttta*t*a | 322 |
| cggcgcgctg*a*a | 323 |
| cggtatt*g*a | 324 |
| cgtaaag*a*a | 325 |
| cgtaaat*a*c | 326 |
| cgtgatc*a*a | 327 |
| cgtttat*t*a | 328 |
| cgwtaat*a*a | 329 |
| ctaattcttc*t*a | 330 |
| ctacttttc*c*a | 331 |
| ctgtagaaga*a*g | 332 |
| ctgttttaga*a*g | 333 |
| cttcacg*a*a | 334 |
| cttcatca*a*c | 335 |
| cttcatctaa*t*a | 336 |
| cttcttctaa*a*a | 337 |
| cttcttcttt*a*a | 338 |
| cttctttc*g*c | 339 |
| cttttagaaaa*t*a | 340 |
| cttttatataa*a*r | 341 |
| cttttatcaat*a*a | 342 |
| cttttcgct*t*c | 343 |
| ctttttatata*a*a | 344 |
| cttttttcwtc*t*a | 345 |
| gaaaaaggat*t*a | 346 |
| gaaacga*t*c | 347 |
| gaaacgt*t*a | 348 |
| gaaattgctg*a*c | 349 |
| gaagaagyga*a*a | 350 |
| gaagatgaaa*a*a | 351 |
| gaagatttat*t*a | 352 |

| Sequence | SEQ ID NO: |
|---|---|
| gaagtattaa*a*a | 353 |
| gaatatgaag*a*a | 354 |
| gatattgata*a*a | 355 |
| gatgaagata*a*a | 356 |
| gatttattat*t*a | 357 |
| gatttcacga*a*a | 358 |
| gcaata*a*c | 359 |
| gccttt*a*c | 360 |
| gcgaaag*a*a | 361 |
| gcgattt*t*a | 362 |
| gcggtat*t*a | 363 |
| gcgttaa*t*a | 364 |
| gcgttta*a*a | 365 |
| gcgtttt*g*a | 366 |
| gckgatt*t*a | 367 |
| gctaaaaaag*a*a | 368 |
| gctattttat*t*a | 369 |
| gctcgcgcga*c*a | 370 |
| gcttcttta*t*a | 371 |
| gcttttcat*c*a | 372 |
| ggcatt*a*c | 373 |
| ggcggta*a*a | 374 |
| ggttgaa*a*c | 375 |
| ggttta*a*c | 376 |
| gtaaaac*g*a | 377 |
| gtaaagcttt*c*a | 378 |
| gtgacga*a*a | 379 |
| gttatcg*c*a | 380 |
| gttgttttac*c*a | 381 |
| sttccgc*a*a | 382 |
| taaaatgggt*g*a | 383 |
| taaagcaatt*a*a | 384 |
| taaatcatct*a*a | 385 |
| taacgaa*g*a | 386 |
| taactcttct*a*a | 387 |
| taatgctt*c*a | 388 |
| tacatcat*c*a | 389 |
| tatcatc*g*a | 390 |

TABLE 3-continued

First Generation Targeted Whole Genome Amplification Primer Set

| Sequence | SEQ ID NO: |
|---|---|
| tatcattaat*a*a | 391 |
| tatcctcttc*c*a | 392 |
| tcttctaata*a*a | 393 |
| tcttctaatt*c*a | 394 |
| tcttcttcta*a*a | 395 |
| tctttttta*c*a | 396 |
| tgacgat*a*a | 397 |
| tgatgcg*a*a | 398 |
| tgcttcttt*a*a | 399 |
| ttagatgaag*a*a | 400 |
| ttagctaaag*a*a | 401 |
| ttattagaag*a*a | 402 |

TABLE 4

Second Generation Targeted Whole Genome Amplification Primer Set

| Sequence | SEQ ID NO: |
|---|---|
| aaaacaat*t*g | 403 |
| aaaacgtt*t*a | 404 |
| aaaagaat*t*a | 405 |
| aaaaggta*t*t | 406 |
| aaaaggtg*a*a | 407 |
| aaataacg*a*t | 216 |
| aaatcgttga*t*a | 409 |
| aaatggtga*a*g | 410 |
| aacaccaa*t*t | 411 |
| aacgaaag*a*t | 412 |
| aacgaaagaa*g*a | 413 |
| aacgaat*a*a | 414 |
| aagaagcga*a*g | 415 |
| aagaagtaaa*a*g | 416 |
| aagcg*g*a | 417 |
| aatcgc*t*a | 418 |
| aatcgcaa*t*t | 419 |
| aatcgcygat*a*t | 420 |
| aatcgttt*c*a | 421 |
| acaacga*t*t | 422 |

TABLE 4-continued

Second Generation Targeted Whole Genome Amplification Primer Set

| Sequence | SEQ ID NO: |
|---|---|
| accgataa*t*a | 423 |
| acgaagc*a*a | 424 |
| agaagcgat*g*a | 425 |
| agcgaaaga*a*g | 426 |
| atacga*t*g | 427 |
| atacgg*a*a | 428 |
| ataaaaa*g*a | 429 |
| atatg*c*g | 430 |
| atattatc*g*t | 431 |
| atcarcgatt*t*t | 432 |
| atcata*c*g | 433 |
| atccgt*t*a | 434 |
| atgaag*c*g | 435 |
| atgtaac*g*a | 436 |
| attaaagat*g*g | 437 |
| attaac*g*c | 438 |
| attacaaa*a*g | 439 |
| attacgat*a*a | 440 |
| attacgt*t*a | 441 |
| attacttg*t*a | 442 |
| attatatg*a*a | 443 |
| attattat*c*g | 444 |
| attgaaaaag*c*a | 445 |
| attgaaac*g*a | 446 |
| attgcttc*t*t | 447 |
| attgtcg*t*t | 448 |
| atttatcg*t*a | 449 |
| caacttct*t*t | 450 |
| caatcgt*a*t | 451 |
| caattaat*a*c | 452 |
| caattgga*a*t | 453 |
| caccaatt*a*c | 454 |
| caccaatt*g*t | 455 |
| caccttta*c*a | 456 |
| catacg*a*a | 457 |
| catataa*c*g | 458 |
| catcaattg*t*t | 459 |
| ccgct*t*t | 460 |

TABLE 4-continued

Second Generation Targeted Whole Genome Amplification Primer Set

| Sequence | SEQ ID NO: |
|---|---|
| cgacttaccg*a*c | 461 |
| cgata*a*c | 462 |
| cgataaag*a*a | 463 |
| cgatataat*t*t | 464 |
| cgatg*t*a | 465 |
| cgattga*a*g | 466 |
| cgattttc*a*a | 467 |
| cgcaa*t*a | 468 |
| cgcttttta*t*t | 469 |
| cggat*a*t | 470 |
| cggtaa*a*t | 471 |
| cggttta*a*t | 472 |
| cgtaat*a*t | 473 |
| cgtata*a*c | 474 |
| cgttaat*t*g | 475 |
| cgttatg*a*a | 476 |
| ctatcg*t*a | 477 |
| ctgattaaag*t*t | 478 |
| cttccata*a*t | 479 |
| cttcgt*a*a | 480 |
| cttctata*t*a | 481 |
| cttctgca*a*t | 482 |
| cttcttca*c*g | 483 |
| cttcttcttt*c*g | 484 |
| cttctta*a*t | 485 |
| cttctttc*g*c | 339 |
| cttctttcg*g*a | 487 |
| ctttcgct*t*t | 488 |
| ctttcgcttc*t*t | 489 |
| cttttaattc*t*t | 490 |
| cttttgtaa*t*a | 491 |
| cttttcg*t*a | 492 |
| cttttttc*a*t | 493 |
| cttttya*t*c | 494 |
| gaaacgat*t*g | 495 |
| gaagaagcga*a*a | 496 |
| gaagaagt*a*a | 497 |

TABLE 4-continued

Second Generation Targeted Whole Genome Amplification Primer Set

| Sequence | SEQ ID NO: |
|---|---|
| gaagaagta*g*c | 498 |
| gatacgaa*a*g | 499 |
| gatgaatt*a*g | 500 |
| gatta*c*g | 501 |
| gattaaagtt*t*c | 502 |
| gcaattgaaa*a*a | 503 |
| gcaattgt*a*t | 504 |
| gcaattgt*t*g | 505 |
| gcgaaagaa*g*c | 506 |
| gcgtaa*t*a | 507 |
| gctactt*a*t | 508 |
| gcttcttt*c*g | 509 |
| gcttttttta*t*t | 510 |
| gtattaaaa*g*a | 511 |
| gttaattg*a*a | 512 |
| gttcg*t*a | 513 |
| gttgc*g*a | 514 |
| taaagataa*t*g | 515 |
| taaagcg*t*t | 516 |
| taaagtgaaa*c*t | 517 |
| taaatcttc*t*a | 518 |
| taacagaa*g*a | 519 |
| taacgaaaga*a*g | 520 |
| taacgga*a*a | 521 |
| taactcttc*t*t | 522 |
| taatam*c*g | 523 |
| taatcg*y*a | 524 |
| taatgaag*a*a | 525 |
| taattgct*t*c | 526 |
| tacaattt*c*a | 527 |
| taccgt*t*a | 528 |
| tacgaaaga*a*g | 529 |
| tacgaatg*a*t | 530 |
| tactcg*t*t | 531 |
| tagaagaa*g*t | 532 |
| tagaagaag*c*g | 533 |
| tagaagc*g*a | 534 |
| tatatcgact*t*a | 535 |

TABLE 4-continued

Second Generation Targeted Whole Genome Amplification Primer Set

| Sequence | SEQ ID NO: |
|---|---|
| tatatcrgcg*a*t | 536 |
| tatcggcgat*t*t | 537 |
| tatgtaa*c*g | 538 |
| tattag*c*g | 539 |
| tattcg*c*t | 540 |
| tattgatg*a*a | 541 |
| tawtacga*a*a | 542 |
| tcaattgc*a*a | 543 |
| tcaattgct*t*c | 544 |
| tcattac*g*a | 545 |
| tccaattg*a*a | 546 |
| tccgaaag*a*a | 547 |
| tccgct*a*a | 548 |
| tccgt*a*t | 549 |
| tcctgtta*c*a | 550 |
| tcgca*t*a | 551 |
| tcgcttta*t*t | 552 |
| tcgtat*t*g | 553 |
| tcgttaca*a*t | 554 |
| tctacaat*t*a | 555 |
| tctactaa*t*t | 556 |
| tcttcaat*a*t | 557 |
| tcttctaa*c*g | 558 |
| tctttata*t*g | 559 |
| tctttatat*t*c | 560 |
| tctttcgc*t*a | 561 |
| tcttttttc*g*c | 562 |
| tgaaaaag*c*g | 563 |
| tgaaacaat*t*g | 564 |
| tgaaacga*a*t | 565 |
| tgaagcga*t*t | 566 |
| tgcaa*c*g | 567 |
| tgcgaaaga*a*a | 568 |
| tgcttcttc*t*a | 569 |
| tgtaaaag*g*t | 570 |
| tgtcggtaag*t*c | 571 |
| tgttctttc*g*t | 572 |
| ttaacgaaa*g*a | 573 |
| ttaacgg*a*a | 574 |
| ttacgaaa*g*a | 575 |
| ttagaaga*t*g | 576 |
| ttattatc*g*g | 577 |
| ttcaata*c*g | 578 |
| ttcacgaa*t*a | 579 |
| ttccgt*a*a | 580 |
| ttcgtaaa*t*t | 581 |
| ttcttta*c*g | 582 |
| ttctttcg*c*a | 583 |
| ttctttcgtt*a*a | 584 |
| ttcttta*t*a | 585 |
| ttgcaatt*g*c | 586 |
| ttgtaatt*g*g | 587 |
| ttgtcggta*a*g | 588 |
| tttattaga*t*g | 589 |
| tttcgtat*a*t | 590 |
| tttcgtta*t*a | 591 |
| tttwtcgt*a*a | 592 |
| twacgat*t*g | 593 |

Table 5 shows a comparison of statistics obtained from the first and second experiments. The statistics indicate the likelihood that more selective and efficient priming of the target *Bacillus anthracis* genome would be expected under the conditions of the second generation proof-of-concept experiment.

TABLE 5

Statistical Comparison of First and Second Experiments

| Statistic | First Generation Experiment | Second Generation Experiment |
|---|---|---|
| Total Frequency of Occurrence of all Selected Genome Sequence Segments | 12822 | 25822 |
| Mean Separation Distance Between Selected Genome Sequence Segments | 815 | 404 |
| Maximum Separation Distance Between Selected Genome Sequence Segments | 5420 | 3477 |
| Average Frequency Bias to Target Genome Over Background Genomes | 3.31 | 4.67 |

The results of the second generation experiment are shown in FIGS. 4A and 4B. It is readily apparent that the modifications to the selection process added in the second experiment result in a more efficient targeted whole genome amplification reaction which is biased toward amplification of the

*Bacillus anthracis* target genome. The primers of Table 4 produce less human DNA and more *Bacillus anthracis* DNA than the traditional whole genome amplification (WGA) and the first generation primer set (Table 3). Furthermore, the frequency bias was found to be even higher for the remaining target genomes as shown in Table 6.

TABLE 6

Statistical Comparison of Genome Sequence Segments for the Target Genomes of the Second Experiment

| Target Genome | Total Frequency of Occurrence of Segments | Mean Separation Distance | Maximum Distance Between Segments | Mean Frequency Bias |
|---|---|---|---|---|
| *Bacillus anthracis* | 25822 | 404.84 | 3477 | 4.67 |
| *Rickettsia prowazekii* | 5606 | 396.41 | 2265 | 5.44 |
| *Escherichia coli* | 23501 | 467.89 | 4822 | 22.70 |
| *Yersinia pestis* | 18597 | 500.43 | 4616 | 35.69 |
| *Brucella* sp. | 13442 | 490.10 | 3527 | 41.96 |
| *Francisella tularensis* | 7925 | 477.56 | 3179 | 50.08 |
| *Burkholderia mallei* | 25218 | 462.73 | 4062 | 291.13 |

Example 4

Targeted Whole Genome Amplification Protocol

The targeted whole genome amplification reaction mixture consisted of: 5 microliters of template DNA, and 0.04025 M TRIS HCl, 0.00975 M TRIS base, 0.012 M $MgCl_2$, 0.01 M $(NH_4)_2SO_4$, 0.8 M betaine, 0.8 M trehalose, 25 mM of each deoxynucleotide triphosphate (Bioline, Randolph, Mass., U.S.A), 0.004 M dithiothreitol, 0.05 mM of primers of the selected primer set, and 0.5 units of Phi29 polymerase enzyme per microliter of reaction mixture.

The thermal cycling conditions for the amplification reaction were as follows:

1. 30° C. for 4 minutes
2. 15° C. for 15 seconds
3. repeat steps 1 and 2×150
4. hold at 95° C. for 10 minutes
5. hold at 4° C. until ready for analysis Example 5

Targeted Whole Genome Amplification of Sepsis-Causing Microorganisms

This example is directed toward design of a kit for targeted whole genome amplification of organisms which are known to cause sepsis. A collection of target genomes is assembled, comprising the genomes of the following microorganisms known to cause bloodstream infections: *Escherichia coli, Klebsiella pneumoniae, Klebsiella oxytoca, Serratia marcescens, Enterobacter cloacae, Enterobacter aerogenes, Proteus mirabilis, Pseudomonas aeruginosa, Acinetobacter baumannii, Stenotrophomonas maltophilia, Staphylococcus aureus, Staphylococcus epidermidis, Staphylococcus haemolyticus, Streptococcus pneumoniae, Streptococcus pyogenes, Streptococcus agalactiae, Streptococcus mitis, Enterococcus faecium, Enterococcus faecalis, Candida albicans, Candida tropicalis, Candida parapsilosis, Candida krusei, Candida glabrata* and *Aspergillus fumigatus*. Because the healthy human bloodstream generally does not contain microorganisms or parasites, only the human genome is chosen as a single background genome. Alternatively, if a human was known to be infected with a virus such as HIV or HCV for example, the genomes of HIV or HCV could be included as background genomes during the primer design process. Genomes commonly found in the human bloodstream are considered background genomes.

The target and background genomes are obtained from a genomics database such as GenBank. The target genomes are scanned by a computer program to identify all unique genome sequence segments between 5 and 13 nucleobases in length. The computer program further determines and records the frequency of occurrence of each of the unique genome sequence segments within each of the target genomes.

The human genome is then scanned to determine the frequency of occurrence of the genome sequence segments. Optionally, the entire list of genome sequence segments is reduced by removing genome sequence segments that have low frequencies of occurrence by choosing an arbitrary frequency of occurrence threshold criterion such as, for example, the mean frequency of occurrence or any frequency of occurrence 25% above or below the mean frequency of occurrence or any whole or fractional percentage therebetween. For example, if the mean frequency of occurrence is 100, 25% above 100 equals 125 and 25% below 100 equals 75 and the frequency of occurrence threshold criterion may be any whole or fractional number between about 75 and about 125. When this step is complete, a subset of the original list of unique genome sequence segments remains. At this point, the subset of genome sequence subsets is analyzed by the computer program to determine the frequency of occurrence of each of the genome sequence segments within the human genome. Upon completion of this step, the genome sequence segments of the subset are associated with the following data; the frequency of occurrence within each of the target genomes and the frequency of occurrence within the human genome. A value indicating the total target frequency of occurrence is calculated by adding the frequency of occurrence of the genome sequence segments in each of the target genomes.

The selectivity ratio is calculated by the computer program for the genome sequence segments of the subset by dividing the total target frequency of occurrence by the background frequency of occurrence. When the series of selectivity ratio calculations are complete, the genome sequence segments are ranked by their selectivity ratio values such that the highest selectivity ratio receives the highest rank. The ranked genome sequence segments are then subjected to the process described Example 2 and illustrated in FIG. 2.

The process of Example 2 and FIG. 2 ends when the predetermined quantity of 200 genome sequence segments is reached and when the stopping criteria are met. The stopping criteria are the following: the mean distance between the selected genome sequence segments on the target genomes is less than 500 nucleobases and the maximum distance between the selected genome sequence segments on the target genomes is less than 5000 nucleobases. These values are calculated by the computer program from the known coordinates of the target genomes and the selected genome sequence segments.

The primer design step begins after completion of the selection process of the genome sequence segments. The genome sequence segments represent primer hybridization sites and a primer is designed to bind to each of the selected genome sequence segments. For an initial round of primer design and testing, primers are designed to be 100% complementary to each of the selected genome sequence segments. Optionally, the primers can be subjected to an in silico analysis to determine if they unfavorable characteristics. Unfavorable characteristics may include poor affinity (as measured by melting temperature) for their corresponding target genome sequence segment, primer dimer formation, or presence of secondary structure. Upon identification of unfavorable characteristics in a given primer, the primer is redesigned by alteration of length or by incorporation of modified nucleobases.

Figure 3:
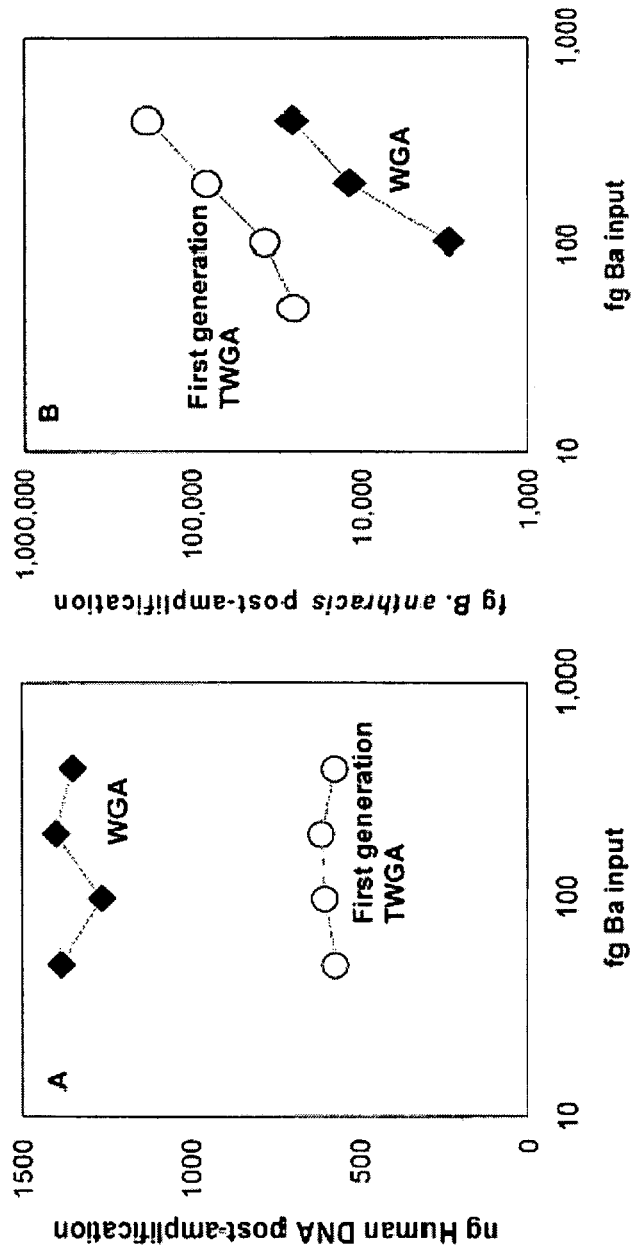
Figure 4:
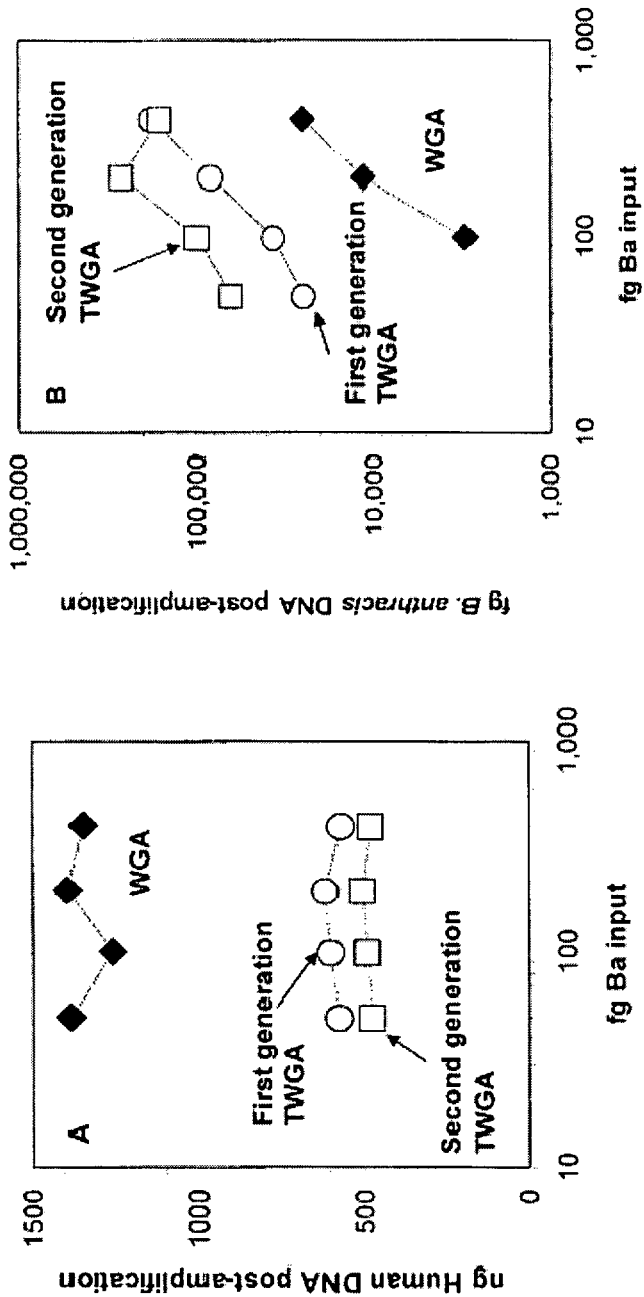
FIG. 4B is a plot indicating the quantity of *Bacillus anthracis* DNA obtained from whole genome amplification (WGA) reactions performed with random hexamer primers (solid diamond) and targeted whole genome amplification (TWGA) method using the primers of Table 3 (clear circle) and the second generation primers of Table 4 (clear square).
Figure 5:
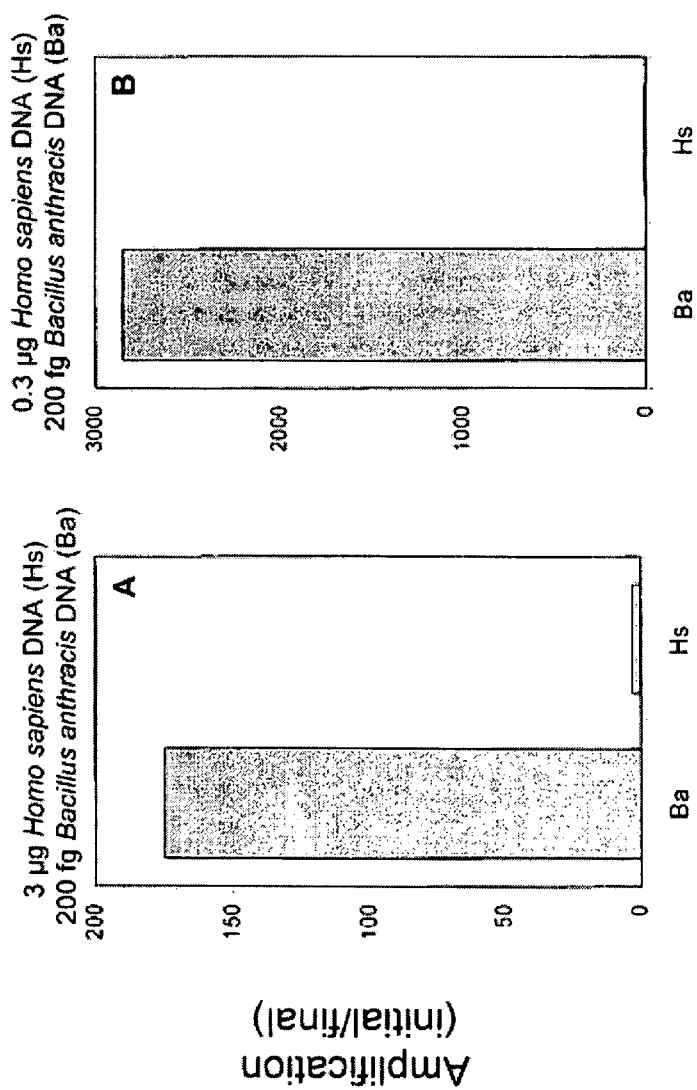
FIGS. 5A and 5B are plots indicating the quantities of *Bacillus anthracis* DNA (target genome) and *Homo sapiens* DNA (background genome) obtained in targeted whole genome amplification reactions with the indicated quantity of background DNA and 200 femtograms (fg) of *Bacillus anthracis* DNA.
Figure 6:
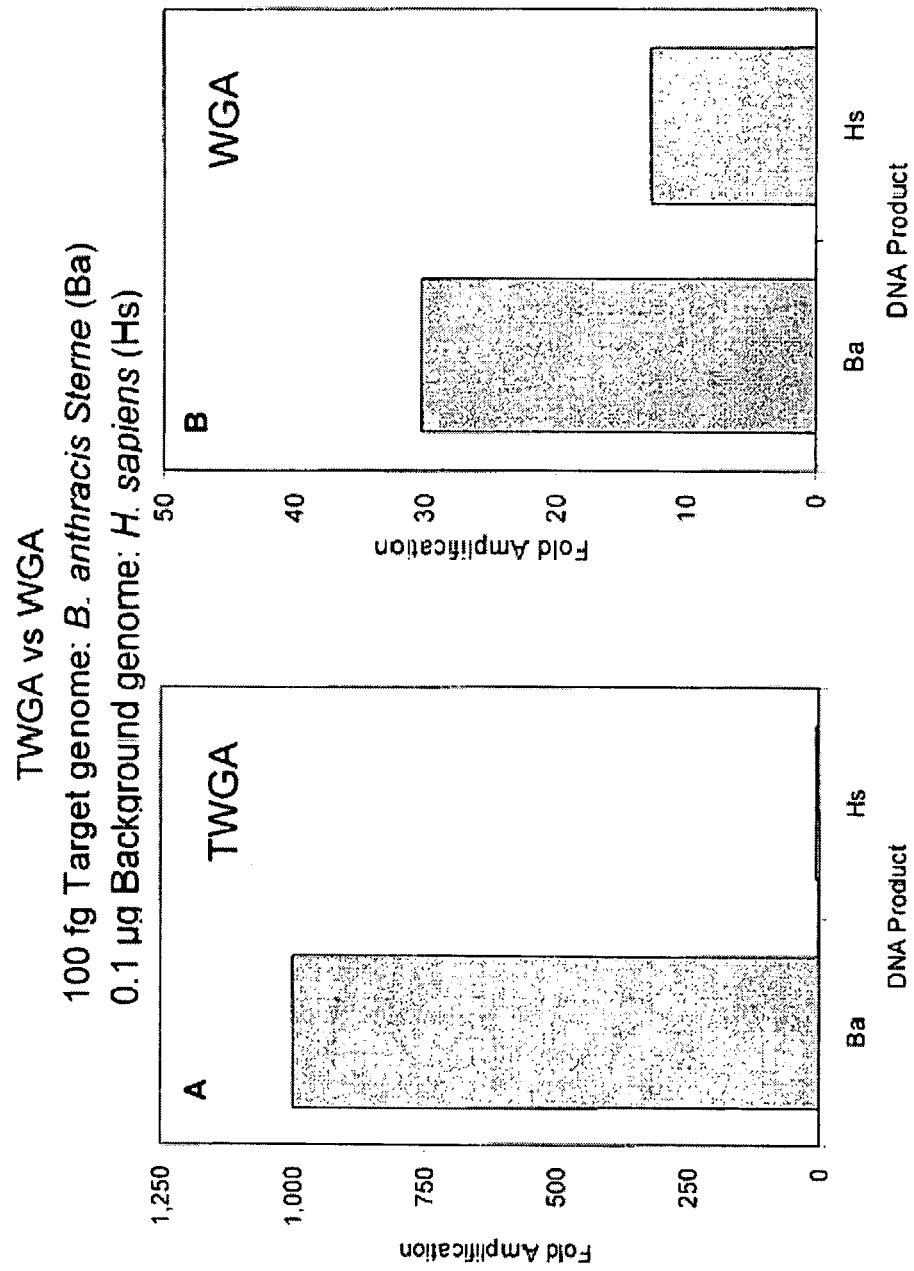
FIGS. 6A and 6B are plots comparing the quantities of *Bacillus anthracis* DNA (target genome) and *Homo sapiens* DNA (background genome) obtained in a targeted whole genome amplification reaction (FIG. 6A) vs. a conventional whole genome amplification reaction (FIG. 6B).

Once primer design (and redesign if necessary) is complete, the primers are synthesized and subjected to in vitro testing by amplification of the target genomes in the presence of human DNA (representing the background human genome) to determine the amplification efficiency and bias toward the target genomes. Analyses such as those shown in FIGS. 3 and 4 are useful for determining these measures. In addition, analyses of statistics such as those shown in Table 6 are useful for obtaining an estimation of bias toward the target genomes relative to the background human genome.

When the primer design and testing is complete, kits are assembled. The kits contain the primers, deoxynucleotide triphosphates, a processive polymerase, buffers and additives useful for improving the yield of amplified genomes. These kits are used to amplify genomic DNA of sepsis-causing organisms from blood samples of individuals exhibiting symptoms of sepsis. The amplified DNA is then available for further testing for the purpose of genotyping. Such tests include real-time PCR, microarray analysis and triangulation genotyping analysis by mass spectrometry of bioagent identifying amplicons as described herein (Examples 6-12). Additionally, genotyping of sepsis-causing organisms is useful in determining an appropriate course of treatment with antibiotics and alerting authorities of the presence of potentially drug-resistant strains of sepsis-causing organisms. Such genotyping analyses can be developed using methods described herein as well as those disclosed in commonly owned U.S. application Ser. No 11/409,535 which is incorporated herein by reference in entirety.

Example 6

Design and Validation of Primer Pairs that Define Bioagent Identifying Amplicons for Identification of Bacteria For design of primers that define bacterial bioagent identifying amplicons, a series of bacterial genome segment sequences are obtained, aligned and scanned for regions where pairs of PCR primers would amplify products of about 39 to about 200 nucleotides in length and distinguish subgroups and/or individual strains from each other by their molecular masses or base compositions. A typical process shown in FIG. 8 is employed for this type of analysis.

A database of expected base compositions for each primer region is generated using an in silico PCR search algorithm, such as (ePCR). An existing RNA structure search algorithm (Macke et al., Nucl. Acids Res., 2001, 29, 4724-4735, which is incorporated herein by reference in its entirety) has been modified to include PCR parameters such as hybridization conditions, mismatches, and thermodynamic calculations (Santa Lucia, Proc. Natl. Acad. Sci. U.S.A., 1998, 95, 1460-1465, which is incorporated herein by reference in its entirety). This also provides information on primer specificity of the selected primer pairs. An example of a collection of such primer pairs is disclosed in U.S. application Ser. No. 11/409,535 which is incorporated herein by reference in entirety.

Example 7

Sample Preparation and PCR

Genomic DNA id prepared from samples using the DNeasy Tissue Kit (Qiagen, Valencia, Calif.) according to the manufacturer's protocols.

PCR reactions are assembled in 50 µL reaction volumes in a 96-well microtiter plate format using a Packard MPII liquid handling robotic platform and M. J. Dyad thermocyclers (MJ research, Waltham, Mass.) or Eppendorf Mastercycler thermocyclers (Eppendorf, Westbury, N.Y.). The PCR reaction mixture includes of 4 units of Amplitaq Gold, 1× buffer II (Applied Biosystems, Foster City, Calif.), 1.5 mM $MgCl_2$, 0.4 M betaine, 800 µM dNTP mixture and 250 nM of each primer. The following typical PCR conditions are used: 95° C. for 10 min followed by 8 cycles of 95° C. for 30 seconds, 48° C. for 30 seconds, and 72° C. 30 seconds with the 48° C. annealing temperature increasing 0.9° C. with each of the eight cycles. The PCR reaction is then continued for 37 additional cycles of 95° C. for 15 seconds, 56° C. for 20 seconds, and 72° C. 20 seconds.

Example 8

Purification of PCR Products for Mass Spectrometry with Ion Exchange Resin-Magnetic Beads For solution capture of nucleic acids with ion exchange resin linked to magnetic beads, 25 µl of a 2.5 mg/mL suspension of BioClone amine-terminated superparamagnetic beads is added to 25 to 50 µl of a PCR (or RT-PCR) reaction containing approximately 10 pM of a typical PCR amplification product. The above suspension is mixed for approximately 5 minutes by vortexing or pipetting, after which the liquid is removed after using a magnetic separator. The beads containing bound PCR amplification product are then washed three times with 50 mM ammonium bicarbonate/50% MeOH or 100 mM ammonium bicarbonate/50% MeOH, followed by three more washes with 50% MeOH. The bound PCR amplification product is eluted with a solution of 25 mM piperidine, 25 mM imidazole, 35% MeOH which includes peptide calibration standards.

Example 9

Mass Spectrometry and Base Composition Analysis

The ESI-FTICR mass spectrometer is based on a Bruker Daltonics (Billerica, Mass.) Apex II 70e electrospray ionization Fourier transform ion cyclotron resonance mass spectrometer that employs an actively shielded 7 Tesla superconducting magnet. The active shielding constrains the majority of the fringing magnetic field from the superconducting magnet to a relatively small volume. Thus, components that might be adversely affected by stray magnetic fields, such as CRT monitors, robotic components, and other electronics, can operate in close proximity to the FTICR spectrometer. All aspects of pulse sequence control and data acquisition were performed on a 600 MHz PENTIUM II data station running Bruker's Xmass software under WINDOWS NT 4.0 operating system. Sample aliquots, typically 15 µl, are extracted directly from 96-well microtiter plates using a CTC HTS PAL autosampler (LEAP Technologies, Carrboro, N.C.) triggered by the FTICR data station. Samples are injected directly into a 10 µl sample loop integrated with a fluidics handling system that supplies the 100 µl/hr flow rate to the ESI source. Ions are formed via electrospray ionization in a modified Analytica (Branford, Conn.) source employing an off axis, grounded electrospray probe positioned approximately 1.5 cm from the metallized terminus of a glass desolvation capillary. The atmospheric pressure end of the glass capillary is biased at 6000 V relative to the ESI needle during data acquisition. A counter-current flow of dry $N_2$ is employed to assist in the desolvation process. Ions are accumulated in an external ion reservoir comprised of an rf-only hexapole, a skimmer cone, and an auxiliary gate electrode, prior to injection into the trapped ion cell where they are mass analyzed. Ionization duty cycles greater than 99% are achieved by simultaneously accumulating ions in the external ion reservoir during ion detection. Each detection event includes 1M data points digitized over 2.3 s. To improve the signal-to-noise ratio (S/N), 32 scans are co-added for a total data acquisition time of 74 s.

The ESI-TOF mass spectrometer is based on a Bruker Daltonics MICROTOF ESI-TOF mass spectrometer. Ions from the ESI source undergo orthogonal ion extraction and are focused in a reflectron prior to detection. The TOF and FTICR are equipped with the same automated sample handling and fluidics described above. Ions are formed in the standard MICROTOF ESI source that is equipped with the same off-axis sprayer and glass capillary as the FTICR ESI source. Consequently, source conditions were the same as those described above. External ion accumulation is also employed to improve ionization duty cycle during data acquisition. Each detection event on the TOF includes 75,000 data points digitized over 75 µs.

The sample delivery scheme allows sample aliquots to be rapidly injected into the electrospray source at high flow rate and subsequently be electrosprayed at a much lower flow rate for improved ESI sensitivity. Prior to injecting a sample, a bolus of buffer is injected at a high flow rate to rinse the transfer line and spray needle to avoid sample contamination/carryover. Following the rinse step, the autosampler injects the next sample and the flow rate is switched to low flow. Following a brief equilibration delay, data acquisition commenced. As spectra are co-added, the autosampler continued rinsing the syringe and picking up buffer to rinse the injector and sample transfer line. In general, two syringe rinses and one injector rinse are required to minimize sample carryover. During a routine screening protocol a new sample mixture is injected every 106 seconds. More recently a fast wash station for the syringe needle has been implemented which, when combined with shorter acquisition times, facilitates the acquisition of mass spectra at a rate of just under one spectrum/minute.

Raw mass spectra are post-calibrated with an internal mass standard and deconvoluted to monoisotopic molecular masses. Unambiguous base compositions are derived from the exact mass measurements of the complementary single-stranded oligonucleotides. Quantitative results are obtained by comparing the peak heights with an internal PCR calibration standard present in every PCR well at 500 molecules per well. Calibration methods are commonly owned and disclosed in PCT Publication Number WO 2005/098047 which is incorporated herein by reference in entirety.

Example 10

De Novo Determination of Base Composition of Amplification Products Using Molecular Mass Modified Deoxynucleotide Triphosphates Because the molecular masses of the four natural nucleobases have a relatively narrow molecular mass range (A=313.058, G=329.052, C=289.046, T=304.046—See Table 7), a persistent source of ambiguity in assignment of base composition can occur as follows: two nucleic acid strands having different base composition may have a difference of about 1 Da when the base composition difference between the two strands is G ↔ A (−15.994) combined with C ↔ T (+15.000). For example, one 99-mer nucleic acid strand having a base composition of $A_{27}G_{30}C_{21}T_{21}$ has a theoretical molecular mass of 30779.058 while another 99-mer nucleic acid strand having a base composition of $A_{26}G_{31}C_{22}T_{20}$ has a theoretical molecular mass of 30780.052. A 1 Da difference in molecular mass may be within the experimental error of a molecular mass measurement and thus, the relatively narrow molecular mass range of the four natural nucleobases imposes an uncertainty factor.

The methods provide for a means for removing this theoretical 1 Da uncertainty factor through amplification of a nucleic acid with one mass-tagged nucleobase and three natural nucleobases. The term "nucleobase" as used herein is synonymous with other terms in use in the art including "nucleotide," "deoxynucleotide," "nucleotide residue," "deoxynucleotide residue," "nucleotide triphosphate (NTP)," or deoxynucleotide triphosphate (dNTP).

Addition of significant mass to one of the 4 nucleobases (dNTPs) in an amplification reaction, or in the primers themselves, will result in a significant difference in mass of the resulting amplification product (significantly greater than 1 Da) arising from ambiguities arising from the G ↔ A combined with C ↔ T event (Table 7). Thus, the same the G ↔ A (−15.994) event combined with 5-Iodo-C ↔ T (−110.900) event would result in a molecular mass difference of 126.894. If the molecular mass of the base composition $A_{27}G_{30}$5-Iodo-$C_{21}T_{21}$ (33422.958) is compared with $A_{26}G_{31}$5-Iodo-$C_{22}T_{20}$, (33549.852) the theoretical molecular mass difference is +126.894. The experimental error of a molecular mass measurement is not significant with regard to this molecular mass difference. Furthermore, the only base composition consistent with a measured molecular mass of the 99-mer nucleic acid is $A_{27}G_{30}$5-Iodo-$C_{21}T_{21}$. In contrast, the analogous amplification without the mass tag has 18 possible base compositions.

TABLE 7

Molecular Masses of Natural Nucleobases and the Mass-Modified Nucleobase 5-Iodo-C and Molecular Mass Differences Resulting from Transitions

| Nucleobase | Molecular Mass | Transition | Δ Molecular Mass |
|---|---|---|---|
| A | 313.058 | A-->T | −9.012 |
| A | 313.058 | A-->C | −24.012 |
| A | 313.058 | A-->5-Iodo-C | 101.888 |
| A | 313.058 | A-->G | 15.994 |
| T | 304.046 | T-->A | 9.012 |
| T | 304.046 | T-->C | −15.000 |
| T | 304.046 | T-->5-Iodo-C | 110.900 |
| T | 304.046 | T-->G | 25.006 |
| C | 289.046 | C-->A | 24.012 |
| C | 289.046 | C-->T | 15.000 |
| C | 289.046 | C-->G | 40.006 |
| 5-Iodo-C | 414.946 | 5-Iodo-C-->A | −101.888 |
| 5-Iodo-C | 414.946 | 5-Iodo-C-->T | −110.900 |
| 5-Iodo-C | 414.946 | 5-Iodo-C-->G | −85.894 |
| G | 329.052 | G-->A | −15.994 |
| G | 329.052 | G-->T | −25.006 |
| G | 329.052 | G-->C | −40.006 |
| G | 329.052 | G-->5-Iodo-C | 85.894 |

Mass spectra of bioagent-identifying amplicons are analyzed independently using a maximum-likelihood processor, such as is widely used in radar signal processing. This processor, referred to as GenX, first makes maximum likelihood estimates of the input to the mass spectrometer for each primer by running matched filters for each base composition aggregate on the input data. This includes the GenX response to a calibrant for each primer.

The algorithm emphasizes performance predictions culminating in probability-of-detection versus probability-of-false-alarm plots for conditions involving complex backgrounds of naturally occurring organisms and environmental contaminants. Matched filters consist of a priori expectations of signal values given the set of primers used for each of the bioagents. A genomic sequence database is used to define the mass base count matched filters. The database contains the sequences of known bacterial bioagents and includes threat organisms as well as benign background organisms. The latter is used to estimate and subtract the spectral signature produced by the background organisms. A maximum likelihood detection of known background organisms is implemented using matched filters and a running-sum estimate of the noise covariance. Background signal strengths are estimated and used along with the matched filters to form signatures which are then subtracted. The maximum likelihood process is applied to this "cleaned up" data in a similar manner employing matched filters for the organisms and a running-sum estimate of the noise-covariance for the cleaned up data.

The amplitudes of all base compositions of bioagent-identifying amplicons for each primer are calibrated and a final maximum likelihood amplitude estimate per organism is made based upon the multiple single primer estimates. Models of all system noise are factored into this two-stage maximum likelihood calculation. The processor reports the number of molecules of each base composition contained in the spectra. The quantity of amplification product corresponding to the appropriate primer set is reported as well as the quantities of primers remaining upon completion of the amplification reaction.

Base count blurring can be carried out as follows. "Electronic PCR" can be conducted on nucleotide sequences of the desired bioagents to obtain the different expected base counts that could be obtained for each primer pair. See for example, ncbi.nlm.nih.gov/sutils/e-pcr/; Schuler, *Genome Res.* 7:541-50, 1997. In one illustrative embodiment, one or more spreadsheets, such as Microsoft Excel workbooks contain a plurality of worksheets. First in this example, there is a worksheet with a name similar to the workbook name; this worksheet contains the raw electronic PCR data. Second, there is a worksheet named "filtered bioagents base count" that contains bioagent name and base count; there is a separate record for each strain after removing sequences that are not identified with a genus and species and removing all sequences for bioagents with less than 10 strains. Third, there is a worksheet that contains the frequency of substitutions, insertions, or deletions for this primer pair. This data is generated by first creating a pivot table from the data in the "filtered bioagents base count" worksheet and then executing an Excel VBA macro. The macro creates a table of differences in base counts for bioagents of the same species, but different strains. One of ordinary skill in the art may understand additional pathways for obtaining similar table differences without undo experimentation.

Application of an exemplary script, involves the user defining a threshold that specifies the fraction of the strains that are represented by the reference set of base counts for each bioagent. The reference set of base counts for each bioagent may contain as many different base counts as are needed to meet or exceed the threshold. The set of reference base counts is defined by taking the most abundant strain's base type composition and adding it to the reference set and then the next most abundant strain's base type composition is added until the threshold is met or exceeded. The current set of data was obtained using a threshold of 55%, which was obtained empirically.

For each base count not included in the reference base count set for that bioagent, the script then proceeds to determine the manner in which the current base count differs from each of the base counts in the reference set. This difference may be represented as a combination of substitutions, $Si=Xi$, and insertions, $Ii=Yi$, or deletions, $Di=Zi$. If there is more than one reference base count, then the reported difference is chosen using rules that aim to minimize the number of changes and, in instances with the same number of changes, minimize the number of insertions or deletions. Therefore, the primary rule is to identify the difference with the minimum sum ($Xi+Yi$) or ($Xi+Zi$), e.g., one insertion rather than two substitutions. If there are two or more differences with the minimum sum, then the one that will be reported is the one that contains the most substitutions.

Differences between a base count and a reference composition are categorized as one, two, or more substitutions, one, two, or more insertions, one, two, or more deletions, and combinations of substitutions and insertions or deletions. The different classes of nucleobase changes and their probabilities of occurrence have been delineated in U.S. Patent Application Publication No. 2004209260 which is incorporated herein by reference in entirety.

Example 11

Selection and Use of Primer Pairs for Identification of Species of Bacteria Involved in Sepsis In this example, identification of bacteria known to cause sepsis was accomplished using a panel of primer pairs chosen specifically with the aim of identifying these bacteria (Table 8). In this current example, the more specific group of bacteria known to be involved in causing sepsis is to be surveyed. Therefore, in development of this current panel of primer pairs, certain established surveillance primer pairs of U.S. application Ser. No. 11/409,535 have been combined with an additional primer pair, primer pair number 2249. The primer members of primer pair 2249 hybridize to the tufB gene and produce a bioagent identifying amplicon for members of the family Staphylococcaceae which includes the genus *Staphylococcus*.

TABLE 8

Names of Primer Pairs in Panel for Characterization of Septicemia Pathogens

| Primer Pair No. | Forward Primer Name | Forward Primer Sequence | Forward Primer (SEQ ID NO:) | Reverse Primer Name | Reverse Primer Sequence | Reverse Primer (SEQ ID NO:) |
|---|---|---|---|---|---|---|
| 346 | 16S_EC_713_732_TMOD_F | TAGAACACCG ATGGCGAAGGC | 594 | 16S_EC_789_809_TMOD_R | TCGTGGACT ACCAGGGT ATCTA | 602 |

TABLE 8-continued

Names of Primer Pairs in Panel for Characterization of Septicemia Pathogens

| Primer Pair No. | Forward Primer Name | Forward Primer Sequence | Forward Primer (SEQ ID NO:) | Reverse Primer Name | Reverse Primer Sequence | Reverse Primer (SEQ ID NO:) |
|---|---|---|---|---|---|---|
| 348 | 16S_EC_785_806_TMOD_F | TTTCGATGCAACGCGAAGAACCT | 595 | 16S_EC_880_897_TMOD_R | TACGAGCTGACGACAGCCATG | 603 |
| 349 | 23S_EC_1826_1843_TMOD_F | TCTGACACCTGCCCGGTGC | 596 | 23S_EC_1906_1924_TMOD_R | TGACCGTTATAGTTACGGCC | 604 |
| 354 | RPOC_EC_2218_2241_TMOD_F | TCTGGCAGGTATGCGTGGTCTGATG | 597 | RPOC_EC_2313_2337_TMOD_R | TCGCACCGTGGGTTGAGATGAAGTAC | 605 |
| 358 | VALS_EC_1105_1124_TMOD_F | TCGTGGCGGCGTGGTTATCGA | 598 | VALS_EC_1195_1218_TMOD_R | TCGGTACGAACTGGATGTCGCCGTT | 606 |
| 359 | RPOB_EC_1845_1866_TMOD_F | TTATCGCTCAGGCGAACTCCAAC | 599 | RPOB_EC_1909_1929_TMOD_R | TGCTGGATTCGCCTTTGCTACG | 607 |
| 449 | RPLB_EC_690_710_F | TCCACACGGTGGTGGTGAAGG | 600 | RPLB_EC_737_758_R | TGTGCTGGTTTACCCCATGGAG | 608 |
| 2249 | TUFB_NC002758-615038-616222_696_725_F | TGAACGTGGTCAAATCAAAGTTGGTGAAGA | 601 | TUFB_NC002758-615038-616222_793_820_R | TGTCACCAGCTTCAGCGTAGTCTAATAA | 609 |

To test for potential interterence of human DNA with the present assay, varying amounts of bacterial DNA from *E. coli* 0157 and *E. coli* K-12 were spiked into samples of human DNA at various concentration levels. Amplification was carried out using primer pairs 346, 348, 349, 354, 358 and 359 and the amplified samples were subjected to gel electrophoresis. Smearing was absent on the gel, indicating that the primer pairs are specific for amplification of the bacterial DNA and that performance of the primer pairs is not appreciably affected in the presence of high levels of human DNA such as would be expected in blood samples. Measurement of the amplification products indicated that *E. coli* 0157 could be distinguished from *E. coli* K-12 by the base compositions of amplification products of primer pairs 358 and 359. This is a useful result because *E. coli* 0157 is a sepsis pathogen and because *E. coli* K-12 is a low-level contaminant of the commercially obtained Taq polymerase used for the amplification reactions.

A test of 9 blinded mixture samples was conducted as an experiment designed to simulate a potential clinical situation where bacteria introduced via skin or oral flora contamination could confound the detection of sepsis pathogens. The samples contained mixtures of sepsis-relevant bacteria at different concentrations, whose identities were not known prior to measurements. Tables 9A and 9B show the results of the observed base compositions of the amplification products produced by the primer pairs of Table 8 which were used to identify the bacteria in each sample. Without prior knowledge of the bacteria included in the 9 samples provided, it was found that samples 1-5 contained *Proteus mirabilis, Staphylococcus aureus*, and *Streptococcus pneumoniae* at variable concentration levels as indicated in Tables 9A and 9B. Sample 6 contained only *Staphylococcus aureus*. Sample 7 contained only *Streptococcus pneumoniae*. Sample 8 contained only *Proteus mirabilis*. Sample 9 was blank.

Quantitation of the three species of bacteria was carried out using calibration polynucleotides as described herein. The levels of each bacterium quantitated for each sample was found to be consistent with the levels expected.

This example indicates that the panel of primer pairs indicated in Table 8 is useful for identification of bacteria that cause sepsis.

In another experiment, two blinded samples were provided. The first sample, labeled "Germ A" contained *Enterococcus faecalis* and the second sample, labeled "Germ B" contained other *Klebsiella pneumoniae*. For "Germ A" the panel of primer pairs of Table 8 produced four bioagent identifying amplicons from bacterial DNA and primer pair numbers 347, 348, 349 and 449 whose base compositions indicated the identity of "Germ A" as *Enterococcus faecalis*. For "Germ B" the panel of primer pairs of Table 8 produced six bioagent identifying amplicons from bacterial DNA and primer pair numbers 347, 348, 349, 358, 359 and 354 whose base compositions indicated the identity of "Germ B" as *Klebsiella pneumoniae*.

One with ordinary skill in the art will recognize that one or more of the primer pairs of Table 8 could be replaced with one or more different primer pairs should the analysis require modification such that it would benefit from additional bioagent identifying amplicons that provide bacterial identification resolution for different species of bacteria and strains thereof.

TABLE 9A

Observed Base Compositions of Blinded Samples of Amplification Products Produced with Primer Pair Nos. 346, 348, 349 and 449

| Sample | Organism Component | Organism Concentration (genome copies) | Primer Pair Number 346 | Primer Pair Number 348 | Primer Pair Number 349 | Primer Pair Number 449 |
|---|---|---|---|---|---|---|
| 1 | *Proteus mirabilis* | 470 | A29G32C25T13 | — | — | — |
| 1 | *Staphylococcus aureus* | >1000 | — | A30G29C30T29 | A26G3C25T20 | — |
| 1 | *Streptococcus pneumoniae* | >1000 | — | A26G32C28T30 | A28G31C22T20 | A22G20C19T14 |
| 2 | *Staphylococcus aureus* | >1000 | A27G30C21T21 | A30G29C30T29 | A26G30C25T20 | — |
| 2 | *Streptococcus pneumoniae* | >1000 | — | — | — | A22G20C19T14 |
| 2 | *Proteus mirabilis* | 390 | — | — | — | — |
| 3 | *Proteus mirabilis* | >10000 | A29G32C25T13 | A29G30C28T29 | A25G31C27T20 | — |
| 3 | *Streptococcus pneumoniae* | 675 | — | — | — | A22G20C19T14 |
| 3 | *Staphylococcus aureus* | 110 | — | — | — | — |
| 4 | *Proteus mirabilis* | 2130 | A29G32C25T13 | A29G30C28T29 | A25G31C27T20 | — |
| 4 | *Streptococcus pneumoniae* | >3000 | — | A26G32C28T30 | A28G31C22T20 | A22G20C19T14 |
| 4 | *Staphylococcus aureus* | 335 | — | — | — | — |
| 5 | *Proteus mirabilis* | >10000 | A29G32C25T13 | A29G30C28T29 | A25G31C27T20 | — |
| 5 | *Streptococcus pneumoniae* | 77 | — | — | — | A22G20C19T14 |
| 5 | *Staphylococcus aureus* | >1000 | — | — | — | — |
| 6 | *Staphylococcus aureus* | 266 | A27G30C21T21 | A30G29C30T29 | A26G30C25T20 | — |
| 6 | *Streptococcus pneumoniae* | 0 | — | — | — | — |
| 6 | *Proteus mirabilis* | 0 | — | — | — | — |
| 7 | *Streptococcus pneumoniae* | 125 | — | A26G32C28T30 | A28G31C22T20 | A22G20C19T14 |
| 7 | *Staphylococcus aureus* | 0 | — | — | — | — |
| 7 | *Proteus mirabilis* | 0 | — | — | — | — |
| 8 | *Proteus mirabilis* | 240 | A29G32C25T13 | A29G30C28T29 | A25G31C27T20 | — |
| 8 | *Streptococcus pneumoniae* | 0 | — | — | — | — |
| 8 | *Staphylococcus aureus* | 0 | — | — | — | — |
| 9 | *Proteus mirabilis* | 0 | — | — | — | — |
| 9 | *Streptococcus pneumoniae* | 0 | — | — | — | — |
| 9 | *Staphylococcus aureus* | 0 | — | — | — | — |

TABLE 9B

Observed Base Compositions of Blinded Samples of Amplification Products Produced with Primer Pair Nos. 358, 359, 354 and 2249

| Sample | Organism Component | Organism Concentration (genome copies) | Primer Pair Number 358 | Primer Pair Number 359 | Primer Pair Number 354 | Primer Pair Number 2249 |
|---|---|---|---|---|---|---|
| 1 | *Proteus mirabilis* | 470 | — | — | A29G29C35T29 | — |
| 1 | *Staphylococcus aureus* | >1000 | — | — | A30G27C30T35 | A43G28C19T35 |
| 1 | *Streptococcus pneumoniae* | >1000 | — | — | — | — |
| 2 | *Staphylococcus aureus* | >1000 | — | — | A30G27C30T35 | A43G28C19T35 |
| 2 | *Streptococcus pneumoniae* | >1000 | — | — | — | — |
| 2 | *Proteus mirabilis* | 390 | — | — | A29G29C35T29 | — |
| 3 | *Proteus mirabilis* | >10000 | — | — | A29G29C35T29 | — |
| 3 | *Streptococcus pneumoniae* | 675 | — | — | — | — |
| 3 | *Staphylococcus aureus* | 110 | — | — | — | A43G28C19T35 |
| 4 | *Proteus mirabilis* | 2130 | — | — | A29G29C35T29 | — |
| 4 | *Streptococcus pneumoniae* | >3000 | — | — | — | — |
| 4 | *Staphylococcus aureus* | 335 | — | — | — | A43G28C19T35 |
| 5 | *Proteus mirabilis* | >10000 | — | — | A29G29C35T29 | — |
| 5 | *Streptococcus pneumoniae* | 77 | — | — | — | — |
| 5 | *Staphylococcus aureus* | >1000 | — | — | — | A43G28C19T35 |
| 6 | *Staphylococcus aureus* | 266 | — | — | — | A43G28C19T35 |
| 6 | *Streptococcus pneumoniae* | 0 | — | — | — | — |
| 6 | *Proteus mirabilis* | 0 | — | — | — | — |
| 7 | *Streptococcus pneumoniae* | 125 | — | — | — | — |
| 7 | *Staphylococcus aureus* | 0 | — | — | — | — |
| 7 | *Proteus mirabilis* | 0 | — | — | — | — |
| 8 | *Proteus mirabilis* | 240 | — | — | A29G29C35T29 | — |
| 8 | *Streptococcus pneumoniae* | 0 | — | — | — | — |
| 8 | *Staphylococcus aureus* | 0 | — | — | — | — |
| 9 | *Proteus mirabilis* | 0 | — | — | — | — |
| 9 | *Streptococcus pneumoniae* | 0 | — | — | — | — |
| 9 | *Staphylococcus aureus* | 0 | — | — | — | — |

Example 12

Design and Validation of Primer Pairs Designed for Production of Amplification Products from DNA of Sepsis-Causing Bacteria The following primer pairs of Table 10 were designed to provide an improved collection of bioagent identifying amplicons for the purpose of identifying sepsis-causing bacteria.

TABLE 10

Primer Pairs for Producing Bioagent Identifying Amplicons of Sepsis-Causing Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 3346 | RPOB_NC000913_3704_3731_F | TGAACCACTTGGTTGACGACAAGATGCA | 616 | RPOB_NC000913_3793_3815_R | TCACCGAAACGCTGACCACCGAA | 627 |
| 3347 | RPOB_NC000913_3704_3731_F | TGAACCACTTGGTTGACGACAAGATGCA | 616 | RPOB_NC000913_3796_3821_R | TCCATCTCACCGAAACGCTGACCACC | 632 |
| 3348 | RPOB_NC000913_3714_3740_F | TGTTGATGACAAGATGCACGCGCGTTC | 623 | RPOB_NC000913_3796_3821_R | TCCATCTCACCGAAACGCTGACCACC | 632 |
| 3349 | RPOB_NC000913_3720_3740_F | TGACAAGATGCACGCGCGTTC | 619 | RPOB_NC000913_3796_3817_R | CTCACCGAAACGCTACCACC | 636 |
| 3350 | RPLB_EC_690_710_F | TCCACACGGTGGTGGTGAAGG | 614 | RPLB_NC000913_739_762_R | TCCAAGCGCAGGTTTACCCCATGG | 630 |
| 3351 | RPLB_EC_690_710_F | TCCACACGGTGGTGGTGAAGG | 614 | RPLB_NC000913_742_762_R | TCCAAGCGCAGGTTTACCCCA | 628 |
| 3352 | RPLB_NC000913_674_698_F | TGAACCCTAATGATCACCCACACGG | 614 | RPLB_NC000913_739_762_R | TCCAAGCGCAGGTTTACCCCATGG | 630 |
| 3353 | RPLB_NC000913_674_698_2_F | TGAACCCTAACGATCACCCACACGG | 617 | RPLB_NC000913_742_762_R | TCCAAGCGCAGGTTTACCCCA | 629 |
| 3354 | RPLB_EC_690_710_F | TCCACACGGTGGTGGTGAAGG | 614 | RPLB_NC000913_742_762_2_R | TCCAAGCGCTGGTTTACCCCA | 631 |
| 3355 | RPLB_NC000913_651_680_F | TCCAACTGTTCGTGGTTCTGTAATGAACCC | 613 | RPLB_NC000913_739_762_R | TCCAAGCGCAGGTTTACCCCATGG | 630 |
| 3356 | RPOB_NC000913_3789_3812_F | TCAGTTCGGTGGCCAGCGCTTCGG | 610 | RPOB_NC000913_3868_3894_R | TACGTCGTCCGACTTGACCGTCAGCAT | 625 |
| 3357 | RPOB_NC000913_3789_3812_F | TCAGTTCGGTGGCCAGCGCTTCGG | 610 | RPOB_NC000913_3862_3887_R | TCCGACTTGACCGTCAGCATCTCCTG | 633 |
| 3358 | RPOB_NC000913_3789_3812_2_F | TCAGTTCGGTGGTCAGCGCTTCGG | 611 | RPOB_NC000913_3862_3890_R | TCGTCGGACTTGATGGTCAGCAGCTCCTG | 635 |
| 3359 | RPOB_NC000913_3739_3761_F | TCCACCGGTCCGTACTCCATGAT | 615 | RPOB_NC000913_3794_3812_R | CCGAAGCGCTGGCCACCGA | 624 |
| 3360 | GYRB_NC002737_852_879_F | TCATACTCATGAAGGTGGAACGCATGAA | 612 | GYRB_NC002737_973_996_R | TGCAGTCAAGCCTTCACGAACATC | 637 |

TABLE 10-continued

Primer Pairs for Producing Bioagent Identifying Amplicons of Sepsis-Causing Bacteria

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 3361 | TUFB_NC002758_275_298_F | TGATCACTGGTGCTGCTCAAATGG | 620 | TUFB_NC002758_337_362_R | TGGATGTGTTCACGAGTTTGAGGCAT | 638 |
| 3362 | VALS_NC000913_1098_1115_F | TGGCGACCGTGGCGGCGT | 621 | VALS_NC000913_1198_1226_R | TACTGCTTCGGGACGAACTGGATGTCGCC | 626 |
| 3363 | VALS_NC000913_1105_1127_F | TGTGGCGGCGTGGTTATCGAACC | 622 | VALS_NC000913_1207_1229_R | TCGTACTGCTTCGGGACGAACTG | 634 |

Primer pair numbers 3346-3349, and 3356-3359 have forward and reverse primers that hybridize to the rpoB gene of sepsis-causing bacteria. The reference gene sequence used in design of these primer pairs is an extraction of nucleotide residues 4179268 to 4183296 from the genomic sequence of *E. coli* K12 (GenBank Accession No. NC_000913.2, gi number 49175990). All coordinates indicated in the primer names are with respect to this sequence extraction. For example, the forward primer of primer pair number 3346 is named RPOB_NC000913_3704_3731 F (SEQ ID NO: 616). This primer hybridizes to positions 3704 to 3731 of the extraction or positions 4182972 to 4182999 of the genomic sequence. Of this group of primer pairs, primer pair numbers 3346-3349 were designed to preferably hybridize to the rpoB gene of sepsis-causing gamma proteobacteria. Primer pairs 3356 and 3357 were designed to preferably hybridize to the rpoB gene of sepsis-causing beta proteobacteria, including members of the genus *Neisseria*, Primer pairs 3358 and 3359 were designed to preferably hybridize to the rpoB gene of members of the genera *Corynebacterium* and *Mycobacterium*.

Primer pair numbers 3350-3355 have forward and reverse primers that hybridize to the rplB gene of gram positive sepsis-causing bacteria. The forward primer of primer pair numbers 3350, 3351 and 3354 is RPLB_EC_690_710_F (SEQ ID NO: 614). This forward primer had been previously designed to hybridize to GenBank Accession No. NC_000913.1, gi number 16127994. The reference gene sequence used in design of the remaining primers of primer pair numbers 3350-3355 is the reverse complement of an extraction of nucleotide residues 3448565 to 3449386 from the genomic sequence of *E. coli* K12 (GenBank Accession No. NC_000913.2, gi number 49175990). All coordinates indicated in the primer names are with respect to the reverse complement of this sequence extraction. For example, the forward primer of primer pair number 3352 is named RPLB_NC000913_674_698_F (SEQ ID NO: 634). This primer hybridizes to positions 674-698 of the reverse complement of the extraction or positions 3449239 to 3449263 of the reverse complement of the genomic sequence. This primer pair design example demonstrates that it may be useful to prepare new combinations of primer pairs using previously existing forward or reverse primers.

Primer pair number 3360 has a forward primer and a reverse primer that both hybridize to the gyrB gene of sepsis-causing bacteria, preferably members of the genus *Streptococcus*. The reference gene sequence used in design of these primer pairs is an extraction of nucleotide residues 581680 to 583632 from the genomic sequence of *Streptococcus pyogenes* M1 GAS (GenBank Accession No. NC_002737.1, gi number 15674250). All coordinates indicated in the primer names are with respect to this sequence extraction. For example, the forward primer of primer pair number 3360 is named GYRB_NC002737_852_879_F (SEQ ID NO: 612). This primer hybridizes to positions 852 to 879 of the extraction.

Primer pair number 3361 has a forward primer and a reverse primer that both hybridize to the tufB gene of sepsis-causing bacteria, preferably gram positive bacteria. The reference gene sequence used in design of these primer pairs is an extraction of nucleotide residues 615036 ... 616220 from the genomic sequence of *Staphylococcus aureus* subsp. *aureus* Mu50 (GenBank Accession No. NC_002758.2, gi number 57634611). All coordinates indicated in the primer names are with respect to this sequence extraction. For example, the forward primer of primer pair number 3361 is named TUFB_NC002758_275_298_F (SEQ ID NO: 612). This primer hybridizes to positions 275 to 298 of the extraction.

Primer pair numbers 3362 and 3363 have forward and reverse primers that hybridize to the valS gene of sepsis-causing bacteria, preferably including *Klebsiella pneumoniae* and strains thereof. The reference gene sequence used in design of these primer pairs is the reverse complement of an extraction of nucleotide residues 4479005 to 4481860 from the genomic sequence of *E. coli* K12 (GenBank Accession No. NC_000913.2, gi number 49175990). All coordinates indicated in the primer names are with respect to the reverse complement of this sequence extraction. For example, the forward primer of primer pair number 3362 is named VALS_NC000913_1098_1115_F (SEQ ID NO: 621). This primer hybridizes to positions 1098 to 1115 of the reverse complement of the extraction.

In a validation experiment, samples containing known quantities of known sepsis-causing bacteria were prepared. Total DNA was extracted and purified in the samples and subjected to amplification by PCR according to Example 2 and using the primer pairs described in this example. The three sepsis-causing bacteria chosen for this experiment were *Enterococcus faecalis, Klebsiella pneumoniae*, and *Staphylococcus aureus*. Following amplification, samples of the amplified mixture were purified by the method described in Example 3 subjected to molecular mass and base composition analysis as described in Example 4.

Amplification products corresponding to bioagent identifying amplicons for *Enterococcus faecalis* were expected for primer pair numbers 3346-3355, 3360 and 3361. Amplification products were obtained and detected for all of these primer pairs.

Amplification products corresponding to bioagent identifying amplicons for *Klebsiella pneumoniae* were expected and detected for primer pair numbers 3346-3349, 3356, 3358, 3359, 3362 and 3363. Amplification products corresponding to bioagent identifying amplicons for *Klebsiella pneumoniae* were detected for primer pair numbers 3346-3349 and 3358.

Amplification products corresponding to bioagent identifying amplicons for *Staphylococcus aureus* were expected and detected for primer pair numbers 3348, 3350-3355, 3360, and 3361. Amplification products corresponding to bioagent identifying amplicons for *Klebsiella pneumoniae* were detected for primer pair numbers 3350-3355 and 3361.

Example 13

Selection of Primer Pairs for Genotyping of Members of the Bacterial Genus *Mycobacterium* and for Identification of Drug-Resistant Strains of *Mycobacterium tuberculosis*

To combine the power of high-throughput mass spectrometric analysis of bioagent identifying amplicons with the sub-species characteristic resolving power provided by genotyping analysis and codon base composition analysis, a panel of twenty-four genotyping analysis primer pairs was selected. The primer pairs are designed to produce bioagent identifying amplicons within sixteen different housekeeping genes indicated by primer name codes in Table 11; rpoB, embB, fabG-inhA, katG, gyrA, rpsL, pncA, rv2109c, rv2348c, rv3815c, rv0041, rv00147, rv1814, rv0005gyrB, and rv0260c. The primer sequences are listed in Table 11.

In *Mycobacterium tuberculosis*, the acquisition of drug resistance is mostly associated with the emergence of discrete key mutations that can be unambiguously determined using the methods disclosed herein.

The evolution of the *Mycobacterium tuberculosis* genome is essentially clonal, thus allowing strain typing through the query of distinct genomic markers that are lineage-specific and only vertically inherited. Co-infections of mixed populations of genotypes of *Mycobacterium tuberculosis* can be revealed simultaneously in the mass spectra of amplification products produced using the primers of Table 11. The high G+C content and of the *Mycobacterium tuberculosis* genome itself greatly facilitates the development of short, efficient primers which are appropriate for multiplexing (inclusion of a plurality of primers in each amplification reaction mixture).

TABLE 11

Primer Pairs for Genotyping and Determination of Drug Resistance of Strains of *Mycobacterium tuberculosis*

| Primer Pair No. | Forward Primer Name | Forward Primer Sequence | Forward Primer (SEQ ID NO:) | Reverse Primer Name | Reverse Primer Sequence | Reverse Primer (SEQ ID NO:) |
|---|---|---|---|---|---|---|
| 3546 | RPOB_L27989-1-5084_2333_2351_F | TGTGGCCGCG ATCAAGGAG | 670 | RPOB_L27989-1-5084_2458_2474_R | TAGCCCGGC ACGCTCAC | 694 |
| 3547 | RPOB_L27989-1-5084_2362_2384_F | TCAGCCAGC TGAGCCAATT CATG | 671 | RPOB_L27989-1-5084_2388_2407_R | TCCGACAG CGGGTTGTTCTG | 695 |
| 3548 | RPOB_L27989-1-5084_2397_2414_F | TCGCTGTCGGG GTTGACC | 672 | RPOB_L27989-1-5084_2418_2434_R | TCCGACAGT CGGCGCTT | 696 |
| 3550 | EMBB_AY727532-1-344_100_119_F | TGCTCTGGCAT GTCATCGGC | 673 | EMBB_AY727532-1-344_209_228_R | TGAAGGGAT CCTCCGGCTG | 697 |
| 3551 | EMBB_AY727532-1-344_134_152_F | TGACGGCTACA TCCTGGGC | 674 | EMBB_AY727532-1-344_160_176_R | TGCGTGGTC GGCGACTC | 698 |
| 3552 | FABG-INHA-PROMOTER_U66801-1-993_169_191_F | TGCTCGTGGAC ATACCGA TTTCG | 675 | FABG-INHA-PROMOTER_U66801-1-993_224_243_R | TCAGTGGCTGT GGCAGTCAC | 699 |
| 3553 | KATG_U06268-1-2324_991_1010_F | TCGGTAAGGAC GCGATCACC | 676 | KATG_U06268-1-2324_1014_1034_R | TGTCCATACG ACCTCGATGCC | 700 |
| 3554 | KATG_U06268-1-2324_1433_1454_F | TGCCAGCCTTA AGAGCCAGATC | 677 | KATG_U06268-1-2324_1458_1480_R | TGTGAGACAGTC AATCCCGATGC | 701 |
| 3555 | GYRA_AF400983-1-385_69_84_F | TCACCCGCAC GGCGAC | 678 | GYRA_AF400983-1-385_103_119_R | TGGGCCA TGCGCACCAG | 702 |
| 3556 | GYRA_AF400983-1-385_80_99_F | TCGACGCGTCG ATCTACGAC | 679 | GYRA_AF400983-1-385_103_119_R | TGGGCCATG CGCACCAG | 702 |
| 3557 | RPSL_AY156733-1-375_65_82_F | TGGCTCTGAAG GGCAGCC | 680 | RPSL_AY156733-1-375_177_195_R | TGCCGTGACCT CGACCTGA | 703 |

TABLE 11-continued

Primer Pairs for Genotyping and Determination of Drug Resistance of Strains of Mycobacterium tuberculosis

| Primer Pair No. | Forward Primer Name | Forward Primer Sequence | Forward Primer (SEQ ID NO:) | Reverse Primer Name | Reverse Primer Sequence | Reverse Primer (SEQ ID NO:) |
|---|---|---|---|---|---|---|
| 3558 | PNCA_AL123456.2_gi41353971-1-4411532_2289165_2289181_F(RC) | TCTGTGGCTGCCGCGTC | 681 | PNCA_AL123456.2_gi41353971-1-4411532_2289303_2289287_R(RC) | TCGGCGCCACCGGTTAC | 704 |
| 3559 | PNCA_AL123456.2_gi41353971-1-4411532_2288970_2288989_F(RC) | TCATCACGTCGTGGCAACCA | 682 | PNCA_AL123456.2_gi41353971-1-4411532_2289119_2289098_R(RC) | TACGTGTCCAGACTGGGATGGA | 705 |
| 3560 | PNCA_AL123456.2_gi41353971-1-4411532_2288815_2288832_F(RC) | TGTGCCTACACCGGAGCG | 683 | PNCA_AL123456.2_gi41353971-1-4411532_2288953_2288933_R(RC) | TCGTCTGCGCACACAATGAT | 706 |
| 3561 | PNCA_AL123456.2_gi41353971-1-4411532_2288710_2288729_F(RC) | TCCGATCATTGTGTGCGCCA | 684 | PNCA_AL123456.2_gi41353971-1-4411532_2288839_2288821_R(RC) | TGGTGCGCATCTCCTCCAG | 707 |
| 3581 | RV2109C_AL123456.2_gi41353971-1-4411532_2369291_2369316_F | TCGACCCGTCGTAGGTAATACGATAC | 685 | RV2109C_AL123456.2_gi41353971-1-4411532_2369342_2369358_R | TGCCGAGGTGGCGCATT | 708 |
| 3582 | RV2348C_AL123456.2_gi41353971-1-4411532_2627916_2627940_F | TGCCCTGTTTGAAACTGCCACATAC | 686 | RV2348C_AL123456.2_gi41353971-1-4411532_2627954_2627974_R | TCGGGCTCAACGACACTTCCT | 709 |
| 3583 | RV3815C_NC000962-1-4411532_4280680_4280699_F | TGCCCTTGGTCGGGCACATTC | 687 | RV3815C_AL123456.2_gi41353971-1-4411532_4280716_4280734_R | TCCACCGGAACCCGGATCA | 710 |
| 3584 | RV0041_AL123456.2_gi41353971-1-4411532_43921_43939_F | TCTGCCCGCCGAGCAATAC | 688 | RV0041_AL123456.2_gi41353971-1-4411532_43960_43976_R | TGGTCCGGGTACGCGGA | 711 |
| 3586 | RV0147_AL123456.2_gi41353971-1-4411532_174655_174678_F | TCCGTAAGTCGGTGTTGACCAAAC | 689 | RV0147_AL123456.2_gi41353971-1-411532_174694_174716_R | TGGCGGGTAGATAAAGCTGGACA | 712 |
| 3587 | RV1814_AL123456.2_gi41353971-1-4411532_2057117_2057135_F | TCGGGTCCACCACGGAATG | 690 | RV1814_AL123456.2_gi41353971-1-4411532_2057151_2057173_R | TGGATGCCGCCATAGTTCTTGTC | 713 |

TABLE 11-continued

Primer Pairs for Genotyping and Determination of Drug Resistance of Strains of Mycobacterium tuberculosis

| Primer Pair No. | Forward Primer Name | Forward Primer Sequence | Forward Primer (SEQ ID NO:) | Reverse Primer Name | Reverse Primer Sequence | Reverse Primer (SEQ ID NO:) |
|---|---|---|---|---|---|---|
| 3599 | RV0083_AL123456.2_gi41353971-1-4411532_92169_92187_F | TGCCGACGCGATCGAACAG | 691 | RV0083_AL123456.2_gi41353971-1-4411532_92220_92238_R | TAACAGCTCGGCCATGGCG | 714 |
| 3600 | RV0005GYRB_AL123456.2_gi41353971-1-4411532_6348_6368_F | TGACCAAGACCAAGTTGGGCA | 692 | RV0005GYRB_AL123456.2_gi41353971-1-4411532_6457_6478_R | TGAGGACACAGCCTTGTTCACA | 715 |
| 3601 | RV0260C_AL123456.2_gi41353971-1-4411532_311588_311604_F | TGCCCAGAGCCGTTCGT | 693 | RV0260C_AL123456.2_gi41353971-1-4411532_311623_311639_2_R | TACACCCACGCCGTGGA | 716 |

The panel of 24 primer pairs is designed to be multiplexed into 8 amplification reactions. Thirteen primer pairs were designed with the objective of identifying mutations associated with resistance to drugs including rifampin (primer pair numbers 3546, 3547 and 3548), ethambutol (primer pair numbers 3550 and 3551), isoniazid (primer pair numbers 3353 and 3354), fluoroquinolone (primer pair number 3556), streptomycin (primer pair number 3557) and pyrazinamide (primer pair numbers 3558, 3558, 3560 and 3561). Four of these thirteen primer pairs were specifically designed to provide bioagent identifying amplicons for base composition analysis of single codons (primer pair numbers 3547 (rpoB codon D526), 3548 (rpoB codon H516), 3551 (embB codon M306), and 3553 (katG codon S315)). In any of these bioagent identifying amplicons used for base composition analysis, detection of a mutation identifies a drug-resistant strain of *Mycobacterium tuberculosis*. The remaining nine primer pairs define larger bioagent identifying amplicons that contain secondary drug resistance-conferring sites which are more rare than the four codons discussed above, but certain of these nine primer pairs define bioagent identifying amplicons that also contain some of these four codons (for example, primer pair 3546 contains two rpoB codons; D526 and H516).

Shown in Table 12 are classifications of members of the bacterial genus *Mycobacterium* according to principal genetic group (PGG, determined using primer pair numbers X and X), genotype of *Mycobacterium tuberculosis*, or species of selected other members of the genus *Mycobacterium* (determined using primer pair numbers X, Y, Z), and drug resistance to rifampin, ethambutol, isoniazid, fluoroquinolone, streptomycin, and pyrazinamide. The primer pairs used to define the bioagent identifying amplicons for each PPG group, genotype or drug resistant strain are shown in the column headings. In the drug resistance columns, codon mutations are indicated by the amino acid single letter code and codon position convention which is well known to those with ordinary skill in the art. For example, when nucleic acid of *Mycobacterium tuberculosis* strain 13599 is amplified using primer pair number 3555, and the molecular mass or base composition is determined, mutation of codon 90 from alanine (A) to valine (V) is indicated and the conclusion is drawn that strain 13599 is resistant to the drug fluoroquinolone.

Primer pair number 3600 is a speciation primer pair which is useful for distinguishing members of *Mycobacterium tuberculosis* PPG1 (including genotypes I, II and IIA) from other species of the genus *Mycobacterium* (such as for example, *Mycobacterium africanum*, *Mycobacterium bovis*, *Mycobacterium microti*, and *Mycobacterium canettii*).

TABLE 12

Classification and Drug Resistance Profiles of Strains of Members of the Genus *Mycobacterium* and Genotypes of *Mycobacterium tuberculosis*

| Strain | Principal Genetic Group (PGG) Primer Pair Numbers: 3554, 3556 | Genotype Primer Pair Number 3581, 3582, 3583, 3584, 3586, 3587, 3599, 3600, 3601 | Drug Resistance to Rifampin Primer Pair Numbers: 3546, 3547, 3548 | Drug Resistance to Ethambutol Primer Pair Numbers: 3550, 3551 | Drug Resistance to Isoniazid Primer Pair Numbers: 3553 | Drug Resistance to Fluoroquinolone Primer Pair Number: 3552 | Drug Resistance to Streptomycin Primer Pair Number: 3555 | Drug Resistance to Pyrazinamide Primer Pair Numbers: 3557 | 3558, 3559, 3560, 3561 |
|---|---|---|---|---|---|---|---|---|---|
| 19422 | PGG-1 | *M africanum* or *M. microti* | wild type | wt | wt | wt | wt | wt | wt |
| 10130 | PGG-1 | *M. bovis* | wt | wt | wt | wt | wt | wt | [part2] C > G |
| 35737 (BCG) | PGG-1 | *M. bovis* | wt | wt | wt | wt | wt | wt | wt |
| *M. Canettii* | PGG-1 | *M. canettii* | wt | wt | wt | wt | wt | wt | [part2] C > G |
| 14157, 15042 | PGG-1 | I | wt | wt | wt | wt | wt | wt | wt |
| 16116 | PGG-1 | IIA | wt | wt | wt | wt | wt | wt | wt |
| 15021 | PGG-1 | IIA | wt | wt | wt | wt | wt | wt | [part2] C > T |
| 5116 | PGG-1 | IIA | wt | wt | S315T | wt | wt | wt | wt |
| 12360, 13876, 14149 | PGG-1 | II | wt | wt | wt | wt | wt | wt | wt |
| 13599 | PGG-1 | II | wt | wt | wt | C-15T | A90V | wt | [part2] A > G |
| 13598 | PGG-1 | II | H528Y | M306V | S315 (N/T) | wt | wt | K43R | wt |
| 10545 | PGG-1 | II | wt | M306I | S315T | wt | wt | wt | wt |
| 13632 | PGG-1 | II | transition | M306I | S315T | wt | wt | wt | [part2] C > T, [part3] G > C |
| 14207 | PGG-1 | III | wt | wt | wt | wt | wt | wt | wt |
| 13866, 13874, 14038 | PGG-2 | III or IV | wt | wt | wt | wt | wt | wt | wt |
| 12578, 12590 | PGG-2 | III or IV | wt | wt | S315T | wt | wt | wt | [part3] G > C |
| 14404 | PGG-2 | IV | wt | wt | wt | wt | wt | wt | wt |
| 14831 | PGG-2 | IV | wt | wt | S315T | T-8C | wt | wt | wt |
| 5170, 13672, 13699, 14424 | PGG-2 | V | wt | wt | wt | wt | wt | wt | wt |
| 13679, 14399 | PGG-2 | VI | wt | wt | wt | wt | wt | wt | wt |
| 13592 | PGG-2 | VI | wt | wt | S315T | wt | wt | wt | wt |
| 13594, 13658, 13869 | PGG-3 | VII | wt | wt | wt | wt | T95S | wt | wt |
| 13821 | PGG-3 | VIII | wt | wt | wt | wt | T95S | wt | wt |
| 35837 (H37Rv7) | PGG-3 | VIII | wt | M306V | wt | wt | T95S | wt | wt |

Example 14

Validation of the Panel of 24 Primer Pairs

Each primer pair was individually validated using the reference *Mycobacterium tuberculosis* strain H37Rv. Dilution To Extinction (DTE) experiments yielded the expected base composition down to 16 genomic copies per well. A multiplexing scheme was then determined in order to spread into different wells the primer pairs targeting the same gene, to spread within a single well the expected amplicon masses, and to avoid cross-formation of primer duplexes. The multiplexing scheme is shown in Table 13 where multiplexed amplification reactions are indicated in headings numbered A through H and the primer pairs utilized for each reaction are shown below.

TABLE 13

Multiplexing Scheme for Panel of 24 Primer Pairs

| Reaction A | Reaction B | Reaction C | Reaction D | Reaction E | Reaction F | Reaction G | Reaction H |
|---|---|---|---|---|---|---|---|
| 3547 | 3548 | 3601 | 3551 | 3553 | 3554 | 3555 | 3556 |
| 3581 | 3584 | 3599 | 3582 | 3583 | 3587 | 3552 | 3586 |
| 3550 | 3600 | 3559 | 3560 | 3546 | 3558 | 3561 | 3557 |

An example of an experimentally determined table of base compositions is shown in Table 14. Base compositions of amplification products obtained from nucleic acid isolated from *Mycobacterium tuberculosis* strain 5170 using the primer pair multiplex reactions indicated in Table 13 are shown. Molecular masses of the amplification products were measured by electrospray time of flight mass spectrometry in order to calculate the base compositions. It should be noted that the lengths of the amplification products within each reaction mixture vary greatly in length in order to avoid overlap of molecular masses during the measurements. For example, reaction A has three amplification products which have lengths of 46 (A13 T11 C15 G07), 68 (A14 T18 C21 G15) and 129 (A21 T37 C44 G27).

TABLE 14

Base Compositions Obtained in the Multiplex Amplification Reactions of Nucleic Acid of *Mycobacterium tuberculosis* Strain 5170

| Reaction | Primer Pair No. | Base Composition (A G C T) |
|---|---|---|
| A | 3547 | 13 11 15 07 |
| A | 3581 | 14 18 21 15 |
| A | 3550 | 21 37 44 27 |
| B | 3548 | 06 13 12 07 |
| B | 3584 | 13 13 24 06 |
| B | 3600 | 37 34 35 25 |
| C | 3601 | 07 20 15 10 |
| C | 3599 | 10 26 22 12 |
| C | 3559 | 26 34 53 28 |
| D | 3551 | 08 13 16 06 |
| D | 3582 | 13 15 17 14 |
| D | 3560 | 28 48 37 26 |
| E | 3553 | 11 15 11 07 |
| E | 3583 | 06 19 16 14 |
| E | 3546 | — |
| F | 3554 | 11 13 14 10 |
| F | 3587 | 15 16 16 10 |
| F | 3558 | — |
| G | 3555 | 09 14 21 07 |
| G | 3552 | 13 26 22 14 |
| G | 3561 | 22 48 39 21 |
| H | 3556 | 07 11 15 07 |
| H | 3586 | 15 11 23 13 |
| H | 3557 | 26 44 39 22 |

Dilution to extinction experiments were then carried out with the chosen triplets of primer pairs in multiplex conditions. Base compositions expected on the basis of the known sequence of the reference strain were observed down to 32 genomic copies per well on average. The assay was finally tested using a collection of 36 diverse strains from the Public Health Research Institute. As expected, the base compositions results were in accordance with the genotyping and drug-resistance profiles already determined for these reference strains.

Example 15

Primer Pairs that Define Bioagent Identifying Amplicons for Hepatitis C Viruses For design of primers that define hepatitis c virus strain identifying amplicons, a series of hepatitis C virus genome sequences were obtained, aligned and scanned for regions where pairs of PCR primers would amplify products of about 27 to about 200 nucleotides in length and distinguish strains and quasispecies from each other by their molecular masses or base compositions.

Table 15 represents a collection of primers (sorted by primer pair number) designed to identify hepatitis C viruses using the methods described herein. The primer pair number is an in-house database index number. The forward or reverse primer name shown in Table 15 indicates the gene region of the viral genome to which the primer hybridizes relative to a reference sequence. In Table 15, for example, the forward primer name HCVUTR5_NC001433-1-9616_9250_9273_F indicates that the forward primer (_F) hybridizes to residues 9250-9275 of the UTR (untranslated region) of a hepatitis C virus reference sequence represented by an extraction of nucleotides 1 to 9616 of GenBank Accession No. NC_001433.1. One with ordinary skill will know how to obtain individual gene sequences or portions thereof from genomic sequences present in GenBank.

TABLE 15

Primer Pairs for Identification of Strains of Hepatitis C Viruses

| Primer Pair No. | Forward Primer Name | Forward Sequence | Forward SEQ ID NO: | Reverse Primer Name | Reverse Sequence | Reverse SEQ ID NO: |
|---|---|---|---|---|---|---|
| 3682 | HCVUTR5_NC001433-1-9616_9250_9273_F | TCAGCGGAGGTGACATGTATCACA | 655 | HCVUTR5_NC001433-1-9616_9313_9337_R | TACTCCTCCTTTCGGTAGCGGTAGA | 662 |
| 3683 | HCVUTR5_NC001433-1-9616_9177_9200_F | TCGACCAACCTTAAACGCACTCCA | 656 | HCVUTR5_NC001433-1-9616_9261_9285_R | GACATGTATCACAACCTGTCGCACA | 663 |
| 3684 | HCVUTR5_NC001433-1-9616_3644_3662_F | TTAGCACCTCGACGGCTGG | 657 | HCVUTR5_NC001433-1-9616_3735_3756_R | CATGCTAATGTCGTTCCGGCGA | 664 |
| 3685 | HCVUTR5_NC001433-1-9616_3708_3731_F | TGCTCGGACCTTTACTTGGTCACG | 658 | HCVUTR5_NC001433-1-9616_3735_3757_R | CATGCTGATGTCATTCCGGTGCA | 665 |
| 3686 | HCVUTR5_NC001433-1-9616_3708_3731_F | TGCTCGGACCTTTACTTGGTCACG | 658 | HCVUTR5_NC001433-1-9616_3822_3840_R | TCGGGTGGTCCACTGCTCA | 666 |
| 3687 | HCVUTR5_NC001433-1-9616_3796_3817_F | TGCCCGTCTCCTACTTGAAGGG | 659 | HCVUTR5_NC001433-1-9616_3876_3893_R | GCTGTGTACACCCGGCGA | 667 |
| 3688 | HCVUTR5_NC001433-1-9616_3855_3872_F | TTTGCGGGCACCTTCCGG | 660 | HCVUTR5_NC001433-1-9616_3876_3893_R | GCTGTGTACACCCGGCGA | 667 |
| 3689 | HCVUTR5_NC001433-1-9616_3855_3872_F | TTTGCGGGCACCTTCCGG | 660 | HCVUTR5_NC001433-1-9616_3942_3962_2_R | ATGCGGTATCCGGTCCTCACA | 668 |
| 3691 | HCVUTR5_NC001433-1-9616_1974_1996_2_F | TGGCTCGGTTGTACAGGGATGAA | 661 | HCVUTR5_NC001433-1-9616_2070_2091 | TGCCCAACGGACTACTTCCTGA | 669 |

Example 16

Primer Pairs that Define Bioagent Identifying Amplicons for Identification of Strains of Influenza Viruses For design of primers that define bioagent identifying amplicons for identification of strains of influenza viruses, a series of influenza virus genome sequences were obtained, aligned and scanned for regions where pairs of PCR primers would amplify products of about 27 to about 200 nucleotides in length and distinguish influenza virus strains of from each other by their molecular masses or base compositions.

Table 16 represents a collection of primers (sorted by primer pair number) designed to identify hepatitis C viruses using the methods described herein. The primer pair number is an in-house database index number. The forward or reverse primer name shown in Table 16 indicates the gene region of the influenza virus genome to which the primer hybridizes relative to a reference sequence. In Table 16, for example, the forward primer name FLUBPB2_NC002205_603_629_F indicates that the forward primer (_F) hybridizes to residues 603-629 of an influenza reference sequence represented by an extraction of nucleotides from GenBank Accession No. NC_002205. One with ordinary skill will know how to obtain individual gene sequences or portions thereof from genomic sequences present in GenBank.

TABLE 16

Primer Pairs for Identification of Strains of Influenza Viruses

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 1261 | FLUBPB2_NC002205_603_629_F | TCCCATTGTACTGGCATACATGCTTGA | 639 | FLUBPB2_NC002205_667_693_R | TATGAACTCAGCTGATGTTGCTCCTGC | 647 |
| 1266 | FLUANUC_J02147_118_148_F | TACATCCAGATGTGCACTGAACTCAAACTCA | 640 | FLUANUC_J02147_188_218_R | TCGTCAAATGCAGAGAGCACCATTCTCTCTA | 648 |

TABLE 16-continued

Primer Pairs for Identification of Strains of Influenza Viruses

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 1275 | FLUBNUC_NC002208_90_116_F | TCCAATCATC AGACCAGCAA CCCTTGC | 641 | FLUBNUC_NC002208_164_189_R | TCCGATATCAG CTTCACTGC TTGTGG | 649 |
| 1279 | FLUAM1_NC004524_369_396_F | TCTTGCCAGTT GTATGGGCCT CATATAC | 642 | FLUAM1_NC004524_451_473_R | TGGGAGTCAG CAATCTGC TCACA | 650 |
| 1287 | FLUAPA_NC004520_562_584_F | TGGGATTCCTTT CGTCAGTCCGA | 643 | FLUAPA_NC004520_647_673_R | TGGAGAAGTT CGGTGGGAG ACTTTGGT | 651 |
| 2775 | FLUANS1_NC004525_1_19_F | TCCAGGACAT ACTGATGAGGAT GTCAAAAATGCA | 644 | FLUANS1_NC004525_29_52_R | TGCTTCCCCA AGCGAATCT CTGTA | 652 |
| 2777 | FLUANS2_NC004525_47_74_F | TGTCAAAAATG CAATTGGGGT CCTCATC | 645 | FLUANS2_NC004525_121_151_R | TCATTACTGCT TCTCCAAGCGA ATCTCTGTA | 653 |
| 2798 | FLUPB1_J02151_1210_1235_F | TGTCCTGGAAT GATGATGGGCA TGTT | 646 | FLU_ALL_PB1_J02151_1313_1337_R | TCATCAGAGG ATTGGAGTCCA TCCC | 654 |
| 1261 | FLUBPB2_NC002205_603_629_F | TCCCATTGTACT GGCATACATG CTTGA | 639 | FLUBPB2_NC002205_667_693_R | TATGAACTCAG CTGATGTTGCT CCTGC | 647 |

Example 17

Primer Pairs that Define Bioagent Identifying Amplicons for Identification of Strains of Staphylococcus aureus For design of primers that define bioagent identifying amplicons for identification of strains of Staphylococcus aureus, a series of Staphylococcus aureus virus genome sequences were obtained, aligned and scanned for regions where pairs of PCR primers would amplify products of about 27 to about 200 nucleotides in length and distinguish Staphylococcus aureus strains of from each other by their molecular masses or base compositions.

Table 17 represents a collection of primers (sorted by primer pair number) designed to identify Staphylococcus aureus strains using the methods described herein. The primer pair number is an in-house database index number. The forward or reverse primer name shown in Table 17 indicates the gene region of the influenza virus genome to which the primer hybridizes relative to a reference sequence. In Table 17, for example, the forward primer name MECA_Y14051_4507_4530_F indicates that the forward primer (_F) hybridizes to residues 4507-4530 of the mecA gene of Staphylococcus aureus sequence represented by GenBank Accession No. Y14051. One with ordinary skill will know how to obtain individual gene sequences or portions thereof from genomic sequences present in GenBank.

TABLE 17

Primer Pairs for Identification of Strains of Staphylococcus aureus

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 879 | MECA_Y14051_4507_4530_F | TCAGGTACTG CTATCCACCC TCAA | 717 | MECA_Y14051_4555_4581_R | TGGATAGACGT CATATGAAG GTGTGCT | 727 |
| 2056 | MECI-R_NC003923-41798-41609_33_60_F | TTTACACATAT CGTGAGCAAT GAACTGA | 718 | MECI-R_NC003923-41798-41609_86_113_R | TTGTGATATGGAGGT TAGAAGGTGTTA | 728 |
| 2081 | ERMA_NC002952-55890-56621_366_395_F | TAGCTATCTTA TCGTTAGAAGG GATTTGC | 719 | ERMA_NC002952-55890-56621_438_465_R | TGAGCATTTTA TATCCATCT CCACCAT | 729 |
| 2086 | ERMC_NC005908-2004-2738_85_116_F | TCTGAACATGA TAATATCTTTG AAATCGGCTC | 720 | ERMC_NC005908-2004-2738_173_206_R | TCCGTAGTTTTG CATAAATTTATG GTCTATTTCAA | 730 |

TABLE 17-continued

Primer Pairs for Identification of Strains of Staphylococcus aureus

| Primer Pair Number | Forward Primer Name | Forward Sequence | Forward SEQ ID NO: | Reverse Primer Name | Reverse Sequence | Reverse SEQ ID NO: |
|---|---|---|---|---|---|---|
| 2095 | PVLUK_NC003923-1529595-1531285_688_713_F | TGAGCTGCATCAACTGTATTGGATAG | 721 | PVLUK_NC003923-1529595-1531285_775_804_R | TGGAAAACTCATGAAATTAAAGTGAAAGGA | 731 |
| 2256 | NUC_NC002758-894288-894974_316_345_F | TACAAAGGTCAACCAATGACATTCAGACTA | 722 | NUC_NC002758-894288-894974_396_421_R | TAAATGCACTTGCTTCAGGGCCATAT | 732 |
| 2313 | MUPR_X75439_2486_2516_F | TAATTGGGCTCTTTCTCGCTTAAACACCTTA | 723 | MUPR_X75439_2548_2574_R | TTAATCTGGCTGCGGAGTGAAATCGT | 733 |
| 3005 | TUFB_NC002758-615038-616222_688_710_F | TGCCGTGTTGAACGTGGTCAAAT | 724 | TUFB_NC002758-615038-616222_783_813_R | TGCTTCAGCGTAGTCTAATAATTTACGGAAC | 734 |
| 3016 | MUPR_X75439_2482_2510_F | TAGATAATTGGGCTCTTTCTCGCTTAAAC | 725 | MUPR_X75439_2551_2573_R | TTATCTGGCTGCGGAGTGAAAT | 735 |
| 3106 | TSST1_NC002758.2_519_546_F | TCGTCATCAGCTAACTCAAATACATGGA | 726 | TSST1_NC002758.2_593_620_R | TCACTTTGATATGTGGATCCGTCATTCA | 736 |
| 2738 | GYRA_NC002953-7005-9668_166_195_F | TAAGGTATGACACCGGATAAATCATATAAA | 737 | GYRA_NC002953-7005-9668_265_287_R | TCTTGAGCCATACGTACCATTGC | 740 |
| 2739 | GYRA_NC002953-7005-9668_221_249_F | TAATGGGTAAATATCACCCTCATGGTGAC | 738 | GYRA_NC002953-7005-9668_316_343_R | TATCCATTGAACCAAAGTTACCTTGGCC | 741 |
| 2740 | GYRA_NC002953-7005-9668_221_249_F | TAATGGGTAAATATCACCCTCATGGTGAC | 738 | GYRA_NC002953-7005-9668_253_283_R | TAGCCATACGTACCATTGCTTCATAAATAGA | 742 |
| 2741 | GYRA_NC002953-7005-9668_234_261_F | TCACCCTCATGGTGACTCATCTATTTAT | 739 | GYRA_NC002953-7005-9668_265_287_R | TCTTGAGCCATACGTACCATTGC | 740 |

Example 18

Comparison of Targeted Whole Genome Amplification Method with an Unbiased Whole Genome Amplification Method A set of algorithms was developed for the design of TWGA primer sets favoring amplification of target DNA from a DNA mixture as described in Example 2. As a test case, a TWGA primer set consisting of approximately 200 primers was designed for the preferential amplification of *Bacillus anthracis* genomic DNA from a mixture of background genomes. The primer set showed high representation of the *Bacillus anthracis* genome and under-representation in a panel of eukaryotic genomes selected from mammals, insects, plants, birds, and nematodes. The primer set was designed with consistent binding of the primers along the *Bacillus anthracis* genome, maintaining representation across the entire genome during amplification. To demonstrate the preferential amplification of target DNA from a DNA mixture, mixtures of *Bacillus anthracis* Sterne DNA and human DNA were amplified using targeted whole genome amplification, and the resulting products were quantified by Quantitative Real-Time PCR-based detection of distinctive genomic sequences. As shown in FIG. 5A, 175-fold amplification of *B. anthracis* DNA was observed in the presence of a ten million-fold excess of human background DNA, with minimal amplification of the background DNA itself. A 3000-fold amplification of target DNA was observed when background was reduced slightly, to a million-fold excess relative to the target DNA levels, again with minimal amplification of background DNA (FIG. 5B).

Results obtained from the targeted whole genome amplification reaction are contrasted with results of an unbiased whole genome amplification reaction in FIG. 6. Target genome was prepared in a million-fold excess of background DNA and amplified by targeted whole genome amplification or by unbiased whole genome amplification. In contrast to targeted whole genome amplification, unbiased whole genome amplification uses random priming which should result in similar amplification of both target DNA and background DNA. In FIG. 6A it can be seen that targeted whole genome amplification favored amplification of the target DNA. In contrast, whole genome amplification produced similar levels of amplification of both components of the DNA mixture (FIG. 6B).

In FIG. 7, it is evident that targeted whole genome amplification increases the sensitivity of detection of target DNA from a mixture, in comparison to unbiased whole genome amplification. Reactions were prepared with human DNA present at 0.1 micrograms per reaction and with *Bacillus anthracis* genomic DNA incremented from 50 to 400 femtograms. Preferential amplification with targeted whole genome amplification primers was compared to unbiased amplification using random unbiased whole genome amplification primers. As shown above, targeted whole genome amplification gave higher yields of *Bacillus anthracis* DNA and lower yields of human DNA than unbiased whole genome amplification (FIGS. 7A and 7B). Significantly, targeted whole genome amplification gave detectable *Bacillus anthracis* product with 50 femtograms of starting material, whereas unbiased whole genome amplification did not.

Targeted whole genome amplification primer sets were developed for six additional target organisms and a cocktail of the primer sets were run in the targeted whole genome amplification reactions. Similar results were obtained when targeted whole genome amplification was formulated with this pool of primer sets or with the *Bacillus anthracis*-specific targeted whole genome amplification primer set, indicating that targeted whole genome amplification can be multiplexed (targeted whole genome amplification seven-set primers vs. TWGA single-set primers, FIG. 7).

CONCLUDING STATEMENTS

The present invention includes any combination of the various species and subgeneric groupings falling within the generic disclosure. This invention therefore includes the generic description of the invention with a proviso or negative limitation removing any subject matter from the genus, regardless of whether or not the excised material is specifically recited herein.

While in accordance with the patent statutes, description of the various embodiments and examples have been provided, the scope of the invention is not to be limited thereto or thereby. Modifications and alterations of the present invention will be apparent to those skilled in the art without departing from the scope and spirit of the present invention.

Therefore, it will be appreciated that the scope of this invention is to be defined by the appended claims, rather than by the specific examples which have been presented by way of example.

Each reference (including, but not limited to, journal articles, U.S. and non-U.S. patents, patent application publications, international patent application publications, gene bank gi or accession numbers, internet web sites, and the like) cited in the present application is incorporated herein by reference in its entirety.

What is claimed is:

1. A method comprising:
   a) amplifying at least one pathogen genome from a sample suspected of comprising at least one pathogen genome and at least one background genome using at least one targeted whole genome amplification primer pair, thereby elevating the quantity of nucleic acid representing said at least one pathogen genome relative to the quantity of nucleic acid representing said at least one background genome, wherein said plurality of targeted whole genome amplification primers is selected by:
      i) identifying at least one pathogen genome;
      ii) identifying at least one background genome;
      iii) identifying a plurality of genome sequence segments having unique sequences within said pathogen genome sequence;
      iv) determining frequency of occurrence of members of said plurality of genome sequence segments within said pathogen genome sequence and determining frequency of occurrence of said plurality of genome sequence segments within said background genome sequences;
      v) calculating a selectivity ratio for said members by dividing said frequency of occurrence within said pathogen genome sequence by said frequency of occurrence of said plurality of genome sequence segments within said background genome sequences;
      vi) selecting a selectivity ratio threshold value, thereby defining a first sub-set of said plurality of genome sequence segments having selectivity ratios equal to or greater than said selectivity ratio threshold value;
      vii) determining the lengths of pathogen genome sequence occurring between genome sequence segments of said first sub-set;
      viii) selecting a second sub-set of genome sequence segments from said first sub-set wherein members of said second sub-set have a mean separation distance of less than a selected length of nucleobases; and
      ix) selecting targeted whole genome amplification primers that hybridize to members of said second sub-set of genome sequence segments such that, under whole genome amplification conditions, said at least one pathogen genome is amplified selectively over said at least one background genomes;
   b) producing one or more amplification products representing bioagent identifying amplicons from said amplified pathogen genome using said at least one primer pair;
   c) measuring molecular masses of said amplification products by mass spectrometry;
   d) calculating base compositions of said amplification products from said molecular masses without sequencing said amplification products; and
   e) comparing said base compositions with a database comprising base compositions of bioagent identifying amplicons of pathogens produced with said at least one primer pair, thereby identifying said pathogen in said sample.

2. The method of claim 1 wherein said mass spectrometry is electrospray time-of-flight mass spectrometry.

3. The method of claim 1 wherein said amplification products are generated using a plurality of primer pairs that define bioagent identifying amplicons.

4. The method of claim 3 wherein said plurality of primer pairs are used in a multiplex reaction to generate a plurality of amplification products.

5. The method of claim 3 wherein said plurality of primer pairs comprises at least two primer pairs from the group consisting of primer pair numbers: 346 (SEQ ID NOs: 594:602), 348 (SEQ ID NOs: 595:603), 349 (SEQ ID NOs: 596:604), 354 (SEQ ID NOs: 597:605), 358 (SEQ ID NOs: 598:606), 359 (SEQ ID NOs: 599:607), 3346 (SEQ ID NOs: 616:631), 449 (SEQ ID NOs: 600:608), 3350 (SEQ ID NOs: 614:629), 2249 (SEQ ID NOs: 601:609), 3361 (SEQ ID NOs: 620:635), and 3360 (SEQ ID NOs: 612:627).

6. The method of claim 3 wherein said plurality of primer pairs comprises primer pair numbers: 346 (SEQ ID NOs: 594:602), 348 (SEQ ID NOs: 595:603), 349 (SEQ ID NOs: 596:604), 3346 (SEQ ID NOs: 616:631).

7. The method of claim 3 wherein said plurality of primer pairs comprises primer pair numbers: 346 (SEQ ID NOs: 594:602), 348 (SEQ ID NOs: 595:603), 349 (SEQ ID NOs: 596:604), and 3361 (SEQ ID NOs: 620:635).

8. The method of claim 3 wherein said plurality of primer pairs comprises primer pair numbers 346 (SEQ ID NOs: 594:602), 348 (SEQ ID NOs: 595:603), 349 (SEQ ID NOs: 596:604) and at least one of the primer pairs selected from the group consisting of 354 (SEQ ID NOs: 597:605), 358 (SEQ ID NOs: 598:606), 359 (SEQ ID NOs: 599:607), 3346 (SEQ ID NOs: 616:631), 449 (SEQ ID NOs: 600:608), 3350 (SEQ ID NOs: 614:629), 3361 (SEQ ID NOs: 620:635), and 3360 (SEQ ID NOs: 612:627).

9. The method of claim 1 wherein a high processivity polymerase enzyme is used at said amplification step.

10. The method of claim 9 wherein said high processivity polymerase enzyme is a recombinant polymerase enzyme.

11. The method of claim 9 wherein said high processivity polymerase enzyme is a genetically engineered polymerase enzyme.

12. The method of claim 9 wherein said high processivity polymerase enzyme is phi29.

13. The method of claim 1, wherein said sample comprises human whole blood.

14. The method of claim 13 further comprising the step of extracting total nucleic acid from said sample before carrying out said amplifying step.

15. The method of claim 1 wherein said sample comprises human buffy coat.

16. The method of claim 15 further comprising the step of extracting total nucleic acid from said sample before carrying out said amplifying step.

17. The method of claim 1 wherein said sample comprises human serum.

18. The method of claim 17 further comprising the step of extracting total nucleic acid from said sample before carrying out said amplifying step.

19. The method of claim 1 wherein said sample comprises human hepatic cells.

20. The method of claim 19 further comprising the step of extracting total nucleic acid from sample before carrying out said amplifying step.

21. The method of claim 1 wherein said sample comprises sputum.

22. The method of claim 21 further comprising the step of extracting total nucleic acid from said sample before carrying out said amplifying step.

23. The method of claim 1 wherein said sample comprises urine.

24. The method of claim 23 further comprising the step of extracting total nucleic acid from said sample before carrying out said amplifying step.

25. The method of claim 1 wherein said sample comprises biopsy tissue.

26. The method of claim 25 further comprising the step of extracting total nucleic acid from said sample before carrying out said amplifying step.

27. The method of claim 1 wherein said at least one pathogen is a bacterium.

28. The method of claim 27 wherein said bacterium is selected from the group consisting of: *Escherichia coli, Klebsiella pneumoniae, Klebsiella oxytoca, Serratia marcescens, Enterobacter cloacae, Enterobacter aerogenes, Proteus mirabilis, Pseudomonas aeruginosa, Acinetobacter baumannii, Stenotrophomonas maltophilia, Staphylococcus aureus, Staphylococcus epidermidis, Staphylococcus haemolyticus, Streptococcus pneumoniae, Streptococcus pyogenes, Streptococcus agalactiae, Streptococcus mitis, Enterococcus faecium, Enterococcus faecalis, Candida albicans, Candida tropicalis, Candida parapsilosis, Candida krusei, Candida glabrata, Mycobacterium tuberculosis*, and *Aspergillus fumigatus*.

29. The method of claim 1 wherein said at least one background genome comprises a human nucleic acid.

30. The method of claim 1 wherein said identifying step indicates the presence of bacterial sepsis in a human patient.

31. The method of claim 1 wherein said identifying step indicates the presence of bacteremia in a human patient.

32. The method of claim 1 wherein said pathogen is a virus.

33. The method of claim 32 wherein said virus is HIV.

34. The method of claim 32 wherein said virus is HCV.

35. The method of claim 32 wherein said virus is influenza virus.

36. A method comprising the steps of:
a) extracting nucleic acids from a sample; and
b) mixing said nucleic acids with at least one targeted whole genome amplification primer pair, a high processivity polymerase enzyme to produce an amplification mixture, wherein said plurality of targeted whole genome amplification primers is selected by:

i) identifying at least one target genome suspected of being present in said sample;
ii) identifying at least one background genome suspected of being present in said sample;
iii) identifying a plurality of genome sequence segments having unique sequences within said target genome sequence;
iv) determining frequency of occurrence of members of said plurality of genome sequence segments within said target genome sequence and within said background genome sequences;
v) calculating a selectivity ratio for said members by dividing said frequency of occurrence within said target genome by said frequency of occurrence of said plurality of genome sequence segments within said background genome sequences;
vi) selecting a selectivity ratio threshold value, thereby defining a first sub-set of said plurality of genome sequence segments having selectivity ratios equal to or greater than said selectivity ratio threshold value;
vii) determining the lengths of target genome sequence occurring between genome sequence segments of said first sub-set;
viii) selecting a second sub-set of genome sequence segments from said first sub-set wherein members of said second sub-set have a mean separation of less than a selected length of nucleobases; and
ix) selecting targeted whole genome amplification primers that hybridize to members of said second sub-set of genome sequence segments such that said at least one target genome is amplified selectively over said at least one background genome;

c) amplifying one or more of said extracted nucleic acids in said mixture of step b wherein said amplifying step is a targeted whole genome amplification reaction;
d) performing a second amplification step using at least one second primer pair that defines a bioagent identifying amplicon to obtain at least one second amplification product;
e) measuring the molecular mass of said at least one second amplification product by mass spectrometry;
f) calculating a base composition of said at least one second amplification product from said molecular mass without sequencing said at least one second amplification product; and
g) comparing said base composition with a database comprising base compositions of bioagent identifying amplicons of pathogens produced with said at least one second primer pair, thereby identifying said pathogen in said sample.

37. The method of claim 36 wherein said mass spectrometry is electrospray time-of-flight mass spectrometry.

38. The method of claim 36 wherein said second amplification step comprises obtaining a plurality of amplification products generated using a plurality of primer pairs that define bioagent identifying amplicons.

39. The method of claim 38 wherein said plurality of primer pairs is used in one or more multiplex reactions to generate a plurality of amplification products.

40. The method of claim 38 wherein said plurality of primer pairs comprises at least two primer pairs from the group consisting of primer pair numbers: 346 (SEQ ID NOs: 594:602), 348 (SEQ ID NOs: 595:603), 349 (SEQ ID NOs: 596:604), 354 (SEQ ID NOs: 597:605), 358 (SEQ ID NOs: 598:606), 359 (SEQ ID NOs: 599:607), 3346 (SEQ ID NOs: 616:631), 449 (SEQ ID NOs: 600:608), 3350 (SEQ ID NOs:

614:629), 2249 (SEQ ID NOs: 601:609), 3361 (SEQ ID NOs: 620:635), and 3360 (SEQ ID NOs: 612:627).

41. The method of claim 38 wherein said plurality of primer pairs comprises primer pair numbers: 346 (SEQ ID NOs: 594:602), 348 (SEQ ID NOs: 595:603), 349 (SEQ ID NOs: 596:604), 3346 (SEQ ID NOs: 616:631).

42. The method of claim 38 wherein said plurality of primer pairs comprises primer pair numbers: 346 (SEQ ID NOs: 594:602), 348 (SEQ ID NOs: 595:603), 349 (SEQ ID NOs: 596:604), and 3361 (SEQ ID NOs: 620:635).

43. The method of claim 38 wherein said plurality of primer pairs comprises primer pair numbers 346 (SEQ ID NOs: 594:602), 348 (SEQ ID NOs: 595:603), 349 (SEQ ID NOs: 596:604) and at least one of the primer pairs selected from the group consisting of 354 (SEQ ID NOs: 597:605), 358 (SEQ ID NOs: 598:606), 359 (SEQ ID NOs: 599:607), 3346 (SEQ ID NOs: 616:631), 449 (SEQ ID NOs: 600:608), 3350 (SEQ ID NOs: 614:629), 3361 (SEQ ID NOs: 620:635), and 3360 (SEQ ID NOs: 612:627).

44. The method of claim 36 wherein said high processivity polymerase enzyme is a recombinant polymerase enzyme.

45. The method of claim 36 wherein said high processivity polymerase enzyme is a genetically engineered polymerase enzyme.

46. The method of claim 36 wherein said high processivity polymerase enzyme is phi29.

47. The method of claim 36, wherein said sample comprises human whole blood.

48. The method of claim 47 further comprising the step of extracting total nucleic acid from said sample before carrying out said amplifying step.

49. The method of claim 36 wherein said sample comprises human buffy coat.

50. The method of claim 49 further comprising the step of extracting total nucleic acid from said sample before carrying out said amplifying step.

51. The method of claim 36 wherein said sample comprises human serum.

52. The method of claim 51 further comprising the step of extracting total nucleic acid from said sample before carrying out said amplifying step.

53. The method of claim 36 wherein said sample comprises human hepatic cells.

54. The method of claim 53 further comprising the step of total nucleic acid from sample before carrying out said amplifying step.

55. The method of claim 36 wherein said sample comprises sputum.

56. The method of claim 55 further comprising the step of extracting total nucleic acid from said sample before carrying out said amplifying step.

57. The method of claim 36 wherein said sample comprises urine.

58. The method of claim 57 further comprising the step of extracting total nucleic acid from said sample before carrying out said amplifying step.

59. The method of claim 36 wherein said sample comprises biopsy tissue.

60. The method of claim 59 further comprising the step of extracting total nucleic acid from said sample before carrying out said amplifying step.

61. The method of claim 36 wherein said sample comprises a bacterium.

62. The method of claim 61 wherein said bacterium is selected from the group consisting of: *Escherichia coli, Klebsiella pneumoniae, Klebsiella oxytoca, Serratia marcescens, Enterobacter cloacae, Enterobacter aerogenes, Proteus mirabilis, Pseudomonas aeruginosa, Acinetobacter baumannii, Stenotrophomonas maltophilia, Staphylococcus aureus, Staphylococcus epidermidis, Staphylococcus haemolyticus, Streptococcus pneumoniae, Streptococcus pyogenes, Streptococcus agalactiae, Streptococcus mitis, Enterococcus faecium, Enterococcus faecalis, Candida albicans, Candida tropicalis, Candida parapsilosis, Candida krusei, Candida glabrata* and *Aspergillus fumigatus*.

63. The method of claim 36 wherein said at least one background genome comprises a human nucleic acid.

64. The method of claim 36 wherein said identifying step indicates the presence of bacterial sepsis in a human.

65. The method of claim 36 wherein said pathogen is a virus.

66. The method of claim 65 wherein said virus is HIV.

67. The method of claim 65 wherein said virus is HCV.

68. The method of claim 65 wherein said virus is influenza virus.

69. The method of claim 1, wherein said calculating a selectivity ratio comprises calculating a mean selectivity ratio.

70. The method of claim 69, wherein said selecting a selectivity ratio threshold value comprises selecting a selectivity ratio at or above said mean selectivity ratio.

71. The method of claim 69, wherein said selecting a selectivity ratio threshold value comprises selecting a selectivity ratio at or below said mean selectivity ratio.

72. The method of claim 69, wherein said selecting a selectivity ration threshold value comprises selecting a whole or fractional percentage between about 25% above or about 25% below said mean selectivity ratio.

73. The method of claim 1, wherein said selecting a selectivity ratio threshold defines said first sub-set of said plurality of genome sequence segments as 80%, 70%, 60% or 50% of said plurality of genome sequence segments within said background genome sequences or any whole or fractional number therebetween.

74. The method of claim 1, wherein both a frequency of occurrence threshold value and a selectivity ratio threshold value are selected, and wherein both of said threshold values are used to define a sub-set of genome sequence segments.

75. The method of claim 1, wherein said genome sequence segments are ranked according to a selectivity ratio such that the highest selectivity ratio receives the highest rank.

76. The method of claim 1, comprising ranking said selectivity ratios using said frequency of occurrence of said plurality of genome sequence segments within said background genome sequences.

77. The method of claim 76, wherein a top ranked genome sequence segment is selected.

78. The method of claim 77, wherein a next highest ranking genome sequence segment is selected.

79. The method of claim 78, comprising determining whether said next ranked genome sequence segment originates from within a largest remaining separation distance.

* * * * *